(12) United States Patent
Labib et al.

(10) Patent No.: US 10,369,263 B2
(45) Date of Patent: Aug. 6, 2019

(54) BLOOD PROCESSING CARTRIDGES AND SYSTEMS, AND METHODS FOR EXTRACORPOREAL BLOOD THERAPIES

(71) Applicant: Princeton Trade & Technololgy, Inc., Princeton, NJ (US)

(72) Inventors: Mohamed E. Labib, Princeton, NJ (US); Stanislav S. Dukhin, Goldens Bridge, NY (US)

(73) Assignee: Novaflux Inc., Princeton, NJ (US)

( * ) Notice: Subject to any disclaimer, the term of this patent is extended or adjusted under 35 U.S.C. 154(b) by 21 days.

(21) Appl. No.: 14/671,186

(22) Filed: Mar. 27, 2015

(65) Prior Publication Data
US 2015/0314057 A1 Nov. 5, 2015

Related U.S. Application Data

(60) Provisional application No. 61/972,312, filed on Mar. 29, 2014.

(51) Int. Cl.
*A61M 1/34* (2006.01)
*B01D 63/02* (2006.01)
(Continued)

(52) U.S. Cl.
CPC .............. *A61M 1/34* (2013.01); *A61M 1/16* (2013.01); *A61M 1/1601* (2014.02);
(Continued)

(58) Field of Classification Search
CPC combination set(s) only.
See application file for complete search history.

(56) References Cited

U.S. PATENT DOCUMENTS

| 3,827,563 A | 8/1974 | Boe et al. |
| 4,038,191 A | 7/1977 | Davis et al. |

(Continued)

FOREIGN PATENT DOCUMENTS

| EP | 0 001 736 A1 | 5/1979 |
| EP | 0 167 162 A2 | 1/1986 |

(Continued)

OTHER PUBLICATIONS

Linneweber et al. ("The effect of surface roughness on activation of the coagulation system and platelet adhesion in rotary blood pumps" Artif Organs May 2007; 31(5): abstract).*
(Continued)

*Primary Examiner* — Ryan B Huang
(74) *Attorney, Agent, or Firm* — Merchant & Gould P.C.

(57) ABSTRACT

In embodiments of the invention, there is provided a dialyzer or filter comprising hollow fibers, in which blood flows on the exterior of the hollow fibers, and dialysate or filtrate may flow on the inside. The external surfaces of the hollow fibers may have properties of smoothness and hemocompatibility. The fiber bundle may have appropriate packing fraction and may have wavy fibers. Optimum shear rates and blood velocities are identified. Geometric features of the cartridge, such as pertaining to flow distribution of the blood, may be different for different ends of the cartridge. Air bleed and emboli traps may be provided. Lengthened service life may be achieved by combinations of these features, which may permit additional therapies and applications or better economics.

32 Claims, 40 Drawing Sheets

(51) Int. Cl.
  *A61M 1/16* (2006.01)
  *B01D 69/08* (2006.01)
  *B01D 61/14* (2006.01)
  *B01D 63/04* (2006.01)

(52) U.S. Cl.
  CPC .......... *A61M 1/1613* (2014.02); *A61M 1/341* (2014.02); *A61M 1/3403* (2014.02); *B01D 63/02* (2013.01); *B01D 63/024* (2013.01); *B01D 69/084* (2013.01); *A61M 2205/3331* (2013.01); *B01D 2313/10* (2013.01); *B01D 2313/12* (2013.01); *B01D 2313/16* (2013.01); *B01D 2313/20* (2013.01)

(56) References Cited

U.S. PATENT DOCUMENTS

| | | |
|---|---|---|
| 4,146,480 A | 3/1979 | Holanek et al. |
| 4,164,468 A | 8/1979 | Raible |
| 4,179,380 A | 12/1979 | Amicel et al. |
| 4,201,673 A | 5/1980 | Kanno et al. |
| 4,212,744 A | 7/1980 | Oota |
| 4,220,535 A | 9/1980 | Leonard |
| 4,271,023 A | 6/1981 | Giovannetti et al. |
| 4,346,006 A | 8/1982 | Kopp et al. |
| 4,374,088 A | 2/1983 | Stenberg |
| 4,620,965 A | 11/1986 | Fukusawa et al. |
| 4,666,603 A | 5/1987 | Madsen et al. |
| 4,707,268 A * | 11/1987 | Shah .................. B01D 63/02 210/650 |
| 4,789,473 A * | 12/1988 | Mathieu .................. B01D 63/02 210/321.8 |
| 4,861,485 A | 8/1989 | Fecondini |
| 4,906,375 A | 3/1990 | Heilmann |
| 4,921,612 A | 5/1990 | Sirkar |
| 4,929,259 A | 5/1990 | Caskey et al. |
| 4,990,251 A | 2/1991 | Spranger et al. |
| 5,037,610 A | 8/1991 | Fukasawa et al. |
| 5,072,498 A | 12/1991 | Raff et al. |
| 5,096,582 A | 3/1992 | Lombardi et al. |
| 5,106,579 A | 4/1992 | Fukazawa et al. |
| 5,139,741 A | 8/1992 | Hagiwara |
| 5,143,612 A | 9/1992 | Hamanaka et al. |
| 5,162,102 A | 11/1992 | Nogawa et al. |
| 5,198,110 A | 3/1993 | Hanai et al. |
| 5,256,294 A | 10/1993 | van Reis |
| 5,522,998 A | 6/1996 | Polaschegg |
| 5,525,144 A | 6/1996 | Gollan |
| 5,578,267 A | 11/1996 | Cosentino et al. |
| 5,626,759 A | 5/1997 | Krantz et al. |
| 5,700,372 A | 12/1997 | Takesawa et al. |
| 5,730,712 A | 3/1998 | Falkvall et al. |
| 5,779,897 A | 7/1998 | Kalthod et al. |
| 5,871,693 A | 2/1999 | Lindsay |
| 5,882,516 A | 3/1999 | Gross et al. |
| 5,942,112 A | 8/1999 | Ishak |
| 6,074,559 A | 6/2000 | Hahmann et al. |
| 6,149,817 A | 11/2000 | Peterson et al. |
| 6,264,627 B1 | 7/2001 | Liska et al. |
| 6,346,090 B1 | 2/2002 | Liska et al. |
| 6,368,557 B1 | 4/2002 | Piplani et al. |
| 6,432,309 B1 | 8/2002 | Fuke et al. |
| 6,478,969 B2 | 11/2002 | Brantley et al. |
| 6,495,101 B1 | 12/2002 | Yokoyama et al. |
| 6,555,006 B2 | 4/2003 | van Reis |
| 6,613,279 B1 | 9/2003 | Elgas et al. |
| 6,623,441 B1 * | 9/2003 | Kihara ................ A61M 1/3693 604/4.01 |
| 6,623,638 B2 | 9/2003 | Watkins et al. |
| 6,638,477 B1 | 10/2003 | Treu et al. |
| 6,719,907 B2 | 4/2004 | Collins et al. |
| 6,764,761 B2 | 7/2004 | Eu et al. |
| 6,811,542 B2 | 11/2004 | Liska et al. |
| 6,890,315 B1 | 5/2005 | Levin et al. |
| 6,994,824 B2 | 2/2006 | Mochizuki et al. |
| 7,128,837 B2 | 10/2006 | Behrendt et al. |
| 7,250,108 B2 | 7/2007 | Boivin et al. |
| 7,267,658 B2 | 9/2007 | Treu et al. |
| 7,285,106 B2 | 10/2007 | Collins et al. |
| 7,316,780 B1 | 1/2008 | Fendya et al. |
| 7,335,334 B2 | 2/2008 | Olsen et al. |
| 7,410,582 B2 | 8/2008 | Bernard et al. |
| 7,537,701 B2 | 5/2009 | Mahendran et al. |
| 7,713,412 B2 | 5/2010 | Heilmann et al. |
| 7,776,219 B2 | 8/2010 | Brugger et al. |
| 7,790,029 B2 | 9/2010 | Dannenmaler et al. |
| 8,182,686 B2 | 5/2012 | Witthaus et al. |
| 8,187,410 B2 | 5/2012 | Noh et al. |
| 8,202,428 B2 | 6/2012 | Heilmann et al. |
| 8,229,546 B2 | 7/2012 | Falkén et al. |
| 8,246,826 B2 | 8/2012 | Wilt et al. |
| 8,343,347 B2 | 1/2013 | Collins et al. |
| 8,387,804 B2 | 3/2013 | Buck et al. |
| 8,394,049 B2 | 3/2013 | Reggiani et al. |
| 8,430,832 B2 | 4/2013 | Humes et al. |
| 8,444,587 B2 * | 5/2013 | Kelly .................. A61M 1/3627 604/4.01 |
| 8,496,826 B2 | 7/2013 | Uchi et al. |
| 8,603,021 B2 | 12/2013 | Levin et al. |
| 8,747,980 B2 | 6/2014 | Bikson et al. |
| 8,795,220 B2 | 8/2014 | Reggiani et al. |
| 8,877,062 B2 | 11/2014 | Mullick et al. |
| 8,883,008 B2 | 11/2014 | Mishkin |
| 8,992,463 B2 | 3/2015 | Hogard et al. |
| 9,005,152 B2 | 4/2015 | Kelly et al. |
| 9,216,246 B2 | 12/2015 | Kelly et al. |
| 9,248,409 B2 | 2/2016 | Noh et al. |
| 9,254,464 B2 | 2/2016 | Keller et al. |
| 9,352,283 B2 | 5/2016 | Ying et al. |
| 2001/0037964 A1 | 11/2001 | Won |
| 2002/0091350 A1 * | 7/2002 | Belson .................. A61M 1/16 604/5.04 |
| 2002/0103453 A1 | 8/2002 | Burbank et al. |
| 2002/0190000 A1 * | 12/2002 | Baurmeister ........ A61M 1/3413 210/650 |
| 2002/0195390 A1 | 12/2002 | Zha |
| 2003/0075498 A1 | 4/2003 | Watkins et al. |
| 2006/0041216 A1 * | 2/2006 | McLaughlin .......... A61M 1/16 604/6.09 |
| 2006/0243653 A1 | 11/2006 | Heinrich et al. |
| 2007/0007193 A1 | 1/2007 | Uchi et al. |
| 2007/0107884 A1 | 5/2007 | Sirkar et al. |
| 2007/0119781 A1 | 5/2007 | Huang et al. |
| 2009/0004053 A1 | 1/2009 | Kenley |
| 2009/0124963 A1 | 5/2009 | Hogard et al. |
| 2009/0218274 A1 | 9/2009 | Sakashita et al. |
| 2009/0234266 A1 * | 9/2009 | Solomon .............. A61M 1/1678 604/6.09 |
| 2009/0321344 A1 | 12/2009 | Lee |
| 2010/0000936 A1 * | 1/2010 | Osabe .................. B01D 63/02 210/487 |
| 2010/0089817 A1 | 4/2010 | Heilmann et al. |
| 2010/0125235 A1 | 5/2010 | Cauley, III et al. |
| 2011/0011786 A1 * | 1/2011 | Feichtner ............ A61B 5/14528 210/321.84 |
| 2012/0043271 A1 | 2/2012 | Maurer |
| 2012/0234746 A1 | 9/2012 | Howard et al. |
| 2012/0318727 A1 | 12/2012 | Kawatani et al. |
| 2013/0094997 A1 | 4/2013 | Wang |
| 2014/0158605 A1 | 6/2014 | Mishkin |
| 2014/0208948 A1 | 7/2014 | Cao |
| 2016/0129172 A1 | 5/2016 | Hornung et al. |
| 2016/0375188 A1 | 12/2016 | Labib et al. |
| 2017/0106341 A1 | 4/2017 | Labib et al. |

FOREIGN PATENT DOCUMENTS

| | | |
|---|---|---|
| EP | 0 217 759 A1 | 4/1987 |
| EP | 1 634 639 A1 | 3/2006 |
| EP | 1 790 364 A1 | 5/2007 |
| EP | 1 964 603 | 9/2008 |
| EP | 2 659 914 A1 | 11/2013 |
| EP | 2796185 A1 | 10/2014 |

(56) References Cited

FOREIGN PATENT DOCUMENTS

| | | |
|---|---|---|
| JP | 53-30990 | 3/1978 |
| JP | S56 100605 | 8/1981 |
| WO | WO2010128044 A1 | 11/2010 |
| WO | WO 2011/032154 A1 | 3/2011 |
| WO | WO 2011/105495 | 9/2011 |
| WO | WO 2013/094533 A1 | 6/2013 |
| WO | WO2015118046 A1 | 8/2015 |
| WO | WO 2015/153370 A2 | 10/2015 |

OTHER PUBLICATIONS

Grudtner et al. ("Histological analysis of cobalt-chromium stents with and without Camouflage polymer coating: experimental porcine carotid artery model" Vascular, vol. 19(2), 2011, pp. 89-96).*

Hashimoto, et al. "Effect of Shear Rate on Clot Growth at Foreign Surfaces". Artificial Organs. Abstract. Nov. 1985. (Year: 1985).*

Feng Ding, et al.; A Biomimetic Membrane Device That Modulates the Excessive Inflammatory Response to Sepsis; PLoS One, Apr. 2011, vol. 6, Issue 4, pp. 1-14.

Feng Shen, et al.; Threshold Response of Initiation of Blood Coagulation by Tissue Factor . . . Arteriosclerosis, Thrombosis, and Vascular Biology. 2008; 28:2035-2041, and Supp.

Ayaka Hirano, et al.; Experimental evaluation of flow and dialysis performance of hollow-fiber dialyzers with different . . . ; Journal of artificial organs (2012) 15:168-175.

John K. Leypoldt, et al.; Hollow Fiber Shape Alters Solute Clearances in High Flux Hemodialyzers; ASAIO Journal 2003, 49:81-87.

Churn K. Poh, et al.; Effect of spacer yarns on the dialysate flow distribution of hollow-fiber hemodializers: a magnetic resonance imaging study; ASAIO Journal 2003 p. 440.

Churn K. Poh, et al.; Effect of flow baffles on the dialysate flow . . . ; Journal of Biomechanical Engineering, Transactions of the ASME, Aug. 2003, vol. 125, pp. 481-489.

Claudio Ronco et al.; Flow distribution analysis by helical scanning in polysulfone hemodialyzers . . . ; Hemodialysis International 2006; 10:380-388.

C. Ronco, et al.; Dialysate flow distribution in . . . ; The International Journal of Artificial Organs, vol. 23, No. 9, 2000, pp. 601-609.

Claudio Ronco; Fluid Mechanics and Crossfiltration in Hollow-Fiber Hemodialyzers; Contributions to Nephrology, 2007, vol. 158, pp. 34-49.

William R. Clark et al.; Solute Removal by Hollow-Fiber Dialyzers; Contributions to Nephrology, 2007, vol. 158, pp. 20-33.

Richard A. Ward et al., Dialysate Flow Rate and Delivered Kt/Vurea for Dialyzers with Enhanced . . . ; Clinical Journal of the American Society of Nephrology; 6: 2235-2239, 2011.

P.W.T. Dierickx, et al.; Blood flow around hollow fibers; The International Journal of Artificial Organs, vol. 23, No. 9, 2000, pp. 610-617.

ReNews® A publication on dialyzer reprocessing, vol. 13, 2008. Downloaded from http://www.medivators.com/renal/renews/.

Stanislav S. Dukhin, et al.; Outside-in hemofiltration for prolonged operation without clogging; Journal of Membrane Science 464 (2014), pp. 173-178.

Ken-ichiro Yamamoto et al. Computational Evaluation of Dialysis Fluid Flow in Dialyzers With Variously Designed Jackets; Artificial Organs, vol. 33, No. 6, 2009.

Norfamilabinti Che Mat, et al.; Hollow fiber membrane modules; Current Opinion in Chemical Engineering 2014, 4:18-24.

Isao Noda, et al.; Effect of Flow Maldistribution on Hollow Fiber Dialysis—Experimental Studies; Journal of Membrane Science 5(1979), 209-225.

M.J. Costello, et al; The effect of shell side hydrodynamics on the performance of axial flow hollow fibre modules; Journal of Membrane Science 80(1993) 1-11.

Jasmin Wu, et al.; Shell side mass transfer performance of randomly packed hollow fiber modules; Journal of Membrane Science 172 (2000) 59-74.

Frank Lipnizki, et al.; Mass transfer performance for hollow fibre modules with shell-side axial feed flow; Journal of Membrane Science 193 (2001) 195-208.

Yujun Wang, et al.; Effect of random packing on shell-side flow and mass transfer in hollow fiber module described by normal . . . ; Journal of Membrane Science 216 (2003) 81-93.

International Search Report and Written Opinion for Application No. PCT/US2015/023114 dated Sep. 30, 2015.

Horng-Ruey Chua et al.; "Circuit lifespan during continuous renal replacement therapy for combined liver and kidney failure;" Journal of Critical Care (2012) 27, 744.e7-744.e15.

Fealy et al.; "The Effect of Circuit "Down-Time" on Uraemic Control During Continuous Veno-Venous Haemofiltration;" Critical Care and Resuscitation Dec. 2002; 4:266-270.

Uchino et al.; "Continuous is not continuous: the incidence and impact of circuit "downtime" on uraemic control during continuous veno-venous haemofiltration," Intensive Care Med. (2003) Apr.; 29:575-578.

Runolfur et al.; "Regional citrate anticoagulation in continuous venovenous hemofiltration in critically ill patients with a high risk of bleeding," Kidney International, vol. 55 (1999), pp. 1991-1997.

Zumoff, Rebecca; "Creating a Wearable Artificial Kidney: A Difficult but Necessary Goal," Nephrology News and Issues, Apr. 21, 2017; https://www.nephrologynews.com/the-wearable-artificial-kidney-a-difficult-but-necessary-goal/.

Dukhin et al., "Outside-in hemofiltration for prolonged operation without clogging," Journal of Membrane Science 464 (2014) 173-178.

* cited by examiner

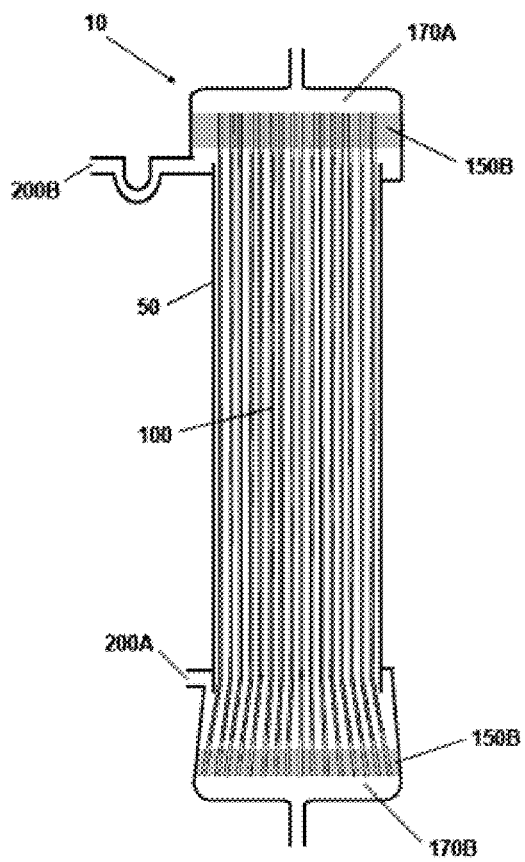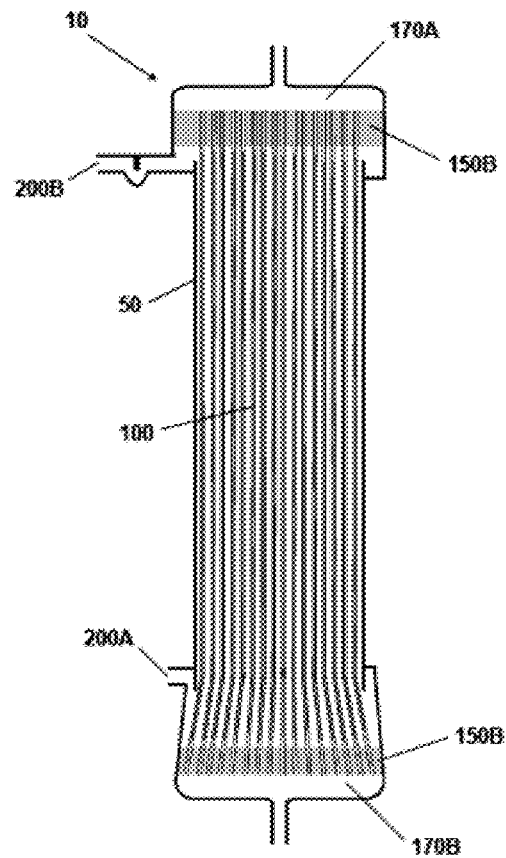

1. Header Section
2. Intermediate Section
3. Middle Section
4. Intermediate Section
5. Header Section

FIG. 19E1
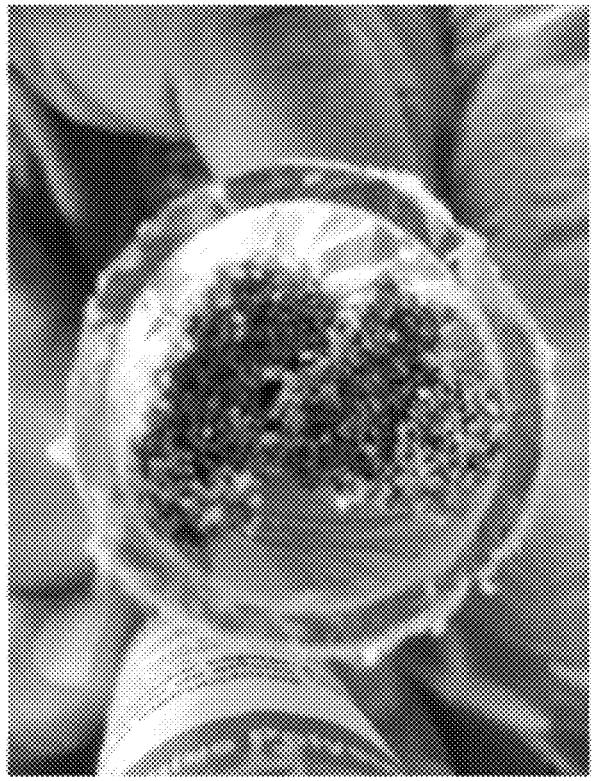
FIG. 19E2

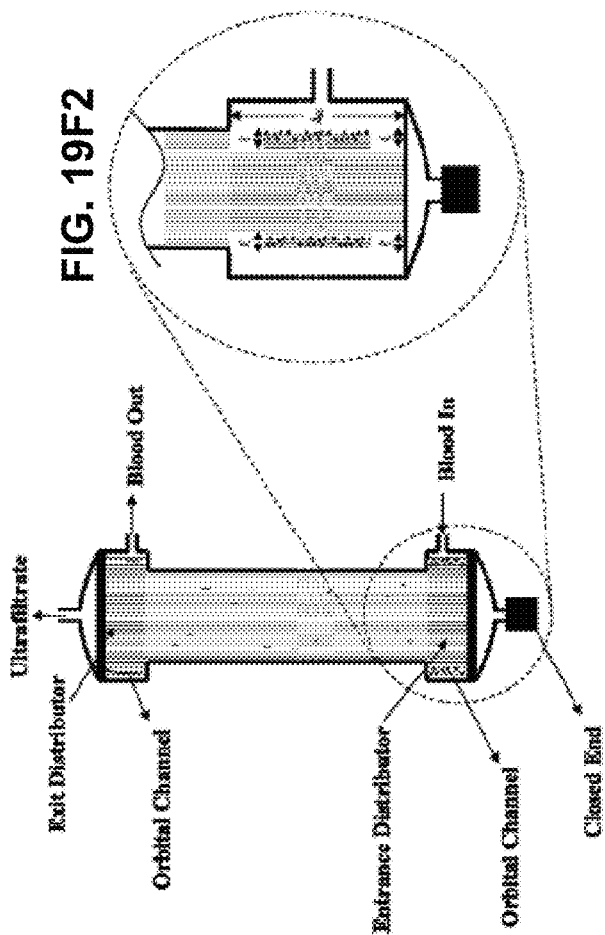
FIG. 19F1
FIG. 19F2
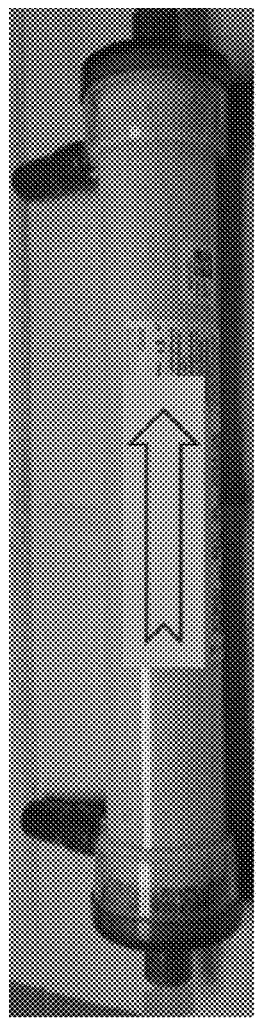
FIG. 19F3

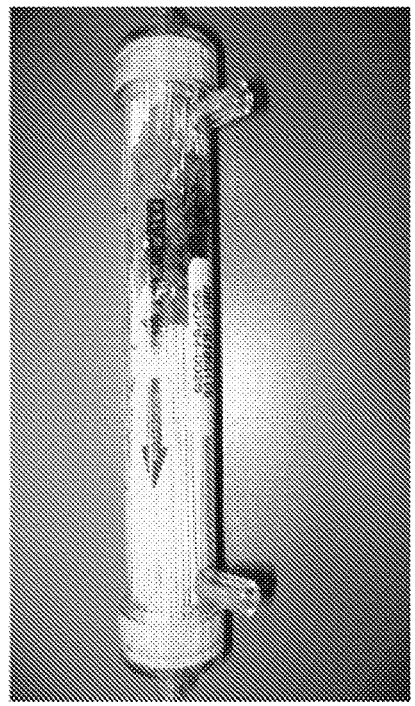
FIG. 19G1
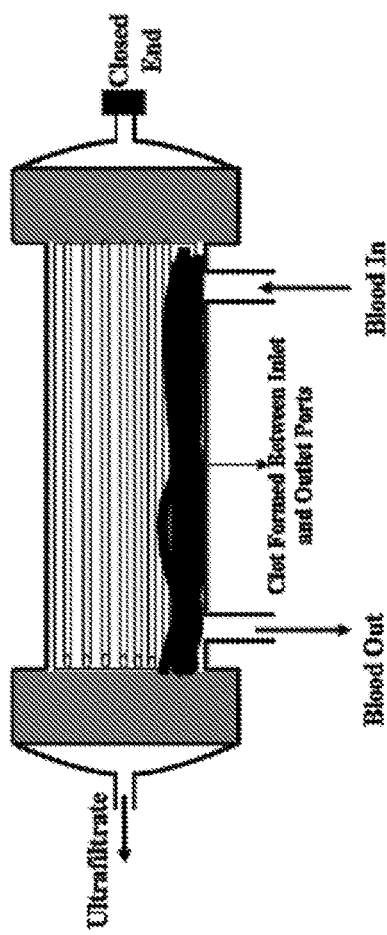
FIG. 19G2

BLOOD PROCESSING CARTRIDGES AND SYSTEMS, AND METHODS FOR EXTRACORPOREAL BLOOD THERAPIES

CROSS-REFERENCE TO RELATED APPLICATION

This application claims priority, to the extent appropriate, to U.S. Provisional Application No. 61/972,312 filed on Mar. 29, 2014. The entire disclosure of U.S. Provisional Application No. 61/972,312 is incorporated herein by reference.

FIELD OF THE INVENTION

Embodiments of the invention pertain to blood processing cartridges and systems, and methods for extracorporeal blood therapies.

BACKGROUND OF THE INVENTION

Hemodialysis, hemofiltration and other forms of extracorporeal blood processing are in widespread and successful use. Nevertheless, one area in which there remains a need for improvement is to allow cartridges to be used for longer periods of time without degradation of performance due to clotting and clogging. There is also need for cartridges and flow system that can minimize the need for complex anticoagulation modalities.

For an understanding of the problems, it is useful to describe some considerations that pertain generally to the extracorporeal processing of blood and to conventional hemodialysis. In general, in an extracorporeal blood flow circuit, there is provided a membrane that is semi-permeable, having a desired small pore size so as to allow some substances to pass through the membrane while other substances do not pass through the membrane, based on the respective molecular weights of the substances. Typically one side of the membrane is exposed to blood and the other side of the membrane is exposed to dialysate or filtrate. Passage of mass through the membrane can be driven by pressure difference across the membrane (convection), or by concentration differences (diffusion), or by a combination of both of these mechanisms.

Fluids and their Properties

Dialysate is an aqueous buffer solution that resembles water in its physical properties, and its fluid mechanical behavior is approximately Newtonian, and it can be used over a wide range of velocities and shear rates. The physical and chemical properties of the surfaces that are in contact with dialysate are relatively unimportant. Dialysate does not form clots. In general, dialysate is a solution that does not impose very demanding requirements on the system or the surfaces that it contacts.

Blood is a complex fluid that tends to form clots if any of various criteria are not satisfied. Clots or thrombi can be very dangerous to the patient if they travel with the blood and enter the patient's body. Also, clots can degrade the performance of the membrane or the cartridge in terms of mass exchange and flow. In general, one property of blood is that motion of blood helps to avoid the formation of clots. This implies it is undesirable for a blood flow system to have flow stagnation points or flow stagnation regions. More specifically, some of the literature characterizes the shear rate of blood flow as a suitable indicator of the tendency for blood to form clots. It is generally considered that there is a preferred shear rate for blood, which is the range of from about 300 $sec^{-1}$ to about 2700 $sec^{-1}$ or more depending on the level and type of anticoagulation and on the surface properties of surfaces in contact with blood. If the shear rate is either below that range or above that range, clots tend to form. A still further belief about the properties of blood is that it is undesirable for the shear rate to change drastically within a short distance along a flowpath. This criterion is referred to as shear rate gradient and is discussed elsewhere herein. Still other criteria pertain to various physical and chemical properties of the blood-facing surface that relate to non-thrombogenicity or hemocompatibility, as discussed in more detail elsewhere herein. Also, exposure of blood to air can result in clots. There are multiple physical and chemical mechanisms that can lead to formation of clots, and the mechanisms of clot formation are not always the same in regard to all of these criteria, but these criteria give general guidance about how to avoid or reduce or minimize clot formation. Also, blood is a non-Newtonian fluid, specifically a shear-thinning non-Newtonian fluid.

Overall Flow Considerations (Conventional Hemodialysis)

Referring now to FIGS. 1 and 2, FIG. 1 illustrates a conventional hemodialysis system and FIG. 2 illustrates a conventional hemodialysis cartridge or filter containing a plurality of hollow fibers that are semi-permeable. A conventional hemodialysis cartridge contains thousands of such hollow fibers arranged in parallel with each other, originating at a supply end header and terminating at a discharge end header. At each end header there is a barrier, formed by potting with a hemocompatible polymer resin, normally polyurethane or equivalent, so that the interiors of the fibers are in fluid communication with a first flow compartment and the exteriors of the fibers are in communication with a second flow compartment distinct from the first flow compartment. The fibers are flexible because they are long and narrow. In a conventional dialyzer containing many hollow fibers, the fibers are bundled inside a housing, usually a cylindrical housing. The housing also has a housing supply fluid connection and a housing discharge fluid connection.

In conventional hemodialysis, blood enters the supply end header, then the blood flows through the lumens of the fibers while undergoing mass exchange through the walls of the hollow fibers, and a roughly similar quantity of blood exits the hollow fibers into the discharge end header to be returned to the patient. This is termed the blood compartment. Dialysate enters at one end of the housing, flows past the exteriors of the fibers, and exits at the other end of the housing. This is termed the dialysate compartment. In conventional hemodialysis, blood and dialysate flow in a counterflow relationship, i.e., in opposite directions. In the housing, pressure drop occurs as dialysate flows from the housing supply end of the housing to the housing discharge end of the housing. Inside the fibers, pressure drop occurs as blood flows from the supply end of the hollow fiber to the discharge end of the hollow fiber. The absolute and relative pressures and pressure drops of the two fluid streams, and other operating parameters, can be controlled so as to result in ultrafiltration. The nature of these fluid flows and pressure drops in the system defines the type of therapy such as hemodiafiltration or hemodialysis, as described elsewhere herein.

In the design of conventional hemodialysis cartridges, some attention is given to the distribution of flow both of blood and of dialysate. The literature suggests that in the absence of appropriate design features, blood flow tends to be distributed nonuniformly among the fibers, typically being greater for fibers located closer to the center of the fiber bundle. Also, dialysate flow tends to be distributed nonuniformly, typically being greater closer to the periphery of the fiber bundle. These nonuniformities and also the nature of the mismatch of these nonuniformities can degrade the effectiveness of the dialyzer in terms of mass (solute) exchange (or clearance) between blood and dialysate. A further area of concern in this regard is that it is possible for some fibers that are near each other to clump together somewhat randomly in localized places, which results in undesirable effects known as channeling. If clumping occurs, there are likely to be some more wide-open regions or channels within the housing and some other clumped-together regions within the housing. The pattern of these regions may vary along the length of the cartridge and might also vary with time. If clumping happens, the open spaces may carry a disproportionate share of dialysate flow. This means that some other fibers or regions of the fiber bundle may carry undesirably small amounts of dialysate, and so do not perform mass exchange as well as intended. Difficulties arising from these issues include not knowing what dose of dialysis the patient actually receives.

Design approaches to reduce or avoid clumping include: the use of appropriate values of the porosity of the fiber bundle inside the housing; the use of wavy fibers; and the use of spacer fibers (which may be either solid or yarn).

Selection of an appropriate porosity or packing factor for the fibers within the housing space has some effect in lessening the tendency for clumping. The porosity fraction of the fiber bundle is the total cross-sectional area of void space between the fibers enclosed in the housing (i.e., the inter fiber space), divided by the total cross-sectional area inside the housing. The packing fraction is the total area enclosed by the external perimeters of the fibers, compared to the total area inside the housing. The relation between the porosity fraction and the packing fraction is that the total of the porosity fraction and the packing fraction is unity. For conventional hemodialysis cartridges that have straight fibers, typical values of the porosity of the fiber bundle range from 70% to 30% (corresponding to a packing fraction ranging from 30% to 70%).

In regard to waviness, the fibers are sometimes manufactured so that instead of being straight, they have a wavy pattern resembling a sinusoid having a small amplitude and a defined spatial period or wavelength. Wavy fibers, if used, typically have a spatial period or wavelength of from 0.5 cm to 2 cm and preferably about 0.8 to 1.0 cm. The wavy fibers provide a tendency toward self-spacing and discouraging of clumping. For conventional hemodialysis cartridges that have wavy fibers, typical values of fiber bundle porosity are normally somewhat less than that for straight fibers.

Another practice sometimes used is to include in the fiber bundle some spacer fibers. Spacers do not carry flow internally, but are potted in the end barriers similarly to the potting of ordinary hollow fibers. Spacers may be either solid fibers or multi-fiber yarns. If the spacers are solid fibers, they may have more rigidity than do corresponding hollow fibers.

Flow Transition at Ends of Housing (Conventional Hemodialysis)

Referring now to FIG. 2, in a conventional hemodialysis cartridge, another area of design is in regard to transition regions that involve changes of flow direction or flow area, particularly regarding flow of dialysate inside the housing flowing past the outsides of the fibers. Such changes may occur at the housing supply port and at the housing discharge port connected to the housing, because these ports generally are directed sideways with respect to the housing while the overall direction of fluid flow between fibers in the bundle is axial, along the length of the housing. As flow progresses into and through and then out of the housing, the flow typically transitions from a sideways connection and a sideways flow direction at the outside of the fiber bundle, to a flow along the axial direction of the fiber bundle where the flow is hopefully distributed as uniformly as possible across the cross-section of the housing, and then back to a sideways connection and a sideways flow direction. One design feature that is sometimes used, when flow enters and exits from the side, is an orbital distributor. An orbital distributor is a channel, having open dimensions substantially greater than the dimension between individual fibers of the fiber bundle, which is adjacent to a side port and which provides or collects fluid to or from substantially 360 degrees around the fiber bundle. Typically, an orbital distributor has an open direction that faces away from the middle of the lengthwise direction of the cartridge. In a conventional hemodialysis cartridge, if an orbital distributor is present, typically it is present at both ends (supply and discharge) of the cartridge, and is geometrically identical at both ends of the cartridge.

Another or related design feature that is sometimes used, especially in designs containing an orbital distributor, is the fanning-out of fibers in the end region, between the orbital distributor and the barrier in which the fibers are potted. Such fanning-out allows the flow to more easily travel transverse to the lengthwise direction of the fibers than would be the case if the inter-fiber spacing were maintained as it is in the main part of the housing. In conventional hemodialysis cartridges, if fanning-out is present, typically it is identical at both ends of the cartridge. If fanning-out is present, typically it is present such that the ratio of the overall cross-sectional area of the fanned fiber bundle to the overall cross-sectional area of the unfanned fiber bundle is in the range of 1.20 to 1.70. There is no known strict requirement or criterion for selection of this ratio.

Fiber Properties (Conventional Hemodialysis)

In a majority of conventional hemodialysis cartridges, the typical pore size of the smallest pores in the semi-permeable membrane is approximately 2 to 7 nanometers, which is suitable for allowing water, small molecules and middle molecules to pass through while retaining large molecules especially albumin. More specifically, the pores having this pore size are typically located at one surface of the membrane, which is a surface that is smooth compared to the opposite surface of the membrane. Such membranes commonly are referred to as asymmetric membranes. Typically for conventional hemodialysis cartridges, the surface that is smooth is the interior lumen surface of the hollow fibers (which is the surface that is contacted by the blood). The term "smooth" can be considered to mean that the rms (root-mean-square) value of the surface roughness is smaller than 100 nanometers. Typically, pores towards the outer surface of such a hollow fiber are larger than pores near the inner surface. In most conventional hemodialysis cartridges, the exterior surface of the hollow fibers (which is contacted by the dialysate) is not smooth. Typically the outside surfaces have surface roughness that is greater than 100 nanometers (root-mean-square). Much of this roughness exists in the form of craters at the surface (rather than pores that are involved in the filtration function).

By far the most common material for making the hollow fibers is a mixture of polyethersulfone (PES) and/or its polymer variants, combined with polyvinylpyrrolidone (PVP). This combination of materials is suitable to make a fiber that is smooth on one surface but not both surfaces, as a function of manufacturing process conditions. The combination of polyethersulfone and polyvinylpyrrolidone is not suitable for making so-called symmetric fibers where both internal and external surfaces of the fiber are smooth.

So-called symmetric fibers have also been made, having a smooth surface on both the inside surface and the outside surface, with both of those smooth surfaces containing the smallest pores. There may be larger pores between the two smooth surfaces. The smoothness on both surfaces generally has not been required for clinical or physiological applications or therapies. Instead, the smoothness on both surfaces has simply happened as a consequence of the manufacturing process in combination with the properties of certain particular polymeric materials. Only a few specific polymeric materials are suitable for manufacturing symmetric fibers. These materials include: polyacrilonitrile (referred to as AN69); cellulose triacetate and other cellulosics; PEPA (polyester polymer alloy, produced by Nikkiso); and polymethylmethacrylate (PMMA).

Some dialyzers use straight fibers, while others use wavy fibers, as discussed in regard to packing fraction. One way of manufacturing wavy fibers is to take hot soft extruded polymer as it leaves the extruder, and put it through a mechanical process that pushes the fiber sideways in one direction out of a straight-line path as it passes through the apparatus, and then pushes the fiber in the opposite direction out of a straight-line path, with this pushing or deforming process being repeated many times. If the resulting fiber shape is considered to be at least approximately sinusoidal, the mechanical parameters of this process can define both the amplitude and the wavelength of the undulations in the fiber.

Further Flow Considerations (Conventional Hemodialysis)

In the conventional arrangement of a hemodialyzer, if a clot forms inside a hollow fiber, the clot generally blocks all blood flow through that fiber and prevents the use of that fiber in filtration or mass exchange for the remainder of the useful life of the cartridge. Such blockage degrades the performance of the cartridge because only the remaining, unclotted fibers are able to carry any blood flow through them and thereby perform a useful function. This is illustrated in FIG. 3 and FIG. 4.

In conventional hemodialysis, the geometric transitions inside the housing near the ends of the fibers, such as orbital distributors and fanning-out of the hollow fibers, if they are present in the design of the cartridge, affect the flow of the dialysate. However, in conventional hemodialysis, the flow details of this transition are important mainly to the extent that they influence the efficiency of the mass exchange. Because of its nature and fluid properties, dialysate is a simple fluid that does not present any possibility of clotting.

In general, passage of substances through the semi-permeable membrane can be due to either diffusion, which results from differences in concentration of chemical species, or convection, which results from pressure difference. It is also possible that both of these processes can be active in the same cartridge, especially with high-flux membranes, which facilitate more connective transport during dialysis.

In conventional hemodialysis, the blood flows inside the lumen along the length of the lumen having a pressure drop from a blood inlet end of the lumen to the blood outlet end of the lumen. Dialysate flows lengthwise the length of the housing, experiencing a pressure drop from the dialysate inlet end of the housing to the dialysate outlet end of the housing. Typically the direction of blood flow is opposite the direction of the dialysate flow, so the end of the housing that has the highest blood pressure is the end of the housing that has the lowest dialysate pressure, and the end of the housing that has the lowest blood pressure is the end of the housing that has the highest dialysate pressure. There can be any desired relation between the absolute levels of those two pressure profiles, because it is possible to adjust the absolute pressure level of either or both of those profiles. This pressure adjustment is now possible with modern dialysis machines that include balancing pressure features.

One common relation is that the two pressure profiles cross each other at some point along the length of the cartridge. In such a situation, for some portion of the length of the cartridge, the direction of the transmembrane pressure difference is outward, causing convective flow from the inside of the fiber outward. In a different portion of the length of the cartridge, the direction of the transmembrane pressure difference is inward, causing convective flow from the outside of the fiber inward. In applications such as high flux hemodialysis where internal filtration is manifested, there is a location somewhere within the cartridge where the pressure of blood inside the hollow semi-permeable fiber equals the pressure of dialysate on the outside of the hollow semi-permeable fiber. In the region between this point and one end of the cartridge, the transmembrane pressure difference causes convective flow of liquid outward through the membrane. In the region between this point and the other end of the cartridge, the transmembrane pressure difference causes convective flow of liquid through the membrane in the opposite direction. Thus, there is offsetting convective flow of liquid across the membrane. This situation is designated Internal Filtration or High Flux Hemodialysis, and is favorable for increased clearance of middle molecules, because liquid that flows from the blood into the dialysate contains middle molecules, but after this liquid mixes with the dialysate and some of the dialysate flows into the blood, that liquid only contains whatever is the concentration of middle molecules is in the dialysate, which is a low concentration. This situation is favorable for clearance of middle molecules. With a higher level of internal filtration, a greater removal of middle molecules can be achieved.

A related conventional technology is ultrafiltration, which has both medical and industrial applications. Ultrafiltration refers only to the passage of substances through the membrane under the action of pressure difference. Fluid to be treated is supplied to the ultrafilter, and a portion of that fluid is discharged from the other side of the membrane as filtrate. Ultrafiltration membranes are defined by the molecular weight cut-off (MWCO) of the membrane used. Typically, for dialysis applications, the pore size in the hollow fiber membranes is approximately 0.2 nanometers to 5 nanometers. In outside-in ultrafiltration, liquid is supplied to the housing, i.e., to the outsides of the hollow fibers, and filtrate is withdrawn from the insides of the hollow fibers through a header. In applications such as water purification, this process is often performed in the dead-end mode. Typically, only one header is used for removal of filtrate, i.e., if both ends of the fibers are potted, one header is a dead-end.

The current standard of practice in extracorporeal blood therapy such as hemodialysis, when mass exchange is desired, is to cause the blood flow through the lumens of the hollow fiber and to cause the dialysate to flow past the exterior of the fibers.

SUMMARY

In an embodiment of the invention, there may be provided a cartridge for use in processing blood. The cartridge may comprise a housing, and within the housing there may be a plurality of fibers contained inside the housing. At least some of the fibers may be hollow and may be made of semi-permeable membranes having respective fiber interiors and fiber exteriors. The fibers may be parallel or almost parallel to each other over at least a substantial portion of their lengths, such as at least 25% of their lengths or at least 50% of their lengths. There may be a first end barrier that joins with the fibers at first ends of the fibers, and joins with a housing interior and bounds a first end plenum and separates the first end plenum from a housing midsection interior region. There may be a second end barrier that joins with the fibers at second ends of the fibers and joins with the housing interior and bounds a second end plenum and separates the second end plenum from the housing midsection interior region. There may be a first fluid flow compartment comprising the first end plenum and the interiors of the hollow fibers and the second end plenum, wherein the first end plenum and the interiors of the hollow fibers and the second end plenum are in fluid communication with each other. There may be a second fluid flow compartment comprising an inter fiber space and a housing supply port and a housing discharge port, all in fluid communication with each other.

In an embodiment of the invention, there may be provided such a cartridge, wherein the second fluid flow compartment contains at least one design feature near a housing supply end of the cartridge that is different from a corresponding feature near a housing discharge end of the cartridge.

In an embodiment of the invention, there may be provided such a cartridge, wherein the fibers comprise polyethersulfone or related polymers, in combination with polyvinylpyrrolidone, and wherein at least some of the fibers are wavy, and wherein the fibers have an outside surface that is hemocompatible, and wherein the fibers have an outside surface that has a root-mean-square surface roughness of less than 100 nanometers.

In an embodiment of the invention, there may be provided such a cartridge, wherein the cartridge further comprises an air bleed.

In an embodiment of the invention, there may be provided such a cartridge, wherein the cartridge further comprises an emboli trap.

In an embodiment of the invention, there may be provided such a cartridge, wherein at least a portion of the housing has on its interior a hemocompatible coating or surface treatment.

In an embodiment of the invention, there may be provided such a cartridge, wherein a portion of the fibers have a hemocompatible coating or surface treatment.

In an embodiment of the invention, there may be provided such a cartridge, wherein certain geometric parameters of a flow transition region have proportions such that 2*L/r is between 0.5 and 2.0.

In an embodiment of the invention, there may be provided a system containing such a cartridge, wherein blood flows in the Inter Fiber Space and the cartridge is used to treat blood in an extracorporeal therapy.

In an embodiment of the invention, there may be provided a system containing such a cartridge, wherein blood flows in the Inter Fiber Space, and plurality of fibers within the housing have a porosity fraction that is between 40% and 70%, and the fibers have an external surface that is hemocompatible and has a root-mean-square surface roughness that is smaller than 100 nanometers.

In an embodiment of the invention, there may be provided a system containing such a cartridge, wherein blood flows in the inter fiber space, and wherein at least some of the fibers in the fiber array are wavy fibers, and wherein in a cross-section of the fiber bundle, the housing and the plurality of fibers, the plurality of fibers within the housing have a porosity fraction that is between 40% and 70%, more preferably between 50% and 62%.

In an embodiment of the invention, there may be provided a system containing such a cartridge, wherein blood flows in the inter fiber space, and wherein the blood flows past a doubly-convex curvature of an external surface of the fiber.

In an embodiment of the invention, there may be provided a system containing such a cartridge, wherein blood flows in the inter fiber space, and wherein the blood flows past a saddle-shaped curvature of an external surface of the fiber.

In an embodiment of the invention, there may be provided a system containing such a cartridge, wherein blood flows in the inter fiber space, and wherein near an inlet end water and small molecules leave said blood by passing from an exterior of said fibers to an interior of said fibers, and near an outlet end of said cartridge, water and small molecules enter said blood by passing from an interior of said fibers to an exterior of said fibers.

In an embodiment of the invention, there may be provided a system containing a cartridge wherein blood flows perpendicular to the hollow fibers. Such a cartridge may be In an embodiment of the invention, there may be provided a system containing a cartridge wherein ratio of said blood flow shear rate to said solution flow shear rate is between 0.5 and 2.0.

In an embodiment of the invention, there may be provided a processing system, comprising a blood flow system and a cartridge within the blood flow system. The cartridge may comprise a housing, and a plurality of fibers contained inside the housing, at least some of the fibers being hollow and being made of semi-permeable membranes having respective fiber interiors and fiber exteriors. The cartridge may comprise a first fluid flow compartment comprising the interiors of the hollow fibers and a second fluid flow compartment comprising an inter fiber space bordering the fiber exteriors. The fibers may occupy space inside the housing at a porosity fraction of between 40% and 70%, and at least a majority of the fibers may have an outside surface that is smooth having a root-mean-square roughness of less than 100 nanometers and is hemocompatible, and at least a majority of the fibers may have a Molecular Weight Cutoff of less than about 50,000 Daltons. The blood flow system may introduce blood into the second fluid flow compartment and may remove processed blood from the second fluid flow compartment.

In such an embodiment of the invention, the porosity fraction may be specifically between 50% and 72%. The fibers may be either mostly wavy fibers or mostly straight fibers, and the fibers may comprise polyethersulfone or related polymers in combination with polyvinylpyrrolidone. The first fluid flow compartment may provide removal of ultrafiltrate, or alternatively dialysate may be both supplied to and removed from the first fluid flow compartment. There may be at least one, or two, barriers in which ends of fibers are potted, and which separate the first fluid flow compartment and the second fluid flow compartment. Blood may flow either mainly parallel to the fibers or mainly perpendicular to the fibers. If parallel, the relative directions of blood flow and dialysate flow may be opposite of each other. The parameters of blood flow may be that the shear rate stays between 300 $sec^{-1}$ and 2700 $sec^{-1}$, and the local average velocity stays above 0.25 cm/sec, and the ratio of maximum to minimum shear rates does not exceed 4. The system may be used in a variety of therapies and also for uses in which the processing system is not connected to a patient during use of the processing system.

Embodiments of the invention may be suitable to operate for extended durations without suffering clogging.

In an embodiment of the invention, there may be provided a method of processing blood. The method includes providing a filter cartridge, supplying blood to a second flow compartment of the filtration cartridge so that the blood flows outside fibers in the filtration cartridge, withdrawing blood from a second flow compartment of the filter cartridge, and withdrawing dialysate or ultrafiltrate from a first flow compartment of the filter cartridge. The filtration cartridge includes a plurality of semi-permeable hollow fibers enclosed within a housing, and includes a first flow compartment comprising lumens of the fibers and comprises the second flow compartment that includes the outsides of the fibers. At least a majority of the fibers have an outside surface that is smooth having a root-mean-square roughness of less than 100 nanometers and is hemocompatible. At least a majority of the fibers have a molecular weight cutoff of less than about 50,000 Daltons. The fibers occupy space inside the housing at a porosity fraction between 40% and 70%.

BRIEF DESCRIPTION OF THE ILLUSTRATIONS

Embodiments of the invention are further described in the following illustrations.

FIGS. 12B and 12C show various possible emboli traps according to the principles of the present disclosure.

Figure 1:
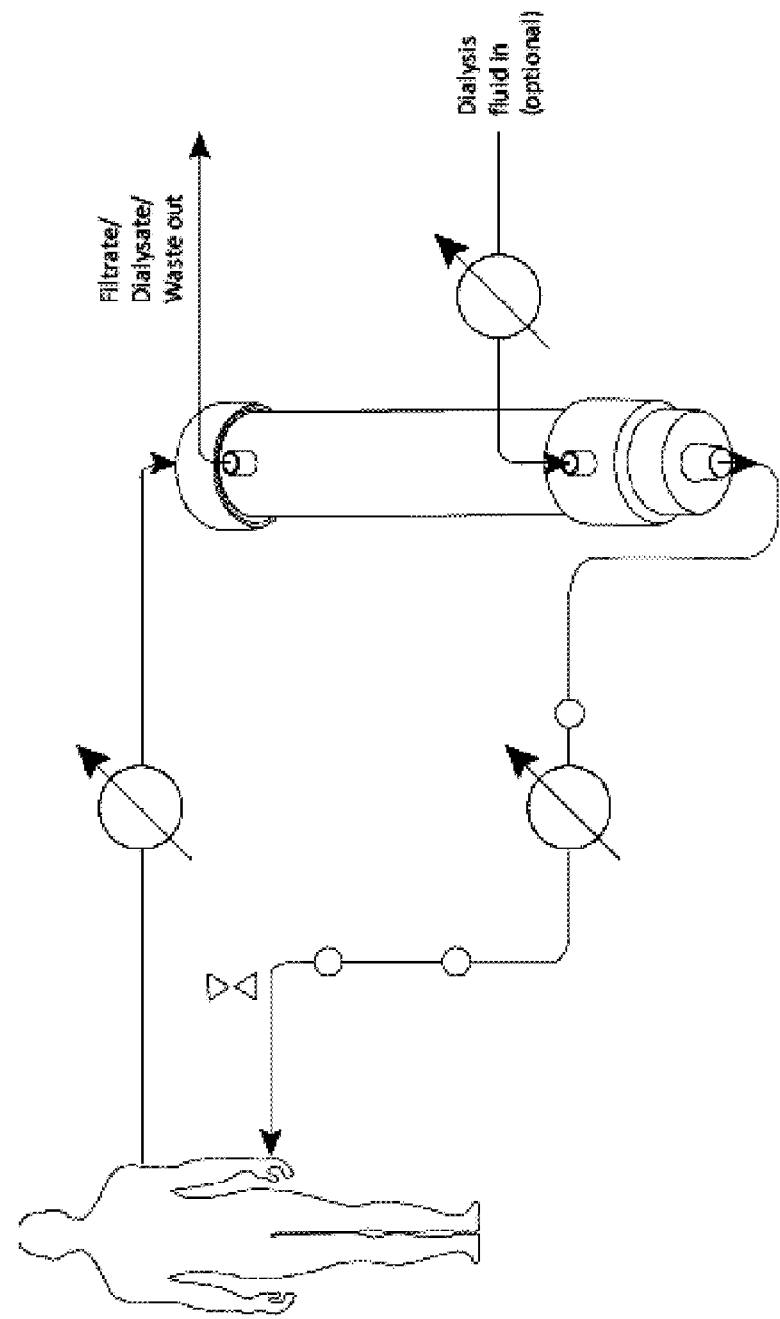
FIG. 1 illustrates a system used in conventional hemodialysis.
Figure 2A:
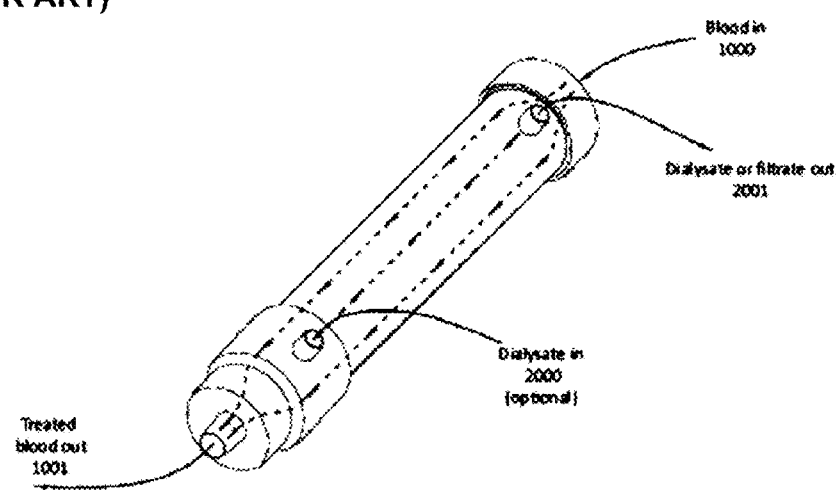
FIGS. 2A and 2B illustrate of a conventional cartridge used in conventional hemodialysis.
Figure 2B:
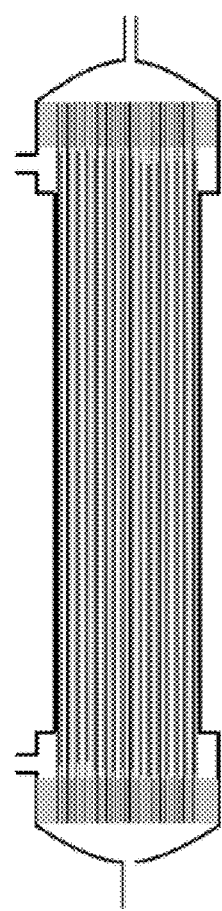
Figure 3:
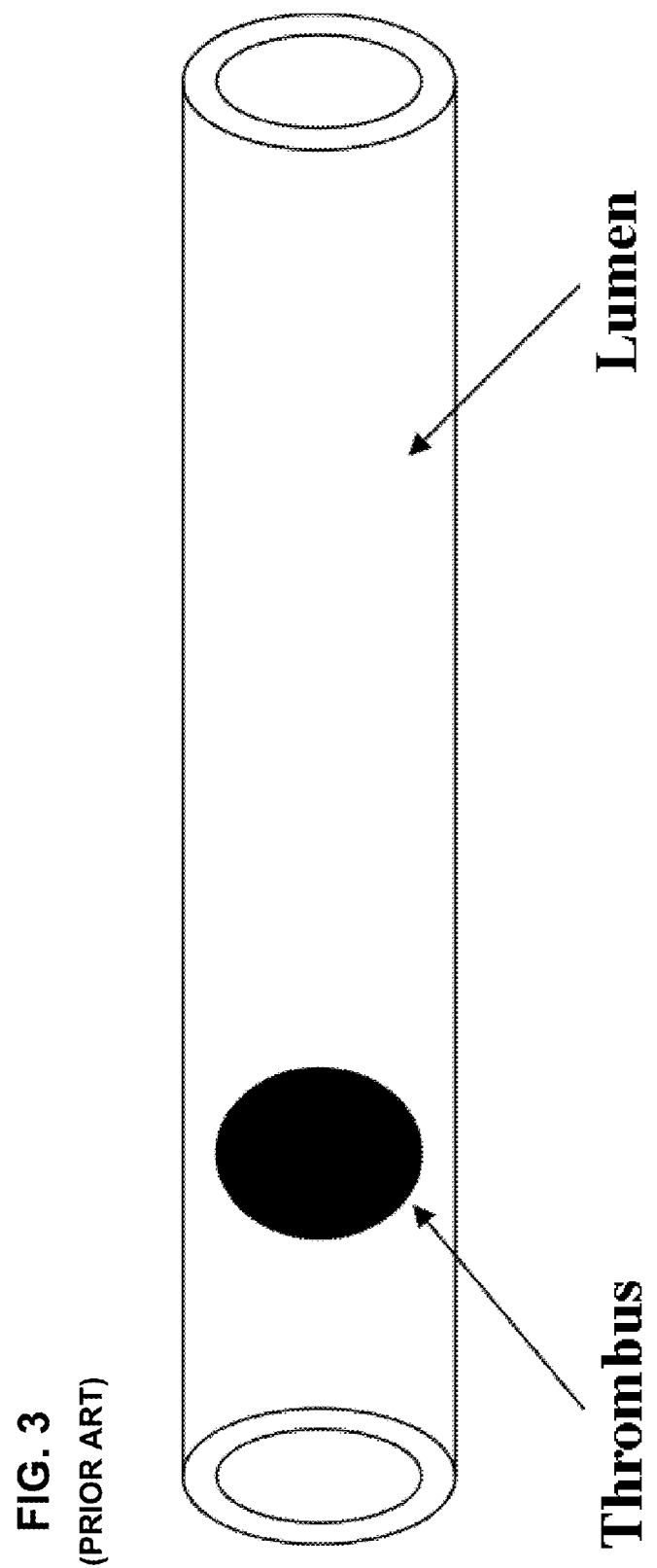
FIG. 3 shows the effect of a hypothetical thrombus inside a hollow fiber in conventional hemodialysis.
Figure 19A:
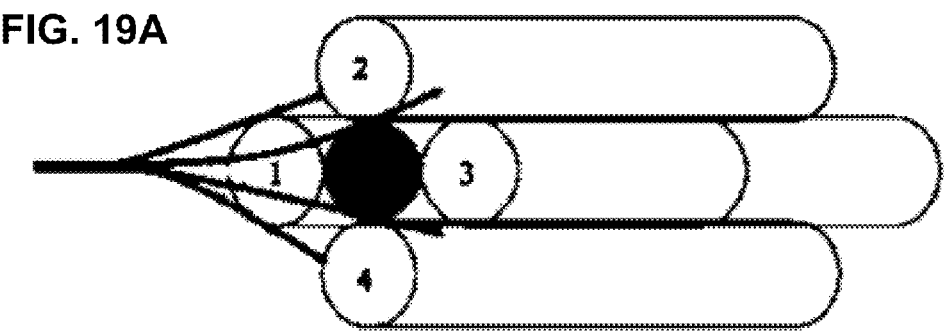
FIG. 19A shows flow distribution for flow around a single thrombus in the inter fiber space according to the principles of the present disclosure.

FIGS. 19E1 and 19E2 show photographs of filter clotting during conventional hemofiltration.

FIGS. 19F1, 19F2, and 19F3 show clot distribution in experiments with embodiments according to the principles of the present disclosure.

FIGS. 19G1 and 19G2 show a photograph and a sketch, respectively, of experimental clot distribution in an embodiment according to the principles of the present disclosure that does not have an orbital distributor.

Figure 19B:
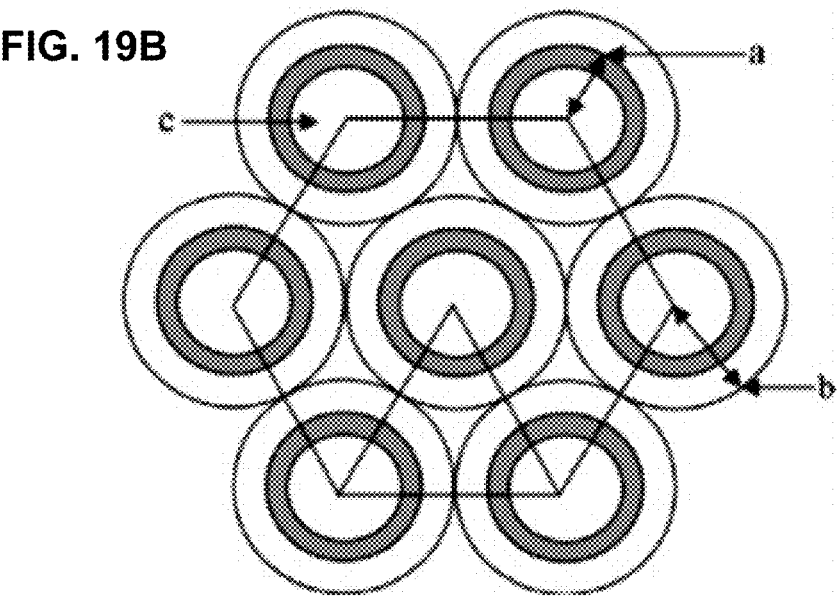
FIG. 19B is a schematic of a hexagonal array of hollow fibers according to the principles of the present disclosure.
Figure 19C:
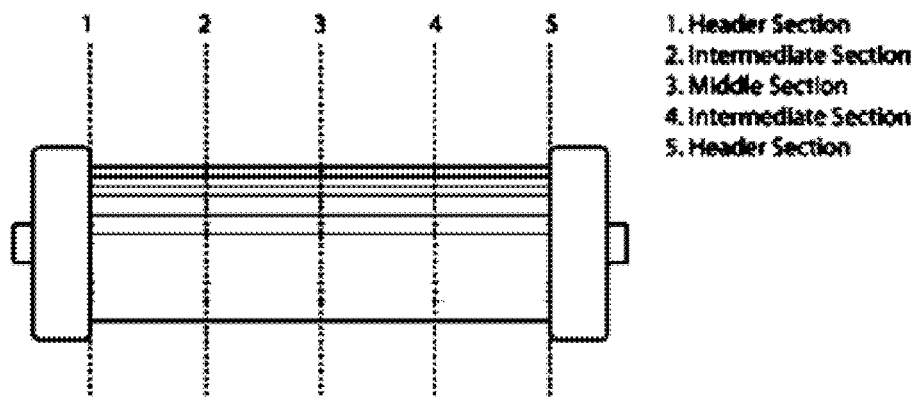
FIG. 19C is a schematic of sectioning along the filter length for microscopic examination of thrombi according to the principles of the present disclosure.
Figure 19D:
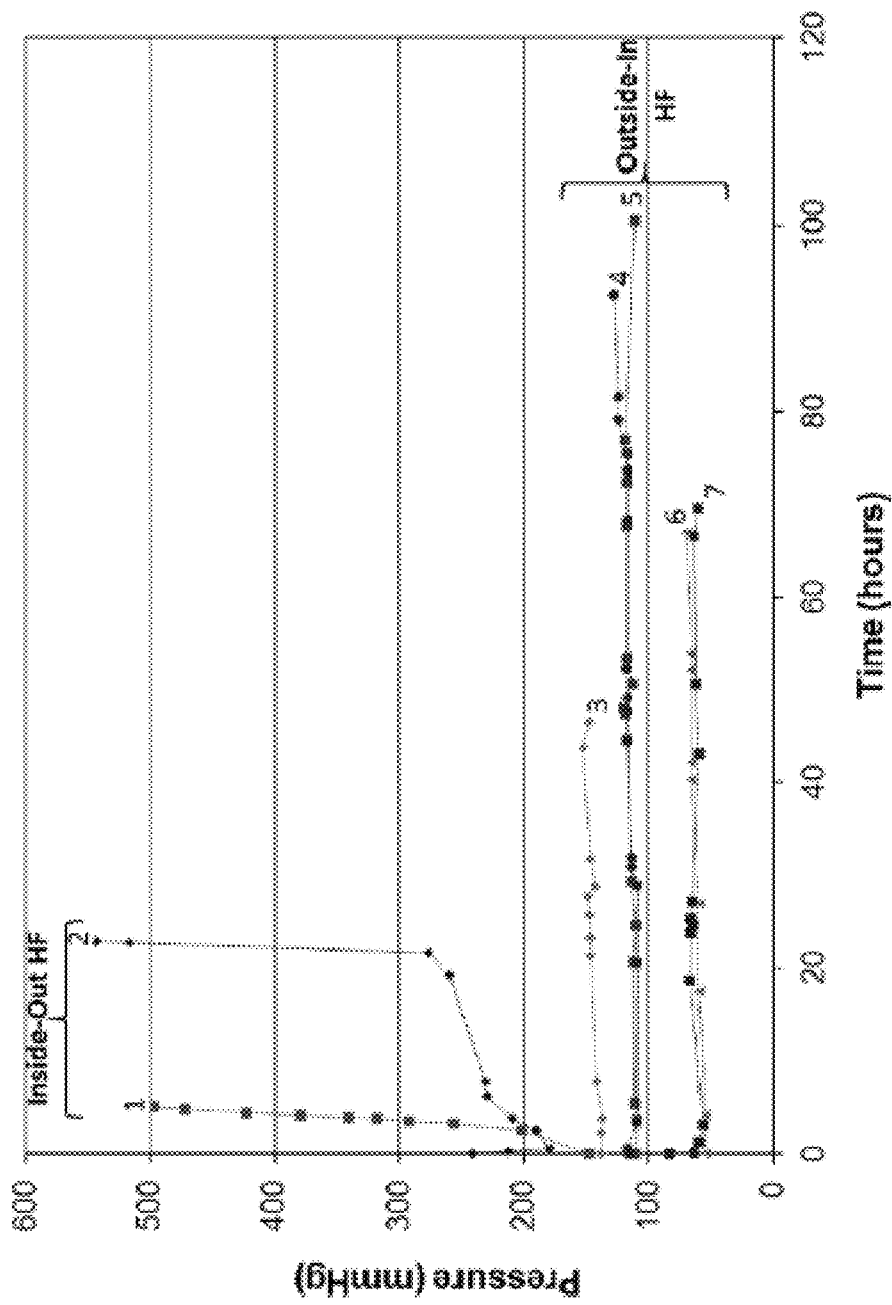
FIG. 19D shows pressure drop across the cartridge for two experiments of conventional practice and for five experiments according to the principles of the present disclosure.
Figure 19H:
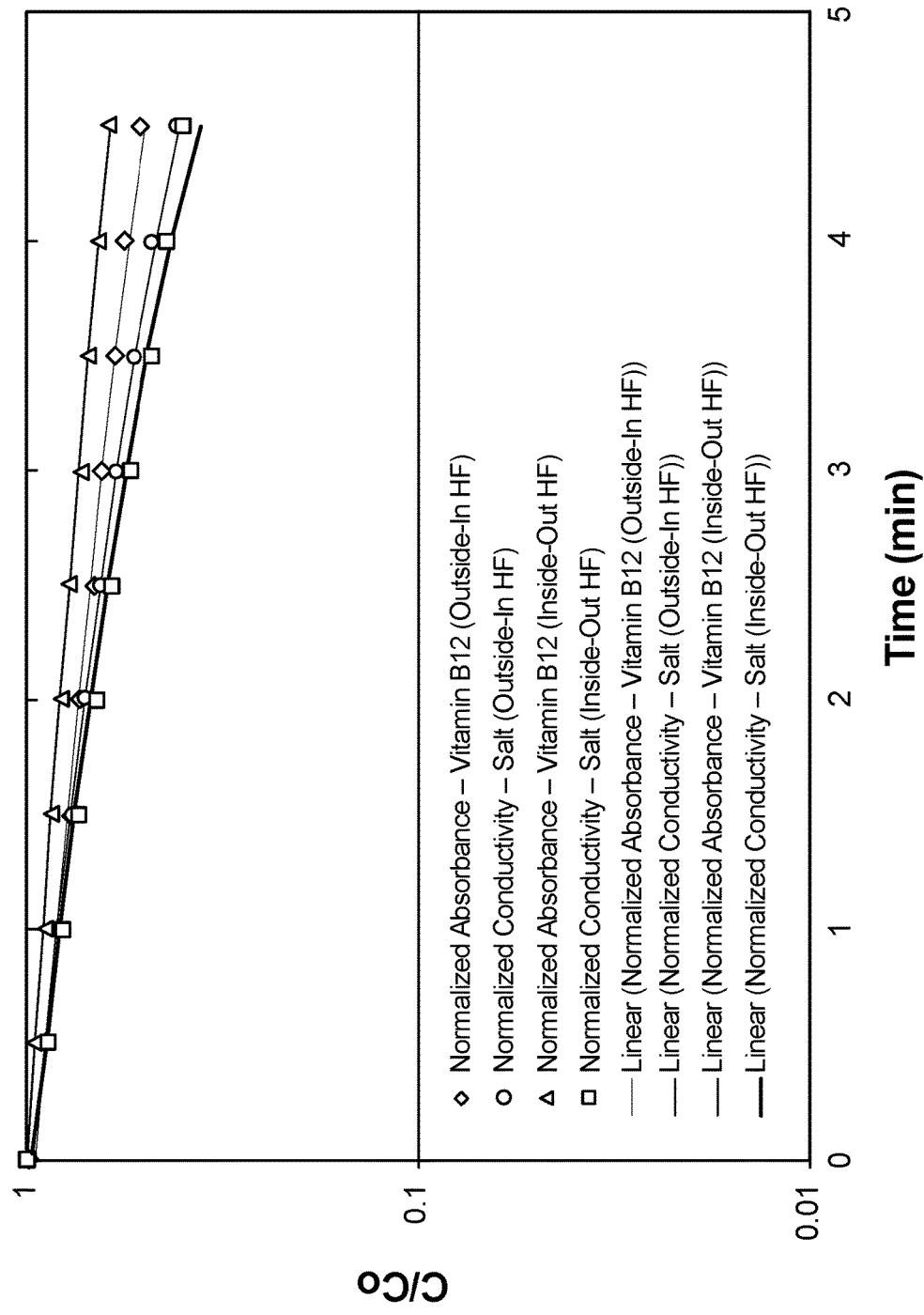

FIG. 19H shows clearance of sodium chloride and vitamin B12 both for conventional dialyzers and for embodiments according to the principles of the present disclosure.

Figure 20A:
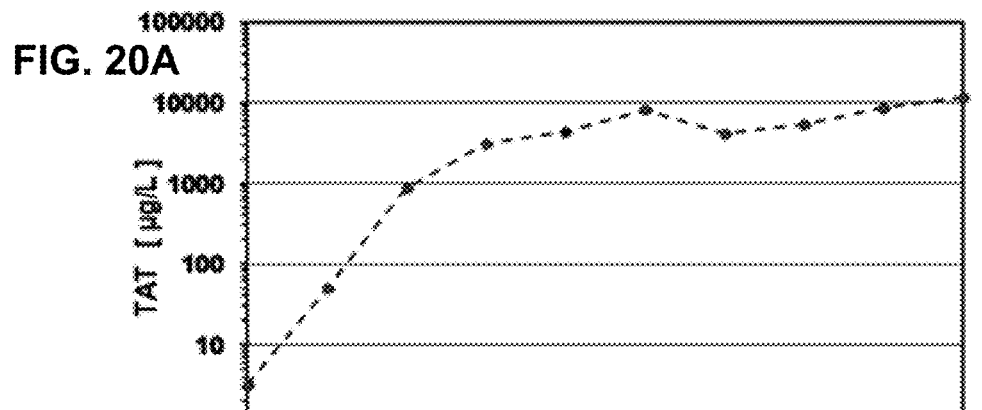

FIG. 20A shows TAT concentration in blood as a function of time for an embodiment according to the principles of the present disclosure.

Figure 20B:
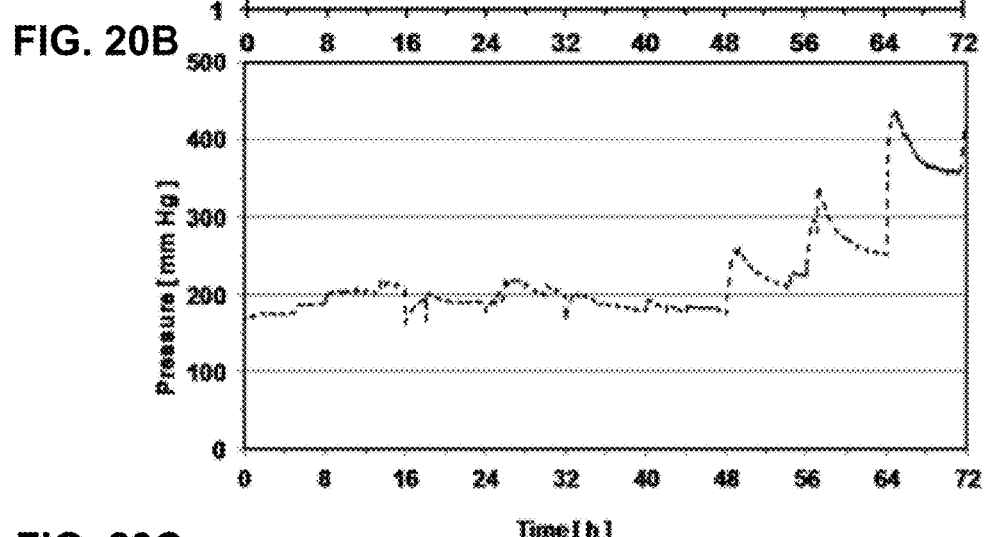

FIG. 20B shows pressure drop across the same dialyzer used in FIG. 20A.

Figure 20C:
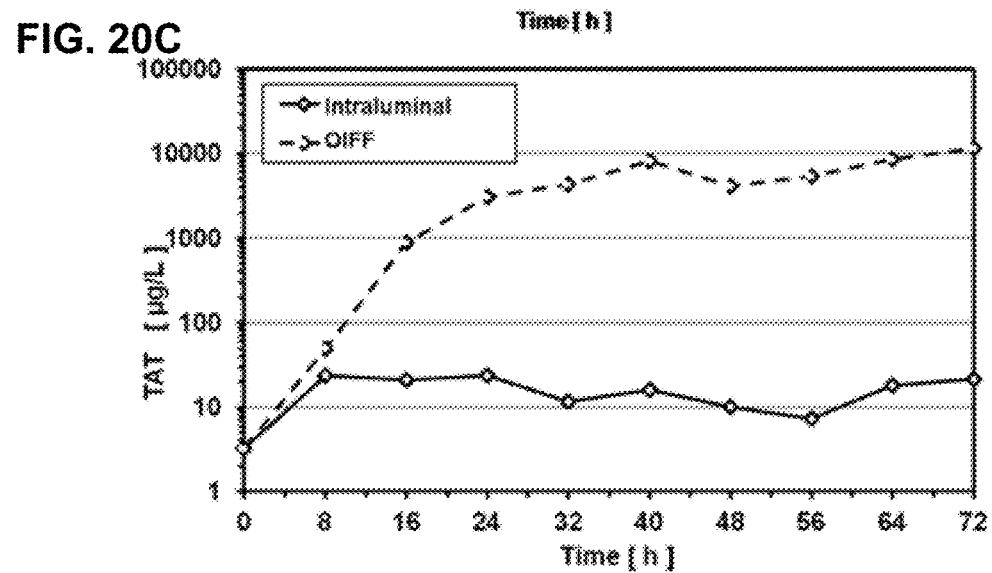

FIG. 20C shows TAT concentration in blood as a function of time for an embodiment according to the principles of the present disclosure, and also shows TAT concentration in blood as a function of time for a conventional dialyzer.

Figure 21A:
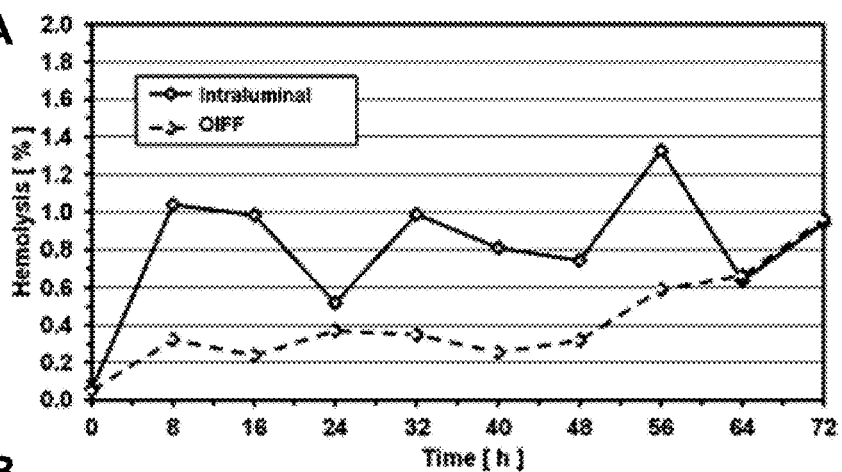

FIG. 21A shows hemolysis as a function of time for an embodiment according to the principles of the present disclosure.

Figure 21B:
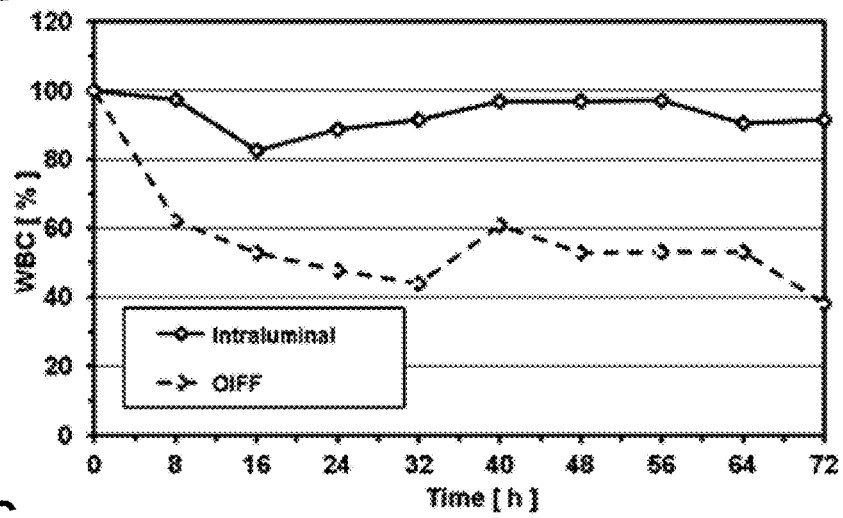

FIG. 21B shows the white blood cell count as a function of time for an embodiment according to the principles of the present disclosure.

Figure 21C:
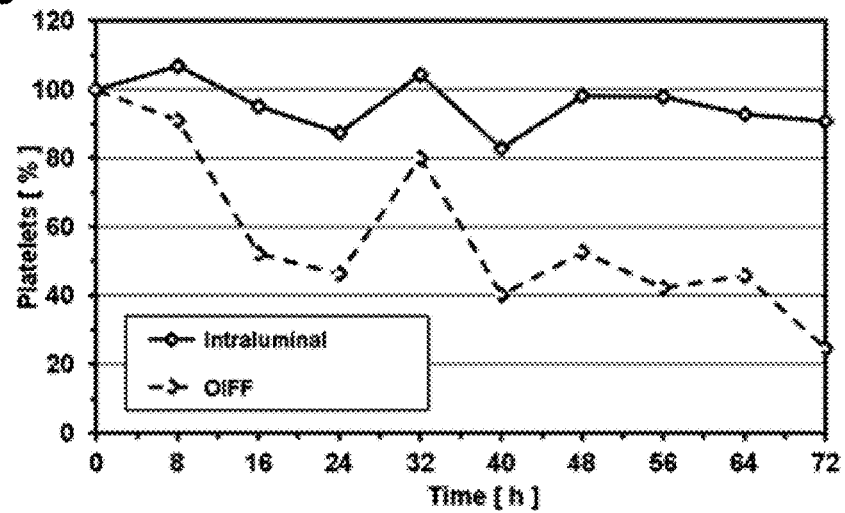

FIG. 21C shows the platelet count as a function of time for an embodiment according to the principles of the present disclosure.

Figure 22A:
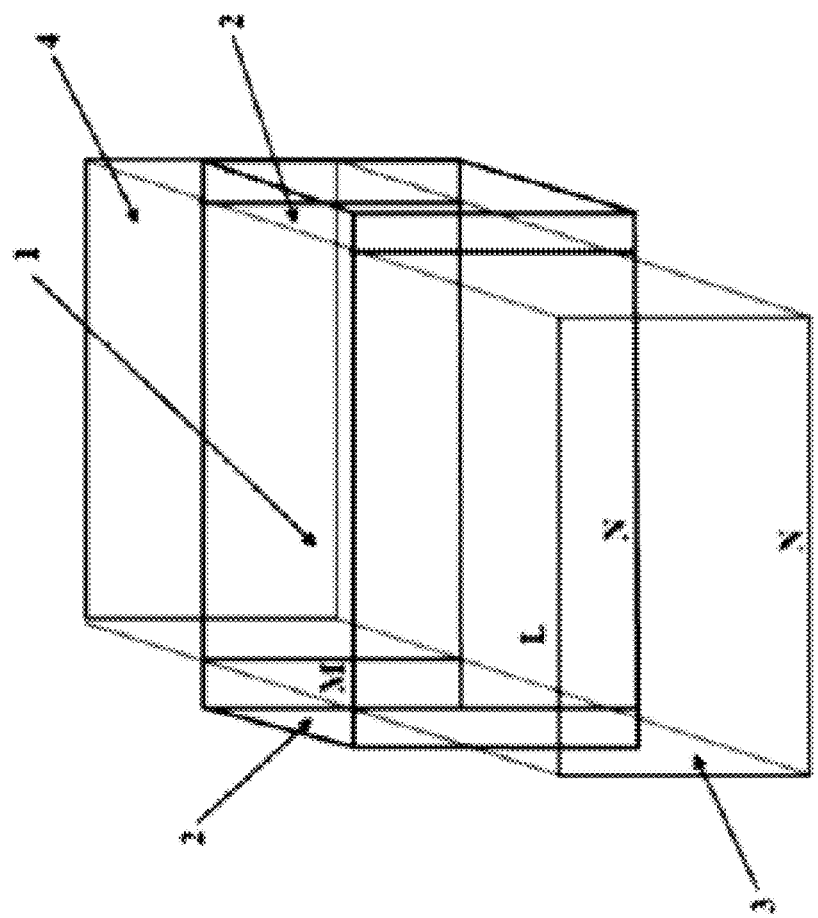

FIG. 22A shows a parallelipipedal geometric construct used in analysis.

Figure 22B:
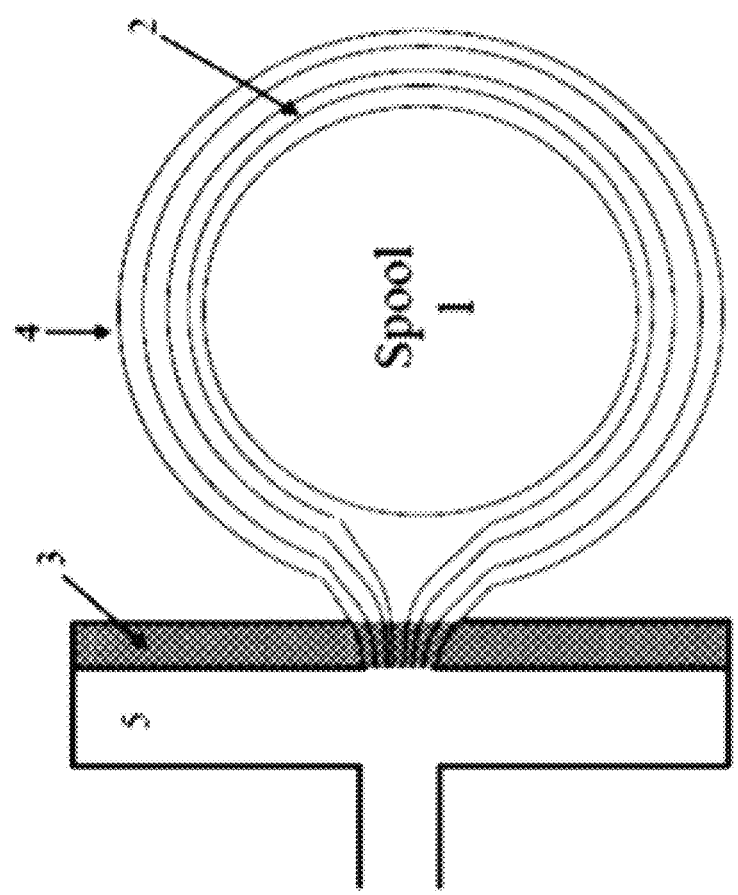

FIG. 22B shows a fiber arrangement of an embodiment according to the principles of the present disclosure.

Figure 22C:
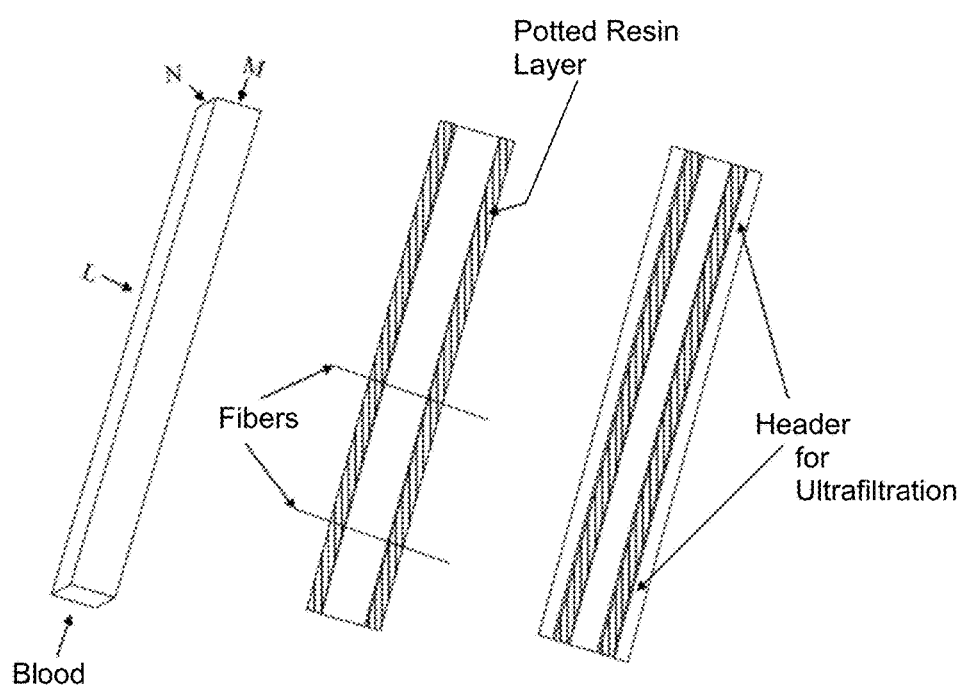

FIG. 22C shows fiber arrangements in an embodiment according to the principles of the present disclosure.

Figure 23A:
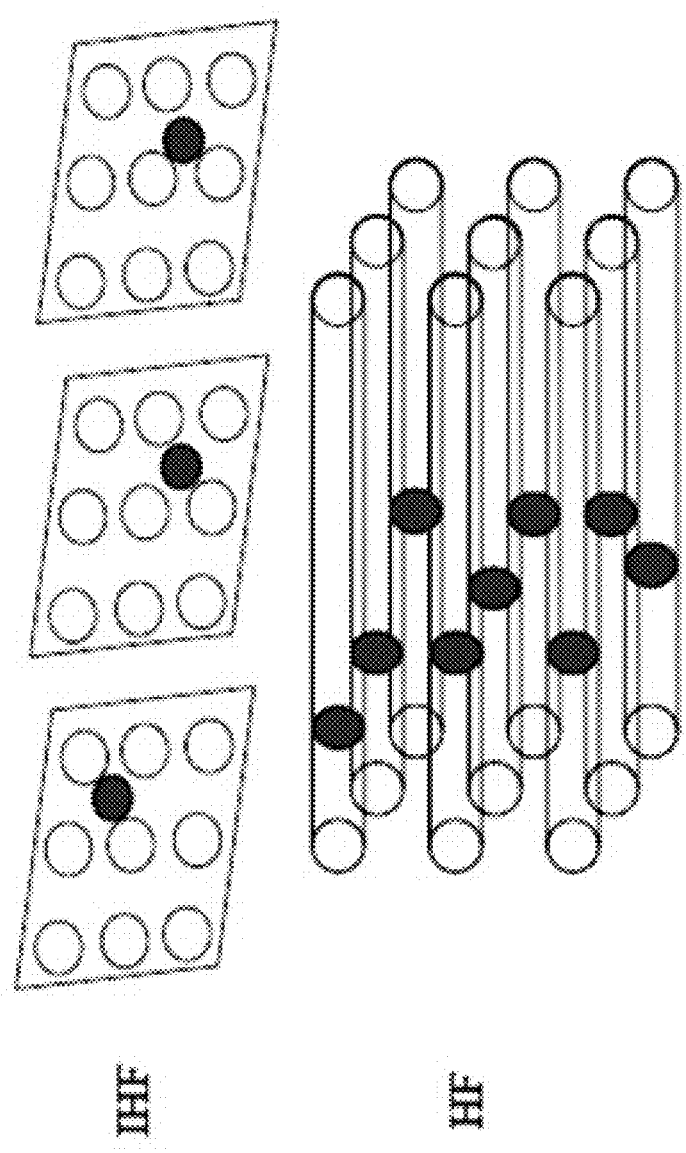

FIG. 23A shows a hypothetical distribution of thrombi.

Figure 23B:
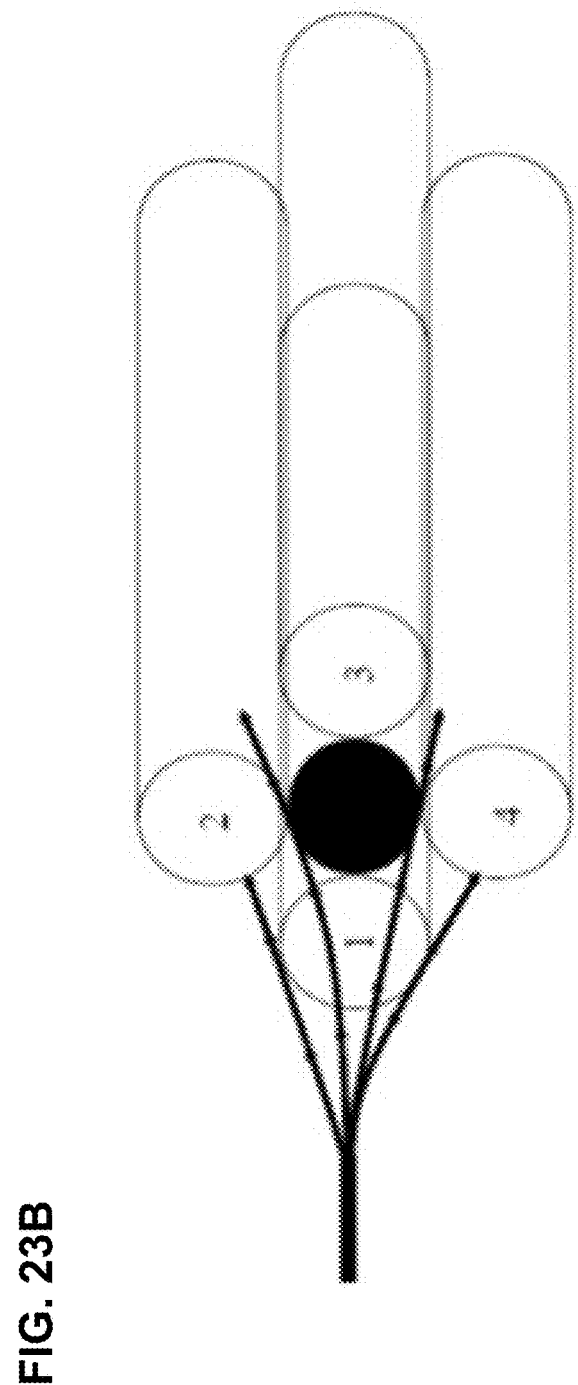

FIG. 23B shows a hypothetical distribution of thrombi among four fibers.

Figure 23C:
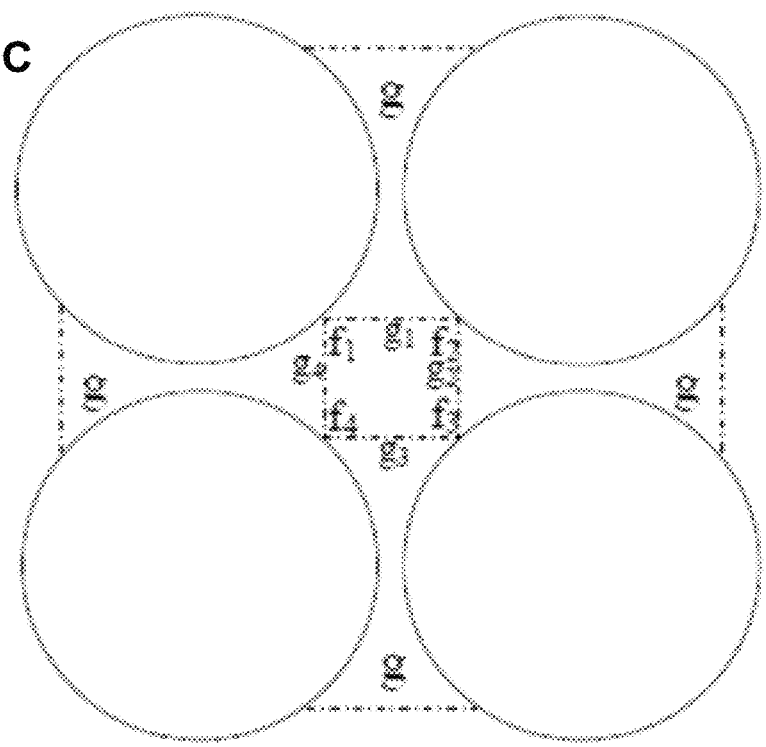

FIG. 23C shows a square cell of identical cylinders.

Figure 23D:
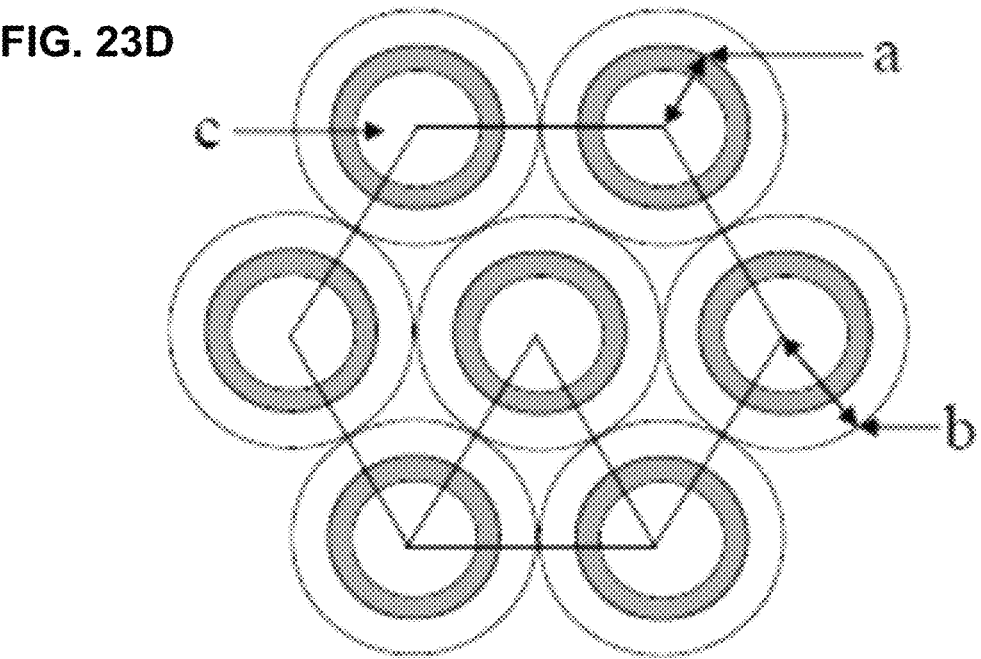

FIG. 23D shows a cell of identical cylinders in a hexagonal arrangement.

Figure 24:
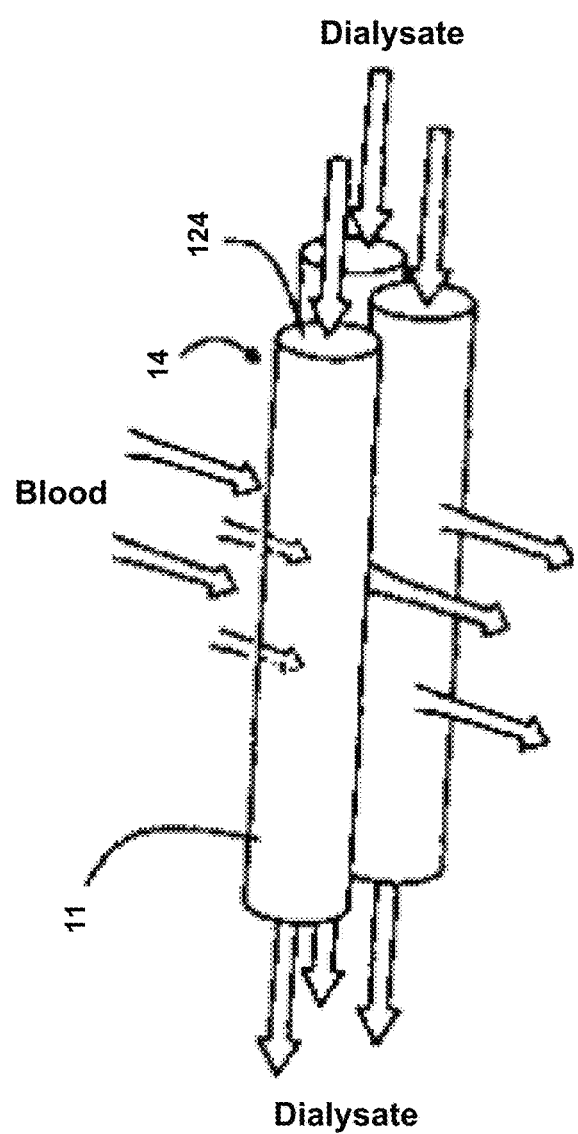

FIG. 24 shows, for an embodiment of the invention, a fiber arrangement in which the blood flows generally perpendicular to the fibers.

Figure 25:
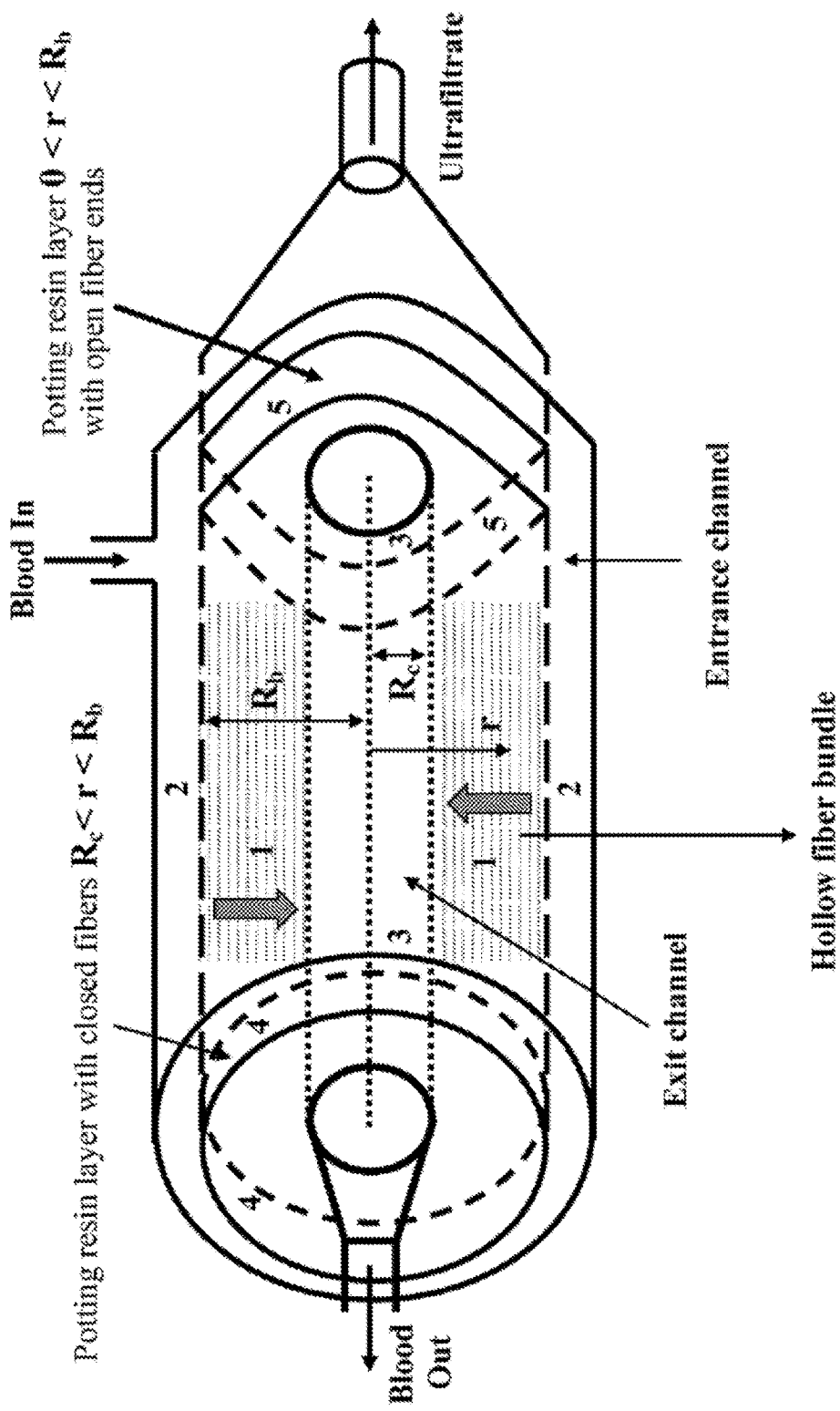

FIG. 25 shows a cartridge design in which the blood flow has a radially outward direction according to the principles of the present disclosure.

Figure 26A:
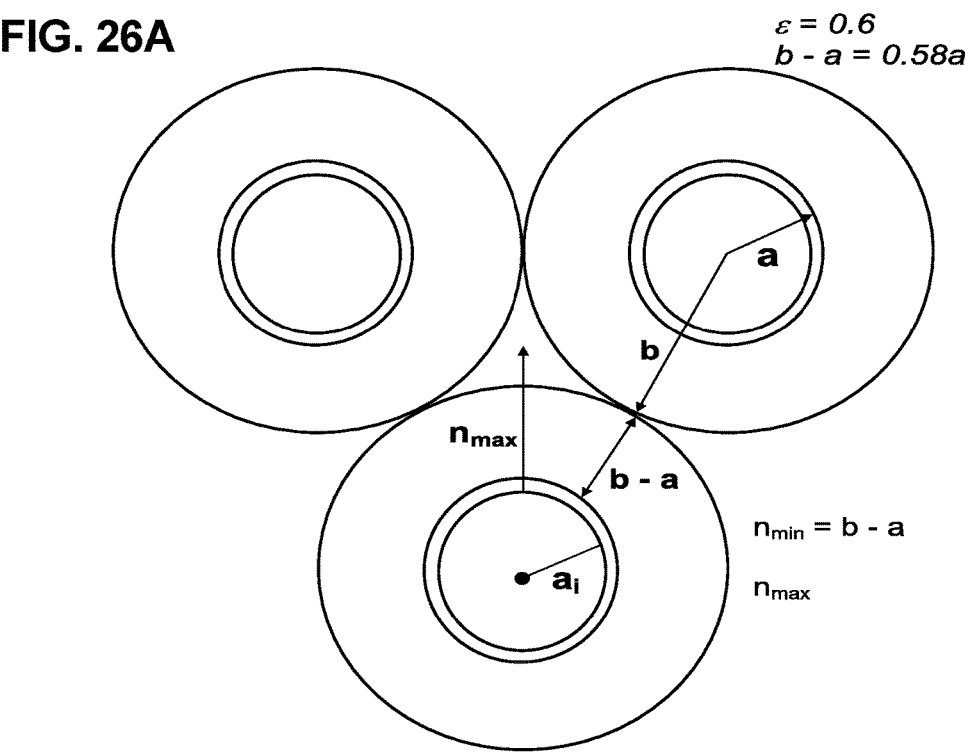

FIG. 26A illustrates certain geometric relationships for a cell of three cylinders that are spaced some distance apart according to the principles of the present disclosure.

Figure 26B:
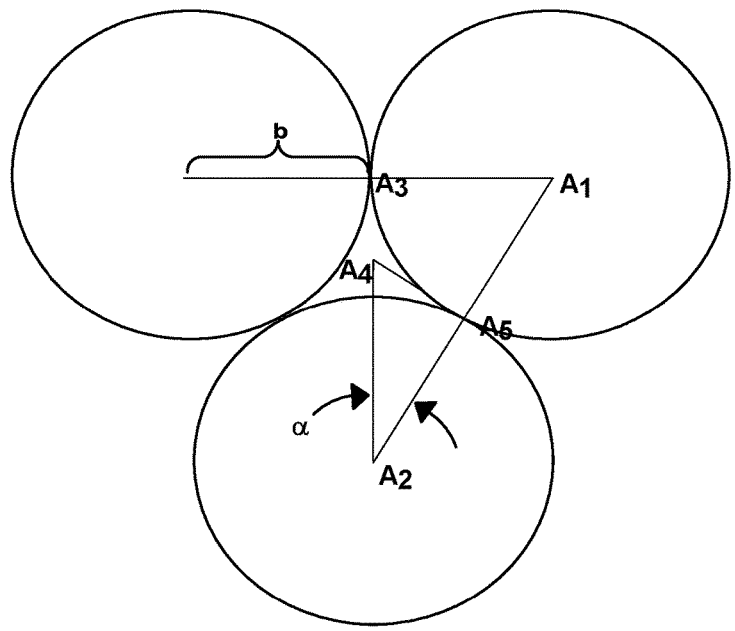

FIG. 26B illustrates a calculation for fiber spacing according to the principles of the present disclosure.

DETAILED DESCRIPTION

Figure 5A:
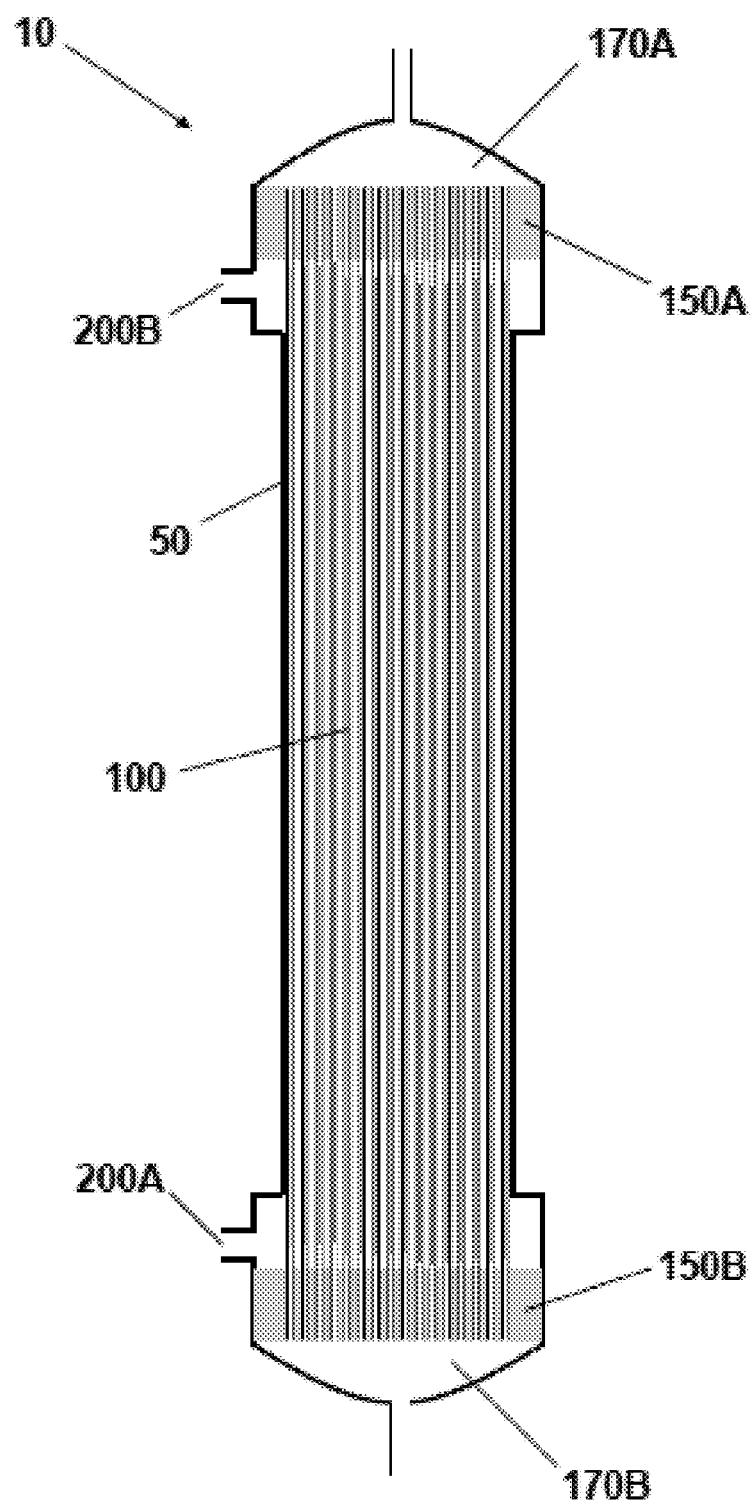
FIGS. 5A and 5B illustrate the overall arrangement of cartridge features and fluid flow for hemodialysis according to principles of the present disclosure.
Figure 5B:
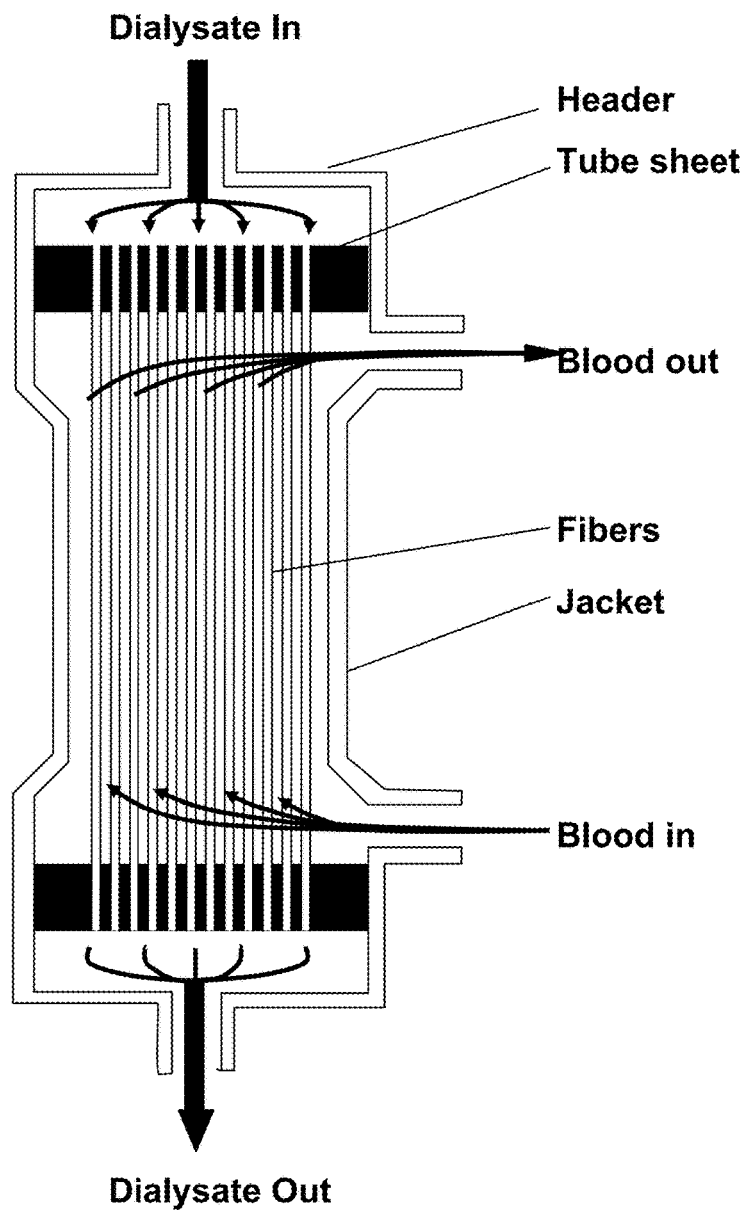

Referring now to FIGS. 5A and 5B, in embodiments of the invention there are provided cartridges 10 that contain a housing 50 that surrounds hollow semi-permeable fibers 100, and blood is arranged to flow in the compartment that contains the inter-fiber space, so that blood flows on the outside of the hollow fibers 100. Dialysate flows in the compartment that contains the lumens of the hollow fibers 100.

Cartridge 10 may comprise a housing 50. Within housing 50 there may be a plurality of fibers 100 contained inside the housing 50. At least some of the fibers 100 may be hollow and may be made of semi-permeable membranes having respective fiber interiors and fiber exteriors. The fibers 100 may be parallel or almost parallel to each other over at least a substantial portion of their lengths. In general, a substantial portion of the their lengths can refer a distance of at least 25% of the total lengths between 150A and 150B. There may be a first end barrier 150A that joins with the fibers 100 at first ends of the fibers 100, and joins with a housing interior of the housing 50 and bounds a first end plenum 170A and separates the first end plenum 170A from a housing midsection interior region. There may be a second end barrier 150B that joins with the fibers 100 at second ends of the fibers 100 and joins with the housing interior of the housing and bounds a second end plenum 170B and separates the second end plenum 170B from the housing midsection interior region.

There may be a first fluid flow compartment comprising the first end plenum 170A and the interiors of the hollow fibers 100 and the second end plenum 170B, with the first end plenum 170A and the interiors of the hollow fibers 100 and the second end plenum 170B being in fluid communication with each other. There may be a second fluid flow compartment comprising an inter fiber space and a housing supply port 200A and a housing discharge port 200B, all in fluid communication with each other.

The hollow fibers 100 may be either smooth or wavy, as discussed herein.

An expected advantage of this situation (although it is not wished to be limited to this explanation) is that if a hypothetical clot occurs somewhere in the inter-fiber space, and if the clot obstructs the local flow of blood near it, the blood can redistribute its flow to alternate flowpaths, such as by flowing at least partially transversely to the overall longitudinal direction of the cartridge 10 and reaching another flowpath that may be generally lengthwise. Such a flow field of blood can be three-dimensional as needed, in contrast to the conventional intra-luminal flow of blood, which is essentially one-dimensional. It is believed that the result of this is that modest quantities of individual clots have little effect on the overall pressure drop across the cartridge 10 and little effect on the mass exchange performance of the cartridge 10. As presented in more detail in one of the Examples, it is expected that if thrombi are distributed in the Inter Fiber Space in an isolated or random manner, the result is that the change in pressure drop is related to the volume fraction of thrombi present in the Inter Fiber Space, which is in contrast to the conventional situation in which the change in pressure drop is related to the number of internally blocked fibers. It is expected, although again it is not wished to be limited to this explanation, that this can result in a cartridge 10 that is longer-lived than the cartridges of conventional technologies, and that this mode of operation also is suitable to be used in a wide range of therapies. As discussed elsewhere herein, cartridges so designed have been demonstrated to have usefully long service lives. There are various design features and strategies that are helpful for such a flow geometry and such a cartridge and such a performance.

Porosity of Fiber Bundle

A design parameter that has significant impact on the flow in the inter-fiber space is the porosity of the fiber bundle.

First of all, as a limiting situation, it is useful to understand that there is a minimum porosity fraction or void fraction simply for geometric reasons. If a plurality of identical cylindrical shapes is arranged so as to fill a region with the cylindrical shapes completely tight against and touching each other, there is always some void space left between the cylindrical shapes. The remaining porosity amounts to a porosity fraction of approximately 10% if the cylinders are packed in a hexagonal array (which is the most dense possible packing), or 22% if the cylinders are packed in a square array. These are situations in which the cylinders actually touch each other.

In embodiments of the invention, the cartridge 10 may be designed such that the fibers 100 are packed somewhat more loosely than that limiting fully tightly-packed situation in which the assumed cylinders touch each other. One reason for this is in order to provide a geometry in which blood can flow at least partly transversely in order to flow around hypothetical clots in order to find an alternate flowpath. Even if the general direction of blood flow is along the longitudinal direction of the cartridge 10, if a clot forms, it is possible for blood flow to shift in a direction that is at least partially transverse to the longitudinal direction of the cartridge 10 and find an alternate flow path. It is believed that such a flow rearrangement capability can contribute to a long service lifetime of the cartridge 10. It can be appreciated that if the bundle were so tightly packed so that fibers 100 essentially touched each other, there would be virtually no cross-flow ability although there still would be flowpaths that conduct flow along the lengthwise direction of the cartridge 10. In essence, there would be parallel flowpaths that would have no ability to communicate sideways with each other. This extreme tight packing situation would not offer the advantages of embodiments of the current invention. The importance of having the alternate flowpaths in the sideways direction may depend on the desired service life of the cartridge 10. For a relatively desired long service life such as 100 hours, the availability of alternate flowpaths in the sideways direction may be more important; for shorter service life such as four hours, this may be less important.

More quantitatively, one of the Examples herein presents mathematically derived results in the form of a ratio between the permeability in the lengthwise direction and the permeability in the lateral direction, as a function of the packing fraction. As the packing becomes extremely dense and the gap between adjacent fibers 100 becomes vanishingly small, the ratio of the parallel permeability to the perpendicular permeability becomes infinite. This limiting mathematical result confirms there is a degree of packing that is so tight that it is undesirable for embodiments of the invention. This basically illustrates that shutting off the lateral permeability is not helpful for embodiments of the invention.

There are some design considerations that may have some importance for the conventional flow of dialysate in the inter fiber space, but that are especially important or different when the fluid flowing on the outsides of the fibers 100 is blood. Even in conventional hemodialysis, it has always been desirable that flow outside of the fibers 100 be distributed as uniformly as possible in the space inside the housing 50, such as for reasons of mass transfer efficiency and knowing accurately the dose of dialysis delivered. However, when blood flows in the inter-fiber space as in embodiments of the invention, there is additional motivation to keep the flow as uniform as possible so as to avoid creating regions such as stagnation regions that could cause formation of clots. It also is important for the blood flow to everywhere be in the proper range of flow parameters for blood flow, such as velocity and shear rate. And, the ability to have alternate flowpaths using transverse interconnections is helpful for clot-prone situations.

In embodiments of the invention, one of the reasons for wanting the spacing of the fibers 100 in the fiber bundle to be as uniform as possible is to avoid the possible clumping-together of the fibers 100. Clumping-together of fibers 100 might form significant void spaces and channels in some places and clumps of fibers 100 in other places. Within clumps of fibers 100, the blood flow might be undesirably slow in certain places such as within clumps, which would favor the formation of clots in the blood. This may also result in local distribution of shear rate that may be undesirable for blood flow and may lead to clot formation.

The porosity fraction of the fiber bundle inside the housing 50 influences the shear rate and velocity distribution and the possible clumping of fibers 100. First of all, it can be understood that in order to avoid clumping of the fibers 100, generally the looser is the packing of the fibers 100, the smaller is the likelihood that fibers 100 will clump. So, this consideration of avoiding clumping favors a fiber packing that is not excessively tight. However, there are also reasons why it is undesirable for the fiber bundle to be excessively loose, i.e., to have a porosity fraction that is excessively large. In embodiments of the invention, empty space inside the housing 50 is occupied by blood, and the volume of that blood occurs as priming volume, i.e., volume of blood that is outside the patient's body during the entire dialysis or other therapy procedure. Furthermore, some fraction of the priming volume of blood may be lost to the patient at the end of the dialysis procedure because it may be difficult to quantitatively return the blood to patient at the end of therapy. For physiological reasons, it is desirable to keep the priming volume below a certain limit as discussed elsewhere herein.

In embodiments of the invention, the hollow fibers 100 may occupy the housing interior space in such a way that there are no significant gaps between the inside of the housing 50 and the fibers 100, i.e., any gap between housing inside surface and a fiber 100 is no larger than a typical fiber-to-fiber gap within the fiber bundle. Another reason for not packing the fibers 100 too loosely is that if the fibers 100 are packed too loosely, there may be the possibility of spaces opening up where the fiber bundle meets the interior of the housing 50, and such gaps or spaces might provide an undesired alternate flowpath for blood, which might affect the flow overall uniformity in the cartridge 10.

So, it may be desirable that the packing of the fiber bundle be loose enough to provide some capability for rearrangement of flow patterns by flow that is at least partially transverse to the direction of the fiber, and loose enough to avoid clumping of the fibers 100, but not so loose as to require an excessively large priming volume or allow gaps at the contact with the housing 50. Taking all of these considerations into account, in embodiments of the invention, experiments show that, if the fibers 100 are straight fibers, the porosity fraction of the fibers within the housing space may be chosen to be within the range of 40% porosity (60% packing fraction) to 70% porosity (30% packing fraction), more preferably within the range of 50% porosity (50% packing fraction) to 60% porosity (40% packing fraction). Good experimental results were obtained at 62% porosity (38% packing fraction). This fraction is somewhat different compared to the fraction typical of conventional hemodialysis cartridges, for which porosity can be as small as 30%. This criterion applies both to straight fibers and to wavy fibers. Lower porosity also may be possible depending on the desired service life; for example, a porosity of 50% could be acceptable, and even a smaller porosity could be acceptable for shorter-term usage.

It may be that control of clotting is a function of both a porosity fraction and the shear rate experienced by the blood flow.

Geometric Proportions of Fiber Bundle

It is believed, although it is not wished to be limited to this explanation, that for embodiments of the invention, a cartridge 10 that is relatively long and slender is favorable. In regard to the flow transition region near either end, if the cartridge 10 is relatively long and slender, whatever region might occur that has low flow velocity or stagnation, that region will be smaller relative to the entire cartridge 10. This should help to reduce the likelihood or amount of formation of clots. Proportions of the cartridge are further discussed in one of the Examples. The proportions of the cartridge may be chosen so that for the flow of blood through the Inter Fiber Space, even if there are any local non-uniformities, the superficial velocity is everywhere greater than 0.25 cm/sec and the shear rate is greater than 300 sec$^{-1}$.

It may be appreciated that these criteria can be used for any of several flow situations and geometries that are discussed elsewhere herein. Such flow situations and geometries include flow generally parallel to fibers in a fiber bundle, and flow generally perpendicular to fibers in a fiber bundle. The perpendicular situation can occur for flow that is generally perpendicular to a plurality of generally straight fibers, or for flow that is generally perpendicular to an array of fibers that themselves occupy a curved path. The perpendicular situation can occur for flows that are generally rectilinear or for flows that are generally radially oriented. These flow orientations can occur in the main part of a fiber bundle, or can occur in a localized transition where the flow may change its direction or its flow area.

Properties of Fiber

In an embodiment of the invention, the hollow fiber 100 may have an exterior surface and an interior surface, and the exterior surface of the hollow fiber 100 may face the blood, and the exterior surface may be hemocompatible. In an embodiment of the invention, the exterior surface of the hollow fiber 100 may have several properties that are believed to enhance hemocompatibility. The exterior surface may be hydrophilic or hemocompatible; it may have certain chemical composition; and it may be smooth. The fibers have an ultrafiltration coefficient of between 5 to 100 ml/hr/m2/mmHg.

In an embodiment of the invention, the hollow fiber 100 may have an exterior surface and an interior surface, and the exterior surface may be hemocompatible. Such a surface may be readily wettable by water in its entirety, that is without substantial hydrophobic patches. The hydrophilic layer may have sufficient hydrophilic moieties per unit surface area to prevent adsorption of fibrinogen and similar molecules. It is preferred to have a thick hydrophilic layer that is fully hydrated such that it would act as a cushion so that it would not damage blood cells during flow. The thickness and packing of the hydrophilic or hemocompatible layer may be chosen to be large enough so that it is larger than the dimension of a fibrinogen molecule, which is 48 nanometers, so as to prevent adhesion of fibrinogen and other molecules implicated in thrombosis from adsorbing on the surface of the fiber. The contact angle of water on such a hydrophilic or hemocompatible surface may be zero or nearly zero.

Hydrophilicity may be determined in part by the surface energy of the material, which is a physical property of the material. It is believed, although it is not wished to be limited to this explanation, that having a hydrophilic blood-facing surface improves hemocompatibility. The presence of a hydrophilic surface in embodiments of the invention contrasts, for example, with the situation in blood oxygenators, which have a hydrophobic external surface and hydrophobic pores of their hollow fibers.

In an embodiment of the invention, the hollow fiber 100 may be made of certain polymers that are known to be advantageous, by virtue of their chemical nature, in terms of hemocompatibility. One example of such polymers is the combination of polysulfone with polyvinylpyrrolidone. Polysulfone by itself is intrinsically hydrophobic and not hemocompatible, but the addition of polyvinylpyrrolidone makes a material that is suitable for use in blood processing. Other appropriate polymers include polyethylene glycols and similar materials.

In embodiments of the invention, the exterior surface of the fibers 100, which is the blood-facing surface, may be smooth, and may have the smallest pores that are found anywhere in the fiber wall. Smooth may be considered to mean having a root-mean-square surface roughness of 100 nanometers or smaller. The interior surface of the fibers 100 may be rough, and may have larger pores than does the smooth surface. Rough may be considered to mean having a root-mean-square roughness of greater than 100 nanometers. Rough may include having relatively large crater-like depressions on the surface. Having the blood-facing surface be smooth is believed to be favorable for hemocompatibility, i.e., avoiding clotting. Also, the described positioning of smoothness and roughness may be consistent with general practice in filtration, in which it is desirable to help avoid clogging of the membrane by depositing the retained material at a surface where it can be sheared off and carried away by a component of flow parallel to the surface, rather than by allowing retained particles to clog pores within the membrane, where they are likely to remain indefinitely thereby increasing hydraulic resistance for flow or permeation through the membrane.

In other embodiments of the invention, in addition to the outer surface being smooth, the interior surface of the fiber may be smooth even though it is not necessary for clinical or physiological reasons that the interior surface be smooth. For example, there are fibers known as symmetric fibers in which the exterior surface is smooth and the interior surface also is smooth.

In embodiments of the invention, the pore size in the walls of the fibers 100 may be such as to give a molecular weight cutoff of approximately 50,000 Daltons. This corresponds to a pore size of approximately 2 nanometers to 7 nanometers. Furthermore, the pores in the walls of the fibers 100 may have a distribution of pore size such that the standard deviation of the distribution is several (e.g., 3) nanometers. In addition to the pore size, the thickness of the semipermeable membrane that is the fiber wall also affects kA0, which is a parameter describing the clearance of middle molecules such as beta2-microglobulin.

The fibers 100 may have an inside diameter such as 200 microns or in the range of from 100 microns to 300 microns, and a wall thickness such as 40 microns, or in the range of from 20 microns to 50 microns. The corresponding outside diameter of the fibers 100 would be less than 400 microns. In embodiments of the invention, it may be possible to use smaller fiber diameter than in conventional hemofilters. Current use and technology of externally smooth fibers only provides fibers that have significantly larger fiber outside diameters than the outside diameters just described.

In embodiments of the invention, the fiber 100 may be provided with a coating, such as on the blood-facing surface of the fiber. A coating may be such as to improve the hemocompatibility of the surface of the fiber 100. Heparin is an example of such a coating material. Heparin is an anionic polyelectrolyte. Perfluorocarbon is another example of a possible coating material. It is possible that the coating may be applied only to portions of the fiber 100, not necessarily to the entire fiber 100. For example, the coating or surface treatment may be applied to regions near the ends of the fiber 100, which is where flow transitions (change of direction and/or area occur). This is discussed elsewhere herein.

In embodiments of the invention, the fibers 100 may have a combination of the following features: manufactured of the combination of polyethersulfone or related polymers, in combination with polyvinylpyrrolidone; smooth on the outside surface; and waviness or undulation along its length.

The smoothness of a particular surface (exterior or interior) of the fibers 100 is a result of choices about the formulation of the solution of solvent and polymers used during manufacture, and also choices about how the fiber 100 is cooled or quenched shortly after it is extruded during manufacture. In order for the outer surface to be smooth, quenching may be applied preferentially to the outer surface of fiber 100.

In embodiments of the invention, the outside diameter of the smooth-outside hollow fiber 100 can be in the range of less than approximately 300 microns, preferably in the range of between 150 and 250 microns. This contrasts with existing technology, in which smooth-outside hollow fibers are only used at substantially larger outside diameters, for purposes other than hemodialysis.

In any discussion of smooth-exterior fibers, it is also possible to include so-called symmetric fibers, which are smooth on both their exteriors and their interiors. Such discussions also apply to fibers that may have a coating.

Waviness of Fiber

In embodiments of the invention, at least some of the fibers 100 may be wavy.

It may be useful to consider the flow conditions experienced by the blood as the blood flows along the length of the fiber bundle in the inter fiber space, and in particular for the situation in which the fibers 100 are wavy. First of all, it may be useful to note what is a typical value of Reynolds number for blood flowing along the length of the fiber bundle in the inter fiber space. The density of blood may be approximated as the density of water, which is 1000 kg/m$^3$. For a typical velocity of blood, one may use a value of 0.02 m/s (2 cm/s). For the dimension of the flow space, it would be correct to use a hydraulic diameter, which would be calculated as 4*Area/Perimeter, using Area=the open cross-sectional area of the inter-fiber space and using Perimeter=total perimeter of all of the fiber exteriors that are exposed to blood in the cross-section. For the present situation, it may be expected that the result is not too different from the fiber diameter, which may be assumed to be 200 microns. It may be assumed that (for a velocity range of interest for present purposes) the viscosity of blood is three times the viscosity of water or 0.003 Pa-s. These quantities combine to give a Reynolds number just slightly larger than 1. This Reynolds number is clearly in the range of laminar flow, indicating that no mixing is likely to occur from internally generated mixing such as turbulence. Thus, there is usefulness in creating disturbances to the flow using local geometric variations. The undulations of wavy fibers 100 may provide such local geometric variations.

Even though a wavy fiber is not strictly a straight line, the fiber may have a generally longitudinal direction that approximately describes the overall path of the fiber on a size scale larger than the wavelength of the waviness. There may be defined a first plane that is perpendicular to the longitudinal direction of the fiber. There may also be defined a second plane, which may be perpendicular to the first plane and may be a plane that the fiber lies in if the shape of the overall path of the fiber lies in a plane, or else the second plane may be a plane that the fiber at least approximately lies in if the shape of the overall path of the fiber is not strictly planar. FIGS. 8A-8D illustrate a fiber 100 that has a generally circular cross-section taken perpendicular to its long direction and is wavy along its long direction. The fiber 100 itself is the envelope of the illustrated suggestive portions of the fiber surface in FIGS. 8A-8D.

Given that the fiber is typically, in cross-section, a circle, the first radius of curvature, R1, may be the radius of the circle that is the cross-sectional shape of the exterior of the fiber. The first radius of curvature may be in the range of 100 microns, or more generally in the range of from 50 to 300 microns. The second radius of curvature, R2, generally describes the waviness of the shape of the path of the fiber. This is discussed in more detail later but may be in the range of millimeters, i.e., larger by some factor than the first radius of curvature R1.

The blood may flow adjacent to the external surface of this fiber 100. The external location of the blood flow may be defined as external with respect to the complete external perimeter that appears in the cross-section of the fiber 100 taken perpendicular to the long direction of the fiber 100.

Figure 8A:
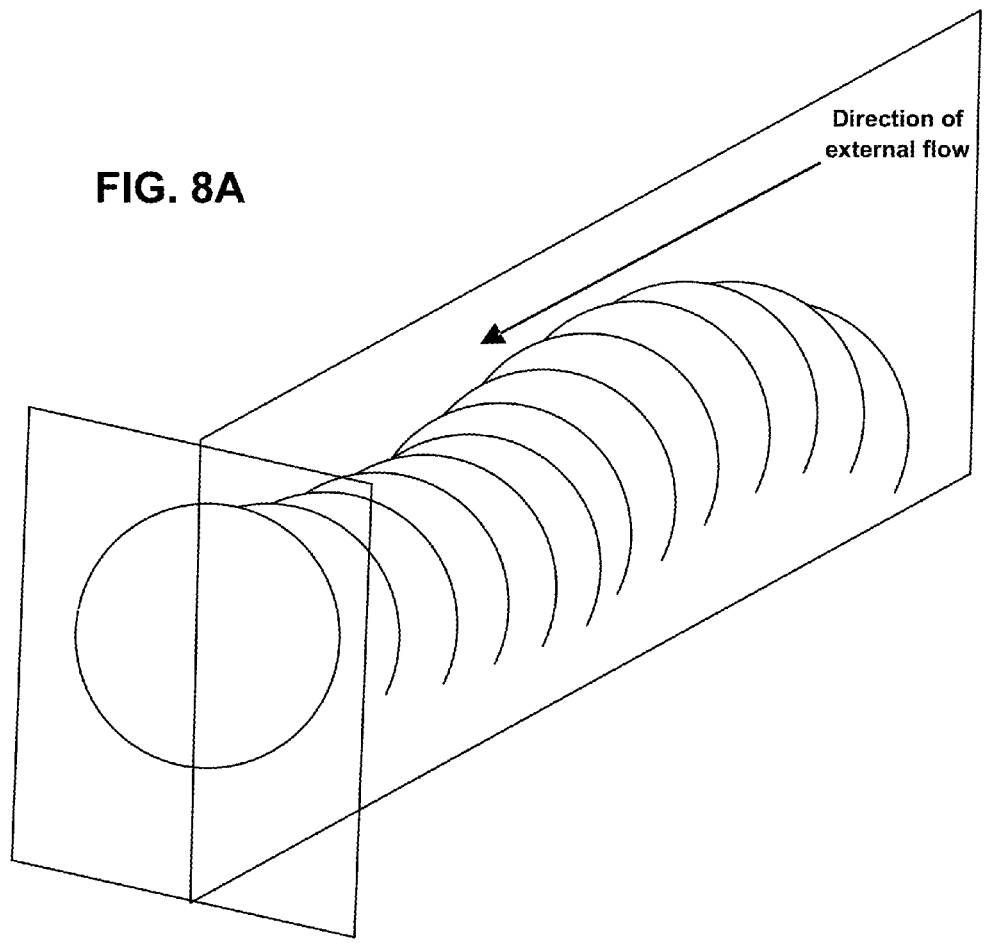
FIG. 8A-8D illustrate geometric details of a wavy fiber of an embodiment according to the principles of the present disclosure.
Figure 8B:
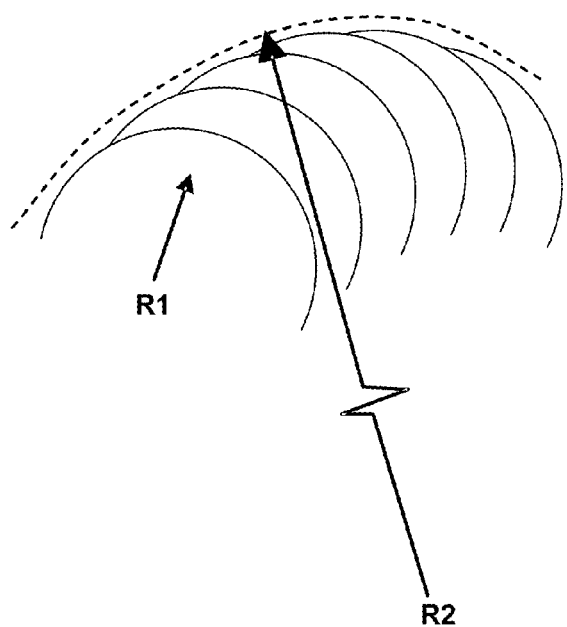

As illustrated in FIG. 8B, in some places the blood flows past exteriors of fibers 100 that have a convexly curved surface in the first plane with the first radius of curvature R1, and have a convexly curved surface in the second plane with the second radius of curvature R2. This can be thought of as the blood flowing past a bump.

Figure 8C:
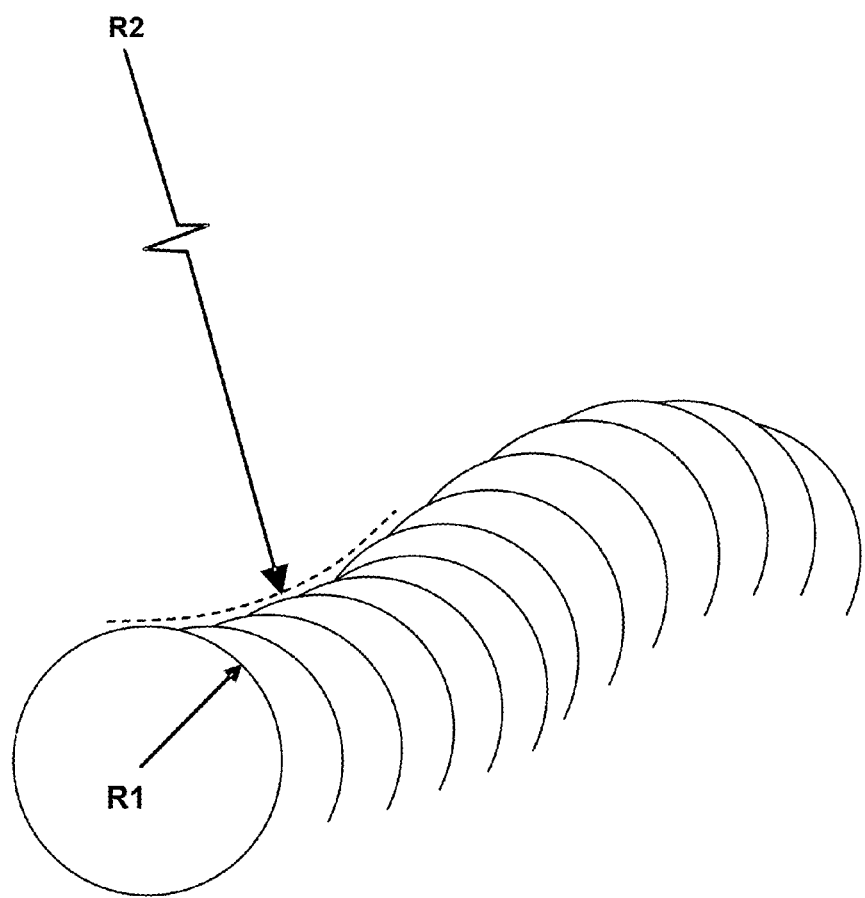

As illustrated in FIG. 8C, another situation also is possible. It is possible that blood flows past the exteriors of fibers 100 that have a convexly curved surface in the first plane with a first radius of curvature R1, and have a concavely curved surface in the second plane with a second radius of curvature R2. This can be thought of as the blood flowing past a saddle.

Figure 8D:
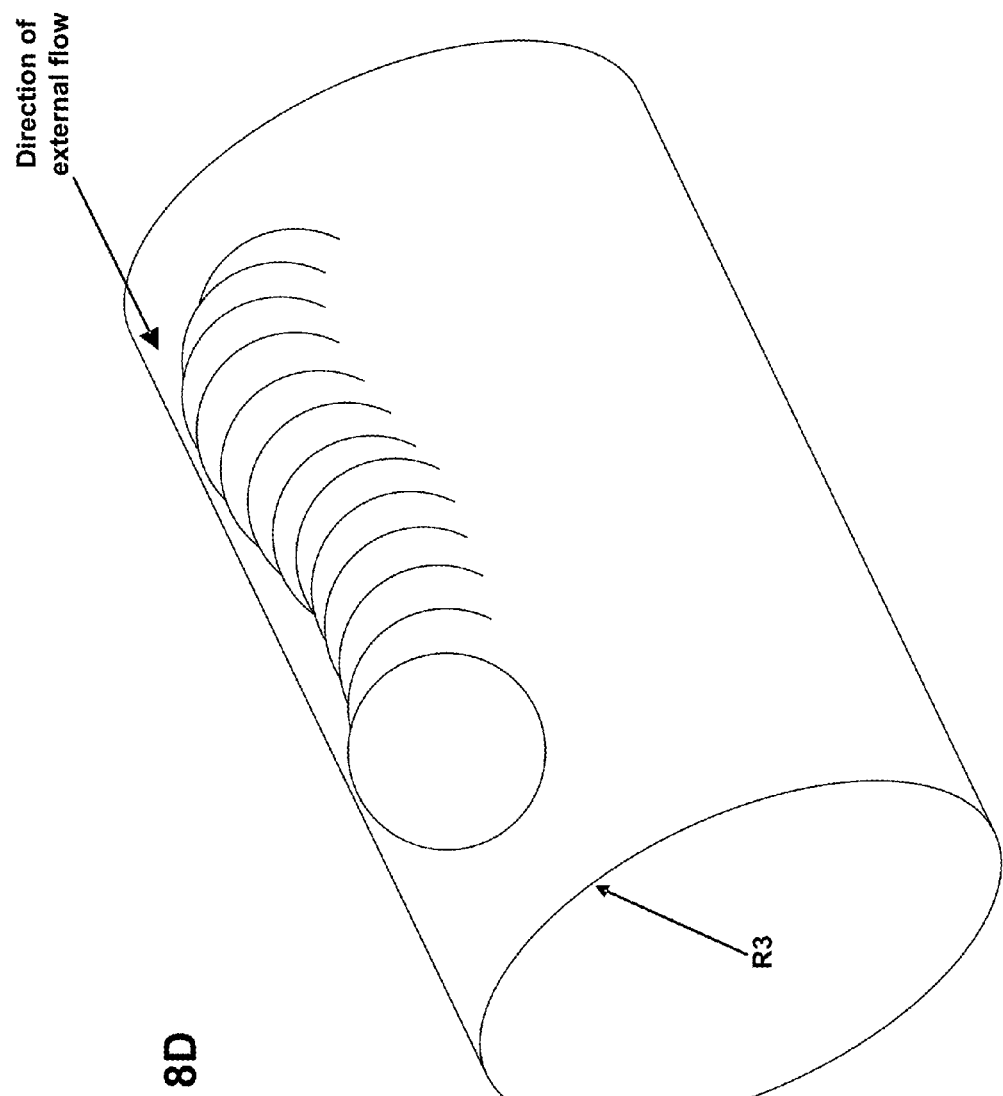

In still further situations, either the "bump" situation or the "saddle" situation may occur where some portion of the fiber 100 touches an internal cylindrical surface, which may be the internal cylindrical surface of the housing 50. The internal cylindrical surface may have a third radius of curvature, R3. This is illustrated in FIG. 8D.

In any of these situations, the variations in shape presented by the external surface of the fiber 100 as the blood flows along it may be useful for mixing the blood and breaking up either fluid boundary layers or diffusion boundary layers or both. This may improve the mass transfer performance of the dialyzer or cartridge 10, and also may help to discourage the formation of blood clots.

In regard to the radius of curvature of the fiber 100 along the length of the fiber 100, given that the shape of the waviness along the fiber 100 may be a generalized oscillatory shape, the second radius of curvature, R2, may be discussed using the mathematical definition of radius of curvature. For a function y=f(x), the radius of curvature is defined as $$R = \frac{[1+(dy/dx)^2]^{(3/2)}}{(d^2y/dx^2)}$$

It may be assumed for sake of analysis that the oscillatory shape of the wavy fiber is a sinusoid. If y=A sin(kx), then dy/dx=A*k*cos(kx) and d$^2$y/dx$^2$=−A*k*k*sin(kx). Then, the formula becomes $$R = \frac{[1+(A*k*\cos(kx))^2]^{(3/2)}}{A*k*k*(-\sin(kx))}$$

It may be useful to evaluate the radius of curvature of a sinusoid at the peak of the sinusoid, which is the location of greatest curvature, and which is where kx has the value pi/2. It may also be useful to consider simply the absolute value of the radius of curvature. Evaluating the above formula for this situation simplifies the formula to $$R=1/(A*k^2)$$

The assumed sinusoidal shape may be described in terms of lambda, which is the wavelength of the sinusoid, and A, which is the amplitude of the sinusoid from middle to peak (i.e., half of the total peak-to-peak amplitude) (which may be referred to as the half-amplitude). So, k=2*pi/lambda. This gives $$R_2 = \text{lambda}^2/[A*4\text{pi}^2]$$

For a numerical example, if the wavelength lambda is assumed to be 0.008 m, and if the half-amplitude of the sinusoid is assumed to be one-twentieth of the wavelength, then the radius of curvature R would be 0.004 m. The ratio of the radius of curvature R$_2$ to a typical fiber radius R$_1$ (which might be assumed to be 100 microns) would be about 40.

In regard to waviness, there are various ways of imparting a wavy shape to the fiber 100. One way is to mechanically deform the fiber 100 sideways first in one direction then in the opposite direction as the fiber 100 passes by after leaving the extruder. This may form a shape that is at least approximately sinusoidal. This may be done while the fiber 100 is at a hot enough temperature so that the fiber can receive a permanent deformation. Alternatively, the fiber 100 may be at least partially quenched on its exterior and then while the fiber is warm, it may be deformed sideways to produce the wavy shape. The quenching process is important for forming the smooth exterior.

As yet another alternative, the fiber 100 may be fully quenched, which aids in forming the smooth exterior, and then may be reheated to an intermediate temperature suitable to soften the fiber enough for the fiber to accept a wavy shape being imposed on it. After formation of the wavy shape, the fiber 100 may then be cooled again. Such a two-step process may be useful for allowing the smooth outer surface of the fiber 100 to form substantially completely, without being disturbed by the rollers or other devices that may be used to form the wavy shape.

In any of these processes, the formation of the wavy shape may be performed at a sufficiently low temperature so that the smooth surface of the hollow fiber 100 is not disturbed during the wave-forming process. For the process of introducing the bends and curves that form the waves, the permanent deformation may be achieved by a combination of temperature-induced softness, and the length of time for which the fiber is held in the deformed position before being cooled, and the extent of over-bending that is used in the wave-forming process. In order to compensate for using a relatively low temperature, the process may use over-bending, i.e., may bend to a larger amplitude than the desired shape so that when the bent fiber springs back, it still retains some of the deformation that was imposed. The process furthermore may use an extended duration of holding time at the softening temperature, which also may help to lessen the required temperature needed for imposing the undulations. The tooling that contacts the fiber to form the undulations may be made with fiber-contacting surfaces that are smooth or polished so as to help maintain the smoothness of the fiber surface during deformation. For example, the smoothness of the tooling surface may be of a root-mean-square dimension that is similar to the smoothness of the exterior surface of the fiber. The fiber-contacting surface of the tooling may have a saddle shape. The convexly curved direction of curvature of the tooling may correspond to the curvature that is imposed onto the fiber. The concavely curved direction of curvature of the tooling may have a curvature that is comparable to the curvature of the fiber in a cross-section taken perpendicular to the fiber's long direction, so that the tooling forms a cradle for the fiber to help prevent the fiber from collapsing due to the deformation of being bent.

In the final formed configuration, the waves in the fibers 100 may have a wavelength of approximately 0.8 cm to 1 cm. The waves in the fibers 100 may have an amplitude of up to approximately 1 mm (which is considered to be the average-to-peak amplitude, which might sometimes be referred to as the half-amplitude). The amplitude can be less than 10% to 30% of the wavelength. The packing of wavy fibers into the housing 50 can be somewhat random. For example, even if the fibers 100 all have the same wavelength, they may be placed in the housing 50 relative to each other such that they are out-of-phase in their lengthwise placement with respect to each other. This may help to maintain separation between the fibers 100 during use.

The parameters of the waviness may be chosen so that the amplitude of the sinusoid is much smaller than the wavelength of the sinusoid.

It is possible that all of the hollow fibers 100 in the bundle can be wavy as described herein, or alternatively it is possible that only some of the hollow fibers 100 in the fiber bundle might be wavy while others of the hollow fibers might be straight.

Although the fibers 100 have been described as having exterior or blood-facing surfaces that are smooth and hydrophilic, in some applications it may be possible to use fibers 100 whose exterior surfaces are rough. This may be especially true for applications and therapies that are of relatively short duration such as emergency situations. In such situations, the damage to blood cells may be tolerable, or an early formation of some number of thrombi may be tolerable.

Geometric Transitions in the Fiber Bundle

It may be desirable to achieve a flow pattern of blood flow along the fiber bundle that is as close to uniform as possible for as much of the fiber bundle length as possible. To achieve this, it may be desirable that the flow transition regions at the inlet and the outlet of the second flow compartment be as short as possible along the main direction of the housing 50. To achieve this, it may be desirable to use a flow distributor at the housing supply port 200A or at the housing discharge port 200B or both.

Figure 9:
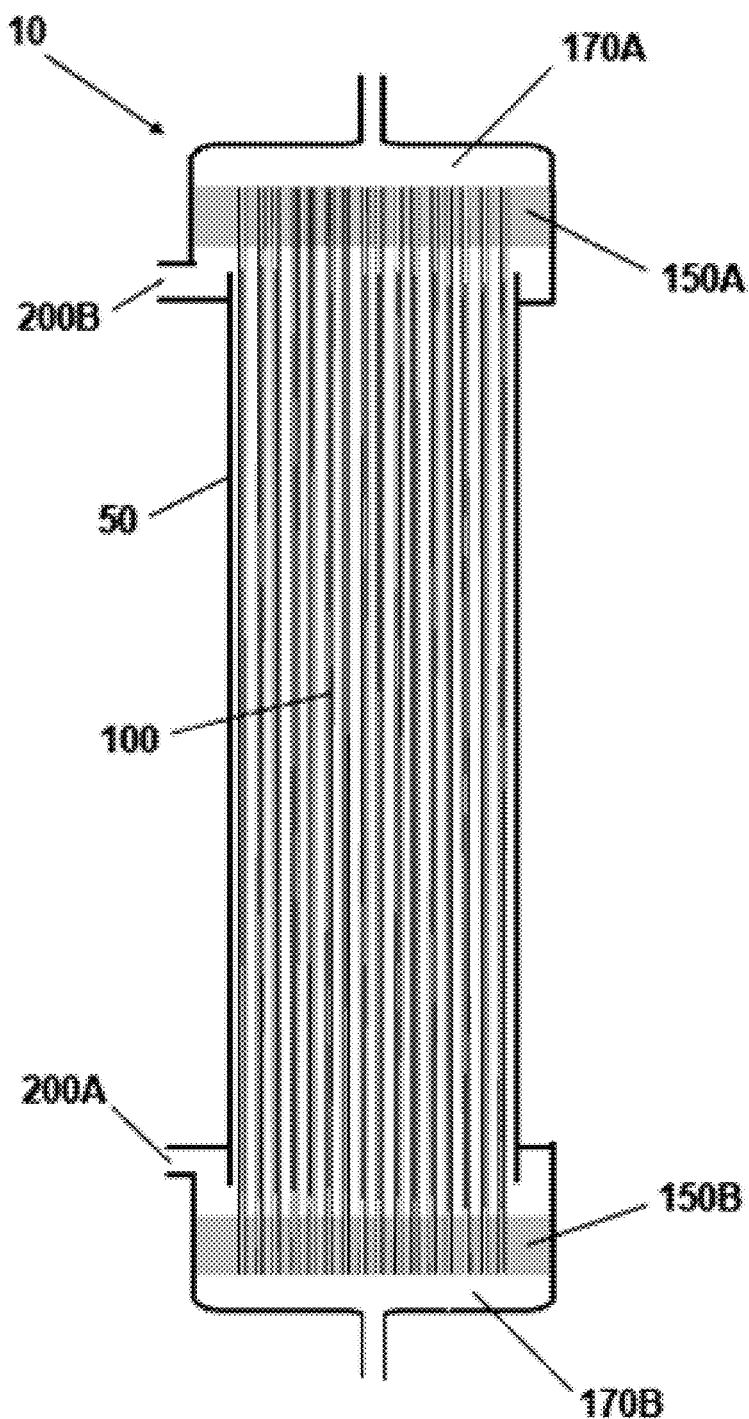
FIG. 9 illustrates an orbital distributor according to the principles of the present disclosure.

Such a distributor may be an orbital distributor. Such an orbital distributor may comprise a flowpath inside the housing 50 near an end of the housing 50, such that the flowpath has open dimensions substantially greater than the spacing between individual fibers 100, and such that the flowpath provides fluid to or collects fluid from a large portion of the housing perimeter, such as substantially 360 degrees around the perimeter of the housing 50. An orbital distributor may have its open direction facing away from the lengthwise middle of the cartridge 10, as illustrated in FIG. 9.

Fanning Out of Fibers

Figure 10A:
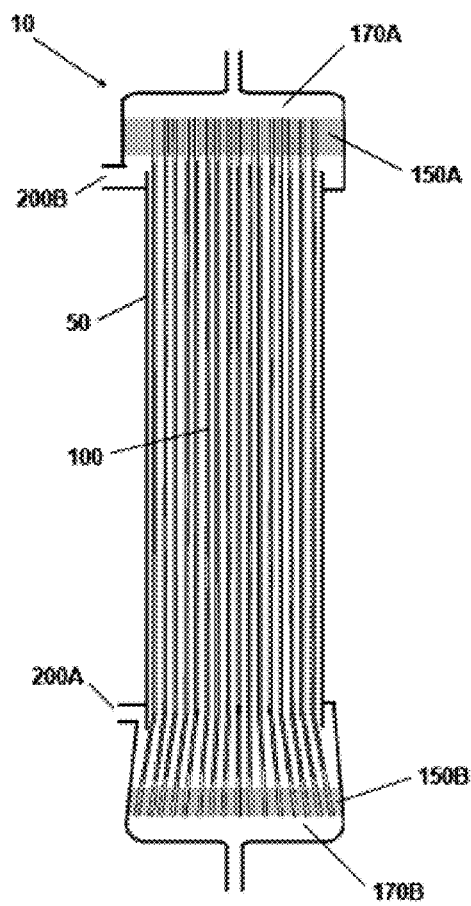
FIG. 10A illustrates a cartridge that is fanned at one end, and unfanned at the other end according to the principles of the present disclosure.
Figure 10B:
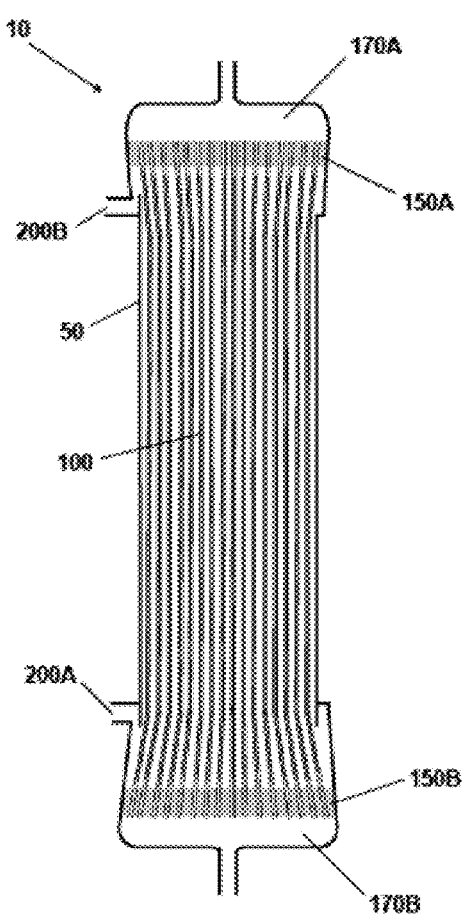
FIG. 10B shows a cartridge that is fanned at one end, and less fanned at other end according to the principles of the present disclosure.

In embodiments of the invention, there is provided a cartridge 10 in which the fibers 100 fan out at at least one end of the housing 50. This is illustrated in FIGS. 10A and 10B. Fanning may be described by a fanning angle, which may be the angle by which the outermost fanned fibers deviate from the direction of fibers that are not fanned or from the direction of that portion of the fibers that is not fanned. Fanning may be described by an area ratio, which may be the total cross-sectional area of the fiber bundle where it joins the barrier 150, compared to the total cross-sectional area of the fiber bundle in the main part of the housing 50. Fanning may be described by the length, in an approximately axial or lengthwise direction of the cartridge 10, of the region in which the fanning occurs, i.e., the region in which the fibers are not substantially parallel to each other. These various fanning parameters may be interrelated with each other. There may be provided fanning near the housing supply end, having a supply end fanning factor and a supply end fanning angle and a supply end fanning length. There may be provided fanning near the housing discharge end having a discharge end fanning factor and a discharge end fanning angle and a discharge end fanning length. Fanning can be provided by virtue of the fibers 100 being confined in certain places by a component of an orbital distributor. Alternatively, it is also possible to provide fanning simply because a portion of the housing interior shape changes from cylindrical to tapered. The presence of fanning means that in the "fan region," the effective porosity of the fiber bundle is larger than it is in the region in the main part of the housing 50 that has generally parallel fibers in the inter fiber space. For example, the ratio of fanned cross-sectional area may be in the range of 1.2 to 1.7, at least at the housing supply end. The fanning angle may be in the range of up to 10 degrees, at least at the housing supply end.

The complete passage of any fluid through the second flow compartment may generally be as described here. Flow at the entrance region arrives through a housing supply port 200A and then undergoes a transition, such that flow enters the fiber bundle in a generally lateral or radial direction flowing from the outside of the fiber bundle towards the center of the fiber bundle across the fibers 100. At the beginning of this transition, flow is at least approximately perpendicular to the bundle of fibers 100. It is also desired that at a more downstream point, after completion of the flow transition, the flow should be generally parallel to the fibers 100 and should have a velocity distribution that is fairly uniformly distributed over the cross-section of the fiber bundle. This latter situation can be idealized as flow parallel to the array of fibers 100. This transition involves at least a change of flow direction of approximately 90 degrees. Continuing, on, at the downstream end of the cartridge 10, after the fluid has flowed almost the full length of the housing 50, the flow transitions in the opposite sense, going from flow that is parallel to the fibers to flow that is in a lateral or radial direction and eventually exits from the housing 50 through a housing discharge port 200B. If an orbital distributor is present, the flow pattern is somewhat more complicated than just described.

Fanning of the fibers 100 can help to achieve this transition of flow. Transition of the flow, which involves flow perpendicular to the overall longitudinal direction of the fibers 100, can be accomplished more easily in a "fanned" fiber array than it could be accomplished in a fiber array lacking the "fan" feature, because of the effective porosity in the "fanned" region being larger than the porosity in the main region. This improved transition means that the transition of the flow can be accomplished in a shorter distance along the path of the flow, which leaves a larger portion of the cartridge 10 experiencing nearly-uniform flow that is believed to be desirable both for clot-free flow and for effective mass transfer. It allows a transition region to be designed to accomplish the transition relatively rapidly, while allowing the main region to be designed somewhat independently with the packing factor that is appropriate for achieving the desired flow and mass transfer properties, priming volume and other design considerations. The usefulness of the fanning feature can be understood from the results for flow past arrays of cylinders, and specifically the characterization of those results in terms of directional permeabilities. The more spaced-apart the fibers in the transition region are, the greater the permeability in the perpendicular direction is, and the shorter the transition region would need to be. In any event, when the fanned region has geometric properties different from those of the main part of the fiber bundle, it is desirable that the blood flow in the fanned region also be within the desired flow parameters, such as shear rate greater than 300 $\sec^{-1}$ and velocity greater than 0.25 cm/sec, just as in other parts of the fiber bundle.

It is believed that it is especially important for the flow transition region at the housing supply end to be effective at creating a highly uniform flow in the inter-fiber space downstream of the supply port 200A transition region and to accomplish the transition within a relatively short transition region. It is believed that at the discharge end, a shorter and less perfect transition region may be sufficient. The flow downstream of this discharge transition region is outside of the dialyzer itself, with the possible result that nonuniformities of flow outside of the dialyzer have less effect or no effect the mass exchange performance of the dialyzer or the flow patterns within the dialyzer. However, it is not wished to be limited to this explanation.

Different Design Features at Different Ends of the Cartridge

It is possible that the fanning of the fibers 100 may be different at the two ends of the cartridge 10. It is possible that at the housing supply end there may be fanning to a greater fanning angle, a greater area ratio, or a greater length of fanned region, compared to the housing discharge end. It is possible that near the housing discharge end either the fibers 100 do not fan out at all or they fan to a discharge end fanning factor that is smaller than the supply end fanning factor or they fan to a discharge end fanning angle that is smaller than the supply end fanning angle, or they fan with a length that is different from the length at the supply end. Fanning out may be reduced or even omitted at the housing discharge end.

In a specific embodiment of the invention, it is possible that there may be fanning of the fibers 100 only at one end of the cartridge 10, that is, the supply end, and that there might be no fanning at all at the housing discharge end. This may be based on the expectation that keeping the fiber packing tighter in the vicinity of the discharge end may help the fiber bundle itself to serve as a sort of an emboli trap for trapping possible emboli that may have formed in the inter-fiber space further upstream in the fiber bundle. This is further illustrated in FIG. 10B.

In the manufacture of a cartridge 10 that has fanned fibers, it is possible to use a stream of air, such as compressed air to separate the fibers. Where the fibers 100 need to be squeezed together, the ring of the orbital distributor may serve that function. Other methods and features are also possible.

Although it is believed that it is good to provide orbital distributors at both ends of the cartridge 10, it is possible that the orbital distributors at the two ends of the cartridge 10 do not have to be identical to each other. The dimensions of the orbital distributor or the flow transition region at one end of the cartridge 10 do not have to equal the dimensions of the orbital distributor or the flow transition region at the other end of the cartridge 10. It is also possible that there could be an orbital distributor at one end of the cartridge 10 and not at the other end of the cartridge 10. For example, an orbital distributor may be provided at the housing supply end but not at the housing discharge end.

In an embodiment of the invention, there may be provided, or there may additionally be provided, a specifically designed emboli trap within the housing 50, such as in the vicinity of the distributor, or external to the housing. An emboli trap can be a space for emboli to settle by gravity and be retained without being swept out of the trap by blood flow, based on the expectation that an embolus is more dense than blood and will tend to sink with respect to blood. An emboli trap can comprise a low point in a flow path. An emboli trap can comprise a baffle that the blood flow impacts.

In an embodiment of the invention, there may be provided an emboli trap in the flow system external to the cartridge 10, either upstream or downstream of the cartridge 10, or both.

The use of color-coding at different ends of a cartridge is not considered a design difference, if the dimensional and other physical features of the cartridge are the same at both ends.

Definitions of Design Parameters

Analytical mathematical solutions are possible for low-Reynolds-number flow involving a two-dimensional array of uniformly spaced identical cylinders. Such solutions are possible both for the situation of flow parallel to a cylinder array and for the situation of flow perpendicular to a cylinder array. [Happel, J., and H. Brenner. Low Reynolds Number Hydrodynamics, Prentice Hall, 1965]. These derivations are discussed in more detail elsewhere herein.

Another available body of literature is for the situation of flow through an isotropic porous medium. An important parameter in this type of analysis is the Darcy constant. The Darcy constant basically quantifies the permeability of the porous medium. The theory of flow through a porous medium is widely used in science, engineering and modeling.

For present purposes one way of summarizing and discussing the mathematical results for flow past arrays of cylinders is by describing those results in terms of parameters from the literature of flow through porous media, specifically the Darcy constant. The fiber bundle of an embodiment of the invention is not isotropic for purposes of flow, but it is possible to take the analytical mathematical results from the two different cases of flow past the array of cylinders, and cast those results in terms of two different Darcy constants, with each Darcy constant representing permeability for flow in a particular direction. There may be a parallel Darcy constant that describes flow parallel to the long direction of the cylinder array or the cartridge 10, and a different, perpendicular Darcy constant that describes flow perpendicular to the long direction of the cylinder array or the cartridge 10. For the present situation, both of these Darcy constants are mainly a function of the porosity fraction of the fiber bundle, the radius of the outside of the fiber, and the fiber-to-fiber spacing.

In general the results indicate that for parameter ranges of present interest, the Darcy constant (representing flow resistance) for flow perpendicular to the fiber bundle is somewhat larger than the Darcy constant (representing flow resistance) for flow along the direction of the fiber bundle. More specifically, if comparison is made in the form of a ratio of the Darcy constant for parallel flow divided by the Darcy constant for perpendicular flow, this ratio is between 1 and 2, when the parameters of fiber bundle porosity, fiber radius and fiber spacing are held constant and are in the range of parameters of interest for present purposes. Both Darcy constants increase with increasing porosity. In the limiting case of extremely tight packing, the perpendicular Darcy constant goes to zero while the parallel Darcy constant remains finite, and so the described ratio of the two Darcy constants goes to infinity. This is so because when the cylinders touch each other no flow is possible in the direction perpendicular to the cylinders, while in the direction parallel to the cylinders there remain paths for flow.

The mathematical analytical derivations for the two cases of flow past arrays of cylinders, which provide the velocity fields used to calculate the two Darcy constants, also provide the shear rate experienced by the flowing blood in embodiments of the invention.

One of the analytical mathematical solutions is for the case of flow parallel to an array of cylindrical fibers, assuming that the cylinders are arrayed in a hexagonal array. In this situation, the distance from a given point on the cylinder surface to the nearest neighboring cylinder varies, and the local flow velocity along the axis also varies among places within the small space between or among neighboring cylinders, and these variables vary together with each other in such a way that the shear rate is identical at all positions around the circumference of the cylinder. The formula for this shear rate for parallel flow is given elsewhere herein.

The other available analytical mathematical solution is for flow perpendicular to the same array of cylinders that represent cylindrical fibers. In this situation, the shear rate does vary with position on the circumference of the cylinders. The most relevant value to examine is the maximum value of shear rate, which occurs at the location of closest approach to another cylinder. This formula for this shear rate for perpendicular flow is given elsewhere herein. It can be understood that one parameter affecting this shear rate is the dimension, in the direction along the axis of the cylindrical fiber, of the channel that carries perpendicular flow, or basically the volumetric flow per unit of depth along the axial direction of the cartridge 10. For a given volumetric flowrate, lengthening that distance decreases the overall velocity and therefore decreases the shear rate.

Although these derivations are presented for cartridges in which the blood flow is lengthwise along the long direction of the cartridge, there are also other possible cartridge designs discussed herein, for which these analyses can also be used.

Shear Rate and Velocity and Flow Transition

As discussed, for flow of blood, shear rate is a parameter that has an influence on thrombus formation and the impact that the processing has upon the blood. In embodiments of the invention, the operating parameters may be chosen such that everywhere the shear rate for blood, is the range of from about 300 $sec^{-1}$ to about 2700 $sec^{-1}$. Furthermore, the choices may be made so that the range is within a smaller subset of that range.

In discussing shear rate, it can be explained that for complicated geometries, the local shear stress may vary spatially. For flow parallel to a geometry such as an array of parallel fibers, there are places within a flow channel at which the shear stress is zero. Examples of such places are planes or lines of symmetry, which may occur between solid surfaces such as midway between solid surfaces. Accordingly, it may be understood that calculation of a shear rate may make use of the shear stress at a fiber surface. Using the shear stress at a fiber surface excludes the zero value of shear stress that may occur in the midst of flow regions at locations of symmetry. Furthermore, even making use of shear stress at a fiber surface, there are geometries, such as flow perpendicular to an array of fibers, in which the local shear stress may vary as a function of position around the perimeter of the fiber. In fact, there may be points on the perimeter of the fiber at which the local shear stress is zero, but there are other points at which the local shear stress is a local maximum. It is the local maximum shear stress among places on the fiber perimeter that is of interest in calculating shear rate.

The design and operational parameters also may be chosen so that the superficial velocity or local average may be greater than 0.25 cm/sec. The superficial or local average velocity may be averaged over a space that is at least as large as a cell or space between fibers or a group of fibers that are near neighbors of each other. This is in view of the fact that there can be extremely localized very small stagnation points that are of the size scale of a fraction of the perimeter of a fiber, but such extremely localized flow features are not of interest for present purposes. A local average velocity or superficial velocity averaged over the described cell or space is used so as to be a good representation of the flow situation.

In regard to shear rate of blood in relation to formation of thrombi or other damaging effects on blood, certain numerical values of shear rate such as 300 $sec^{-1}$ and 2700 $sec^{-1}$ are used for discussion herein to represent an appropriate range of operation. However, it may be understood that those limits, especially the upper limit, can be a function of certain variables. One such variable is the use of heparin. If the patient is administered a greater dose of heparin, the upper limit shear rate can be larger than that value. Similarly, if the membrane contains heparin such as in the form of a coating, that would raise the allowable upper limit of shear rate similarly as if the patient is given a heparin dose. Also, if the duration of treatment is relatively short, that would allow the use of a shear rate higher than the given value of shear rate. It may be understood that the shear rate for flow along the long direction parallel to the fibers is determined by the overall volumetric flowrate and the geometric parameters of the spacing between the fibers. It may further be understood that the shear rate for flow perpendicular to the fiber bundle, such as occurs at the housing entrance and the housing exit, is determined by the overall volumetric flowrate, and the geometric parameters of the spacing between the fibers, and furthermore is also affected by one additional variable, namely the lengthwise dimension of the transition region. So, this additional variable can be used to adjust the relative values of the two shear rates. It similarly can be used to adjust the relative values of certain fluid velocities. Thus, the lengthwise dimension of the transition region is a variable that affects the shear rate in perpendicular flow in the transition region but does not affect the shear rate in the parallel flow region.

Similarly, it may be understood that the average velocity for flow along the long direction parallel to the fibers 100 is determined by the overall volumetric flowrate and the geometric parameters of the spacing between the fibers 100. It may further be understood that the average velocity for flow perpendicular to the fiber bundle is determined by the overall volumetric flowrate, the geometric parameters of the spacing between the fibers 100, and the lengthwise dimension of the transition region. Thus, the lengthwise dimension of the transition region is a variable that affects the average velocity in perpendicular flow in the transition region but does not affect the average velocity in the parallel flow region. The geometry is illustrated in FIG. 11.

The circumferential area for flow entering the fiber bundle from the orbital distributor is 2*pi*r*H, where r is the radius of the fiber bundle, and H is the dimension illustrated as $l_a$ or $l_b$ in FIG. 11. The cross-sectional area for axial flow, is proportional to pi*r². The ratio of these two areas is proportional to the dimensionless parameter 2*H/r. This parameter can be used to describe how abrupt or smooth a transition is provided for flow to transition between a predominantly radial direction and a predominantly longitudinal direction. The cartridge 10 may be designed such that for the transition region near the housing supply port, 2*H/r has a value between 0.5 and 2.0. The cartridge may be designed such that the supply and discharge distributors have respective axial lengths L, and the housing midsection interior region has a radius r, and the supply distributor has a value of 2*L/r that is greater than 1.0, and the discharge distributor has a value of 2*L/r that is less than 1.0.

Figure 11A:
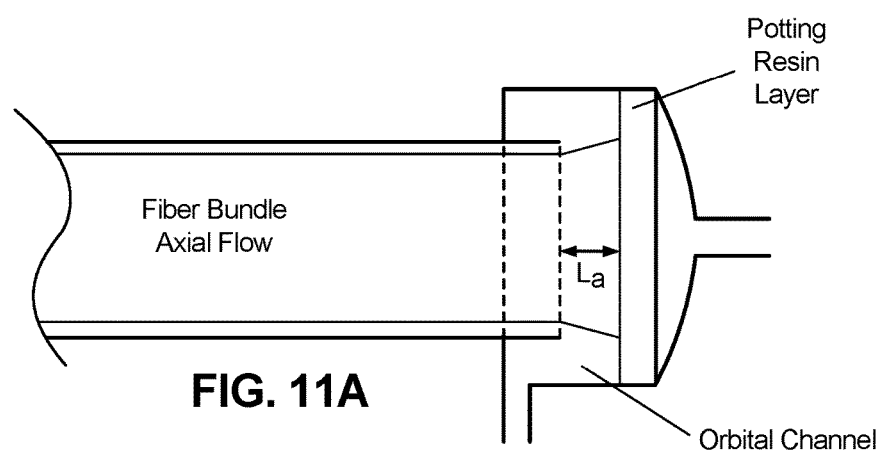
FIGS. 11A and 11B show end transition regions and measurement of length dimensions thereof according to the principles of the present disclosure.
Figure 11B:
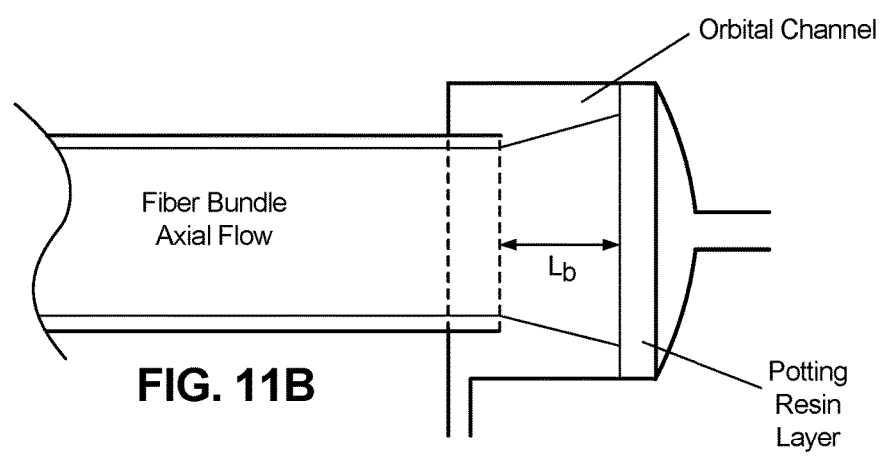

In the situation of an end region that includes an orbital distributor, within a short distance, the flow transitions from flow that is perpendicular to fibers 100 to flow that is parallel to fibers 100. This means that the flow transitions from a shear rate and an average velocity that are characteristic of perpendicular flow, to a shear rate and an average velocity that are characteristic of parallel flow, within a short distance. It is believed that for blood in particular, it is undesirable for the shear rate to change quickly, a criterion that is referred to as shear rate gradient. It is believed, although it is not wished to be limited to this explanation, that it is beneficial if the shear rate in the perpendicular-flow region is not drastically different from the shear rate in the parallel-flow region. Based on these insights, in an embodiment of the invention, the design parameters may be chosen so that the velocity for perpendicular flow entering the fiber bundle in the transition region is approximately equal to the velocity for parallel flow in the main region of the fiber bundle, or is equal to between 50% and 200% of the velocity for parallel flow in the main region of the fiber bundle. One such design parameter that may be appropriately chosen is the lengthwise dimension of the supply-distribution region. This dimension is illustrated in FIG. 11A and FIG. 11B as $l_a$ and $l_b$ respectively, for two different dimensions of orbital distributor or flow transition region.

Another parameter that affects the flow transition for flow entering and for flow exiting the fiber bundle is the "fanning out" of the fiber bundle. The "fanning out" area ratio can determine the Darcy constants (both the parallel Darcy constant and the perpendicular Darcy constant) for the fan region. In view of the fact that the fan region has some variation in geometry along its length, it may be appropriate to use average values of the two Darcy constants for the fan region. Both Darcy constants for the fan region can be expected to be different from the Darcy constants for the main region of the fiber bundle, because in general the porosity and dimensions in the fanned region are different from the porosity and dimensions in the main part of the fiber bundle. The shear rate for perpendicular flow in the fanned region may be calculated using the formula for shear rate at the narrow inter-fiber places in perpendicular flow, using the average porosity that is characteristic of the fanned region. The shear rate for parallel flow in the main body of the housing may be calculated using the formula for shear rate in the inter-fiber places using the porosity that is characteristic of the main part of the housing. In embodiments of the invention, the design parameters may be chosen so that the shear rate for perpendicular flow entering the fiber bundle in the transition region is between 50% and 200% of the shear rate for parallel flow in the main region of the fiber bundle.

Air Bleed Feature

In general for hemodialysis, if there were any air bubbles contained in blood that re-enters the patient's body, the presence of those air bubbles would be a serious medical problem. Also, exposure of blood to air can encourage the formation of clots. Clots are also a problem if they enter the patient's body, and also if clots form inside fiber of conventional hemofiltration, they block flow through those fibers. In conventional hemodialysis practice, typically the cartridge is primed with saline solution before blood is introduced into the cartridge, so that air can be purged from the fiber interiors by saline solution, but sometimes not every fiber interior is successfully purged by saline. Because embodiments of the invention contain blood flowing in the inter-fiber space, it may be particularly important to provide for elimination of air in or near the inter-fiber space.

Figure 12A:
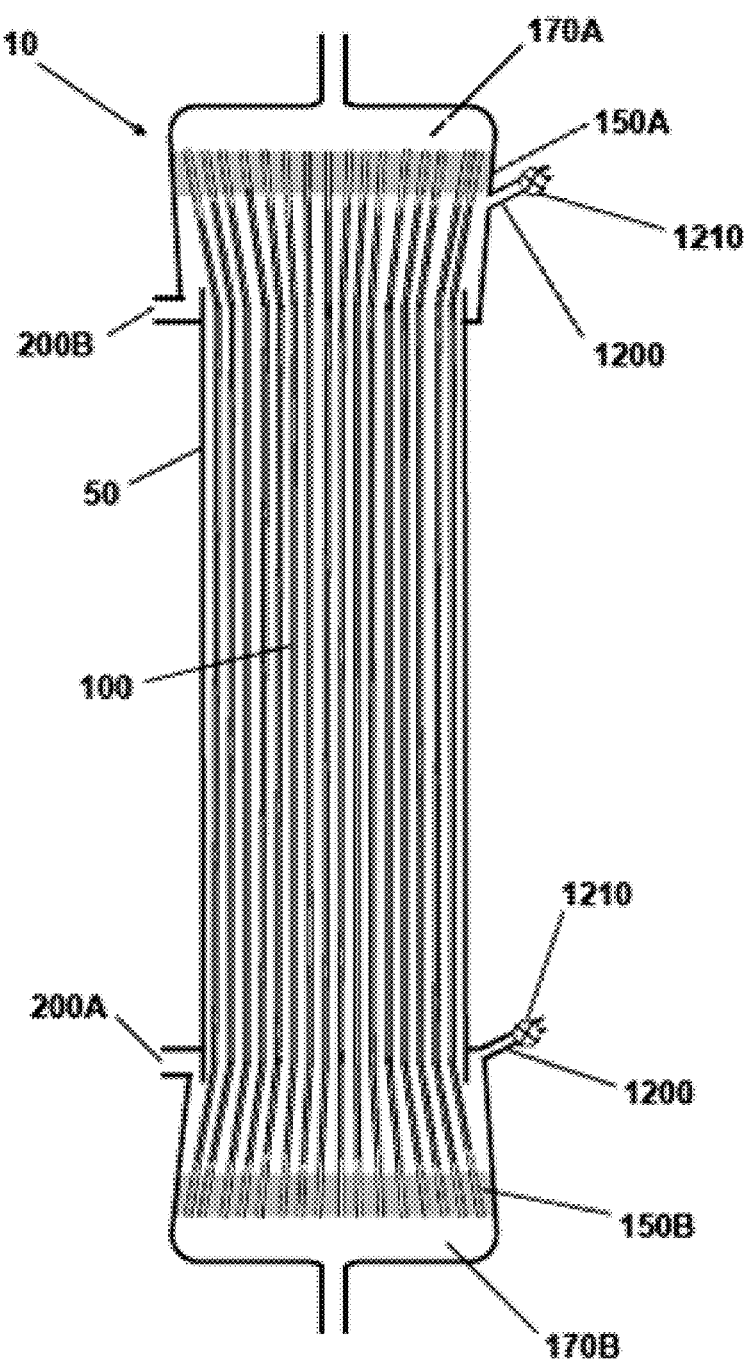
FIG. 12A shows a cartridge with an air bleed according to the principles of the present disclosure.

Referring now to FIG. 12A, in an embodiment of the invention, there may be provided an air bleed 1200 connecting to the inter fiber space at a desired location, or, more generally, connected to the second fluid flow compartment at a desired location. It is possible that when liquid such as blood or saline solution is introduced into an initially air-filled housing that contains an orbital distributor, there may be pockets of air that do not easily escape. This may be true for almost any orientation of the cartridge 10 with respect to gravity. Accordingly, there may be provided, at a place where air is likely to collect, such as at a corner or edge of an orbital distributor, an air bleed such as a vent connection with a valve 1210. This is an air bleed connected to the housing interior space, which is the second fluid flow compartment. The air bleed 1200 may be connected to a place in the second fluid compartment that is a local high point when the cartridge 10 is oriented in an intended orientation for use. Either one or two air bleeds 1200 may be provided as desired at either or both ends of the cartridge 10. The location or design of an individual air bleed 1200 may be unique to the particular location on the cartridge 10.

For example, a cartridge 10 may have a cartridge end that is intended to be downwardly oriented during use. At the intended downwardly oriented end of the cartridge 10, the location of the air bleed may be at or near a local high point where a pocket or bubble of air may be likely to collect. For example, if the cartridge 10 contains an orbital distributor a at the intended lower end of the cartridge 10, an air bleed may be provided connecting to the cartridge 10 at a location such as a local high point of the orbital distributor.

A cartridge 10 may have an end that is intended to be upwardly oriented during use. At the intended upwardly oriented end of the cartridge 10, the location of that air bleed 1200 may be at or near a local high point where a pocket of air may be likely to collect. For example, an air bleed 1200 may be provided at a location that is close to the potted barrier 150 at that upwardly oriented end of the cartridge 10.

If there are two air bleeds, the design of the air bleeds may be non-symmetric with respect to the midplane of the cartridge 10.

If the cartridge 10 does not contain an orbital distributor at the downwardly located end, it may be sufficient for only one air bleed 1200 to be provided, located at the intended upper end of the cartridge 10 such as close to the potted barrier 150. If the cartridge 10 contains only one orbital distributor, an air bleed 1200 may be provided at whatever end of the cartridge 10 is intended to be the more upwardly located end during intended use of the cartridge 10.

An air bleed or either or both of the air bleeds may point upward, in the direction away from the cartridge 10, when the cartridge 10 is oriented in an intended orientation for use. An air bleed 1200 may be located 180 degrees away from the corresponding port at that orbital distributor or from the corresponding port at that place on the cartridge 10.

It is further possible that there may be provided certain internal features that slope upward toward any air bleed 1200 when the cartridge 10 is oriented in its intended orientation for use. For example certain internal surfaces may be oriented so that even if the main longitudinal direction of the cartridge 10 is oriented vertically, the local surfaces near the air bleed 1200 may slope upwardly toward the air bleed connection. Any air bleed may be provided with an appropriate valve as illustrated.

An air bleed may also be provided at any other desired location that is in fluid communication with the inter fiber space or generally in fluid communication with the second fluid compartment.

There also may be provided anywhere desired in the tubing or other components of the blood handling system, an air trap or an emboli trap or both, either upstream or downstream of the cartridge or both in the blood flow system, as desired.

Referring now to FIGS. 12B and 12C, there are shown embodiments of the invention in which a cartridge comprises a density-based emboli trap. The basis for operation of a density-based trap is the fact that a clot has a density that is slightly greater density than the density of blood. The density of clotted blood (Acousto-mechanical and thermal properties of clotted blood, Volodymyr M Nahirnyak, Suk Wang Yoon and Christy K Holland, J Acoust Soc Am. 2006 June; 119(6):3766-3772) is about 1080 kg/m$^3$, whereas the density of ordinary human blood is about 1060 kg/m$^3$. This represents a density difference of about 2%. It may be desirable to provide a flow geometry that tends to retain higher-density particles while at the same time not creating a local stagnation region in the blood flow, because of the undesirability of stagnation regions as discussed herein.

Such an emboli trap may comprise a local low point in the flowpath of the blood. Such a local low point may be located between a descending portion of the blood flowpath and an ascending portion of the blood flowpath. There may be provided a flowpath such that downstream of the local low point, the flow proceeds upward at an angle 45 degrees or more with respect to horizontal. It is possible, for example, that the flow can go through a U-shaped flowpath that is in a vertical plane or at least has a vertical component, as illustrated in FIG. 12A. As illustrated in Figure B, an emboli trap can be an impact baffle such that there is a space for emboli to flow at least partially downward and settle out by gravity and be retained after they impact the baffle.

A density-based emboli trap as described could be internal to the housing 50 or could be external to the housing 50 while still being part of the cartridge 10. In embodiments of the invention, there also or alternatively may be provided a filtration-based emboli trap. In such an emboli trap, the blood may be caused to flow through a sieve-like structure whose openings are such as to retain emboli while allowing blood to pass through. In an embodiment of the invention, there may be provided an Emboli trap in the flow system external to the cartridge 10, either upstream or downstream of the cartridge 10, or both.

Surface Treatment of Inside of Housing or in Places on Fibers

In an embodiment of the invention, the housing 50 may be made of polymers such as polycarbonate or polypropylene. The same is true of orbital distributors, which may be joined to or integral with parts of the housing 50. First of all, the blood-facing surfaces of those components may be smooth, such as having a root-mean-square roughness of less than 100 nanometers. It is also possible that those materials could be manufactured so that they contain no plasticizer or only minimal amounts of plasticizer, so as to eliminate or minimize the possibility of objectionable materials that might diffuse into the blood or might compromise the hemocompatibility of the surface.

In an embodiment of the invention, the housing 50 may have an inside surface that has been treated with a coating or a surface treatment that increases its hemocompatibility. This may refer to the housing interior overall, or to only portions of the housing interior such as parts of a distributor, or both. It is possible that there may be more coated locations or more coating at some places in the housing interior (such as preferentially near the housing supply end) than other places. Heparin is one example of a possible housing surface coating substance that improves hemocompatibility. Heparin is an anionic polyelectrolyte substance. Fluoropolymers are another example. Still other examples are polyvinylpyrrolidone, polyethylene glycol, and vitamin E.

Figure 13:
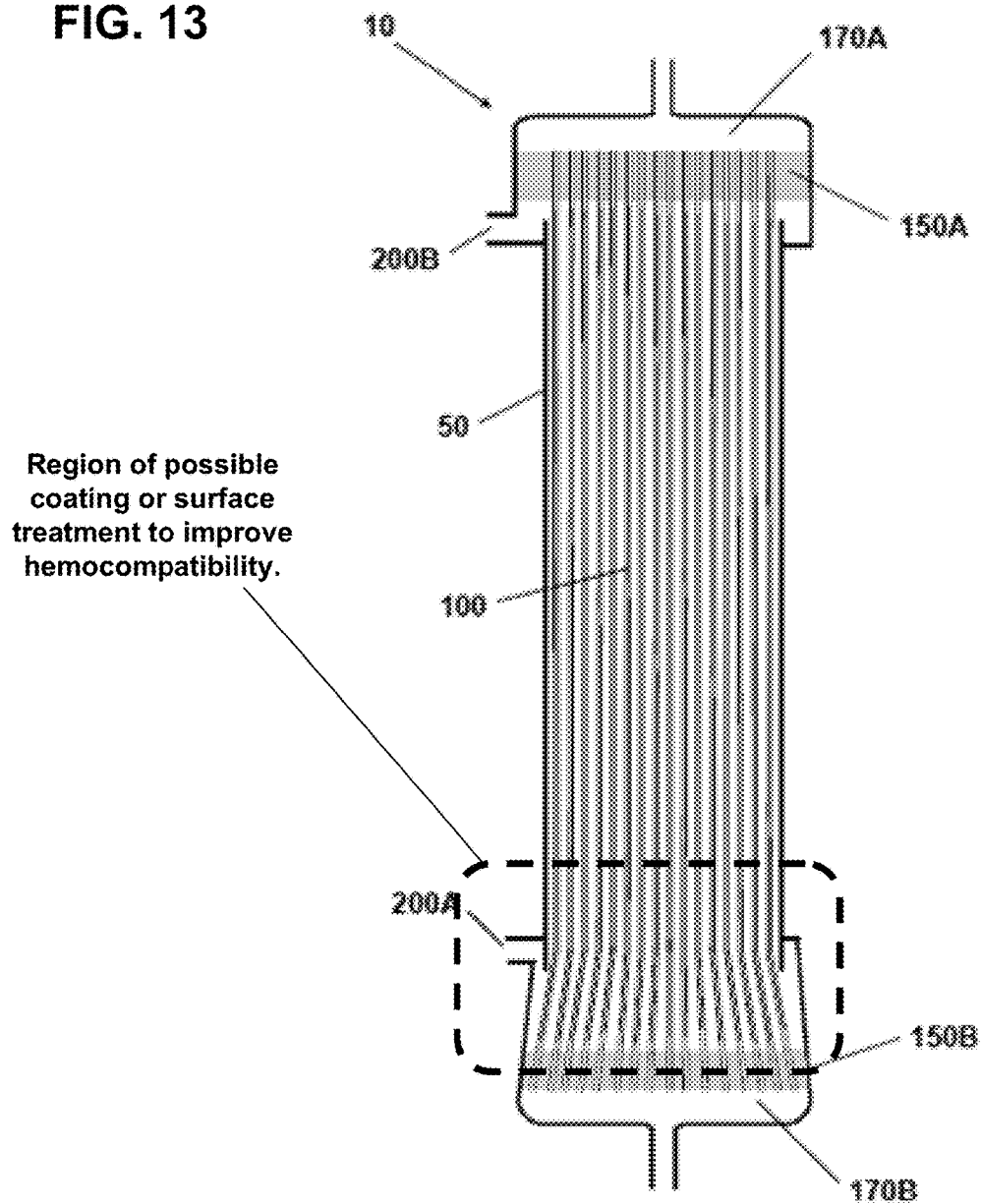
FIG. 13 shows locations inside the housing or on the fibers that might be given a coating or surface treatment according to the principles of the present disclosure.
Figure 14:
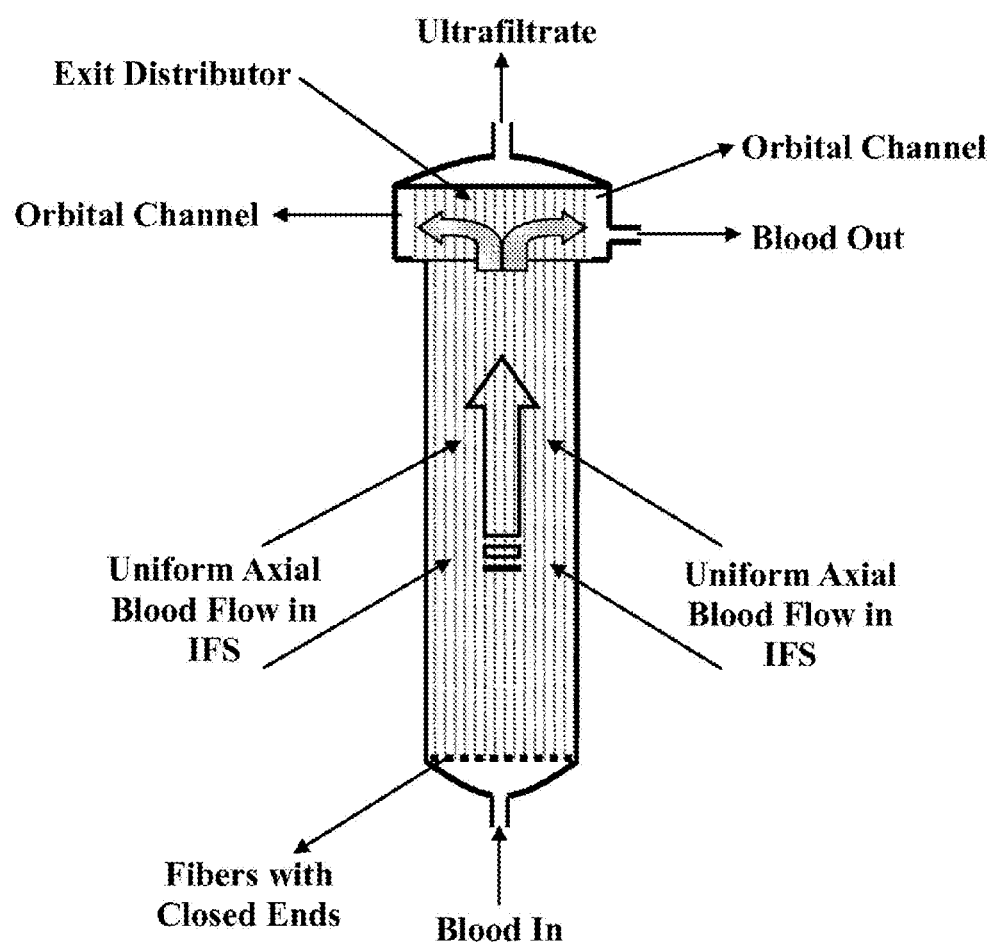
FIG. 14 shows a cross-sections of an ultrafilter according to the principles of the present disclosure.

Referring now to FIG. 13, in an embodiment of the invention, there may be provided a surface treatment or coating on the outside surface of the hollow fibers 100. Specifically, there may be a surface treatment or coating on only a portion of the outsides of the hollow fibers 100, which may be the portions of the hollow fibers 100 that are near the ends of the housing 50. This is also illustrated in FIG. 13. The regions near the ends of the housing 50 would be where flow transition (change of direction or change of area) takes place, bringing with it the possibility of regions of low blood velocity or stagnation regions. Again, possible coating substance include heparin, fluoropolymers, polyvinylpyrrolidone, polyethylene glycol, and vitamin E.

It is further possible, with regard to either the housing 50 or the fibers 100, that a surface treatment could precede the application of a heparin or other coating. For example, as is known in the art, a heparin coating could be preceded by a pre-coating of polyethyleneimine (PEI), which is a cationic polymer to which heparin binds.

Connector Fittings

In an embodiment of the invention, the design of fluid connection fittings on respective places on the cartridge 10 may be chosen to be consistent with fittings that are in current use for the flow of blood and for the flow of dialysate. For example, in tubing and connections for conventional hemodialysis, the blood connection is a Luer-Lock connection. In an embodiment of the invention, the connection that goes to the sides of the housing 50, which are intended to carry blood, may be Luer-Lock connections. In tubing and connections for conventional hemodialysis, the dialysate connection is a Hansen connector. In an embodiment of the invention, the connection that goes to the headers at the ends of the housing 50, which are intended to carry dialysate, may similarly be Hansen connections.

Design for Low Priming Volume of Blood

Also in regard to embodiments of the invention that have blood flow outside the fibers, there are considerations about the amount of volume of that region that has to be filled by the patient's blood. In situations involving extracorporeal blood flow, blood fills the space between the housing interior and the exterior surfaces of the fibers 100. This blood comes from the patient. It is commonly considered that for an adult patient, the priming volume should be no greater than 150 milliliters. In more detail, the allowable priming volume may be a function of the body mass of the patient. The priming volume includes the described empty volume inside the cartridge 10, and also the volume of relevant tubes and other features of the blood flow circuit. The amount of blood used for the purpose of "priming," that is, filling the blood-containing region of the cartridge 10 with blood, comes from the patient, and some fraction of that blood might be lost, unavailable to be returned to the patient's body. In embodiments of the invention, the cartridge 10 and other apparatus may be designed so as to keep the priming volume to a desirably small value.

It can be noted that the same design trends that favor keeping the superficial velocity above a minimum value or above a value such as 1 cm/sec, and keeping the shear rate at or above a value such as 1000 $sec^{-1}$, also favor keeping the priming volume relatively small. Reducing the porosity also reduces the priming volume. Keeping the porosity of the fiber bundle as small as possible, such as less than 80%, is helpful.

Recapture of Priming Blood

It may be desirable that out of a priming volume of 150 milliliters or so of blood, the amount that is unrecovered and is lost to the patient be no more than 5 to 10 milliliters of blood per dialysis treatment. First of all, it may be noted that when blood or some other liquid is being introduced into an Inter Fiber Space that is dry, the Inter-Fiber Space may act as a wick to help liquid (either saline or blood) fill that space. The Inter Fiber Space may be filled directly with blood, or the Inter Fiber Space may first be filled with saline to displace air and then the saline may be displaced by blood.

Figure 15:
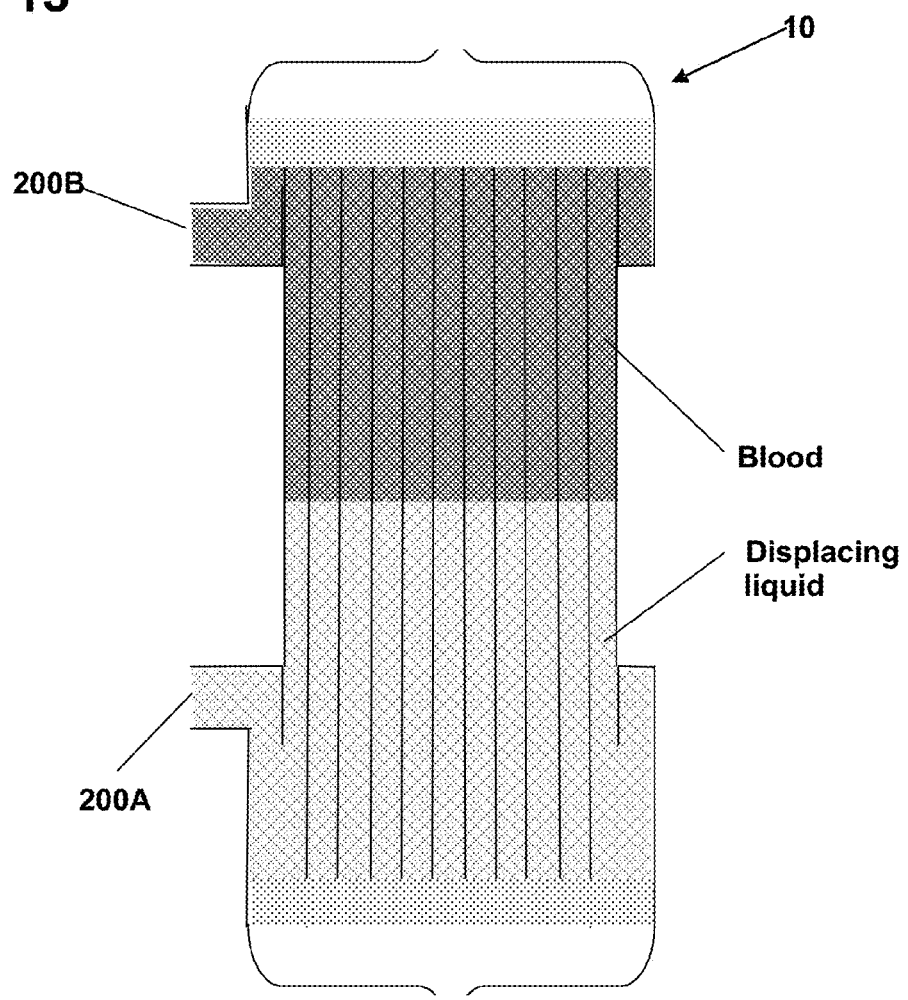
FIG. 15 shows the recapture of blood that was used to fill the priming volume of the cartridge according to the principles of the present disclosure.

Referring now to FIG. 15, one way to help minimize the amount of non-recovered priming blood is that, after dialysis, the blood-containing compartment may be slowly filled with a displacement liquid so as to displace blood while maintaining as sharp a boundary as possible between the blood and the displacement liquid. Displacing blood from the fiber bundle might be done by displacement downward or displacement upward, depending on circumstances.

Displacement and recovery of blood from the filter or dialyzer, in this case the inter fiber space of the filter or dialyzer, can be considered to be a problem of flow through a porous medium. In order to displace blood from the dialyzer while maintaining a fairly sharp interface between the blood and the displacing liquid, several considerations are believed to be helpful. These considerations are discussed in "An Experimental Study of Miscible Displacements in Porous Media with Variation of Fluid Density and Viscosity" by Chao-Ying Jiao and Heinz Hotzl, Transport in Porous Media 54: 125-144, 2004. First of all, in general, it is believed that it is helpful if the displacing of blood is done slowly.

One consideration is that the displacement should be done in a gravitationally stable manner, such that the more-dense liquid is located vertically below the less-dense liquid. This avoids the Rayleigh-Benard instability. This means that if the liquid being introduced to displace blood is more dense than blood, it may be introduced from below the blood. This is believed to be the more likely case. Alternatively, if the liquid being introduced to displace blood is less dense than blood, it may be introduced from above the blood. This is believed to be the less likely case.

Another consideration is that it is believed to be helpful if the displacing liquid has a viscosity different from the viscosity of the displaced liquid, which is blood, and specifically that the displacing liquid be more viscous than the blood that is being displaced. This avoids the Saffman-Taylor instability.

One possible displacing liquid, which is both more dense and more viscous than blood, is a solution of glycerin and water. In the limit of pure glycerin, the density of glycerin is greater than the density of water or blood by several tens of percent, and pure glycerin has a viscosity that is hundreds of times the viscosity of water. For a solution of water and glycerin, these properties can be adjusted over a wide range by the proportions of water and glycerin in a water-glycerin solution. Water and glycerin are soluble or miscible with each other in all proportions. Furthermore, glycerin is physiologically benign. Also, performing the displacing as slowly as possible is believed to be helpful for maintaining a sharp boundary between the displacing fluid and the blood, and minimizing the amount of blood that must be discarded.

Overall System, Including Both Cartridge and Fluid Handling Components

There are also embodiments of the invention that comprise a cartridge 10 as described herein, in combination with a system that provides flow of blood and flow of dialysate. First of all, as already discussed, the system may cause blood to flow in the inter-fiber space, and may cause dialysate or filtrate to flow inside the lumens of the fibers 100. In more detail, blood may be supplied to housing supply port 200A and may be withdrawn from housing discharge port 200B. Dialysate may be supplied to first end plenum 170A and may be withdrawn from second end plenum 170B. First end plenum 170A and second end plenum 170B and housing supply port 200A and housing discharge port 200B may be arranged so that blood and dialysate flow through the cartridge 10 in generally opposite directions, creating a counterflow arrangement. For example, the dialysate inlet and the blood outlet may be near one end of the cartridge 10. The dialysate outlet and the blood inlet may be near the opposite end of the cartridge 10.

Figure 16:
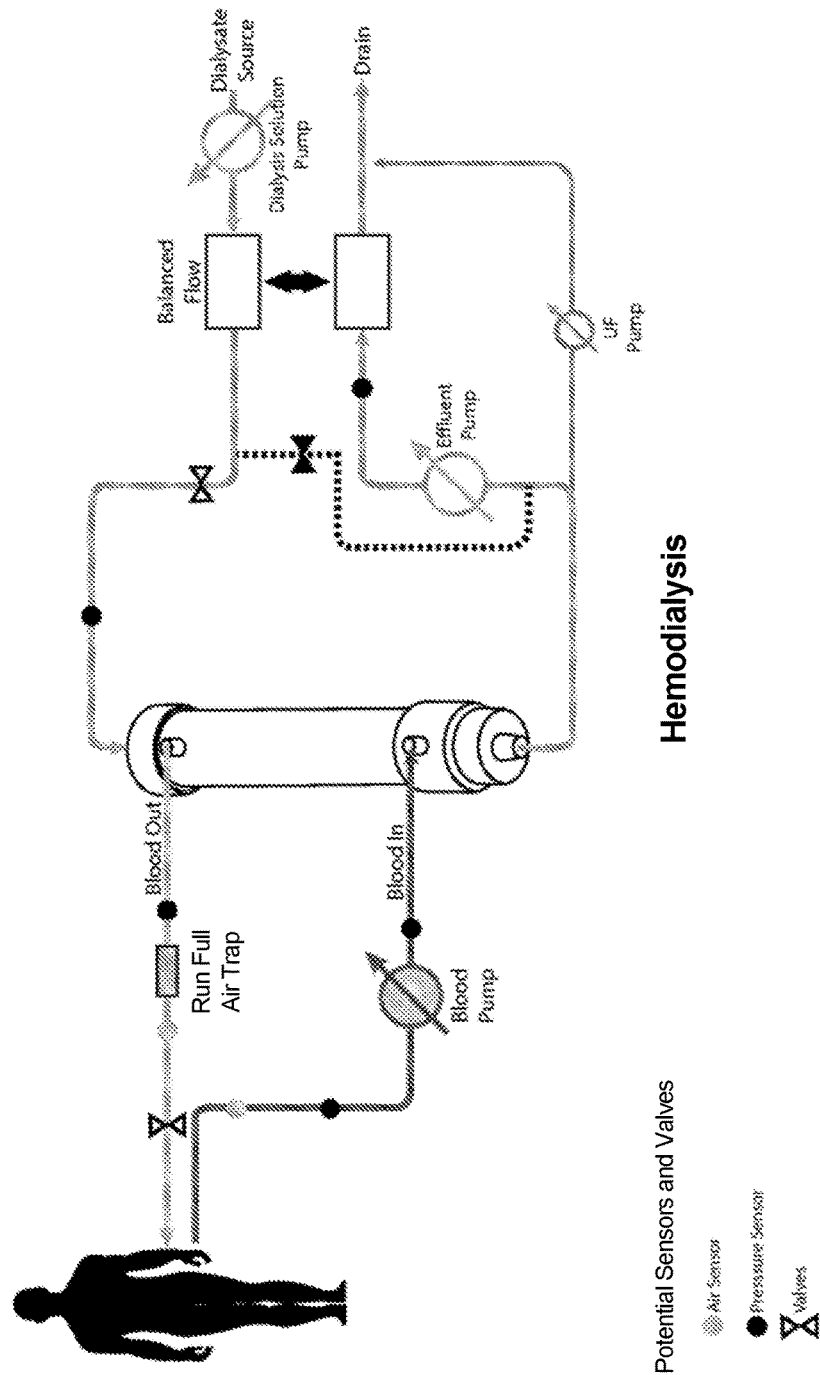
FIG. 16 shows a system for hemodialysis according to the principles of the present disclosure.

FIG. 16 illustrates a system for performing hemodialysis according to an embodiment of the invention. There is shown a blood supply to the housing 50 and a blood discharge from the housing 50. There is also shown a dialysate supply to the cartridge header and a dialysate discharge from the other cartridge header.

Figure 17:
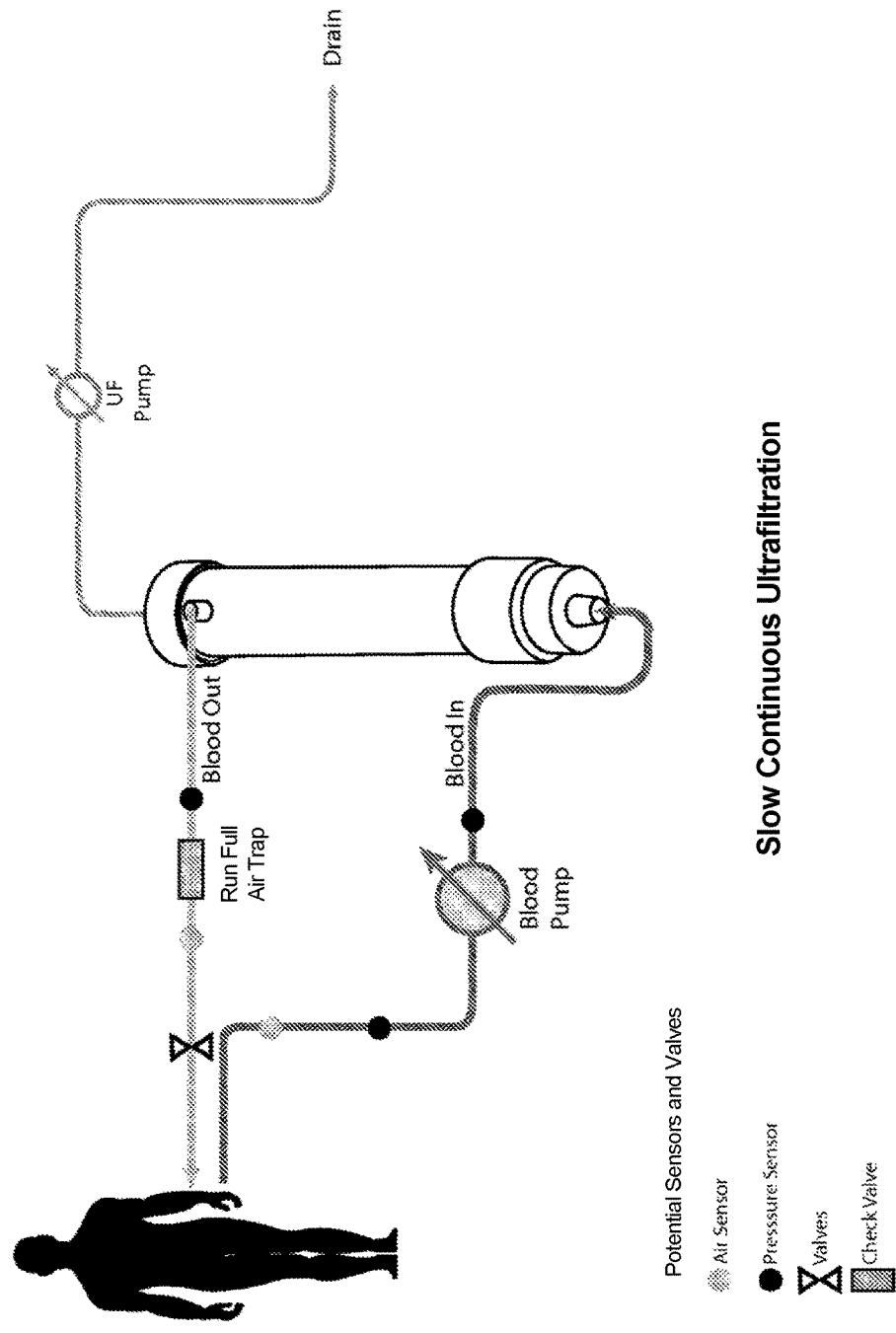
FIG. 17 shows a system for ultrafiltration according to the principles of the present disclosure.

FIG. 17 illustrates a system for performing ultrafiltration according to an embodiment of the invention. In ultrafiltration, there is convective mass transfer driven by pressure difference across the hollow membrane. On the upstream side of the hollow fiber membrane, there may be provided both a supply port and a discharge port, as illustrated, in the housing 50 of the cartridge 10. On the downstream side of the hollow fiber membrane, there only needs to be one active port. As illustrated, the downstream side of the hollow fiber membrane is the lumens of the hollow fibers 100. In Figures such as FIG. 9, it was illustrated that both ends of the hollow fibers 100 are potted in first barrier 150A and second barrier 150B at respective ends of the cartridge 10. However, only one of the headers or plenums actually needs to be used to collect filtrate. In FIG. 17, it is illustrated that the hollow fibers only need to be potted in a barrier 150 at one end. The hollow fibers are shown as being dead-ended, i.e., individually closed, at their other end. As illustrated, the dead-ended hollow fibers have flow of blood coming toward them. The fiber bundle may be contained inside housing 50 snugly enough so that it maintains its position relative to the housing 50 despite the flow of blood toward the otherwise unsupported ends of the hollow fibers.

Use of Wavy Fibers in Conjunction with Blood Flowing Outside the Fibers

It is possible that the fibers may be wavy. In this regard, it is possible that all of the fibers may be wavy, but more generally, at least a majority of the fibers may be wavy.

Alternatively, it is possible that the fibers may be straight. In this regard, it is possible that all of the fibers may be straight, but more generally, at least a majority of the fibers may be straight.

In an embodiment of the invention, as discussed elsewhere herein, there may be provided a system in which the blood flows past the exterior surfaces of the fibers 100, and the packing fraction of the fibers 100 in the fiber bundle may be chosen to be in the range of a packing fraction 40% (porosity 60%) to a packing fraction of 70% (porosity of 30%), and the external surfaces of the fibers may be smooth and hydrophilic.

In general, as discussed, it is believed that wavy fibers are helpful for preventing clumping of fibers, as compared to straight fibers under similar conditions. In general, it is also believed that a liquid flowing lengthwise past wavy fibers will experience more local mixing and stirring than the same liquid flowing past straight fibers. It can be expected that this mixing would interrupt fluid boundary layers and diffusion boundary layers. This mixing should improve mass transfer or clearance. Further, it is possible that the irregular nature of flow past the outsides of wavy fibers may increase the shear rate experienced by the blood, which may prevent the blood from thickening, due to the non-Newtonian behavior of blood. This is a helpful result.

In an embodiment of the invention, blood flow outside of the fibers can be provided in combination with wavy fibers. Blood is more viscous than dialysate by a factor of several times. The exact ratio of the viscosities is complicated by the fact that blood has different viscosities at different shear rates due to its non-Newtonian nature, and also is complicated by compositional variation of blood and other factors. Nevertheless, in all situations, there is some greater viscosity for blood as compared to dialysate, and this increased viscosity tends to make fluid boundary layers become thicker or grow more rapidly than would be the case for a less-viscous liquid such as dialysate flowing in the same dialyzer compartment and geometry. One function of a dialyzer is to provide the opportunity for diffusion, which partially is accomplished by continually refreshing a supply of liquid near the diffusion surface or boundary. A thicker fluid boundary layer, or a more viscous fluid, would generally work against this purpose. Mixing or stirring of the liquid would help.

As discussed herein, in the situation where the liquid that is flowing past the exteriors of wavy fibers is blood (a liquid that can form clots), the frequent local changes of blood flow direction caused by the frequent local geometry changes of the exteriors of the wavy fibers may help to prevent clotting, as discussed herein. Additionally, the waviness of the fibers causes a mixing and stirs up the blood as the blood passes the undulations of the fibers, so that blood that has not recently been exposed to mass transfer is exposed afresh to the surface of the fiber. This mixing would disrupt the formation of mass transfer boundary layers, resulting in more thorough mass exchange.

However, it is noted that there are also other embodiments of the invention that comprise straight fibers.

In regard to avoiding the formation of clots, another criterion relevant to blood is that the superficial velocity for blood be greater than 0.25 cm/sec, while being less than 2 cm/sec. These values may be slightly influenced by the amount of anti-coagulant used, and by the condition of the blood-facing surface of the fiber 100 (such as smooth or not, and coated with a hemocompatible coating or not). The superficial velocity is the volumetric flowrate of blood divided by the total cross-sectional area of the empty space of the Inter Fiber Space, which is the total amount of empty space area outside the fibers 100 but inside the housing 50.

Pressure Profiles in the Blood Flowpath and the Dialysate Flowpath

Figure 18:
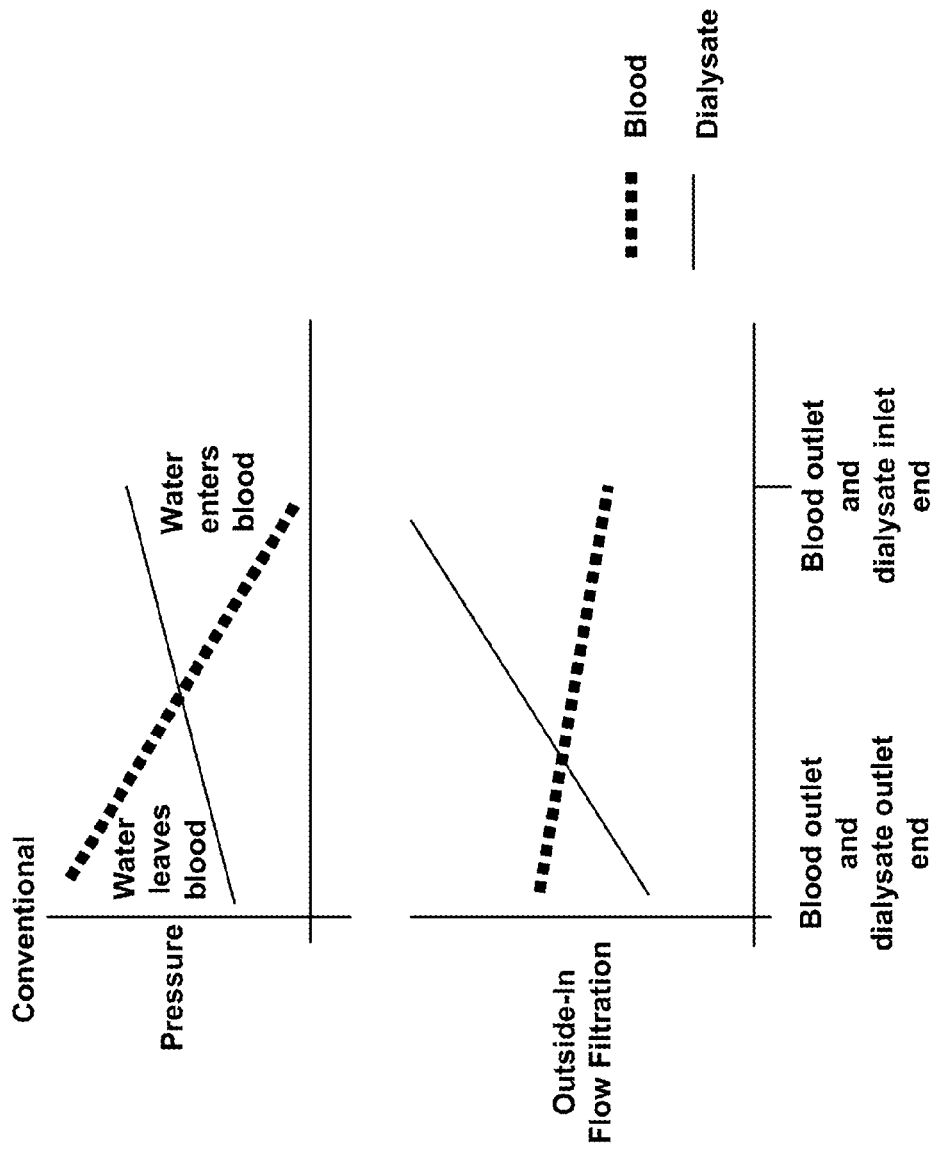
FIG. 18 shows pressure profiles, schematically, for embodiments according to the principles of the present disclosure.

As illustrated in FIG. 18, in a conventional dialyzer that operates using internal filtration, at the end of the dialyzer where blood enters the fibers of the dialyzer, the pressure of the blood is higher than the pressure of the dialysate, so in this part of the dialyzer the direction of convective transport is away from the blood, into the dialysate. With continuing description of a conventional dialyzer, at the end of the dialyzer where blood exits the fibers of the dialyzer, the pressure of the blood is lower than the pressure of the dialysate, so the direction of convective transport is such as to move water from the diaysate back into the blood.

In contrast, in embodiments of the invention as are also illustrated in FIG. 18, near upstream end of the dialysate flowpath through the cartridge 10, the direction of convective transport is for water and small molecules to flow out of the fiber lumen into the housing region. At the downstream end of the dialysate flowpath through the cartridge 10, the direction of convective transport such as for water and small molecules is to go from the housing 50 into the lumen of the fiber 100. This flow pattern also can be influenced by the absolute pressure levels of the various fluid streams.

It is possible that the pressure profiles may vary substantially linearly from one end of the housing 50 to the other, and from one end of the fiber to the other. However, variations other than linear are also possible.

As discussed elsewhere herein, in embodiments of the invention, the packing fraction of the fibers 100 in the housing 50 may be in the range of approximately 40% of the space inside the housing (i.e., porosity fraction 60%). This number represents looser than the maximally-packed limit of fiber-to-fiber contact, but still snugly packed. Within the fibers 100 themselves, space may be apportioned between a fraction of their space that is devoted to the wall thickness of the fibers 100 and a fraction of their space that represents the lumens inside the fibers 100. Typical actual dimensions of fibers 100 are an inside diameter in the range of 175 to 250 microns, and a wall thickness of 20 to 40 microns. If the inside diameter is assumed to be 200 microns and the wall thickness is assumed to be 30 microns (giving an outside diameter of 260 microns), then the fiber contains about 60% of its cross-sectional area as lumen and 40% of its cross-sectional area as wall. This apportioning may be used for estimation purposes.

So, with all area-related quantities being expressed in relation to the housing cross-sectional area, the allocation of space within the housing 50 may be approximately as follows: 60% inter-fiber space, 16% for the walls of the fibers 100, and 24% lumen space within the fibers 100. It may further be realized that typically in dialysis, the volumetric flowrate of the dialysate is larger than the volumetric flowrate of blood, such as for example twice the volumetric flowrate of blood. An average velocity is a volumetric flowrate divided by the applicable flow area. A normalized average velocity can be calculated using normalized values of any of these quantities. So it is possible to calculate, as shown in Table 1, normalized relative values of the average velocity of dialysate and the average velocity of the blood. The ratio of these two average velocities can also be calculated. These parameters are shown both for the conventional situation and for the situation of an embodiment of the invention.

TABLE 1

| | Conventional | Outside-In |
| --- | --- | --- |
| Volumetric Flowrate, Blood (relative) | 1 | 1 |
| Volumetric Flowrate, Dialysate (relative) | 2 | 2 |
| Cross-Sectional area for flow of Blood (fraction of housing area) | 0.24 | 0.6 |
| Average Velocity, Blood | 4.17 | 1.67 |
| Cross-Sectional area for flow of Dialysate (fraction of housing area) | 0.6 | 0.24 |
| Average Velocity, Dialysate | 3.33 | 8.33 |
| Ratio V Dialysate/V Blood | 0.8 | 5 |
| Volumetric Flowrate, Blood (relative) | 1 | 1 |
| Volumetric Flowrate, Dialysate (relative) | 1 | 1 |
| Cross-Sectional area for flow of Blood (fraction of housing area) | 0.24 | 0.6 |
| Average Velocity, Blood | 4.17 | 1.67 |
| Cross-Sectional area for flow of Dialysate (fraction of housing area) | 0.6 | 0.24 |
| Average Velocity, Dialysate | 1.67 | 4.17 |
| Ratio V Dialysate/V Blood | 0.4 | 2.5 |

It can be seen that for the assumed values of respective parameters, in embodiments of the invention, the dialysate velocity is significantly increased compared to the blood velocity. Compared to conventional hemodialysis, while maintaining the same dialysate flowrate and blood flowrate, the blood average velocity is decreased because the blood is flowing through a larger cross-sectional area than conventionally, and the dialysate average velocity is increased because the dialysate is flowing through a smaller cross-sectional area than conventionally. In conventional hemodialysis practice, the ratio Vdialysate/Vblood is generally in the range of approximately unity, having a value of 0.8 for the input values assumed in Table 1. In contrast, for embodiments of the invention, for the assumed parameter values, the ratio Vdialysate/Vblood is about 5. More generally, in embodiments of the invention, the ratio Vdialysate/Vblood may be greater than 1, or greater than 2, or greater than 3, or greater than 4.

The comparison of pressure drop for the dialysate flowpath and pressure drop for the blood flowpath is influenced by the just-described velocity ratio. Another factor influencing the pressure drops is the comparison of the viscosity of blood to the viscosity of dialysate. The viscosity of dialysate is approximately the viscosity of water. The viscosity of the blood is not a single number, but rather is affected by the flow conditions, because blood is a non-Newtonian fluid. Also influencing the pressure drops is the comparison of the effective dimensions of the flowpaths. For flow inside a lumen, the effective dimension would be the inside diameter of the lumen. For flow past the external surfaces of fibers 100, the effective dimension would be a hydraulic diameter of the interfiber space. The effect of all of these variables on pressure drop is somewhat complicated, but their combined effect may be smaller than the rather large velocity ratio just discussed and exemplified in Table 1. This suggests that in embodiments of the invention, the pressure drop across the dialysate flowpath may be larger than twice the pressure drop across the blood flowpath, or larger than 1.5 times the pressure drop across the blood flowpath, or larger than 1.2 times the pressure drop across the blood flowpath, or still more generally, larger than the pressure drop across the blood flowpath.

As illustrated for Outside-In Flow Filtration, blood is introduced near the bottom of the dialyzer and the blood flows upward and is withdrawn near the top of the dialyzer. However, it may be possible to use the opposite orientation also. Also, having robust internal filtration (flow of water back and forth through the membrane in opposite directions at different places within the cartridge) may be helpful in achieving mixing of the blood.

For clinical purposes, the dialysate that is supplied may be ultrapure dialysate, because in a portion of the dialyzer, some of the dialysate passes through the membrane into the patient's blood and into the patient. Ultrapure dialysate is available at many dialysis facilities.

In an embodiment of the invention there may be provided a blood flow system; and a cartridge connected to the blood flow system. The cartridge may comprise a housing, which contains a plurality of fibers inside the housing. At least some of the fibers may be hollow and may be made of semi-permeable membranes having respective fiber lumens and fiber exteriors, and the membranes may have a molecular weight cutoff of approximately 50,000 Daltons. There may be a first fluid flow compartment comprising the lumens of the hollow fibers; and a second fluid flow compartment comprising an inter fiber space inside the housing. Blood may flow in the inter fiber space at a blood flowrate, and an aqueous buffer solution may flow inside the fiber lumens at a solution flowrate. The blood may have, based on the blood flowrate and on blood properties and on dimensional parameters of said inter fiber space, a blood flow shear rate, and the aqueous buffer solution has, based on the solution flowrate and on solution properties and on dimensional parameters of the .lumens, a solution flow shear rate. A ratio of the blood flow shear rate to the solution flow shear rate may be between 0.5 and 2.0, or more particularly between 0.67 and 1.50, or more particularly between 0.8 and 1.2.

It is believed, although it is not wished to be limited to this explanation, that having the shear rate for the blood and the shear rate for the dialysate be more nearly equal to each other, means that mass transfer on the two sides of the membrane will be more nearly equal to each other, which provides good dialyzer performance. With the geometry of Outside-In Flow Filtration, approximate equality of shear rates for blood and for dialysate can be achieved with less dialysate flow, relative to blood flow, than in conventional hemodialysis. Thus, the dialysate flowrate could be lowered, perhaps to equal the blood flowrate. This would save on the amount of dialysate used during treatment.

Embodiments of the invention are further described, but are in no way limited, by the following Examples.

EXAMPLE 1

An experiment was conducted in which bovine blood was flowed in the inter fiber space inside the housing 50. The fibers were made of polyethersulfone combined with polyvinylpyrrolidone, and were asymmetric in that they were smooth on their interiors and rough on their exteriors. The surface area was 1.5 $m^2$, and the porosity was 62% (packing fraction 38%). When the blood was being circulated for embodiments of the invention, it had a flowrate of 100 to 300 milliliters/minute and in the inter-fiber space it had a superficial velocity, as determined by the volumetric flowrate of the blood and the open cross-sectional space inside the housing but outside of the fibers, of 0.25 to 0.75 cm/sec. The blood was circulated for 248 hour periods and was changed daily without flushing the system The time that is reported here is cumulative time during which the blood was flowing.

Hollow fiber membranes are employed in numerous applications due to their high membrane packing density (membrane area per unit device volume) and low manufacturing costs. However, fiber clogging can be a major limitation in some systems. The impact of fiber clogging becomes particularly significant when the feed contains a high volume fraction of dispersed particles that can aggregate and adhere to the lumen of the hollow fibers.

Fiber clogging is a particular issue in blood hemofiltration used for removal of fluid and uremic toxins in renal replacement therapy. The pores of hemofiltration membranes have to be sufficiently small to prevent protein loss from blood plasma, while the surface properties of the fiber lumens need to provide high membrane hemocompatibility and minimal thrombosis. However, despite significant advances in membrane materials development, fiber clogging due to thrombus deposition in the fiber lumens currently limits the maximum filter life to 15-40 hrs in applications of both Continuous Renal Replacement Therapy (CRRT) and hemodialysis. The development of wearable hemodialysis and ultrafiltration devices that can effectively prevent hypervolemia in congestive heart failure patients and treat patients with acute or chronic kidney disease is currently limited by the lack of reliable long-term hemofiltration without filter clogging.

One approach that has been used to minimize fiber clogging in many industrial applications is to use "outside-in filtration." In this case, the feed flows into the inter-fiber space (IFS) of the fiber bundle while permeate is removed through the fiber lumens. Outside-in filtration has been an enabling technology in immersed (or submerged) membrane bioreactors and removal of particulates in water purification, allowing activated sludge with high particulate loadings to be processed for extended periods of time. However, these systems use suspended hollow fibers that are free to move, with the fiber surface kept clean (at least in part) by aeration of the fluid in the bioreactor.

The objective of this study was to examine the potential of using outside-in filtration for long-term hemofiltration. The outside-in configuration has been used previously in membrane oxygenators, although in this case the primary motivation was the improved mass transfer characteristics with blood flow outside of the fibers. Limited previous work has shown that this configuration may be attractive in blood microfiltration using hydrophobic membranes (plasmapheresis), but we are unaware of any previous work on outside-in hemofiltration. Initial work was focused on developing a simple mathematical model to describe the effects of thrombus deposition on fluid flow in conventional versus outside-in hemofiltration. Experimental studies were performed to demonstrate for the first time successful blood processing in hemofiltration for >100 hours using the outside-in mode of operation. These results have important implications for the development of improved hemofiltration processes capable of providing long-term renal replacement therapy and in the treatment of hypervolemia in congestive heart failure patients.

An advantage of the outside-in configuration is the 3-dimensional and highly interconnected flow path in the inter-fiber space (IFS). Thrombus deposition in intraluminal conventional hemofiltration typically occurs at or near the entrance of an individual hollow fiber, completely blocking the entire length of that fiber leading to a significant increase in the axial pressure drop for flow through the module. Thus, in principle, the deposition of N thrombi (where N is the number of hollow fiber membranes in the module) would lead to complete blockage of the module. In contrast, thrombus deposition in the inter-fiber space will have little effect on the axial pressure drop since the blood flow is able to pass around the blockage as shown schematically in FIG. 19A. Deposition of the same N thrombi would occupy only a very small volume fraction of the inter-fiber space, providing minimal disturbance to the blood flow.

The effect of "interconnectivity" on flow has been examined previously in both depth filters and membranes. Ho and Zydney [Ho, C-C., and A. L. Zydney, "Effect of membrane morphology on protein fouling during microfiltration," J. Membrane Sci., 155, 261-276 (1999)] evaluated the flow distribution around a blockage on the upper surface of a symmetric membrane as a function of the pore interconnectivity, defined as the ratio of the Darcy permeability in the normal and transverse flow directions. Surface blockage on membranes with highly interconnected pores had minimal effect on the total hydraulic resistance to flow (until the upper surface is nearly totally blocked) since the fluid is able to flow around and under the surface blockage as it percolates through the porous structure of the membrane. The same phenomenon occurs in depth filters, with particle blockage occurring throughout the filter but causing relatively little change in the total resistance until the pore space within the filter is very highly plugged.

In order to obtain additional insights into the effects of thrombus deposition on the fluid flow behavior in conventional and outside-in hemofiltration, a simple mathematical model was developed to describe the axial pressure drop due to flow in the inter-fiber space. We assume that thrombi are mono-disperse with diameter (d) approximately equal to the inter-fiber spacing [FIG. 19B]. Two limiting cases are examined: (a) uniform distribution of thrombi within the inter-fiber space, i.e., the number of thrombi in any cross-section of the fiber bundle is constant, and (b) preferential clotting near the entrance region of the module.

As discussed by Herzig et al. [Herzig, J. P., D. M. LeClerc, and P. Le Goff, "Flow of suspensions through porous media: Application to deep filtration," Ind. Eng.

Chem., 62, 8-35 (1970).], the pressure drop in a partially clogged bed can be approximated as:

$$\frac{\Delta P}{P_o} = \left(\frac{\varepsilon_o}{\varepsilon}\right)^3 \quad (1)$$

where $\Delta P_o$ and $\varepsilon_o$ are the axial pressure drop and porosity of the initial (unclogged) IFS, and $\varepsilon$ is the porosity of the partially clogged IFS. For a uniform hexagonal array of hollow fibers [FIG. 19B], the initial porosity is given as:

$$\varepsilon_0 = 1 - \left(\frac{a}{b}\right)^2 \quad (2)$$

where a is the outer radius of the hollow fiber membrane and b is the radius of the cylinder defined by the mid-point between adjacent fibers. Equation (2) neglects the "triangular" gap between the fibers. The porosity of the partially clogged IFS is evaluated by simple geometric considerations as:

$$\varepsilon = \varepsilon_0\left[1 - \frac{2n}{3N}\left(\frac{d}{L}\right)\right] \quad (3)$$

where n is the number of deposited thrombi, N is the number of hollow fibers, L is the fiber length, and d is the diameter of a thrombus, assumed to be equal to the interfiber spacing, i.e., d=2(b−a). A typical hollow fiber hemofilter (see Table 1) has d=200 μm and L=20 cm, which corresponds to $\varepsilon=0.9993\varepsilon_o$ and $\Delta P=1.002\Delta P_o$ when n=N. It would take n=1500 N for the porosity of the inter-fiber space to drop to zero (at which point the axial pressure drop would become infinite).

If all of the thrombi deposit in the entrance region of the hollow fiber module (Lent), the porosity in this region will be given by Eq. (3) but with L=Lent. In this case, the total axial pressure drop is given by the sum of the pressure drop across the entrance length (clogged) and the remainder of the fiber (unclogged):

$$\frac{\Delta P}{P_0} = 1 + \frac{L_{ent}}{L}\left(\frac{\varepsilon_0}{\varepsilon}\right)^3 - \frac{L_{ent}}{L} \quad (4)$$

If Lent=1 cm, then $\Delta P$ is again equal to $1.002\Delta P_o$ when n=N due to the highly interconnected nature of the flow. However, under these conditions, the pressure drop would become infinite when n=75N, leading to a 20-fold reduction in the number of thrombi that can be accommodated within the inter-fiber space.

As discussed by Fraser et al. [Fraser, K. H., T. Zhang, M. E. Taskin, B. P. Griffith, and Z. J. Wu, "Computational fluid dynamics analysis of thrombosis potential in left ventricular assist device drainage cannulae," ASAIO J., 56(3), 157-163 (2010)], thrombus formation is governed by the nature of the surface, the condition of the blood (e.g., the extent of anticoagulation), and the local flow conditions. The presence of low shear (less than 250 sec−1) or stagnant flow tends to increase thrombogenicity. In addition, high shear rates can activate platelets leading to thrombosis; the use of intermediate shear rates is generally considered to provide minimal thrombosis and clogging. The wall shear in conventional hemofiltration can be calculated using the Hagen-Poiseuille equation:

$$\gamma_w = -\frac{du}{dr} = \frac{R}{2\mu}\left(\frac{dp}{dz}\right) \quad (5)$$

where R is the inner fiber radius, μ is the blood viscosity, and dp/dz is the axial pressure gradient in the hollow fiber.

The axial velocity in the IFS can be evaluated assuming a hexagonal array of hollow fibers (FIG. 19B), neglecting the "triangular" gaps between fibers, as discussed by Happel and Brenner [Happel, J., and H. Brenner. Low Reynolds Number Hydrodynamics, Prentice Hall, 1965]:

$$u = -\frac{1}{4\mu}\frac{dp}{dz}\left[(a^2 - r^2) + 2b^2\ln\frac{r}{a}\right] \quad (6)$$

where r is the radial coordinate and a and b are the inner and outer radii of the cylinders that define the inter-fiber space. The wall shear rate on the external surface of a hollow fiber is thus:

$$\gamma_w = -\left.\frac{du}{dr}\right|_{r=a} = \frac{1}{2\mu}\left(\frac{a^2-b^2}{a}\right)\left(\frac{dp}{dz}\right) = -\frac{1}{2\mu}\left(\frac{a\varepsilon}{1-\varepsilon}\right)\left(\frac{dp}{dz}\right) \quad (7)$$

For the Asahi Rexeed® dialyzers used in the subsequent experiments, a=120 μm and ε=0.62. Blood flow in this unit with μ=3.5 cP gives dp/dz≈ΔP/L with ΔP=40 mm Hg and L=33.4 cm. This yields a wall shear rate of $\gamma_w=450$ s$^{-1}$, which is consistent with the recommended shear rates for minimal thrombosis.

The volumetric flow rate in the inter-fiber space can be evaluated by integration:

$$Q = 2\pi N_f \int_a^b u r\, dr = -\frac{\pi N_f}{8\mu}\left[4a^2b^2 - a^4 - 3b^4 + 4b^4\ln\left(\frac{b}{a}\right)\right] \quad (8)$$

where Nf is the number of hollow fibers. Thus, a pressure drop of 40 mm Hg in the Asahi Rexeed® dialyzer (Nf=7700) would yield a blood flow rate of 370 mL/min, which is about twice that observed experimentally. This discrepancy likely reflects the more complex, non-uniform, flow distribution in the inter-fiber space between the randomly arrayed hollow fibers.

Hemofiltration experiments were performed using a modified version of the hemodialysis system described by Morti and Zydney. Blood was pumped into the hollow fiber module through the lumen feed port (conventional operation) or through the port in the inter-fiber space (outside-in configuration) using a peristaltic pump (Cole Parmer, Model No. 77200-62). The ultrafiltration rate was set at a predetermined rate using an ultrafiltrate metering pump (Fluid Metering, Inc. Model No. QV1 with V200 Controller). Digital pressure gauges (Cecomp Electronics, Inc., U.S.A.) were used to continuously record the pressure at the module inlet and outlet. The system was operated with total recycle, with the ultrafiltrate returned directly to the blood reservoir, using a constant temperature of 37° C., maintained by placing the blood reservoir on a hot plate (VWR Model No. 12365-382).

Solute clearance was evaluated using NaCl and vitamin B12 following the procedures described by Morti and Zydney [Morti, S. M., and A. L. Zydney, "Protein-membrane interactions during hemodialysis," Am. Soc. Artif. Internal Organs J., 44, 319 (1998).]. NaCl concentrations in the "blood reservoir" were measured using a conductivity meter (Myron L. Company, Ultrameter) with vitamin B12 evaluated spectrophotometrically using the absorbance at 360 nm (Beckman, DU® 530). Data were obtained in dialysis mode using the solutes dissolved in saline.

In vitro hemofiltration experiments were performed with bovine blood purchased from Lampire Biological Laboratories (Pipersville, Pa.). Heparin was added at concentrations ranging from 2.5 to 10 IU/mL. Blood flow rates were varied between 75 and 300 mL/min, using ultrafiltrate flow rates from 1.5-2.0 mL/min. During outside-in operation, the filter was positioned vertically with blood introduced from the bottom dialysate port and exiting from the top dialysate port. Ultrafiltrate was collected from the top lumen port with the bottom lumen port closed. Both low flux (Kuf≤10 ml/hr/mmHg) and high flux hemodialyzers and hemofilters were examined (Table 2).

TABLE 2

Dialyzers/filters used, with key geometric characteristics.

| Name | Type | Surface Area (m2) | Fiber ID (μm) | Fiber Length (cm) |
|---|---|---|---|---|
| Gambro H6 | High Flux | 0.6 | 200 | 10 |
| Sorin DHF0.2 | High Flux | 0.25 | 200 | 14.5 |
| Fresenius F3 | Low Flux | 0.4 | 200 | 20 |
| Minntech HF 400 | High Flux | 0.3 | 200 | 12 |
| Spectrum P-D1-030E-100-01N | High Flux | 0.0115 | 500 | 20 |
| Asahi Rexeed 15R | High Flux | 1.5 | 185 | 33.4 |
| Asahi Rexeed 15LX | Low Flux | 1.5 | 185 | 33.4 |
| Minntech Renaflo Mini | High Flux | 0.05 | 620 | 15 |

Experiments were normally terminated when the axial pressure drop between the inlet and outlet of the filter reached a value between 250 and 300 mmHg. Blood was changed daily without flushing the filter to appropriately simulate the conditions needed for long-term continuous hemofiltration. Immediately after filter failure, the filter was rinsed with saline to remove all visible blood. Visual observations were made to determine the mode and distribution of thrombi in the various sections of the filter.

FIG. 19D shows the axial pressure drop (blood inlet minus blood outlet) as a function of time for long-term blood processing performed with the Asahi Rexeed® 15R and 15LX hemodialyzers using both conventional (intra-luminal) and outside-in hemofiltration. The two repeat experiments using conventional hemofiltration showed unacceptable pressure drops (greater than 300 mm Hg) after less than 25 hr (and in one case after only 5 hr). The small decline in pressure at the very end of these experiments was due to the inability of the blood (feed) pump to maintain a constant flow rate under these conditions. In contrast, operation using the outside-in configuration provided stable operation for up to 100 hr. It is likely that these filters could be used for much longer filtration runs given the very small (typically less than 20 mm Hg) increase in pressure after even 100 hr of operation. This improved performance was seen over a range of blood flow rates (100 to 200 mL/min) and using both low flux (Asahi Rexeed® 15LX) and high flux (15R) modules. Similar results were obtained with the other filters listed in Table 1, with all filters showing at least 100 hr of continuous operation when used in the outside-in configuration.

A very simple mathematical model for the increase in axial pressure drop seen with intra-luminal (conventional) operation was developed using the classical fouling model based on fiber (or pore) blockage [Hlavacek, M., and F. Bouchet, "Constant flow-rate blocking laws and an example of their application to dead-end microfiltration of protein solutions," J. Membrane Sci. 82, 285 (1993).]:

$$\frac{\Delta P}{P_o} = 1/(1 - \alpha t)$$

where α is the fiber blockage parameter and t is the filtration time. Although the actual situation is likely to be quite complex, with some degree of fiber constriction due to blood cell deposition as well as partial fiber blockage by smaller thrombi, Equation (9) does correctly predict that the pressure rises very rapidly at a critical time $t=1/\alpha$ when all of the fibers become blocked. Based on the data in FIG. 19D, the fibers become fully blocked after between 6 and 24 hr. In contrast, for the outside-in configuration (n≈10 N after 100 hr of operation), Eq. (3) predicts an increase in axial pressure drop of only 3%, which is in fairly good agreement with the results in FIG. 19D.

Visual examination of failed filters used in the conventional mode showed that the lumens of the hollow fibers became clotted with thrombi mostly within the first 1 to 2 cm from the entrance header (FIG. 19E1) with minimal clotting observed in the downstream regions (FIG. 19E2). This finding was consistent for all filter types and membrane materials when used for conventional hemofiltration.

In contrast to the results in FIG. 19E1-19E2, the modules used for outside-in hemofiltration showed a small number of isolated thrombi distributed within the main section of the fiber bundle past the entrance zone of the distributor. There was a clear indication of visible clot formation in the entrance zone of the filter within the distributor section where blood enters the fiber bundle, while the exit distributor was mostly clean with no visible clots (FIG. 19F). Microscopic examination of sections of the fiber bundle after long-term hemofiltration showed a very low volume fraction of small size thrombi dispersed within the bundle. There were no observable differences in the number or distribution of thrombi between the low and high flux dialyzers.

Figure 6A:
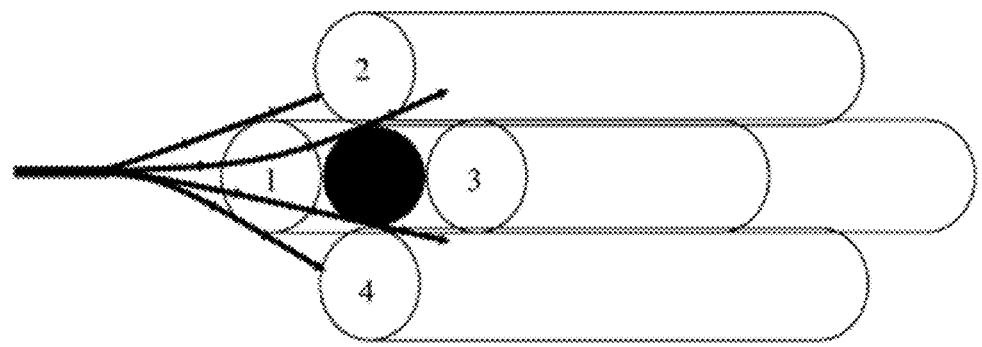
FIG. 6A illustrates the flow of blood past the outside surfaces of hollow fibers, flowing past a single thrombus.
Figure 6B:
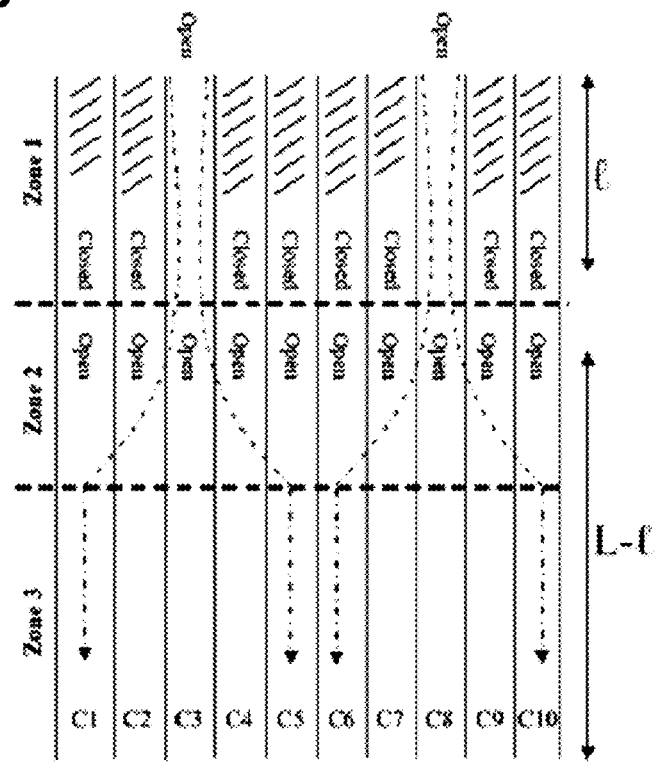
FIG. 6B illustrates the rearrangement of flow patterns around a thrombus.
Figure 7A:
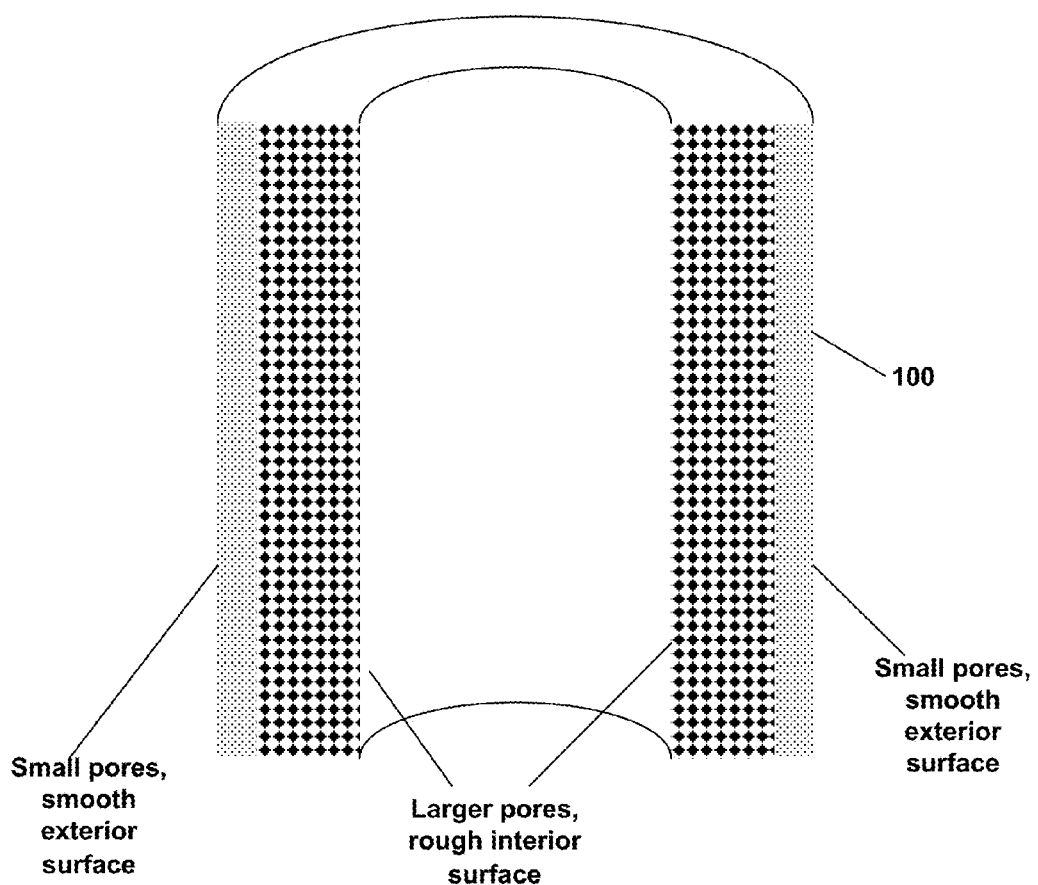
FIG. 7A illustrates a straight fiber that has a smooth exterior and a rough interior.
Figure 7B:
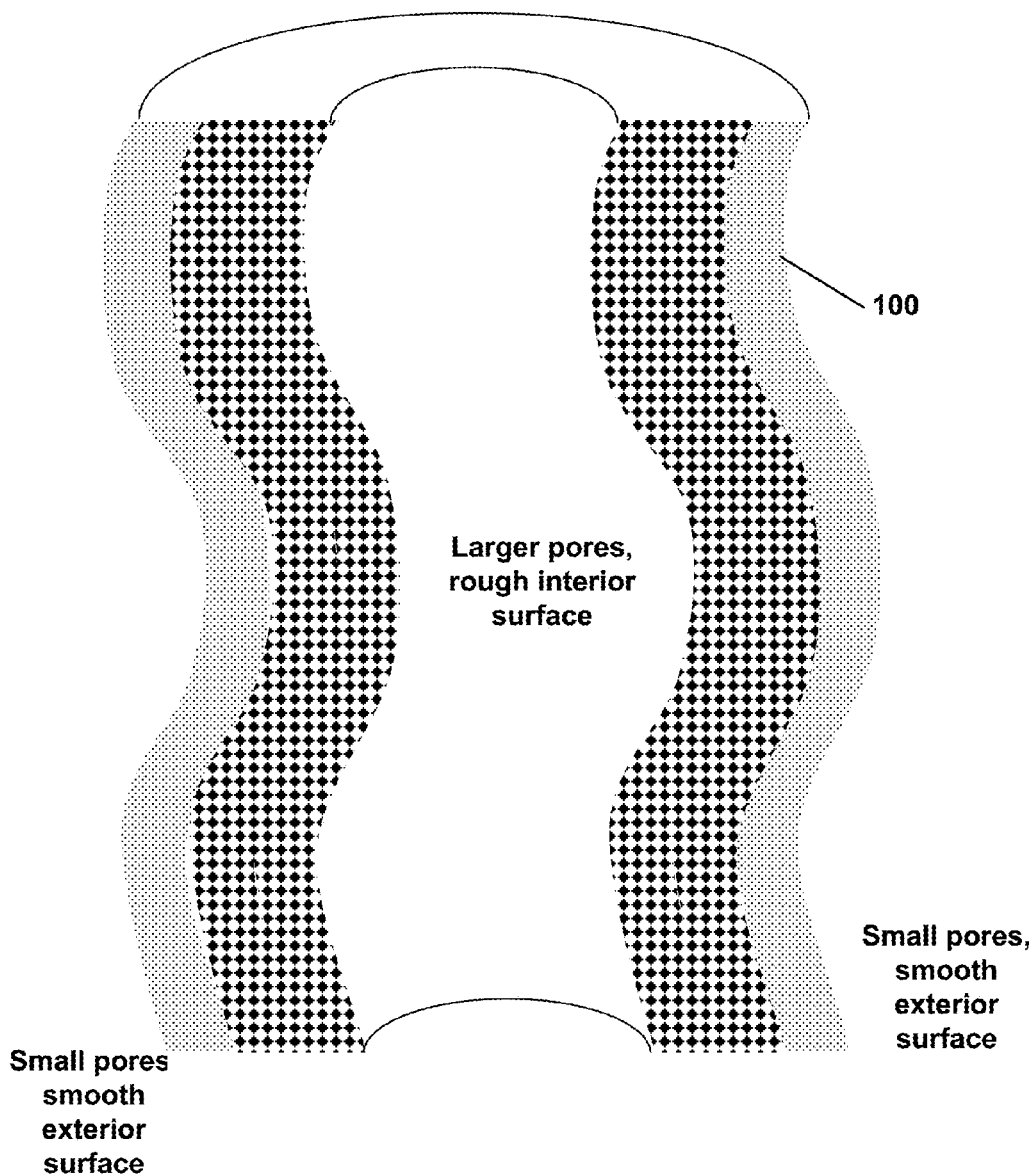
FIG. 7B illustrates the same for a wavy fiber having a smooth exterior and a rough interior.

Limited experiments were also performed with the Minntech Renaflo Mini® hemofilter made without the orbital distributor that is used to provide better flow distribution in the inter-fiber space of the module. Although this module could still be used for as much as 94 hours in the outside-in configuration, it showed a large extended clot in the space between the outer shell and the fiber bundle where blood enters the system (shown schematically in FIG. 6A). Other clots were also found within the large irregular spaces of the fiber bundle. These results clearly demonstrate the importance of uniform flow within the inter-fiber space during outside-in hemofiltration.

The results in FIGS. 19D-19G were obtained using 10 IU/mL of heparin. Hemofiltration experiments performed with only 2.5 IU/mL showed severe clotting during handling. Data obtained with a heparin concentration of 5 IU/mL showed more thrombi formation in the entrance zone compared to that seen with 10 IU/mL, although these filters could still be successfully operated for >100 hr. Thrombus deposition was also greater when using higher blood flow rates (e.g., 300 mL/min), although there was still relatively little increase in axial pressure drop over 100 hr of operation (data not shown).

In order to demonstrate that the outside-in configuration provided adequate solute removal, clearance experiments were performed using NaCl and vitamin B12. Typical data for the Asahi Rexeed® 15R module are shown in FIG. 19H for the solute concentration in a "blood" reservoir as a function of time (where the reservoir was filled with water containing the solutes). The clearance can be calculated directly from the slope of the data on a semi-log plot [15]. The calculated clearance for both NaCl and vitamin B12 were statistically identical in the two flow configurations, demonstrating that outside-in hemofiltration can provide adequate solute clearance for clinical applications in treatment of renal failure.

The data obtained in this study clearly demonstrate that the use of an outside-in configuration dramatically increases the lifetime of hemofiltration modules during blood filtration. This increase is a direct result of the hydrodynamic advantage of the outside-in mode of hemofiltration. When the hollow fiber module is operated with conventional (intra-luminal) flow, thrombi deposited within the fiber lumens cause a significant increase in the axial pressure drop and a maximum life of less than 30 hr. This effect is not seen when using the outside-in configuration due to the 3-dimensional interconnected hydrodynamic flow channels in the inter-fiber space. The small volume fraction of trapped thrombi observed in the inter-fiber region causes only a small increase in axial pressure drop (less than 20 mm Hg), consistent with predictions of the simple mathematical model developed earlier. A small thrombus trap could easily be used in the return blood line to insure that no shed thrombi are returned to the patient. The much longer operation possible with the outside-in configuration would reduce filter replacement costs, minimize blood loss, significantly reduce nursing requirements, minimize disturbances in patient blood pressure, and reduce the likelihood of infection.

The low level of thrombi formation seen during outside-in operation is likely due to a number of phenomena. First, the gaps between fibers are considerably larger than the 200 µm inner diameter of the hollow fibers. Second, it is possible that albumin deposited on the external surface of the fibers may protect against platelet adhesion. This phenomenon may be more important in the outside-in configuration due to the greater degree of concentration polarization associated with the somewhat lower mass transfer coefficient in the inter-fiber space. It is also possible that there is some protection associated with the asymmetric structure of the hollow fiber membranes, with the surface facing the blood now having a larger pore size. Third, the lower shear rate in the inter-fiber space may reduce clot formation; data obtained with higher blood flow rates clearly showed greater thrombus deposition near the device inlet when using the outside-in configuration. Thrombus deposition also increased at low heparin concentrations due to the development of bulk thrombi (emboli) within the blood.

It may well be possible to use outside-in hemofiltration at lower heparin concentrations and/or for longer times by re-designing the inter-fiber space to provide more uniform flow distribution and/or by adding an emboli trap in the blood flow path immediately before the entrance to the filter. For example, a more axially uniform flow within the IFS could be achieved by appropriate modification of the entrance header. It would also be possible to consider other filter configurations (e.g., employing radial flow) to ensure more uniform blood flow in the inter-fiber space. Such enhanced hemofiltration modules could potentially enable successful long-term renal replacement therapy and treatment of hypervolemia in congestive heart failure patients.

For certain applications involving extracorporeal blood treatment, it is useful if a duration of lifetime for a dialyzer or filter can achieve at least approximately 100 hours without clogging or suffering other significant degradation of performance. Such a duration makes possible medical procedures that are more in the nature of continuous treatment rather than intermittent treatment. Such a duration not only has economy in terms of the cost of dialyzers or filters, but also has value in terms of not subjecting the patient to overly frequent changes of apparatus possibly associated with concomitant loss of blood by the patient for purposes such as priming of the filter or cartridge 10.

The cartridges used in experiments for outside-in hemofiltration showed a small number of isolated thrombi distributed within the main section of the fiber bundle past the entrance zone of the distributor. There was a clear indication of visible clot formation in the entrance zone of the filter within the distributor section where blood enters the fiber bundle, while the exit distributor was mostly clean with no visible clots. Microscopic examination of sections of the fiber bundle after long-term hemofiltration showed a very low volume fraction of small size thrombi dispersed within the bundle. There were no observable differences in the number or distribution of thrombi between the low and high flux dialyzers.

EXAMPLE 2

In this Example, there is presented experimental evidence that the hydrodynamic advantage of Outside-In Flow Filtration is maintained despite evidence of thrombosis. This experiment was conducted with donated human blood, which flowed through the filter for eight-hour time periods. In between those time periods, the blood was drained and replaced by saline solution. Each new day of the experiment was re-started using fresh donated human blood.

For purposes of this experiment, it may be realized that there are at least two types of measurements that can indicate the presence of blood clots may be detected. One is a chemical test, which detects the presence of thrombin antithrombin complex (TAT). TAT is released during clot formation and is an excellent indicator for thrombosis, so the presence of this substance is a chemical indicator of the presence of clots. A second way of detecting the presence of clots or more specifically clogging is an overall physical manifestation in the form of pressure drop for the flow of blood through a geometry such as the geometry of embodiments of the invention. The presence of significant clotting, perhaps together with some influence of the particular location or spatial distribution of the clots, may be expected to manifest itself as increased pressure drop for the flow of blood in the flowpath that goes through the inter fiber space.

Referring now to FIG. 20A, there is shown, as a function of time, the level of TAT measured through chemical analysis of the blood. At the beginning of the experiment the TAT concentration had a low baseline value, but then the TAT concentration rose steadily. Also shown in FIG. 20B, on the same time scale, is the pressure drop for flow of the blood from the housing supply port to the housing discharge port, through the inter fiber space of the dialyzer. At the beginning of the experiment the pressure drop had a baseline value, and it maintained that baseline value for a fairly long time of about 48 hours into the experiment. Only after a time of 48 hours did the pressure drop increase rapidly. It can be noted that the time when the pressure drop began to increase noticeably is much later than the time when the TAT concentration began to increase. From this it can be inferred that some clots began forming early, as indicated by the beginning of the increase in the TAT concentration. However, for a long time those clots did not have any noticeable effect on the pressure drop or the hydrodynamic resistance of the filter. It can be inferred that when those early clots formed, the blood found alternate flowpaths around the clots without incurring much additional pressure drop. Only when the TAT concentration reached a level of almost 10,000 micrograms per liter, which presumably indicated a significant level of clotting in the fiber space or at significant places in the fiber space, was there any noticeable increase in the pressure drop for blood flow through the cartridge. This implies that a modest amount of clotting (assuming it is well distributed spatially) has almost no effect on the pressure drop of the blood flow for Outside-In Flow Filtration, and a fairly extensive amount of clotting needs to occur before there is any noticeable change in the pressure drop characteristics of the blood flow. This is in contrast to the situation with conventional hemodialyzers, in which the impact on blood flow pressure drop is closely related to the amount of clotting, by virtue of the amount of fibers that are blocked.

This experiment lasted for 65 hours of blood flow time before severe clotting occurred. The fibers used in this experiment were not optimal because the fibers were rough on their blood-facing surface, i.e., the fiber exteriors. It can be expected that if the fibers were constructed of materials and had external surface smoothnesses and high hemocompatibility that were better suited to the intended purpose, the formation of clots would have been even slower and the cartridge would have lasted even longer before clogging. So, this is still considered an encouraging result.

FIG. 20C shows a comparison between the data of FIG. 20A and some experimental data for conventional hemofiltration. FIG. 20C shows that the TAT concentration for conventional hemofiltration is less than it is for Outside-In Flow Filtration, which by itself is not a good thing. It is believed that the comparison of TAT concentration for Outside-In Flow Filtration and the TAT concentration for conventional operation mainly illustrates that having a smooth blood-facing surface is preferable. Ideally, for Outside-In Flow Filtration, the fibers would be manufactured with the smooth surface on the outside, which is the blood-facing surface.

EXAMPLE 3

Hemolysis is the destruction, such as the lysis or rupture, of red blood cells, accompanied by the release of free hemoglobin. Red blood cells are relatively large, compared to platelets and white blood cells, and also red blood cells are especially fragile and easily ruptured. Accordingly, experience teaches that it may be expected that hemolysis may especially be associated with situations where the blood flows past sharp flow geometries.

Hemolysis occurs to some degree in conventional hemodialysis. It is possible that in conventional dialysis, hemolysis results from the sharp edges where the lumens meet the potting barrier 150, and from the need for blood cells to pass by those sharp edges. In contrast, for embodiments of the invention, there are not nearly as many sharp edges or corners that blood needs to flow past.

Experiments were conducted with donated human blood using the Outside-In Flow Filtration of embodiments of the invention, as described elsewhere herein. Experiments were also conducted using conventional systems. The occurrence of hemolysis was inferred from measurements of hemoglobin, which is released when red blood cells are ruptured. Measurements of hemoglobin were taken as a function of time during the experiment.

Amounts of hemolysis are shown in FIG. 21A, for conventional hemodialysis and for embodiments of the invention having outside-in filtration of blood. It is found that in embodiments of the invention, the rate of hemolysis is significantly smaller compared to conventional hemodialysis. The only time when hemolysis fraction for embodiments of the invention became equal to the hemolysis fraction for conventional techniques was near the very end of the data acquisition, when the filter became significantly clogged.

It is thought, although it is not wished to be limited to this explanation, that the reduced amount of hemolysis for outside-in filtration results from the lack of sharp edges exposed to blood flow in embodiments of the invention. This characteristic is believed to advantageous for long-term therapies such as Continuous Renal Replacement Therapy (CRRT), slow continuous hemodialysis and when using filter in wearable therapies including hemodialysis and ultrafiltration.

Here, hemolysis results show that conventional situation is breaking red blood cells at sharp entrances to fibers at the potting. OIFF shows better results because blood never enters sharp entrances but rather has smooth boundaries. So this is a good result for OIFF Two other blood analysis measurements that are indicative of dialyzer performance are the measurement of white blood cell count and the measurement of platelet count. As background information, both white blood cells and platelets are smaller than red blood cells, and also are more robust with respect to mechanical disturbance. So, experience suggests that if they are depleted, the reason for depletion would be a non-mechanical source such as a hemocompatibility issue. It can further be postulated that the hemocompatibility issues are related to the smoothness or roughness of the blood-facing surface on a size scale of nanometers, and on other factors such as hydrophilicity and intrinsic chemistry of surface molecules.

In regard to this comparison between outside-in flow filtration and conventional dialysis, it must be remembered that the experiment used conventional hemodialysis cartridges, because of their ready availability. For the conventional part of the experiment, blood was put through the lumens as usual, and the lumens had smooth interior walls with high hemocompatibility. For embodiments of the invention, the blood was supplied to inter fiber space of similar dialyzers, and the blood was exposed to the fiber outside surfaces, which were rough and less hemocompatible. Based on the underlying assumptions and expectations, it would have been preferable for the fiber outside surfaces facing the blood to have been smooth and hemocompatible in the Outside-In Flow Filtration case. However, such dialyzers were not available for the experiment.

The data that were obtained with donated human blood are plotted in FIGS. 21B and 21C. The data show that the preservation of white blood cells and platelets was worse for embodiments of the invention, as compared to the conventional situation. Accordingly, it can be expected that those rough external surfaces resulted in the depletion of white blood cells and platelets during long-term experiments. However, the same understanding and assumptions imply that if the outsides of the fibers, i.e., the blood-facing surfaces, had been smooth and hemocompatible, probably there would not have been so much damage to white blood cells and platelets. This provides motivation to manufacture fibers for embodiments of the invention so that the fibers have smooth hemocompatible exterior surfaces.

It should be noted that these experiments were conducted using a quantity of 250 mL of donated human blood, which was continuously recirculated. For embodiments of the invention, the measured depletion of white blood cells and platelets may seem large. However, an actual adult patient would have about 5 Liters of blood, which is 20 times as large. Accordingly, the depletion of white blood cells and platelets that was measured and is plotted in FIGS. 20A-20C would be reduced by a factor of approximately 20 if that same amount of damage was experienced by the actual quantity of blood present in a human body. It may also be expected that homeostasis would have further minimized depletion of white blood cells and platelets.

EXAMPLE 4

In this Example, guidelines are derived for the sizing and proportioning of dialyzers or the filter. In summary, for any given ultrafiltration coefficient, the ultrafiltration flowrate is proportional to the total surface area of the fibers, which makes it proportional to the number of the fibers and to the length of the fibers, which makes the ultrafiltration flowrate proportional to the volume of the fiber bundle. Second, for any given volume of the fiber bundle, making the fiber bundle relatively long and slender is better for achieving a larger blood flow velocity and shear rate. The recommended ranges of superficial velocities and shear rates have been detailed elsewhere herein. In embodiments of the invention, the geometric characteristics need to chosen so that geometric dimensions of the filter will provide the recommended ranges of velocities and shear rates.

In one filter design, a fiber bundle with rectangular cross-section is may be used to achieve uniform Outside-In Flow Filtration operation. Referring now to FIG. 22A, in the axial direction, the bundle is symmetrical with potted resin layers near both edges of the bundle and the fibers penetrating though them. Hence, the bundle has a shape of parallelpiped assembly. The designations of ribs of rectangular edges of rectangular bundle are L and M. The designation of rib in the axial direction, in directions parallel to fibers, is N. When blood flows outside the fibers in a direction perpendicular to the fibers, ultrafiltration occurs. The pressure in the fiber lumens increases and the filtrate flows to the nearest extremity of fiber, where pressure is almost atmospheric. Hence, two headers for the collection of filtrate have to be attached symmetrically to both potted resin layers. The blood uniformly flows perpendicular to fibers. Two opposite sides of the parallelipiped bundle, among the four sides, can be used for blood flow. The other two sides have to be sealed with a plastic shell. For example, bundle surfaces NL have to be sealed, while two surfaces NM remain free for perpendicular blood flow. Two similar headers with internal cross-section NM have to be attached to the opposite sides of bundle NM. One header serves for blood entrance into the Inter Fiber Space, the second header serves for blood exiting. In this design there is no need for orbital distributors since blood enters directly to the fiber bundle enclosed in the rectangular housing.

The method for determining dimensions is proposed for the combination of N, M, L parameters of a filter for uniform Outside-In Flow Filtration to provide the required ultrafiltration rate and blood velocity, where N, M, L are length of edges of the assumed rectangular fiber bundle respectively. A single possibility to characterize filter is its dependence on N, M, L quantitatively is the development of mathematical models, which determine the dependence of blood linear velocity U and ultrafiltration volumetric velocity $Q_u$ on geometrical parameters N, M, L. $Q_u$ is important for medical treatment during hemofiltration, control of the blood velocity U is important, because a sufficiently large value of U helps to suppress thrombosis. $Q_u$ and U are input parameters in modeling, which will be described later. The reliability of the equation for the Darcy constant is important for this modeling. We confirmed the equations for the Darcy constant by experiment. The embodiments on the invention detailed herein are necessary to design an Outside-In Flow Filtration filter for the various applications and therapies. In the absence of such embodiment, thousands of experimental combinations will be required, a task that is both prohibitive and expensive to achieve.

Analytical modeling for predicting Outside-In Flow Filtration filter design becomes possible because Reynolds number (Re) is small and the structure of the Inter Fiber Space of this geometry is uniform. Small Reynolds number means that the dependence of superficial velocity on pressure gradient within Inter Fiber Space is linear. The superficial velocity in porous media, which represents the case of Inter Fiber Space, is the velocity averaged over a volume whose dimension is much larger than the pore dimension and equals to the volumetric velocity through a certain cross-section divided on this cross-section. In this geometry, the velocity distribution along the bundle is one dimensional due to the uniformity of the Inter Fiber Space. Although the superficial velocity decreases downstream because of ultrafiltration, this decrease is negligible when the ultrafiltration volumetric velocity $Q_u$ is very small in comparison with $Q_b$, $$Q_u << Q_b \qquad (1)$$

The invariance of velocity, for practical purposes, means that the pressure gradient is uniform as well. The local pressure gradient and local superficial velocity may be related to each other according to the hydrodynamics of porous media with the use of Darcy's law $$U = -\frac{K}{\mu} grad p \qquad (2)$$

where K is the Darcy constant. As gradp is invariant, it may be represented as a ratio for the difference between inlet and outlet pressures and the distance between inlet and outlet headers.

$$U = \frac{K_\perp}{\mu} \frac{(P_{in} - P_{out})}{L} \qquad (3)$$

where the index $\perp$ corresponds to blood flow perpendicular to fiber axis in this case, $$K_\perp = \frac{(1-\alpha)^3}{4k\alpha^2} a^2 \qquad (4)$$

a is the external radius of fibers, k is Kozeny number, α is the solidity, α=1−ε, where ε is porosity of the Inter Fiber Space. As the cross-section for blood flow is NM $$Q_b = NMU \qquad (5)$$

where the definition of superficial velocity (Example 1) is used. Combining Equation (3) and Equation (5) yields $$Q_b = \frac{NM}{L}(P_{in} - P_{out})\frac{K_\perp}{\mu} \qquad (6)$$

Transmembrane pressure, ultrafiltration coefficient (uc) and the total membrane surface area ($S_u$) are required to derive an equation for $Q_u$. Transmembrane pressure is the difference between local pressure within IFS and corresponding local pressure in the lumen of a hollow fiber. Both vary along the bundle. There is coupling between blood flow and filtrate flow because of the ultrafiltration flux. However, there is decoupling, at first approximation, when the condition (1) is valid. This condition allows us to consider axial dependence of pressure within Inter Fiber Space as a linear dependence. In addition, this leads to the conclusion that the pressure variation along the lumens is very small in comparison with that within Inter Fiber Space, and consequently it may be disregarded. In turn, the pressure within the lumens may be considered as an invariant one when an expression for transmembrane pressure is derived because in this expression the pressure drop along the lumen is very small in comparison with the pressure drop along the Inter Fiber Space. The pressure within the lumen may be represented as $P_l$. For uniform Outside-In Flow Filtration, the ultrafiltration is controlled by a special pump located near the exit for filtrate and hence $P_l$ is negative.

Transmembrane pressure decreases linearly downstream because the pressure within Inter Fiber Space decreases linearly from $P_{in}$ till $P_{out}$. Hence, the total ultrafiltration flux is proportional to averaged transmembrane difference $$\frac{P_{in} - P_{out}}{2} - P_l = \frac{P_{in} - P_{out}}{2} + |P_l| \qquad (7)$$

The total ultrafiltration flux $Q_u$ is proportional to membrane area $S_u$ and the ultrafiltration coefficient which is specific for different membranes and depends on pore dimension and on pore surface concentration of the membrane.

$$Q_u = S_u(uc)\left[\frac{P_{in} - P_{out}}{2} + |P_l|\right] \qquad (8)$$

$Q_u$ and pressures can be controlled, that allows to determine the product $S_u(uc)=UC$, which may be called the dialyzer ultrafiltration coefficient. Accordingly, the information about the product $$UC = S_u(uc) \qquad (9)$$

is usually available for a particular dialyzer.

In order to clarify the influence of geometrical parameters N, M, L on the ultrafiltration flux, we need to express $S_u$, which is a surface area of the fibers, as a function of the fiber amount n and the fiber radius a.

$$S_u = n2\pi aN \qquad (10)$$

where N is the fiber length, n is the number of fibers in the bundle. The area of the bundle cross-section LM may be represented as a product of the area per one fiber cross-section $\pi b^2$ multiplied on fiber amount n $$LM = \pi b^2 n \qquad (11)$$

where b is the outer radius of the cylindrical cell.

The substitution n according to Eq (11) into Eq (10) yields $$S_u = \frac{2a}{b^2}LMN = \frac{2\alpha}{a}LMN \qquad (12)$$

The dependence of ultrafiltration flux on geometrical parameters follows from the substitution $S_u$ according to Equation (12) into Equation (8)

$$Q_u = \frac{2\alpha}{a}LMN(uc)\left[\frac{P_{in} - P_{out}}{2} + |P_l|\right] \qquad (13)$$

The dependence of ultrafiltrate flowrate on uc and transmembrane pressure is apparent. Increasing either of these variables enhances $Q_u$. It means that high flux membrane has to be chosen. LMN is the bundle volume. The notion of specific surface, i.e., surface per unit volume, is well known for porous media in colloid science. It is proportional to 1/a, where a is the pore radius. Membrane surface with respect to the bundle volume is analog of specific surface. As the membrane surface belongs to bundle volume, the specific surface has to be multiplied by the bundle volume. The aforesaid establishes similarity in notions of membrane surface and specific surface in colloid science.

If the equation is solved for LMN so that LMN is expressed through $Q_u$ $$LMN = \frac{Q_u a}{2\alpha(uc)}\left[\frac{P_{in} - P_{out}}{2} + |P_l|\right]^{-1} \qquad (14)$$

It becomes apparent that the required ultrafiltration volumetric flowrate determines the volume of the bundle.

We shall specify Equation (14), using the bundle packing parameters of the Asahi dialyzer, α=1−ε=0.4
a=(185+70)/2=255/2 micron, where 185 micron is the internal diameter, wall thickness 35 micron. UC=75 ml/mmHg·hr, $S_u$=1.5 m²=1.5×10⁴ cm².

The substitution of this data into Equation (9) yields $$uc = \frac{UC}{S_u} = 1.4 \times 10^{-6} \text{ cm}^3/\text{mmHg·sec} \qquad (15)$$

The substitution of these values for uc, a, α and $Q_u$=1.5 ml/min=2.5×10⁻² cm³/sec into Equation (14) yields LMN values presented in Table 3. These very small bundle volumes confirm the possibility of creating a miniature wearable filter that uses Outside-In Flow Filtration.

Equations (6) and (13) forms the system of two equations for determination of two unknown values L and NM. Alternately this system can be used for determination of dependencies $Q_b$ and $Q_u$ on chosen values of L and NM. In order to establish what maximal value of blood linear velocity is favorable for suppression of thrombosis development, L has to be found from this system of equations. The larger U, the smaller L will be. The substitution NM according to Equation (6) into Equation (13) yields $$L^2 = \frac{aK_\perp P_{in} Q_u}{2\alpha\mu(uc)\left(\frac{P_{in}}{2} + |P_l|\right)Q_b} \quad (16)$$

Two independent presentations for U are possible. L according to Equation (16) may be substituted into Equation (3) or U can be expressed with the use of Equation (5)

$$U = \frac{Q_b}{NM} \quad (17)$$

These two presentations have to be identical $$U = \frac{Q_b}{NM} = U = \frac{K_\perp P_{in}}{\mu L} \quad (18)$$

On the other hand, L satisfies Equation (16), while LMN satisfies Equation (14). This identity is possible only at certain dependencies L and NM on the other parameters. Meantime, NM and L are already determined by Equations (14) and (16). Hence, we need to obtain Equation (16) for L by means of substitution into $$\frac{Q_b}{NM} = \frac{K_\perp P_{in}}{\mu L} \quad (18b)$$

MN according to Equation (14) is substituted into rewritten Equation (18b)

$$L = \frac{K_\perp P_{in} NM}{Q_b \mu} = \frac{K_\perp P_{in} a Q_u}{Q_b \mu 2\alpha(uc)\left(\frac{P_{in}}{2} + |P_l|\right)L} \quad (18c)$$

Equation (18c) and Equation (16) are identical, that demonstrates the consistency of the derivation. Let us consider $|P_l| = P_{in}$ that simplifies Equation (16) and makes L independent of pressure $$L = \left[\frac{aK_\perp Q_u}{3\alpha Q_b \mu(uc)}\right]^{0.5} \quad (19)$$

Equation (3) may be multiplied by the ratio 1330 dyne (mmHg·cm²)⁻¹ for conversion of units, which enables us to substitute $P_{in}$ in mmHg although $\mu$ is expressed in dyne, $\mu = 3.5 \times 10^{-2}$ dyne cm⁻² sec.

$$U = \frac{10^{-5} \times 1330 \Delta P(mmHg)}{3.5 \times 10^{-2} L(cm)} = 0.37\frac{P_{in}(mmHg)}{L(cm)} \quad (20)$$

The values of L and U calculated with Equations (19) and (20) are given in Table 3 for two values of $P_{in}$. NM has to be represented through LMN and L, corresponding to a certain $P_{in}$ in Table 3

$$NM = \frac{LMN}{L} \quad (21)$$

$$Q_b = U(P_{in}, L)\frac{LMN(P_{in})}{L} \quad (22)$$

TABLE 3

| $P_{in}$ (mmHg) | | | | | 33 | | | | 100 | | | |
|---|---|---|---|---|---|---|---|---|---|---|---|---|
| TMP (mmHg) | | | | | 50 | | | | 150 | | | |
| LMN (cm³) | | | | | 5.56 | | | | 1.85 | | | |
| L (cm) | U (cm/sec) | $Q_b$ (ml/min) | NM (cm²) | $S_u$ (m²) | | U (cm/sec) | $Q_b$ (ml/min) | NM (cm²) | $S_u$ (m²) |
| 7.7 | 1.62 | 71 | 0.72 | 0.03 | | 4.86 | 71 | 0.24 | 0.01 |

Self-consistency: Input parameters are a, α, $|P_l| = P_{in}$, $Q_u$ and $Q_b$. Output parameters are L and NM. In addition, U and $Q_b$ may be calculated using Eqs. (20) and (22). Hence, $Q_b$ is input parameter and $Q_b$ can be calculated a posteriori, $Q_b^c$. $Q_b$ as input parameter and $Q_b^c$ have to be almost equal.

A complication in modeling is that the condition of a small Reynolds number, used in the theory based on Darcy Law becomes violated at higher blood velocities. The Reynolds number is the dimensionless ratio $$\frac{2aU}{\nu} < 1 \quad (23)$$

where 2a is the external fiber diameter; $\nu = 3.5 \times 10^{-2}$ cm²/sec is blood viscosity.

The role of inertial forces was investigated in relevant process of filtration with the use of granular bed. It was found that Kozeny equation is quite acceptable up to Re=6. The non-linear Navier-Stokes equation was used in a recent simulation of shear rate within the hollow fiber bundle. The linear dependence between shear stress and Re (blood flow rate) is predicted for the range of Re values 1 to 10. This means that the contribution of non-linear inertial term is small. Consequently, the approach based on cylindrical cell model Example initially developed for Re<1, perhaps, continue to be approximately valid for 1<Re<10 as well. We compared numerical information about shear stress dependence on Re and our calculations with the use of Example 6 (Equation E1.3b) for shear rate based on cylindrical cell model and found that the differences in results are not large.

Hence, the recent simulation shows that Table 3 may be used for estimates even for Re that are not small, in spite of the fact that inertial forces are not accounted for in approach, based on the hydrodynamic cylindrical cell model.

The method of determination of geometrical parameters for filter for uniform hemofiltration which corresponds to a certain high blood superficial velocity U consists of the following steps:

Selection of a standard dialyzer in which hollow fibers have a hemocompatible surface. If there is a possibility for preparation of hollow fiber with a better quality of hemocompatible external surface, a standard dialyzer has to be fabricated using such a surface. The ultrafiltration coefficient of dialyzer UC and $S_u$ have to be measured for the standard dialyzer.

The ultrafiltration coefficient of membrane uc has to be calculated with the use of Eq (9) on the basis of the dialyzer testing, namely with the use of measured UC and $S_u$.

Selection of sufficient high pressures $P_{in}$ and TMP. Usually linear dependence between $Q_u$ and TMP exists for pressures lower than 150 to 200 mmHg a.) Determination of membrane surface $S_u$ for miniature filter with the use of Eq (8) required for $Q_u$=1.5 ml/min at selected $P_{in}$ and TMP.

b.) The calculation of bundle volume LMN for miniature filter by means of the substitution of its membrane surface area $S_u$ into Eq (12).

c.) After LMN corresponding to selected values $P_{in}$ and $Q_u$=1.5 ml/min is established, the specification of L value with the use of Eq. (19) determines U($P_{in}$, L) according to Eq (3).

d.) NM is specified according to Eq (21) after LMN and L are selected.

In addition to the bundle having the theoretical parallelepiped shape, it would also be possible to build a fiber bundle of circular cross-section formed by coiling hollow fiber around a spool may be used for uniform Outside-In Flow Filtration (FIG. 22B). Two extremities of fibers cut in axial direction are compressed against each other and stabilized by potted resin layers which isolate the filtrate from the blood stream. Internal and external surfaces of the bundle are sealed by means of coverage by a plastic barrier. Inlet and outlet headers of conical shape may be attached to opposite surfaces of the bundle, which have the shape of a hollow disk. There is some similarity with the design of a cardiopulmonary bypass oxygenator only with respect to blood flow, because the collection of filtrate from outlets of all hollow fibers add an additional portion of design, namely outlet header for filtrate. Hence, the design combines features of an oxygenator and of a hemofilter that uses Outside-In Flow Filtration. One embodiment describes the design of filter for uniform Outside-In Flow Filtration based on the bundle with coiled hollow fibers (FIG. 22B).

An even larger difference exists between relationships that dictate the determination of operational parameters, in particular, geometrical parameters. This is necessity of enhancement of oxygen transport in blood that is achieved by increasing of blood velocity. In an oxygenator, the volumetric flowrate of blood past the fibers is several times larger than the volumetric flowrate of blood out of and into the patient's circulator system. In contrast, for a hemofilter, these two parameters are equal to each other.

The theory of oxygen mass transport from fiber surface into the blood stream is the basis for the specification of geometrical parameters of an oxygenator. Although high velocities are required in OIUF too in order to suppress thrombosis, the condition for its achievement is different. The membrane has to be sufficiently large for providing the required ultrafiltration flux, i.e., this dictates the bundle volume. In contrast, the entrance area for blood flow has to be sufficiently small to achieve high entrance linear velocity; which cannot be large for miniature wearable hemofilter. In distinction, the volumetric velocity of blood which undergoes oxygenation does not affect essentially the geometrical parameters of oxygenator. The required ultrafiltration flux and restricted volumetric velocity of blood are input parameters in program for specification of geometrical parameters for the outside-in hemofilter which makes it very different from modeling for oxygenator design.

The required ultrafiltration flow determines the membrane surface area and bundle volume in case of bundle formed from coiled fibers too. It is almost small as in the case for parallelepiped bundle. Three geometrical parameters $L_1$, $R_1$, $R_2$, interconnected by the condition of the chosen value for volume $\pi(R_2^2-R_1^2)$ are specified by the condition of maximal linear velocity at acceptable volumetric velocity.

A large similarity between two versions of uniform Outside-In Flow Filtration is illustrated in FIG. 22C where a) is bundle of parallelepiped shape and b) is bundle in shape of hollow cylinder with internal radius $R_1$ and external radius $R_2$. The length of blood path in both cases is nominated as L. The difference exists in cross-section area for blood stream, which is MN in rectangular case and $\pi(R_2^2-R_1^2)$ in cylindrical case. In order to obtain the dependencies for $Q_u$ and $Q_b$, first an analog of (Eq 10) for $S_u$ has to be derived. It turned out, that the derivation is longer, because fibers of different length in the range $2\pi R_1$ to $2\pi R_2$ contribute to $S_u$.

$$S_u = \frac{\pi^2 \alpha L}{2a}(R_2^2 - R_1^2) = \frac{\pi \alpha}{2a}\pi(R_2^2 - R_1^2)L \tag{24}$$

As there is so much similarity in determination of output parameter LMN or $\pi(R_2^2-R_1^2)L$ and $L_{cy}$ (length of coiled bundle) or L, we repeat all derivations described above for parallelepiped design using Eq. (24) instead of Eq. (12). The results are presented in next equations:

$$\pi(R_2^2 - R_1^2)L_{cy} = \frac{4}{\pi}LMN \tag{25}$$

$$L_{cy} = \left(\frac{4}{\pi}\right)^{0.5} L \tag{26}$$

$$U_{cy} = \left(\frac{\pi}{4}\right)^{0.5} U \tag{27}$$

$$\pi(R_2^2 - R_1^2) = \frac{\pi(R_2^2 - R_1^2)L_{cy}}{L_{cy}} = \frac{4}{\pi}\left(\frac{\pi}{4}\right)^{0.5}\frac{LMN}{L} = \left(\frac{4}{\pi}\right)^{0.5} MN \tag{28}$$

where $L_{cy}$ and $U_{cy}$ are length of hollow cylindrical bundle and axial blood velocity, i.e., volumetric velocity along bundle. $Q_{bcy}$ may be obtained with the use of Eqs. (27) and (28)

$$Q_{bcy} = \pi(R_2^2 - R_1^2)U_{cy} = \left(\frac{4^{0.5}}{\pi}\right)\left(\frac{\pi}{4}\right)^{0.5} NMU = NMU = Q_b \tag{29}$$

$Q_b$ is an input parameter. As $Q_{bcy}$ which is output parameter is equal to $Q_b$, this demonstrates the self-consistency of derived equations.

As $4/\pi$ differs from 1 by only about 25%, Eqs. (25), (26), (27) and (28) characterize $\pi(R_2^2-R_1^2)L$, $L_{cy}$, $U_{cy}$, $\pi(R_2^2-R_1^2)$, $Q_{bcy}$ almost by dependencies for LMN, i.e., Eq. (14) for L, i.e., Eq. (19) for U, i.e., Eq. (20) for NM, i.e., Eq. (21) for $Q_b$, i.e., Eq. (22)

The small difference in output parameters for parallelepiped design and hollow coiled cylinder design when the set of input parameters is the same, make it unnecessary to perform further numerical illustration, because Table 1 shows data which with account for multipliers $(4/\pi)$, $(4/\pi)^{0.5}$ and $(\pi/4)^{0.5}$ may be addressed to coiled hollow cylindrical bundle. There is almost the same result with respect to hydrodynamic conditions for thrombosis, when $Q_b$, U and consequently shear rate are the same for both designs. The shear rate is calculated with equations of example (E1). There may, however, be differences with respect to the ease or methods of fabrication of the various different hemofilters.

Additional analysis were made and support that the above design methods apply to outside-in filter where blood flow in direction parallel to the fiber axis. Such designs are detailed in the embodiments of the invention provided elsewhere herein.

EXAMPLE 5

This Example describes in more detail the hydrodynamics of Outside In Flow Filtration as compared to conventional hemofiltration practice. This derivation demonstrates that in Outside-In Flow Filtration, a moderate accumulation of clots results in only a much smaller percentage increase in pressure drop A semiquantitative estimation of thrombi volume fraction (ratio of total thrombi volume to total volume of IFS) is possible assuming they are uniformly distributed downstream, which resembles their intuitively random distribution within blood cross-section. Naturally, they are distributed randomly downstream as well. However, the random distribution can be replaced by a periodic distribution (in first approximation), according to an approach which is often used in hydrodynamic porous (disperse) system.

The amount of thrombi required for essential clogging (decrease in blood flow rate) is L/4a times as large in Outside-In Flow Filtration as in conventional practice. A crude estimate follows that therapeutic treatment may be longer due to Outside-In Flow Filtration by about a factor of L/2a, assuming that the amount of thrombi grows linearly with time.

To illustrate the notion of isolated distribution of thrombi within the Inter Fiber Space, in FIG. 23A we show nine fibers of radius a and introduce flat layers perpendicular to fibers with the thickness 2a.

Thrombosis depends on a combination of factors including blood properties, anticoagulation treatment, membrane materials, hemocompatibility and flow parameters used during the process.

In regard to conventional hemodialysis or hemofiltration, researchers have focused for many years on improving the hemocompatibility of the internal lumen surface of hollow fiber membranes in order to retard thrombosis for the blood flowing inside the lumens. However, for embodiments of the Outside-In Flow Filtration invention, the blood flows on the outside of the hollow fibers. Accordingly, it becomes desirable to provide hemocompatibility for the external surface of hollow fibers. Experience with conventional hemodialysis and other forms of extracorporeal blood treatment also focuses on the use of anticoagulants such as heparin. It may be useful, when making experimental comparisons, to standardize the amount of heparin treatment used. Also important are the values of key process parameters that influence the hydrodynamic detachment force of thrombi or platelet activation or adhesion, such as the shear stress and consequently the shear rate. Hence, in order to properly compare filter life or clogging during experiments comparing conventional intra-luminal hemofiltration and Outside-In Flow Filtration, it is appropriate to use similar shear rate and blood anticoagulation properties.

However, even with appropriate choices for all of these parameters, it is still possible for thrombi to form, and this brings the major question of how the blood flow path can be designed so that thrombi that do form have as little impact as possible on pressure drop of blood flow through the cartridge.

One important step related to the influence of the total amount of thrombi on the filter hydrodynamic resistance. The distribution of thrombi within inter-fiber space (IFS), for example, uniform or non uniform distribution, strongly affects the growth of hydrodynamic resistance during long-term blood processing. In this context, we have not found a suitable definition for the term clogging in the literature to describe this particular case. Sometimes clogging is identified with the filling of Inter Fiber Space which may be quantified as the ratio of the total volume of thrombi to the volume of total Inter Fiber Space. The definition of local volume fraction used here assumes that a volume exists which contains numerous thrombi and simultaneously is small in comparison to the linear dimension of the fiber bundle (its length L and diameter d). These conditions are satisfied if the thrombi dimension l is not very large, for example, when the thrombi dimensions are approximately the fiber diameter (2a), because the condition $$2a<<d<<L$$

is satisfied due to the large difference between d=2 cm and 2a~0.03 cm.

The notion of local volume fraction allows us to characterize clogging which is non-uniform in space. The notion of Inter Fiber Space as the space available for blood flow during Outside-In Flow Filtration changes when the clogging occurs during blood processing. The space available for blood flow is confined by fibers and by thrombi. In summary, the situation may be characterized as the change in geometric conditions for blood flow.

As soon as the geometric conditions corresponding to fiber and thrombi distribution in space are known, the task of theoretical hydrodynamics, which describes blood flow within a fiber bundle change due to thrombosis, is determined. Indeed, the equation for blood flow is known, while the boundary conditions are given for surfaces of fiber and thrombi as zero velocity along them, which is the known universal boundary conditions in the hydrodynamics of viscous flow. The uniqueness of the theoretical problem is that the locations of boundary surface, i.e. thrombi locations are unknown. The current level of knowledge is not sufficient to predict the spatial distribution of thrombi.

Taking into account this indefiniteness, different possibilities for thrombi distribution in space have to be considered. In fact, the choice of such characteristic distributions for thrombi represents the second step in the analysis.

The third step in the analysis is the hydrodynamics analysis. A contribution of certain characteristics of thrombi distribution due to the growth of entrance filter pressure, for example growth of hydrodynamic resistance at constant blood flow rate, has to be quantified.

There has been am imbalance in research of thrombosis influence on blood flow. In fact all attention has been focused on the first sub-process, while even qualitative notions about second and third sub-process are not formulated or even discussed. At first glance, this may be justified because the first sub-process predetermines what will happen in the third step.

A significant advantage of Outside-In Flow Filtration compared to conventional intra-luminal hemofiltration is caused by the significant difference between blood flow patterns in the Inter-Fiber Space (IFS) compared to the blood flow pattern inside fiber lumens, and by how thrombi affect the hydrodynamic resistance in each case. The hydrodynamic resistance of Outside-In Flow Filtration as a function of thrombi accumulation within the filter follows completely different behavior. The property which causes hydrodynamic resistance in the Inter Fiber Space during Outside-In Flow Filtration to be relatively unaffected by the presence of moderate amounts of thrombi is the fact that the flow field can be characterized as a three-dimensional (3D) system of interconnected hydrodynamic channels (similar to what is sometimes referred to as pores). In contrast, blood flow in the fiber lumens during conventional intra-luminal hemofiltration only follows a one dimensional (1D) flow pattern.

In conventional intra-luminal hemofiltration, one thrombus is sufficient to clog any one fiber. As a result, N thrombi are sufficient to clog the flowpaths through N hollow fibers. In this case, the increase in hydrodynamic resistance during treatment is very closely related to the number of fibers that are clogged by thrombi.

In contrast, for the case of blood flow in the inter-fiber space during Outside-In Flow Filtration, the same number of thrombi within the Inter Fiber Space of an identical fiber bundle will only cause a slight increase in the hydrodynamic resistance of the filter during blood processing.

A thrombus formed within the Inter Fiber Space during Outside-In Flow Filtration may form a local obstacle for blood movement in the axial direction or other specified direction, depending on the details of the filter design. However, when a blood stream encounters a thrombus, the blood stream will change its trajectory in the 3-D space of the Inter Fiber Space to avoid the thrombus and will flow around the thrombus (FIG. 23B). This rearrangement of flow will result in only a small increment of increase in the overall hydrodynamic resistance of the flowpath, and follows an entirely different mathematical and physical relationship.

To further illustrate this property, it is possible to introduce the notion of isolated distribution of thrombi within the Inter Fiber Space. As illustrated for sake of example, we show nine (9) fibers of radius (a). Further, we imagine subdividing the flowpath length into flat layers each layer being perpendicular to the long direction of the fibers, and each layer having thickness (2a) (FIG. 23A). For the fiber bundle of a typical hemodialyzer the number of these layers would be L/2a~700 (assuming a=150 micron, L=20 cm). However, we only show three layers crossing with fibers, while the fibers themselves are not shown. Assuming that thrombi formation is a random process, there are nine (9) layers that have one thrombus per layer, while there remain almost 700 other layers that do not contain any thrombi. Three layers are shown only with blood streaming lines obviating the thrombi during flow. It is clear without any computations that thrombi in this example will almost not affect the hydrodynamics of the filter and therefore they essentially cannot affect the overall axial pressure drop. In a striking distinction, in conventional hemofiltration with intra-luminal blood flow, these nine (9) thrombi will completely stop blood flow inside nine (9) hollow fibers. This example illustrates the fundamental difference between conventional intra-luminal hemofiltration and Outside-In Flow Filtration with respect to the influence of thrombi on the overall axial pressure drop of blood flow.

The understanding of the Inter Fiber Space as a system or network of interconnected hydrodynamic channels is the central notion for understanding the advantages of Outside-In Flow Filtration in comparison with conventional intra-luminal hemofiltration. The notion of imaginary hydrodynamic channels for axial flow can be illustrated (FIG. 23C), when the fibers are arranged in a square lattice, and the porosity is not high, i.e. the fiber volume fraction is rather high such as 0.4-0.5.

A portion of the Inter Fiber Space confined by four fibers is depicted in (FIG. 23C). In the narrow gaps between fiber surfaces the liquid velocity is very low because viscous retardation of movement is strong the narrower the gaps. Narrow gap boundaries are marked as g in FIG. 23C. In addition, the cross-section for flow is small within the gap. Hence the contribution by the gap to the overall flow is negligible. It is sufficient to account for flow only within the broad portion of the hydrodynamic pore or channel, which is surrounded by the boundary $f_1g_1f_2g_2f_3g_3f_4g_4$. For example, narrow gaps may serve as walls for the imaginary hydrodynamic channels surrounded by the mentioned boundaries.

The difference between imaginary channels and narrow gaps, shown in FIG. 23C) disappears if a fiber is surrounded by 6 equidistant fibers in a hexagonal array (FIG. 23D). Nevertheless, the conclusion obtained with the notion of imaginary channels, introduced for the square array, continues to be true for the case of a hexagonal array of fibers. Indeed, as thin gaps with large hydrodynamic resistance are absent, the interconnection within the Inter Fiber Space becomes stronger and this will result in further reducing the influence of thrombi on the hydrodynamic resistance.

While only thrombi with dimension of approximately the fiber diameter are considered here, in reality both larger thrombi and smaller thrombi may exist. However, our microscopic examination of cartridges, after an Outside-In Filtration experiment that extended for 100 hours of hemofiltration time, revealed the presence of only very few thrombi that could be described as larger than a fiber diameter. Even when a thrombus with dimension larger than fiber diameter exists and may overlap some adjacent hydrodynamic channels, there will still be adequate opportunity for blood to flow around such a thrombus through other adjacent channels.

In contrast to the simplicity of the qualitative proof of the hydrodynamic advantage of Outside-In Flow Filtration in comparison with conventional intra-luminal hemofiltration, the quantitative analysis is very difficult. Nevertheless, there are several factors which may simplify the problem.

As a semi-quantitative estimate, it is sufficient for practical purposes to show that the filter lifetime maybe increased by at least about five times in the case of Outside-In Flow Filtration in comparison with the average 20 hours achievable in conventional intra-luminal hemofiltration. Essentially, the modeling simplifies the task as long as the volume fraction of thrombi remains sufficiently small. We discovered that this condition may be satisfied during 100 hours of Outside-In Flow Filtration according to our experimental results as described herein.

The modes of filter clogging may depend significantly on the level of anticoagulation used during Outside-In Flow Filtration. These differences are manifested when comparing the cases when blood is unstable (without adding heparin) and when blood stability is increased by heparin addition. Our success in determining the prevailing clogging mode at typical heparin concentrations by microscopic visualization of Inter Fiber Space clogging in long-term experiments establishes the main manifestation or indication that the thrombi are distributed in an "isolated" thrombi distribution. The discovery that the thrombi are distributed in an isolated thrombi distribution simplifies the modeling and makes it possible to demonstrate the hydrodynamic advantages of the Outside-In Flow Filtration mode.

It is possible that for situations of low heparin concentration, the assumption of isolated thrombi distribution might not be valid. Such a case becomes more difficult to model. In the absence of isolated thrombi distribution within Inter Fiber Space, such as at low heparin concentration, the hydrodynamic advantages of Outside-In Flow Filtration may be less apparent or less dramatic.

For purposes of this analysis, we follow a classical assumption regarding the design, modeling and analysis of hemofiltration, in which the central goal is that the process be uniform in space to the greatest possible degree. This condition might not be perfectly satisfied when considering flow either inside thousands of fibers or outside them.

We assume the deposited thrombi within Inter Fiber Space to be mono-disperse and their diameter ($d_{tr}$) is approximately equal to the internal diameter of a fiber. We also assume the presence of imaginary hydrodynamic channels within Inter Fiber Space and disregard the small differences in their dimensions. With respect to the case of conventional intra-luminal hemofiltration, one thrombus is sufficient to clog one fiber lumen. In the case of Outside-In Flow Filtration, one thrombus only influences the local hydrodynamics.

The consequence of local clogging is very sensitive to the axial dependence of thrombi distribution within Inter Fiber Space. In one example, uniform axial distribution of thrombi within Inter Fiber Space is considered, i.e., the same number of thrombi ($n_{tr}$) is located within any cross-section of the fiber bundle. However, as the thrombus dimension is 2a, it is more convenient to represent the fiber bundle during Outside-In Flow Filtration as a sequence of layers, called imaginary layers, perpendicular to the lengthwise axis of the fiber bundle, with each layer having a thickness 2a.

As the comparison of conventional intra-luminal hemofiltration and Outside-In Flow Filtration is accomplished for identical total numbers of thrombi (NO equal to the total number of channels n, and as the thrombi are assumed to be uniformly distributed among the imaginary layers (and the quantity of such layers is L/2a), the mean quantity of thrombi per layer $n_{tr}$ is:

$$n_{tr} = n\left(\frac{L}{2a}\right)^{-1} = n\frac{2a}{L} \qquad (2)$$

This in turn characterizes the decrease in the number of unclogged channels for each imaginary layer.

As the decrease of in the number of open channels, $n_{tr}$, is the same for all 2a layers, it means that $n_{tr}$ is the decrease in the amount of imaginary channels for the Inter Fiber Space as a whole according to the assumption of axially uniform clogging. On the other hand, the hydrodynamic permeability of the Inter Fiber Space as a whole is proportional to the amount of imaginary channels that remain open. Thus, the decrease ΔK in hydrodynamic permeability is proportional to $n_{tr}$. Hence, $$\frac{\Delta K}{K} = \frac{n_{tr}}{n} \qquad (3a)$$

where K is the Darcy constant (discussed elsewhere herein) for a clean Inter Fiber Space (no thrombi present), or $$\frac{\Delta K}{K} = \frac{2a}{L}\frac{N_{tr}}{n} \qquad (3b)$$

when the total amount of thrombi $N_{tr}$>n.

While for the conventional situation of intra-luminal blood flow, $N_{tr}$=n is sufficient to stop flow in all the fibers, in the situation of Outside-In Flow Filtration the same total amount of thrombi leads to a negligible relative decrease of Darcy constant (2a/L), according to Equation (3a). This is for the particular case of the Equation (3b) for $N_{tr}$=n. During Outside-In Flow Filtration, $N_{tr}$ may exceed n by as much as orders of magnitude, and according to this relationship, even for that severe situation, the decrease in the hydrodynamic permeability for the Outside-In Flow Filtration case remains small according to Equation (3b) because 2a/L is very small, only about $1.4 \times 10^{-3}$.

The linear dependence between ΔK and $N_{tr}$ exists for $N_{tr}$ sufficiently small in comparison with n. A crude estimate for the maximal $N_{tr}$ in Equation (3a) may be obtained considering the condition for the possibility of blood flow from an imaginary channels clogged by thrombus into adjacent imaginary channels. This is always possible when a free adjacent channel exists. Meantime, the adjacent channel may be clogged as well. Hence, a free adjacent channel has to exist for any clogged channel. This means that the amounts of clogged channels $n_{tr}$ has to be approximately equal to the amount of free channels (n−$n_{tr}$) for any imaginary cross-section, for example $n_{tr}$=0.5n. In this case, approximately half length of any fiber is covered by thrombi. So, this exercise illustrates the potential of Outside-In Flow Filtration to be much less affected by a given number of thrombi than the conventional practice, at least for the assumption of thrombi being isolated.

Experimentally, our microscopic examination of the Inter Fiber Space after 100 hours of Outside-In Flow Filtration operation revealed an axially non-uniform thrombi distribution where thrombi were mostly found to predominate near the entrance layer of the orbital distributor with thickness (l), and their amount depended on the concentration of heparin in the blood. Beyond this entrance region, there was found to be a gradual decrease in thrombi concentration within the entrance layer with increasing distance past the entrance. This complicates the experimental determination of l. It appears that the consistent modeling of the influence of thrombi accumulation in the entrance zone on the hydrodynamic permeability requires the investigation of how the thrombi concentration depends on x. This is hard to quantify because of practical considerations that are hard to quantify. As a preliminary approach, we will only consider here that the thrombi distribution within the entrance zone is uniform. So, in other words, we may take the previous modeling approach that had been applied to the entire Inter Fiber Space of the entire fiber bundle, and instead now apply it only to a small region near the entrance of the fiber bundle. This means that thrombi amount $N_{tr}$ is uniformly distributed between the number of ½a imaginary layers within the entrance section, and that Equation (3b) addresses only the entrance zone with thickness l, i.e., $$\frac{\Delta K(l)}{K} = \frac{2a}{l}\frac{N_{tr}}{n} \quad (4)$$

$$\text{or } \frac{\Delta K(l)}{K} = \frac{2a}{l} \quad (5)$$

when $N_{tr}=n$. The designation $\Delta K(l)$ relates to the decrease of Darcy coefficient in the entrance zone only, while $\Delta K$ is the decrease in the hydrodynamic permeability of the bundle caused by the decrease of $\Delta K(l)$. The more narrow the entrance section is, the smaller l is in Equation (4), the larger will be the decrease in Darcy constant at the invariant $N_{tr}$, because the amounts of clogged imaginary channels increases as (l) decreases. While the flow in conventional intra-luminal Hemofiltration is completely stopped as already discussed, the decrease in hydrodynamic permeability remains small when the thickness of entrance zone l>>2a. However, $\Delta K(l)$ is orders of magnitude larger than $\Delta K$ in Equation (2), when l is orders of magnitude smaller than L at the same $N_{tr}$, because $$n_{tr} = n\frac{2a}{l} \quad (6)$$

is L/l times larger than that according Equation (2). With increasing $N_{tr}$, Darcy constant decreases. However, this decrease remains relatively small as long as $$N_{tr}/n < l/2a \quad (7)$$

Analysis of Equation (7) points to the conclusion that the significant advantage of Outside-In Flow Filtration at $N_{tr}>n$ remains with the exception of the case of very large $N_{tr}/n$. This is because while the fiber lumens are completely clogged in conventional Hemofiltration, some imaginary channels are preserved when l is large in the entrance section of the Outside-In Flow Filtration filter. These advantages may not be as significant when l is small.

Basically, the first calculation that assumed the thrombi were uniformly distributed of the entire filter Length L. This calculation uses calculation methods that are analogous, but it essentially concentrates the thrombi into a similar uniform distribution over just a short entrance length l of the fiber bundle rather than the entire length L of the fiber bundle. It can be understood that the impact of this thrombi pattern on the pressure drop across the cartridge is magnified by the factor L/l, in comparison to the previous result. Nevertheless, even in this situation, the dialyzer can still tolerate more thrombi than a conventional dialyzer, while remaining within a reasonable overall pressure drop.

At first glance, the direct prediction of the filter life for Outside-In Flow Filtration case seems impossible. However, some estimate is possible because filter life of about 20 hours is known from experience in CRRT (Continuous Renal Replacement Therapy) and because the ratio of filter life for Outside-In Flow Filtration and Hemofiltration may be estimated, when the condition, (7), is valid. Our analysis has shown that long term Outside-In Flow Filtration is possible at condition (7) which in turn is valid if the heparin concentration is not too low. When the condition (7) is not satisfied, the model based on isolated thrombi becomes invalid and another approximation is required. The model of remaining channels may be proposed when the condition (7) is not valid and volume fraction is not small. It is shown, that hydrodynamic advantage of Outside-In Flow Filtration still exists, even when the accumulated thrombi are only partially isolated as long as some channels remain open for flow.

Blood flow in the fiber lumens may only provide partial control in this case because the pressure and velocity distributions in the Inter Fiber Space might not be uniform, which leads to angular and axial dependence in ultrafiltration flow and hence in solute clearance. These facts forced Ronco to pay attention to the spatial distribution of dialysate flow in the Inter Fiber Space of conventional dialyzers. A recent technological achievement in this respect pertains to modifications in the dialyzer design by incorporating orbital distributors in an attempt to optimize the pressure and velocity distributions in the dialysate compartment Although many dialyzer manufacturers employ orbital distributors, some designs are better than others with respect to achieving uniform velocity distribution in the dialysate compartment. Although this may be relevant to the present invention, flow in the dialysate compartment is only concerned with the flow of the dialysate buffer which is basically water and does not provide insight as to handle flow for the development of Outside-In Flow Filtration. According to the present invention, achieving uniform distribution of velocity not only in the Inter-Fiber Space but also in every section of the filter during Outside-In Flow Filtration is one of the requirements needed to achieve hemofiltration with a very long service life of the cartridge. Specifically, thrombosis, which controls the onset of and the growth of the hydrodynamic resistance in the Inter-Fiber Space (IFS) during Outside-In Flow Filtration, is very sensitive to shear stress. It is possible to quantify the axial symmetric blood flow in some filters, and accordingly to control it, as described herein.

The Inter Fiber Space may be characterized as a three-dimensional (3D) system of interconnected hydrodynamic channels as distinguished from conventional hemofiltration, which is defined by one-dimensional (1D) flow inside fiber lumens. In conventional intra-luminal hemofiltration, N thrombi will block blood flow inside N fibers. During Outside-In Flow Filtration, orders of magnitude larger number of thrombi cannot block the Inter Fiber Space as long as the thrombi are mainly isolated from each other and blood can flow around the deposited thrombi. This mechanism explains the unique long-term blood processing achieved by Outside-In Flow Filtration in these experiments. Microscopic examination of sections of the fiber bundle showed that the deposited thrombi found in the Inter Fiber Space had dimensions about the size of the hydrodynamic channels and that they were isolated from each other.

While the outside-in flow methodology has been used in industrial processes such as microfiltration used in water purification, these applications primarily deal with removing solid particles from stable dilute suspensions such as suspended silt particles in water using the "dead end" filtration mode. There are many differences between this industrial water application as compared to blood processing or hemofiltration. The hydrodynamics of blood flow, the complex processes of thrombosis, modes of thrombi formation/deposition, and issues related to the irreversible deposition of molecules, cells and thrombi (aggregate of cells) within the filter and the concomitant clogging of the filter are sensitive to specific blood properties and to complex inter-dependent process variables. Due to these specific blood properties, researchers have primarily focused on improving the hemocompatibility of the internal lumen surface of hollow fibers to retard thrombosis during conventional intra-luminal hemodialysis or hemofiltration (the only mode currently used worldwide). While hemocompatibility has been shown to provide some small improvement in lowering thrombus formation, heparin coating of blood contact surfaces has not provided the necessary filter life increase. One of the reasons for this is that a single clot will block a fiber, and so development of multiple clots essentially increases the number of blocked fibers eventually leading to a clotted and unusable filter.

Other membrane improvements include tight thin skin luminal surfaces with larger voids on the outside of the fiber to allow for the ability of larger molecular weight solutes to move across the membrane while retaining a sharp cutoff to prevent protein leakage. Albumin and other protein leakage is not desirable in most situations due to the nutritional profile of the patients who use these modalities, as lower albumin levels are associated with higher mortality. Even though hemocompatibility of the lumenal surfaces has not significantly improved the thrombus formation profile and hence filter life for traditional hollow fiber blood filtration devices, these surface treatments can also be used in embodiments of the invention. Further development of Outside-In Flow Filtration may be accomplished by making the external surface of hollow fibers truly hemocompatible. Such a feature would lower thrombi formation, increasing the likelihood that formed thrombi are isolated from each other and blood can flow around the isolated deposited thrombi.

The mode of isolated thrombi distribution may not be valid for cases of low heparin concentration and this case become more difficult for modeling. In the absence of isolated thrombi distribution within the Inter Fiber Space, the hydrodynamic advantages of Outside-In Flow Filtration may diminish at low heparin concentrations. Later, this central topic will be discussed in detail.

The effect of the total amount of thrombi on the hydrodynamic resistance, thrombi distribution within the Inter Fiber Space, for example, uniform or non uniform, strongly affects the growth of hydrodynamic resistance during long-term Outside-In Flow Filtration processing. In this context, we have not found a suitable definition for the term clogging in the literature to describe this particular case. Sometimes clogging is identified with the filling of the Inter Fiber Space, which may be quantified as the ratio of the total volume of thrombi to the volume of total Inter Fiber Space. Numerous distributions for local volume fraction are possible for the same mean volume fraction. The definition of local volume fraction assumes that a volume exists which contains many thrombi and simultaneously is small in comparison to the linear dimension of the fiber bundle (its length 2a and diameter d). These conditions are satisfied if the thrombi dimension l is not very large, for example, when their dimensions are about fiber diameter (2a) because the conditions $$2a \ll d \ll L$$

does not cause an essential constraint due to the large difference between d=2 cm and 2a~0.03 cm.

The notion of local volume fraction allows us to characterize the clogging, which is non-uniform in space, in contrast to the traditional blood filtration devices. The notion of the Inter Fiber Space as the space available for blood flow during Outside-In Flow Filtration changes when only when severe clogging occurs during Outside-In Flow Filtration. The space available for blood flow is confined by fibers and by thrombi. In summary, the situation may be characterized as the change in geometrical conditions for blood flow. The main advantage of Outside-In Flow Filtration compared to conventional blood filtration devices lies in the significant difference between blood flow in the Inter Fiber Space compared to blood flow inside fiber lumens. The main advantage of the Outside-In Flow Filtration mode arises because the conditions for hydrodynamic resistance growth between the two modes are very different. In Outside-In Flow Filtration the resistance is lower. Even when a thrombus with a dimension larger than fiber diameter may overlap within the Inter Fiber Space, some adjacent channels formed by wall of the fiber remain and the blood will still flow through a different trajectory through other adjacent channels formed by the outside wall of the fiber.

One may believe that these surface thrombi may lower clearance of waste products, which is a critical outcome traditional intra lumen blood flow devices, because the effect of intraluminal clot formation on solute removal due to the reduction surface area of the membrane bundle. A clot blocks a fiber in these devices. This effect is more pronounced with the diffusive therapies Hemofiltration and Hemodiafiltration. With the conventional approach a clot in the intraluminal area of the fiber, blocks the flow in the fiber, eliminating the surface area of the entire fiber. In the Outside-In Flow Filtration filter, the size of the clot or thrombus reduces the surface area of the fiber bundle only by the specific dimension of the clot, with much lower loss of surface area. In addition the external surface of the fiber is 1.2 to 1.25 greater than the internal diameter of the fiber so even with some thrombus formation in the Inter Fiber Space with Outside-In Flow Filtration filters our testing has demonstrated that Outside-In Flow Filtration can achieve the same clearance of salt and vitamin $B_{12}$ as conventional dialysis, and may be considered for both diffusive and convective therapies such as Continuous Renal Replacement Therapy at the Ultrafiltration rates used in current therapy.

EXAMPLE 6

This Example is a discussion about the Darcy Constant and shear and mathematical derivations of low Reynolds number flow past two different orientations of arrays of identical circular cylinders.

Thrombosis tends to occur at conditions of undesirably low shear rate and undesirably high shear rate, while there is a range of intermediate shear rates at which the rate of thrombosis is not very large. In conventional intra-luminal blood flow, the shear rate can be easily quantified by an equation derived from Poiseuille flow. In contrast, the task for calculating shear rate during Outside-In Flow Filtration requires different considerations due to the more complex flow within the Inter Fiber Space.

The velocity distribution is characterized by local velocities at any point in the system. The simplest case is for a velocity distribution that is uniform, i.e., any local velocity is the same and consequently it is equal to velocity averaged over the entire space of the system. This means uniform velocity may be easily determined because the product of its value and area of cross-section perpendicular to flow is the measurable volumetric velocity flow rate. This velocity is called superficial velocity and is equal to the ratio of volumetric velocity to cross-section area.

The notion of superficial velocity allows one to describe transport within heterogeneous system, i.e., porous system, as within a homogeneous system. The notion of superficial velocity is useful for measurement and for formulation of the main empirical regularity in hydrodynamics porous media, known as Darcy's law, which interconnects superficial velocity and pressure gradient. Uniform structure of porous space predetermines uniformity of superficial velocity, if condition of flow at entrance and exit of the system is uniform.

The notion of superficial velocity may be used for characterization of non-uniform flow as well. Around any point a physically small volume may be considered, i.e., volume within which the velocity variation is small, and relevant cross-section perpendicular to flow. The ratio of flow rate within this physical small volume to relevant cross-section is local superficial velocity.

Although superficial velocity is proportional to pressure gradient, the superficial velocity is not sufficient to describe the system because the constant coefficient (Darcy constant, K) in this relationship is unknown. In addition, the knowledge of the superficial velocity is not sufficient for calculation of shear rate. The shear rate is required for the external surface of fibers while the use of the superficial velocity considers the disperse phase (fiber) and the dispersion media (pores) as a single homogeneous system, where inter-phase surface (fiber surface) is absent. Hence, a further level of detail of flow characterization is required to quantify shear rate, namely velocity distribution along individual fibers between them (superficial velocity parallel to fibers) or velocity distribution around fibers (superficial velocity perpendicular to fibers). This is referred to herein as the microscopical level in characterization of velocity distribution, or microscopic velocity when fibers are identical. If fibers of a bundle have the same diameter, and are parallel and equally spaced, every fiber may be surrounded by identical hydrodynamic cell and the velocity distribution within this cell will be valid for any fiber of the bundle. This allows one to quantify shear rate for surface of any bundle. The superficial velocity characterizes the velocity distribution on the level of the fiber bundle, microscopic velocity characterizes velocity distribution on the level of single fibers. Their interconnection is obtained by means of integrating microscopic velocity on the cross-section of cell that yields flow rate in cell, whose ratio to cell cross-section yields superficial velocity and consequently, its interconnection with microscopic velocity. The integration of superficial velocity over bundle cross-section yields flow rate through the bundle. Consequently, the microscopic velocity distribution and shear rate are expressed in terms of the volumetric flowrate through bundle, which is measurable or easily known.

Two analytical results are available in the literature, both in Happel and Brenner [Happel, J., and H. Brenner. Low Reynolds Number Hydrodynamics, Prentice Hall, 1965]. These results are for flow parallel to an array of identical cylinders, and for flow perpendicular to an array of identical cylinders. Both of these situations are worth analyzing because both situations occur for flow in the housing regions of typical dialyzers.

The viscous flow along an array of parallel equally spaced cylinders at low Reynolds number is one of the basic hydrodynamics of porous media. It is considered in Chapter 8 of Happel and Brenner on the basis of a cell model. The identical cells around any equidistant cylinder may be formed as it is shown in FIG. 23D. b is the radius of the cylindrical surface of the cell as determined by Equation (E1.1).

$$\frac{a^2}{b^2} = \alpha \quad (E1.1)$$

The axial flow within the Inter Fiber Space is completely characterized by the flow within a single cell. The flow along the cell is the flow between coaxial cylinders, which is a well-known example of a hydrodynamic problem that has an exact solution. The flow velocity is given by Equation (8.4.19) in [Happel and Brenner].

$$u = -\frac{1}{4\mu} \times \frac{dp}{dz}\left[(a^2 - r^2) + 2b^2 \ln\frac{r}{a}\right] \quad (E1.2)$$

where $\mu$ is viscosity, r is radial coordinate, i.e., the distance to cylinder axis. Equation (E1.2) satisfies the boundary condition of viscous liquid that its velocity equals zero on the solid surface, i.e., at r=a. The derivative for u(r)

$$\frac{du}{dr} = \frac{1}{2\mu} \times \frac{dp}{dz}\left[r - \frac{b^2}{r}\right] \quad (E1.3a)$$

satisfies the well-known boundary condition that shear on cell surface du/dr(b) has to be equal to zero. The shear rate on external surface of fiber is $$\frac{du}{dr}(a) = \frac{1}{2\mu} \times \frac{dp}{dz} \times \frac{(a^2 - b^2)}{a} = -\frac{a\varepsilon}{2\mu(1-\varepsilon)} \times \frac{dp}{dz} \quad (E1.3b)$$

where Equation (E1.1) is used with account that porosity $\varepsilon = 1 - \alpha$ where $\alpha$ is solidity.

The substitution $\mu$=3.5 centipoise, a=150 micron, dp/dz~$\Delta$p/L, $\Delta$p=40 mmHg, L=20 cm and $\varepsilon$=0.62 as measured porosity for Asahi Rexeed® dialyzers and the transformation to common system of units yield shear rate 960 sec$^{-1}$ in Zone 2 of the filter which agrees with optimal shear rate range recommended for blood flow.

The volumetric velocity in the cell between coaxial cylinders is obtained (Equation 8.4.20 in Happel and Brenner) by means of integration $$Q = 2\pi \int_a^b urdr = -\frac{\pi}{8\mu} \times \frac{dp}{dz}\left(\frac{4a^2b^2 - a^4 - 3b^4 + 4b^4 \ln\frac{b}{a}}{b^2}\right) \quad (E1.4)$$

The filtration velocity for the Inter Fiber Space is determined as $$U = \frac{Q}{\pi b^2} \quad (E1.5)$$

and satisfies the general equation of Darcy for porous media $$U = -\frac{K}{\mu}\left(\frac{dp}{dz}\right) \quad (E1.6)$$

Combining Equations E1.4, E1.5 and E1.6 yields the coefficient of permeability for Darcy equation in the particular case of an array of parallel cylinders (Equation 8.4.21 in Happel and Brenner)

$$K = \frac{\pi}{8}\left(\frac{4a^2b^2 - a^4 - 3b^4 + 4b^4\ln\frac{b}{a}}{a}\right) \quad (E1.7)$$

The well-known Carman-Kozeny Equation, derived on the basis of semi-empirical considerations, also presents an expression for K in Darcy equation (Eq. 8.4.22 in [Happel and Brenner])

$$K = \frac{\varepsilon m^2}{k} \quad (E1.8)$$

where $\varepsilon$ is porosity, m is hydraulic radius defined for porous media as ratio of free pore volume to the area of their wetted surface while k is so called Kozeny constant. k is a dimensionless number. It was assumed that k is an invariant for all random porous media, no matter what are the particle dimensions and porosity, which is confirmed approximately by much experimental data. In the case of the flow parallel to cylinders $$m = \frac{(b^2 - a^2)}{2a} \quad (E1.9)$$

The substitution in Equation (E1.8) yields K for the inter-fiber space $$K_{ifs} = \frac{(1-\alpha)^3 a^2}{4k\alpha^2} = \frac{\varepsilon^3 a^2}{4k(1-\varepsilon)^2} \quad (E1.10)$$

where Equation (E1.1) is used.

A small difference between Equation (E1.10 and Equation (E1.8) transformed with the use of Equation (E1.1) was found for values of $\alpha$=0.4 and 0.5 inherent in dialyzer design.

There is also another ideal situation that is useful to analyze, namely the situation for flow perpendicular to an array of equally-spaced parallel cylinders. In the Asahi dialyzer, near the distributor, flow between the fibers is mainly perpendicular to the fibers, while in the main part of the dialyzer, the flow in the Inter Fiber Space is mainly parallel to the fibers. In our experiments, with blood flowing between the fibers, thrombi were mainly observed near the supply distributor. Thus, it is important to characterize the case of blood flow perpendicular to fibers.

A similar cylindrical cell model may be used to quantify blood flow perpendicular to cylinder. In this case the velocity distribution depends on two cylindrical coordinates, r and angle $\theta$. Angle $\theta$ increases in direction of flow. Two components characterize the velocity distribution. The component $U_\theta(r,\theta)$ characterizes the movement in direction of increasing angle $\theta$, the component $U_r(r,\theta)$ is radial one. The pressure gradient has two components too. The vector form of Stokes equation is represented as a system of two equations. The approach to solve the mathematical problem is described in [Happel and Brenner].

An auxiliary function $\phi(r,\theta)$ is introduced which allows to represent the distributions for velocity components (Equation 8.4.25 in [Happel and Brenner])

$$U_r(r,\theta) = \frac{1}{r} \times \frac{\partial \phi}{\partial \theta}, \quad (E1.11)$$

$$U_\theta(r,\theta) = -\frac{\partial \phi}{\partial r}$$

After the substitution of velocity component in Stokes equation, biharmonic equation for $\phi$ arises. Its solution in general form is given in [Happel and Brenner] as Equation (8.4.27), where 4 unknown coefficients have to be determined from 4 boundary conditions $$\psi = \sin\theta\left[\frac{1}{8}Cr^3 + \frac{1}{2}Dr\left(\ln r - \frac{1}{2}\right) + Er + \frac{F}{r}\right] \quad (E1.12)$$

In [Happel and Brenner] it is considered that cylinder moves with velocity U inside cylindrical cell that determines the velocity distribution for liquid in contact with moving cylinder surface $$U_r(a,\theta)=U\cos\theta \quad U_\theta(a,\theta)=-U\sin\theta \quad (E1.13)$$

The radial velocity on imaginary cylindrical surface with radius b equals to zero $$U_r(b,\theta)=0 \quad (E1.14)$$

The absence of momentum transfer through the external surface of cell is accounted for in the fourth condition. As the transfer may occur to viscous flow, the condition may be addressed to shear rate on the external surface. However, it is shown in hydrodynamics of viscous flow that tangential viscous stress in the case of linear flow is expressed by vorticity. Its equation in cylindrical system coordinate for external surface of cylindrical cell has to be equal to zero, $$U_r(b,\theta)=0 \quad (E1.15a)$$

as well as normal component of velocity, i.e., $$\sigma_{r\theta}(b,\theta) = \mu\left[\frac{\partial U_0}{\partial r}(b,\theta) + \frac{1}{b} \times \frac{\partial U_r}{\partial \theta}(b,\theta) - \frac{U_r(b,\theta)}{b}\right] = 0 \quad (E1.15b)$$

This Equation is (8.4.28b) in [Happel and Brenner].

When the left hand side of boundary conditions are represented through the derivatives of function $\phi(r,\theta)$ with the use of Equations (E1.11) a system of four linear algebraic equations for determinations of C, D, E and F are obtained. The equation is given for only D in [Happel and Brenner]

$$D = -\frac{-2U}{\ln\frac{b}{a} + \left[\frac{a^4}{b^4 + a^4}\right] - \frac{1}{2}} \quad (E1.16)$$

It turns out, that E and D are cancelled when the velocities and their derivatives are substituted into Equation (E1.15). F and C remain in the equation $$-\frac{Cb}{2} - \frac{4F}{b^3} = 0 \qquad (E1.17)$$

that yields $$F = -\frac{Cb^4}{8} \qquad (E1.18)$$

The other three equations allow us to determine D, C, and E. We obtained for D Equation (E1.16) that confirms the consistency of the calculation. The derived equation for C is $$C = \frac{8\alpha^2 U}{2\ln\frac{b}{a}(a^4 + b^4) + (a^4 - b^4)} \qquad (E1.19)$$

The tangential viscous stress on the external surface of fibers which affects the onset of thrombosis is expressed by Equation (E1.15) where b has to be replaced by a.

It can be expressed by the left hand side of Equation (E1.17) which follows from Equation (E1.15) by means of substitution a instead of b $$\sigma_{r\theta}\left(a, \frac{\pi}{2}\right) = \frac{a}{2}\left(C + \frac{8F}{a^4}\right) = \left(\frac{b^4}{a^4} - 1\right)\frac{aC}{2} \qquad (E1.20)$$

where F is replaced by C using Equation (E1.17).

The final equation follows from Equation (E1.20) after C substitution according to Equation (E1.19) and replacement of the ratio a/b by solidity using Equation (E1.1)

$$\sigma_{r\theta}\left(a, \frac{\pi}{2}\right) = \frac{4\mu U}{a} \times \frac{1 - \alpha^2}{2\ln\alpha^{-0.5}(1 + \alpha^2) - 1 + \alpha^2} \sin\theta \qquad (E1.21)$$

It is seen that the angular dependence of tangential force is similar to that of tangential component of velocity (E1.13) and that it increases with decreasing solidity, i.e., with the increasing porosity. The derived Equation (E1.21) is illustrated in Table E1.1 for normalized function $\sigma_{r\theta}\mu$, $\theta=\pi/2$, $\alpha=0.4$ and $\alpha=125$ micron.

TABLE E1.1

| | U, cm/sec | | | |
|---|---|---|---|---|
| | 1 | 2 | 5 | 10 |
| $\sigma_{r\theta}/\mu$, sec$^{-1}$ | 1400 | 2800 | 7000 | 14000 |

The Table E1.2 presents the result of calculation for K made with the use of cell model and Carman-Kozeny equation (E1.10) for flows parallel and perpendicular to fibers.

TABLE E1.2

| | K$_{\text{II}}$/a$^2$ | | K$_\perp$/a$^2$ | |
|---|---|---|---|---|
| | Model | | | |
| | Cell Model | Carman-Kozeny Model | Cell Model | Carman-Kozeny Model |
| | Equation | | | |
| ε | E1.7 | E1.10 | E1.22 | E1.10 |
| 0.6 | 0.087 | 0.085 | 0.07 | 0.06 |
| 0.8 | 0.54 | 0.66 | 0.42 | 0.47 |

The Table demonstrates excellent agreement between predictions according to cell model and Carman-Kozeny model. Both methods systematically reveal anisotropy. However, the orientation of flow with respect to fiber orientation affects permeability rather weakly. At least, the difference in geometry of the Inter Fiber Space and ideal bundle with equidistant fibers and their exact parallelism may cause larger difference in permeation. Taking this into account, we will use only one among two models and apply only one equation, no matter what is the orientation of blood flow respective to fiber is. We will use Eq. (E1.10) because of its simplicity.

Anisotropy of the Darcy Constant:

When K is determined according to Carman-Kozeny theory, i.e., by means of Eq. (E1.8), the anisotropy is characterized by difference in value of Kozeny constant, namely $k_{\text{II}}$, when flow is parallel to cylinder and $k_\perp$, when the flow is perpendicular to it. Table E1.1, which is a portion of Table 8.4.2 in [Happel and Brenner].

| ε | k$_{\text{II}}$ | k$_\perp$ |
|---|---|---|
| 0.9 | 7.31 | 11 |
| 0.8 | 5.23 | 7.46 |
| 0.7 | 4.42 | 6.19 |
| 0.6 | 3.96 | 5.62 |
| 0.5 | 3.67 | 5.38 |

Kozeny constant is present in denominator of Eq. (E1.8). As it is systematically larger for perpendicular case, Darcy constant is for all porosities smaller when flow is perpendicular to fibers. As to the numerator of Eq. (E1.8), it is invariant because the hydraulic radius m according to Eq. (E1.9) does not depend on direction of flow.

While Eq. (E1.7) yields Darcy constant for parallel flow, derived with the use of cylindrical model, the same model allows us to derive the equation for the case of perpendicular flow, namely Eq. (8.4.32) in [16].

$$K_\perp = \frac{b^2}{4}\left[\ln\left(\frac{b}{a}\right) - \frac{1}{2}\left(\frac{b^4 - a^4}{b^4 + a^4}\right)\right] = \frac{a^2}{4\alpha}\left[\ln\left(\frac{1}{\alpha^{0.5}}\right) - \frac{1}{2}\left(\frac{1 - \alpha^2}{1 + \alpha^2}\right)\right] \qquad (E1.22)$$

EXAMPLE 7

Referring now to FIG. 22B, in yet another embodiment of the invention, there may be provided blood flow outside the fibers, and the flow of dialysate or filtrate may be through the interior of the fiber. As in the previous Example, the blood flow external to the fibers may be generally perpendicular to the fibers, but the fibers may have yet another configuration. In this embodiment, the fibers may proceed in the form of a loop, such that both ends of the fibers are potted in a common barrier of potting material. On the side of the barrier away from the loop, for operation in the mode of hemodialysis, appropriate connections may be provided to supply and withdraw dialysate to or from ends of fibers. For example there may be a separator between supply and return. The illustrated configuration could also be operated in a mode of ultrafiltration. In such a situation, filtrate could exit from both ends of the fiber into a common region on the side of the barrier that is opposite the loop of fiber.

In this configuration, the interior region or central region of the loop may be occupied by a filler or spacer or spool suitable to prevent flow in that space. The filler or spacer may be solid and may have a surface that is hemocompatible and smooth as discussed elsewhere herein. The fibers and other illustrated components may further be surrounded by a housing (not illustrated).

EXAMPLE 8

Referring now to FIG. 24, in yet another embodiment of the invention, there may be provided an array of hollow fibers. As with other embodiments of the invention, there may be provided dialysate flow through the lumens of the hollow fibers. There may be provided blood flow past the exteriors of the hollow fibers. However, in this situation, the blood may flow generally perpendicular to the long direction of the hollow fibers. So, in this situation the blood flow passing the hollow fibers has a main flowpath and also, as in other embodiments, there are sideways connections that provide opportunities for the blood flow to rearrange itself sideways if necessary.

In such an embodiment of the invention, the housing (not illustrated) may have any geometry that supplies blood at an appropriate location and withdraws blood at another appropriate location and distributes the blood flow in an appropriate pattern.

It is possible that the fibers need not be uniformly distributed. For example, the fibers could be arranged such that at a more upstream location, the fibers might have a porosity such that the fibers are less densely packed, and at a more downstream location, the fibers might have a porosity such that the fibers are more densely packed. With such an arrangement, the more-downstream fibers could serve as an emboli trap for possible thrombi that occur further upstream. Of course, the opposite spatial variation of porosity could also be constructed, or any other desired variation. Of course, distributors could also be used with such fiber arrangements to help introduce blood or withdraw blood desired flow patterns. The cartridge could be designed so that the flow pattern could be as uniform as is achievable.

Referring now to FIG. 25, there is shown a cartridge in which the blood flows past the exteriors of hollow fibers, in a direction that is generally radially outward. The blood may be introduced into this configuration by a central tube that has generally good fluid conductance so that it can supply fluid to the fiber bundle for the full length of the fiber bundle, along its long direction. Outside the fiber bundle, the blood after it has passed the fibers may be collected by an appropriate collection feature or header in the housing.

EXAMPLE 9

It is also useful to note and explain comparative features of some other technologies that involve extracorporeal processing of blood.

Cardiopulmonary bypass (often referred to as a "heart-lung machine") performs oxygenation of blood, using a blood oxygenator. The blood oxygenator uses an extracorporeal blood treatment technology that has some similarities to dialysis. A blood oxygenator contains a semi-permeable membrane in the form of hollow fibers, and blood flows on the outside of the hollow fibers. However, in blood oxygenation, one side of the porous membrane is in contact with blood, and the other side of the porous membrane is in contact with oxygen. The only substance that passes through the membrane is oxygen. No liquid passes through the membrane. This contrasts with hemodialysis, in which liquid contacts both surfaces of the membrane and liquid does pass through the membrane. The flow velocity of blood in an oxygenator is substantially larger than in a dialyzer.

Physically, the hollow fibers used in an oxygenator are different from the hollow fibers used in dialyzers such as embodiments of the invention. In an oxygenator, the fiber surface facing the blood in an oxygenator is hydrophobic, so as to help prevent liquid from passing through the membrane.

Another technology that involves extracorporeal processing of blood is a Selective Cytopheretic Device (SCD) (A Biomimetic Membrane Device That Modulates the Excessive Inflammatory Response to Sepsis, Ding, PLoS ONE, Volume 6, Issue 4, April 2011) Such a membrane is a hollow fiber synthetic biomimetic membrane that binds and sequesters activated leukocytes from the systemic circulation along an extracorporeal blood circuit. In such a device, blood does flow on the outside of the hollow fibers. The SCD used in the reference was a dialysis cartridge containing polysulfone hollow fibers with a molecular weight cut off (MWCO) of 65 kDa. A distinguishing feature of such a technology is that the exterior surfaces of the fibers, which face the blood, are rough, for the purpose of capturing leukocytes.

EXAMPLE 10

This Example pertains to how clearance and mass transport are affected by the design change of having blood on the outside of the fibers, as opposed to conventional practice.

The convective component of clearance is determined by ultrafiltration flux which is the product mean transmembrane pressure (TMP) and ultrafiltration coefficient. In order to provide identical conditions for ultrafiltration a new type of hollow fiber has to produce with an active layer on the outer surface of the fiber, because this layer has to be adjacent to the blood compartment. This new type of asymmetrical membrane has to be a high-flux membrane, because high $Q_{uf}$ and high clearance are achieved in traditional hemodialysis using high-flux membrane. Naturally, the same sieving coefficient has to be provided.

Direct control of transmembrane pressure (TMP) is impossible but central control of boundary pressures for both blood $P_{bi}$ and $P_{bo}$ and dialysate $P_{di}$ and $P_{do}$ (i—inlet, o—outlet) is possible. TMP is generally expressed in average values with simplified formula.

$$\overline{TMP} = \frac{p_{bi} + p_{bo}}{2} - \frac{p_{di} + p_{do}}{2} - \frac{\pi_i + \pi_o}{2} \quad (1)$$

Where $\pi_i$ and $\pi_o$ are inlet and outlet oncotic pressures.

This simple equations becomes possible due to approximation of axial pressure distributors as liner functions. This approximation is valid because ultrafiltration flux $Q_u$ is essentially lower than blood flow rate $Q_b$ and dialysate flow rate $Q_d$.

As transmembrane flux is proportional to local transmembrane pressure TMP(x) and both vary along fiber. The averaging of transmembrane flux leads to an equation for total ultrafiltration flow $$Q_{uf}^{io} = 2\pi auc \int_o^L (p_b^{exp}(x) - p_d^{ifs}(x))dx = \qquad (2)$$

$$2\pi auc \left[ \frac{p_b^{cap}(o) - p_b^{cap}(L)}{2} - \frac{p_d^{ifs}(x) - p_d^{ifs}(x)}{2} \right] = 2\pi aLuc\overline{TMP}^{io}$$

where equation (1) is accounted for and the equation is specified for in-outside (index io) ultrafiltration, cap and ifs mean capillary and IFS (interfiber space)

A similar equation for outside-in hemodialysis may be obtained from Equation (2) by means of exchange of indexes cap→ifs, ifs→cap $$Q_{uf}^{io} = 2\pi auc \left[ \frac{p_b^{ifs}(o) - p_b^{ifs}(L)}{2} - \frac{p_a^{cap}(o) - p_a^{cap}(L)}{2} \right] L \qquad (3)$$

uc in Equations (2) and (3) is ultrafiltration coefficient of device UC normalized on unit area membrane, uc=UC/$2\pi aL$.

While indexes i and o in Equation (1) means inlet and outlet of capillary (bundle), the application of the same indexes for inlet and outlet of ultrafiltration fluxes may cause a misunderstanding. In order to prevent this misunderstanding we use indexes i and o in combination io or of to characterize ultrafiltration flux and to discriminate in-outside and outside-in in version of dialysis.

As soon as coordinate x is introduced to characterize axial flow, nominations for its inlet and outlet are $$P^i=P(x=0)=P(0) \text{ and } P_o=(x=L)=P(L)$$

The physical model for clearance is rigorous. However, its exact quantification is problematic, because only poor characterization for porous space of membrane is possible and formation of protein polylayer (secondary membrane) and its influence on solute transport is difficult to quantify.

In spite this constraint, the clarification of perspective, whether that level of clearance, which is achieved using hemodialysis can be achieved on the base of OIHD or not possible. As soon as conditions which control clearance during hemodialysis are known, the providing the same conditions during OIHD has to provide the same clearance.

One among set of necessary conditions to establish link for clearance during OIHD and HD is achievement that high ultrafiltration flow during OIHD which provides optimal clearance during HD $$Q_{uf}^{oi} = Q_{uf}^{oi} \qquad (4)$$

that requires $\overline{TMP}^{oi} = \overline{TMP}^{io}$ $$\text{and } (2\pi rucL)^{oi} = (2\pi rucL)^{oi} \qquad (5)$$

Accepted definitions of convective and diffusive clearance. Mathematical statements of clearance in CRRT can be derived from analyses of solute mass balance across the hemodialyzer/hemofilter based on either blood-side disappearance or dialysate-side appearance. Blood-side clearance is calculated based on the disappearance of solute from the blood compartment over the length of the hemodialyzer/hemofilter and may be calculated as $$K=(Q_{Bi}C_{Bi}-Q_{Bo}C_{Bo})/C_{Bi} \qquad (6)$$

Where $Q_b$ and $C_B$ represent the blood flow rate and solute concentration in the blood, respectively, and the subscripts I and o designate the inlet and outlet of the hemodialyzer/hemofilter respectively.

Since the ultrafiltration rate (QUF) is equal to the difference between inlet ($Q_{Bi}$) and outlet ($Q_{Bo}$) blood flow, Equation (6) can be written as $$K=Q_{Bi}(C_{Bi}-C_{Bo})/C_{Bi}+Q_{UF}C_{Bo}/C_{Bi} \qquad (7)$$

The first term in this equation $Q_{Bi}(C_{Bi}-C_{Bo})/C_{Bi}$ represents diffusive clearance in the absence of ultrafiltration, while the second term $Q_{UF}C_{Bo}/C_{Bi}$, represents convective clearance in the absence of diffusion.

Since the change in solute concentration in the blood over the length of the dialyzer tends to be small, oncotic pressure contributes to transmembrane flux.

It is caused by formation of protein polylayer on the blood side of membrane due to its accumulation during ultrafiltration, the protein polylayer is the thinner, the higher tangential velocity of blood. In fact the same shear rate to be provided in blood compartment during Outside-In Hemodialysis and Hemodialysis. But the shear rate is smaller at the same $Q_b$ in the Inter Fiber Space case, that is unfavorable for $Q_{UF}$ in the Outside-In Hemodialysis case. The shear rate is smaller because $K^{ifs}$ is 4 times larger than $K^{cap}$ at ε=0.6, while shear rate proportional to 1/K.

The shear rate on external surface of fiber is $$\frac{du}{dr}(a) = \frac{a\varepsilon}{2\mu(1-\varepsilon)} \times \frac{dp}{dz} \qquad (8)$$

As it is shown in Example E.1) namely Equation (E1.3b) derived in framework of cell mode. It may be transformed to form which better for practical application by presentation $$\frac{dp}{dz}$$

with the use of the Darcy law, namely Equation (E1.6)

$$\frac{1}{\mu}\frac{dp}{dz} = -\frac{U}{K} = \frac{Q_b}{KS_b} \qquad (9)$$

Where K is the Darcy Constant, $S_b$ is area of dialyzer cross-section, $$K_{ifs} = \frac{\varepsilon^3 a^2}{4k(1-\varepsilon)^2} \qquad (10)$$

That is Equation (E1.10), ε is the bundle porosity, K is Kozeny constant, K≅5, $K^{ifs}$=10$^{-5}$, $K^{ifs}$=10$^{-5}$, $K^{cap}$=2.5×10$^{-6}$ cm$^2$, when α=125 micron. The equation for $K^{cap}$. The equation for $K^{cap}$ is derived on the base of well known Poissenille law for viscous laminar flow inside cylindrical capillary lumens. The substitution according to Equations (9) into Equation (8) yields for shear rate in the Inter Fiber Space $$\frac{du^{ifs}}{dr}(\alpha) = \frac{a\varepsilon}{2(1-c)} \times \frac{Q_b^{ifs}}{K^{ifs}S_b} \quad (11)$$

The equation for shear rate on internal surface of the capillary can be obtained using known possible velocity distribution within capillary $$\frac{du}{dr}(a) = \frac{a_i}{2} \times \frac{Q_b^{cap}}{K^{cap}S_b} \quad (12)$$

The substitution of numerical values for $K^{ifs}$ into Equation (11) and for $K^{cap}$ into Equation (12) yields shear rates of 200 sec$^{-1}$ and 1000 sec$^{-1}$ for capillary and the Inter Fiber Space respectively when $\varepsilon$=0.6.

In order to increase the shear rate within the Inter Fiber Space, a change of porosity from $\varepsilon$=0.6 to $\varepsilon$=0.5 is proposed. This leads to essential decrease of $K^{ifs}$ according to Equation (11) and to the associated increase in shear rate.

The shear rate becomes 2.7 times as high within the Inter Fiber Space at the same $Q_b$. However, this estimate is made in framework of cell model while within junction axial velocity and shear rate may be much lower than shear rate averaged over orbital angle. Another estimate, accomplished in assumption of equidistant fiber (but without cylindrical symmetry inherent in cell models has shown, that the orbital variation of shear rate is much smaller than 700 sec$^{-1}$. It means that transition to s=0.5 may provide lower oncotic pressure, lower correction to modular $Q_{uf}$ in case of Outside-In Hemodialysis.

The deviation from equidistant model naturally leads to weaker local ultrafiltration in most narrow junctions but this causes a negative contribution to $Q_{uf}$ in both cases of Outside-In Hemodialysis and conventional Hemodialysis. Application of wavy fibers may eliminate very narrow junctions with their harmful influence on local ultrafiltration. Simultaneously with application of wavy fibers, compression of bundle can be used to discourage channeling.

On the other side, the cell model, which is the first approximation in accomplished analysis, fails respective to wavy fibers because waves violate cylindrical symmetry. However, if wave length is large in comparison with the wave amplitude, the deviation from symmetrical to cylindrical symmetry is small.

With respect to the diffusive component of clearance it has to be considered as a combination of transport within membrane pores, transport in the blood stream near the membrane, and transport in the dialysate stream near the internal surface of the membrane. At the same $Q_{uf}$ the condition for convective diffusion inside membrane are identical in Outside-In Hemodialysis and Hemodialysis. In the blood compartment, these conditions are additionally controlled by the shear rate, because the shear rate controls convective diffusion. As soon as change in the Inter Fiber Space porosity from $\varepsilon$=0.6 to $\varepsilon$=0.5 is made, the shear rate in the Inter Fiber Space becomes larger than the shear rate in capillaries for blood in Hemodialysis. Hence, the condition for convective diffusion in blood compartment becomes better in Outside-In Hemodialysis than in Hemodialysis at $\varepsilon$=0.5. As to the dialysate compartment, the shear rate is higher and convective diffusion is faster at the same $Q_d$ upon changing from Hemodialysis to Outside-In Hemodialysis. In addition, the absence of stagnant zones and channeling in capillary case leads to more regular and faster dialysate convective diffusion. Naturally the rate of convective diffusion will decrease with proposed decrease in $Q_d$. But it will remain higher than in the Inter Fiber Space of traditional Hemodialysis as long as $Q_d$ will decrease too much. The relevant modeling is possible.

Possibility for decreasing dialysate consumption

Because of the change from Hemodialysis to Outside-In Hemodialysis, the lumens become the dialysate compartment, and the shear rate in dialysate compartment approximately doubles at least for geometric reasons. That is valuable for convective diffusion and convective clearance. Meantime, $Q_d$ does not have to be kept the same, as it was assumed above, but may even decreased.

First, $Q_d$ may be decreased by a factor of 2 while providing that shear rate, which existed in the Inter Fiber Space at twice higher $Q_d^{ifs}$.

$Q_d^{cap}$ twice larger than $Q_d^{ifs}$ in Hemodialysis is possible in Outside-In Hemodialysis at the same shear rate but conditions for convective diffusion within the lumens are much better than that with IFS. There are flow stagnation zones within the Inter Fiber Space, namely at junctions between channels.

Higher shear rate in the Inter Fiber Space is required to enhance axial flow along junctions. Then upon changing from Hemodialysis to Outside-In Hemodialysis, i.e. upon changing from dialysate flowing through the Inter Fiber Space compartment to dialysate flowing within the lumen compartment for dialysate flow rate is sufficient. This means that it is possible to decrease $Q_d^{OIHD}$ in comparison with $Q_d^{HD}$ essentially by a factor of more than 2. Although this will increase the difference $C_d(L)-C_d(o)$, it may be shown that $C_d(L)$ remains small.

Upon changing from Hemodialysis to Outside-In Hemodialysis, the backfiltration becomes less possible as long as $K^{ifs}$ is larger than $K^{cap}$ with $K^{ifs} \sim 4K^{cap}$ at $\varepsilon$=0.6. This advantage of Outside-In Hemodialysis may be explained on the basis of Ronco's analysis of FIG. 4A and FIG. 4B in [C. Ronco, Problems related to backfiltration in hemodialysis, NEPHROLOGIA, Vol. 10, Sep. 3, 1990].

Figure 4:
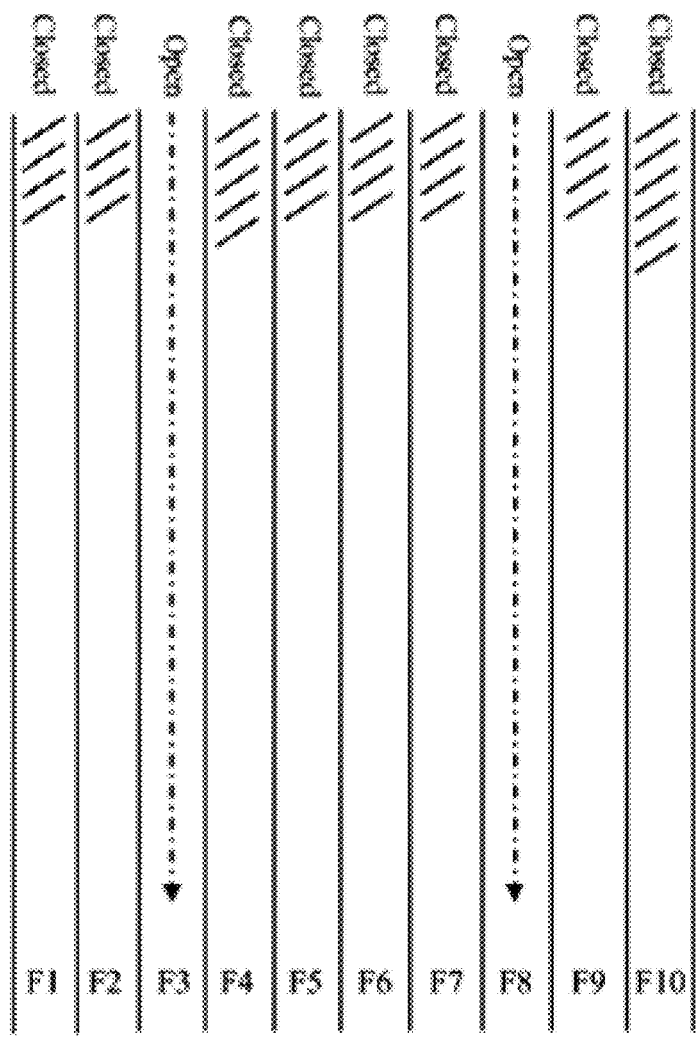
FIG. 4 shows the effect of hypothetical thrombi inside a number of hollow fibers in conventional hemodialysis.

FIG. 4 of Ronco shows examples of three different pressure profiles that may be encountered inside a dialyzer which employs a countercurrent configuration. Part(A) shows the ideal situation in which the entire surface and length of the filter is utilized for filtration, and no backfiltration occurs. The Trans Membrane Pressure is always positive because of the hydrostatic pressure drop in the blood compartment is low and $P_{bo}$ is slightly greater than $n_o$+Pdi (where $P_{di}$=inlet dialysate pressure). Part(B) shows the case in which for any of a number of possible reasons (higher resistance of the filter, higher permeability of the membrane and higher ultrafiltration in the proximal segment of the filter) the pressure drop in the blood compartment is larger and the increased pressure is generated by plasma proteins causes an oncotic flux of dialysate into the blood in the distal segment of the filter. The amount of backfiltration in this condition of the oncotic pressure as blood is diluted by the backfiltration flux.

The change from Part(B) "to part" is the change from a larger axial gradient of pressure $$\frac{dp}{dz}$$

to a smaller one.

Meantime $\frac{1}{\mu}\frac{dp}{dz} = -\frac{Q_b}{S_b K}$ (8.1)

according to Darcy's law. Upon changing from HD to Outside-In Hemodialysis, K increases: $K^{ifs} > K_{cap}$ (8.2). Consequently, $$\frac{dp}{dz}$$

decreases upon changing from Hemodialysis to Outside-In Hemodialysis. Hence, the harmful backfiltration is less possible for Outside-In Hemodialysis, than for Hemodialysis. It is noteworthy, that $K^{ifs}$ remains larger than $K^{cap}$ even upon changing to a more favorable lower porosity value of $\varepsilon$=0.5.

The contribution of dialysate pressure drop to Trans Membrane Pressure in FIG. 4 of Ronco is much smaller than that of blood because of the smaller viscosity of water (whose properties substantially represent the properties of dialysate) and the larger amount of cross-sectional flow area in the Inter Fiber Space. As $K^{cap} > K^{ifs}$ the contribution of dialysate flows to Trans Membrane Pressure increases for Outside-In Hemodialysis. In spite of this increase, this contribution remains small due to the lower viscosity of water. This contribution may be even smaller at a useful decrease in $Q_d$, possibly due to better condition for convective diffusion within the capillary in comparison with the Inter Fiber Space.

Further analysis was done for data of the Vitamin B12 and NaCl clearance curve of FIG. 19H. In those experiments there were equal volumetric flowrates of dialysate and blood, at approximately 285 milliliters/minute. (This is in contrast to conventional dialysis practice in which the dialysate flowrate is usually double the blood flowrate.) This is experimental confirmation of the mathematical prediction that good clearance results could be obtained when the dialysate flowrate and the blood flowrate are approximately equal to each other.

Specification of Operational Parameters for Hemodialysis

An overall parameter useful for comparing the performance of hemodialyzers is convective clearance. This clearance depends on, among other parameters, four pressures, i.e., the inlet and outlet pressures of the blood flowpath and the dialysate flowpath. It is reasonable to consider first how the four pressures are specified in conditions of typical conventional Hemodialysis. After that, a similar approach may be used for specifying the pressures for Outside-In Flow Filtration. This will allow finally to specify four pressures for Hemodialysis using Outside-In Flow Filtration in such a way as to provide the same convective clearance as is achieved during conventional Hemodialysis. In addition to the requirement of high TransMembranePressure, at least two conditions have to be satisfied during Hemodialysis, namely providing certain blood flow rate $Q_b^{10}$ and dialysate flow rate $Q_d^{4s}$. As we use a cell model we designate $q_b^{ifs}$ and $q_d^{cap}$ respectively for a single hydrodynamic cell and for a single fiber (capillary). An analogous Darcy constant $K^{ifs}$ for the Inter Fiber Space may be derived as described elsewhere herein.

For assumed dimensional and numerical values $a_i$=95 micron, $a$=125 micron, $\varepsilon$=0.6, it can be calculated that $K^{cap}$ is 4 times smaller than that $K^{ifs}$ for the Inter Fiber Space.

$K^{cap} \cong \frac{1}{4}K^{ifs}$ (9.1)

While $K^{ifs} = 10^{-5}$ cm$^2$.

$U_b = \frac{q_b}{\pi b^2} = \frac{K^{cap}1300}{\mu_b L}(P_c^{cap}(o) - P_b^{cap}(L))$ (9.2)

A similar equation may be written for dialysate with $K^{ifs}$ and $\mu$ (water) for dialysate flow. In order to simplify description of the derivation, we represent Equation (3.2) in the form $(P_b^{cap}(o) - P_b^{cap}(L)) = \tilde{q}_b^{cap}$ (9.3)

where $\tilde{q}_b^{cap} = \frac{\mu_b L \cdot q_b^{cap}}{1300 \cdot K^{cap} \cdot \pi b^2}$ (9.4)

Then the equation for dialysate takes the form $P_d^{ifs}(o) - P_d^{ifs}(L) = \tilde{q}_d^{ifs}$ (9.5)

where $\tilde{q}_d^{ifs} = \frac{\mu L \cdot q_d^{cap}}{1300 \cdot K^{ifs} \cdot \pi b^2}$ (9.6)

The third equation is the Equation (1.6) for TransMembrane Pressure $TMP^{io} = \frac{p_b^{cap}(o) - p_b^{cap}(L)}{2} - \frac{p_d^{ifs}(o) - p_d^{ifs}(L)}{2}$ (9.7)

Hence there are three equations, i.e., Equation (9.3), Equation (9.5), and Equation (9.7), for the four unknown variables $P_b^{cap}(o)$, $P_b^{cap}(L)$, $P_d^{ifs}(o)$, $P_d^{ifs}(L)$ $q_b$, $q_d$, TMP are input parameters. In fact, it can be found in the Hemodialysis literature, which specifies these parameters, that $q_b$ (or $Q_b$ per dialyzer) is in range 150-300 ml/min, and $Q_d$ is in the range of 200-500 ml/min. But it is unclear where there is a justification for the choice of TransMembrane Pressure being about 100 mmHg In fact, higher TransMembrane Pressure leads to better convective clearance.

Although these questions regarding clearance optimization in Hemodialysis are relevant, it is not the primary focus. Our task is to show that these typical operational parameters of Hemodialysis, which are $Q_u$, $Q_d$, and TMP, may be achieved for Outside-In Hemodialysis. Hence, $TMP^{oi} = TMP^{io}$ may be achieved.

The next task is to specify $P_b^{oi}(o)$, $P_b^{oi}(L)$, $P_d^{oi}(o)$, $P_d^{oi}(L)$, such as to provide $TMP^{oi} = TMP^{io}$ (9.8)

The determination of four pressures through input values $q_b^{cap}$, $q_d^{ifs}$, $TMP^{oi}$, may first be addressed to Outside-In Hemodialysis.

$P_b^{cap}(o) = P_b^{cap}(L) + \tilde{q}_b^{cap}$ (9.9)

$P_b^{cap}(L)$=is unknown (9.10)

There is no additional condition and $P_b(L)$ remains arbitrary. (Possibly, some attention to venous and arterial pressure may be required.)

$$P_d^{ifs}(o) = P_d^{ifs}(L) + \tilde{q}_d^{ifs} \tag{9.11}$$

When TMP is considered as an input parameter in Equation (1.6), one obtains $$P_d^{ifs}(L) = P_b^{cap}(L) - TMP^{io} + \frac{\tilde{q}_b^{cap}}{2} - \frac{\tilde{q}_d^{ifs}}{2} \tag{9.12}$$

Specification Operational Parameters for Outside-In Hemo-Dialysis

We may use Equation (9.9), Equation (9.10), Equation (9.11) and Equation (9.12) and obtain similar equations for conventional Inside-Out Hemodialysis by means of interchanging the indices so that cap→ifs, and ifs→cap, as follows:

$$P_b^{ifs}(o) = P_b^{ifs}(L) + \tilde{q}_b^{ifs} \tag{9.13}$$

$P_b^{ifs}(L)$ is unknown venous pressure (9.14)

$$P_d^{ifs}(o) = P_d^{ifs}(L) + \tilde{q}_d^{ifs} \tag{9.15}$$

$$P_d^{cap}(L) = P_b^{ifs}(L) - TMP^{oi} + \frac{\tilde{q}_b^{ifs}}{2} - \frac{\tilde{q}_d^{cap}}{2} \tag{9.16}$$

where $$\tilde{q}_b^{ifs} = \frac{\mu_b L \cdot q_b^{ifs}}{1300 * K^{ifs} \cdot \pi b^2} \tag{9.17}$$

$$\tilde{q}_d^{cap} = \frac{\mu_b L \cdot q_d^{cap}}{1300 * K^{cap} \cdot \pi b^2} \tag{9.18}$$

where
$\tilde{q}_b^{ifs}$, $\tilde{q}_d^{cap}$, and $TMP^{oi}$ input parameters.

Four pressures are output parameters.

We can obtain numerical values for pressures using for $q_b$ and $q_d$ the values $Q_b^{ifs}$ and $Q_d^{cap}$, which are the same values as in conventional Hemodialysis, for example, $$Q_b^{ifs} = 180 \frac{ml}{min} = 3 \frac{cm^3}{sec}, \; Q_d^{cap} = 120 \; ml/min = 2 \frac{cm^3}{sec},$$

while, $b^2 = a^2/1-\varepsilon = (1.25 \times 10^{-2})^2/0.4 = 3.9 \times 10^{-4}$; $\pi b^2 = 1.2 \times 10^{-3}$, $L=20$ cm the q and $\pi b^2$ can be replaced by using the identity $$\frac{q}{\pi b^2} = \frac{q}{S_B} \tag{9.20}$$

Where $$S_B = \frac{\pi D^2}{4} = 5 \; cm^2$$

is the bundle cross-section for $D_b = 2.5$ cm.

Equation (9.20) is valid because $Q=nq$, $S_B=n\pi b^2$, where n is the number of fibers, and n cancels out of the equation.

Substitution of the numerical values into Equations (9.17) and (9.18) yields $$\frac{\tilde{q}_b^{ifs}}{2} = 0.5 \frac{3.5 \times 10^{-2} \times 20 \times 3}{1300 \times 10^{-5} \times 5} = \frac{3.5 \times 10 \times 3}{1.8 \times 5} = 16 \tag{9.21}$$

$$\frac{\tilde{q}_d^{cap}}{2} = 0.5 \frac{10^{-2} \times 20 \times 2}{1300 \times 0.26 \times 10^{-5} \times 5} = \frac{20}{1.3 * 0.26 * 5} = \frac{4}{0.34} = 11.6 \tag{9.22}$$

Substituting these numbers into equation (9.19) yields)

$P_b^{ifs}(o) = P_b^{ifs}(L) + 32$ mmHg $P_d^{cap}(L) = P_b^{cap}(L) - 100 + 16 - 11.6 = P_b^{ifs}(L) - 95.6$ mmHg (9.22)

$P_d^{ifs}(o) = P_b^{ifs}(L) - 95.6 + 18.6 = P_b^{ifs}(L) - 77$ mmHg

There remain options as to how $P_b(o)$ and $P_b(L)$ may be independently controlled. For example, there could be a resistance installed between the vascular access and the dialyzer exit. The higher the resistance is, the larger $P_b(L)$ is. Afterwards, $P_b(o) = P_b(L) + \tilde{q}_b$.

The calculated exit and entrance pressures Equation (9.23) do not reveal any constraint that would prevent us from obtaining operation at a condition of $Q_b = Q_d = 300$ ml/min during Outside-In Hemodialysis.

This supports the use of a dialysate flowrate that is equal to the blood flowrate. This would be in notable contrast to the practice in conventional dialysis, in which the dialysate flowrate is typically twice the blood flowrate. There would be economic as well as other benefits in reducing the dialysate flowrate while maintaining equivalent performance.

Comparison of shear rate and convective diffusion for blood flow within the Inter Fiber Space and for blood flow within the capillary Because $K^{ifs} \sim 4K^{cap}$, changing from conventional Hemodialysis to Outside-In Hemodialysis, i.e. replacing the capillary by the Inter Fiber Space for the blood compartment, leads to a decrease in blood shear rate from 2000 sec-1 to 1000 sec-1 in the blood compartment at assumed equal blood and dialysate flowrates of $Q_b=300$ ml/min, $Q_d=300$ ml/min. This does not affect TMP and convective clearance, but this may decrease diffusive clearance. A protein polylayer forms a membrane surface in the blood compartment due to ultrafiltration. The higher the shear rate is, the smaller may be the thickness of this mobile polylayer. So, it is advantageous to increase the shear rate of blood flowing in the Inter Fiber Space. An obvious possibility to increase shear rate is to increase the volumetric blood velocity. However, $Q_b$ greater than about 300 ml/min may be harmful for blood shear rate in the vascular system.

Next, at first glance, it appears possible to increase $q_b^{ifs}$, which would enhance the shear rate without increasing $Q_b^{ifs}$ decreasing the total number of fibers n. However, this would mean there would be a corresponding decrease in the total ultrafiltration flow, which is not acceptable.

Such a decrease of total ultrafiltration flow would mean a decrease in total rate of impurities removed from the patient's blood, which would be able to be compensated for only by unacceptably prolonging a dialysis treatment session.

Instead, Equation (10) indicates another possible approach based on the fact that $\tau^{ifs}$ increases very rapidly with decreasing porosity. For example, a porosity of 0.6 is used in some dialyzers and for sample calculations here, but it is also quite reasonable to design a dialyzer having a porosity of 0.5. Upon changing from ε=0.6 to ε=0.5, the parameter $$\frac{e^3}{(1-e)^2}$$

decreases from 1.35 to 0.5, i.e., by a factor of 2.7 times.

This change means that $K^{ifs}$ decreases by a factor of 2.7, and it also means that the shear rate within the Inter Fiber Space becomes 2700 sec$^{-1}$, which is 700 sec$^{-1}$ higher than in the lumen of the capillary fiber. In other words, there are some grounds to assume, that in the case of ε=0.5, clearance in the case of Outside-In Hemodialysis may at least not be lower than in conventional Hemodialysis. However, some additional analysis is required.

Although the shear rate calculated in the framework of a cell model is higher, this advantage is addressed to mean shear rate, i.e. shear rate averaged with respect to orbital angle for the entire circumference around a cross-section of the fiber, because at some local places around the circumference the shear rate is minimal while at other local places it increases to a maximum.

FIG. 26A illustrates certain geometric relationships for a cell of three cylinders that are spaced some distance apart, having a fiber radius a and a spacing radial dimension b. FIG. 26A illustrates the orbital (angular) dependence for the characteristic distance h, which is used in characterizing the shear rate value. This distance h is the distance between the fiber surface and the midpoint between three fibers, with the midpoint between three fibers being a place where the shear rate is zero. $h=b-a=h_{min}$ at the minimal distance between fiber surfaces. Progressing from the narrow portion of a junction, h monotonically increases up to the maximum distance, corresponding to a point which is located equidistantly from three surfaces. The difference between $h_{max}$ and $h_{min}$ characterizes the orbital (angular) dependence of shear rate. The larger the difference is, the larger is the variation of shear rate.

It can be appreciated that the difference is large at minimal porosity, when fibers almost touch each other and $h_{min} \to 0$. While $h_{max}$ decreases slightly with increasing porosity, $h_{min}$ increases rapidly and the difference between $h_{min}$ and $h_{max}$ becomes less significant with increasing porosity.

FIG. 26B helps to calculate $h_{min}(\varepsilon)$ and $h_{max}(\varepsilon)$ for a fiber spacing that is essentially tight packing where the fibers touch each other, as a limiting situation.

$h_{max}$ equals to length $A_2A_4$, which is the hypotenuse.

With reference in FIG. 26B to right triangle $A_2A_4A_6$, according to the definition of the cosine function, $$\cos\alpha = \frac{A_2A_3}{A_2A_4},$$

which leads to $$A_2A_4 = \frac{A_2A_3}{\cos\alpha} = \frac{b}{\cos 30°} = b\frac{2}{\sqrt{3}} = 1.15b \quad (E10.1)$$

$$h_{max} = 1.15b - a = 1.15\frac{a}{\sqrt{1-e}} - a \quad (E10.2)$$

While $$b - a = \left(\frac{1 - \sqrt{1-e}}{\sqrt{1-e}}\right)a \quad (E10.3)$$

$h_{max}$ and $h_{min}$ are calculated for 2 values of ε in

| ε | 0.6 | 0.5 |
|---|---|---|
| $\sqrt{1-\varepsilon}$ | 0.63 | 0.71 |
| $\frac{1}{\sqrt{1-\varepsilon}}$ | 1.58 | 1.41 |
| $\frac{1}{\sqrt{1-\varepsilon}} - 1$ | 0.58 | 0.41 |
| $\frac{1.15}{\sqrt{1-\varepsilon}} - 1$ | 0.82 | 0.62 |
| $\frac{h_{max} - h_{min}}{h_{max}}$ | $\frac{0.82 - 0.58}{0.82} = 0.29$ | $\frac{0.62 - 0.41}{0.62} = 0.34$ |

When the porosity is decreased from 0.6 to 0.5, the orbital (angular) variation of shear stress increases only 15% while the averaged shear stress increases by a factor of 2.7 times. One concludes that ε=0.5 is better for Outside-In Hemodialysis rather than ε=0.6. This suggests that if the fiber bundle is fabricated with a porosity of 0.5, the condition of convective transport affecting blood within the Inter Fiber Space may not be worse than the condition of convective transport affecting blood inside the lumen in conventional Hemodialysis.

However, some uncertainties remain. The proposed argument may be valid to the extent that is inherent in model of equal spacing of the fibers. This does not necessarily mean that the diffusive clearance is lower. The situation is not certain. If the fibers happen to be unequally spaced, the convective diffusion will be suppressed for pairs or groups of fibers with decreased $h_{min}$. However, when $h_{min}$ decreases for a certain pairs or groups of fibers, there is a corresponding increase in $h_{min}$ for other pairs or groups of fibers. In principle, the influence of deviation from the equally-spaced model may be mostly eliminated, especially if the fibers are wavy so as to tend to keep themselves uniformly distributed in space.

Additional Comments

Applications of the cartridges, systems, apparatus and methods described herein could, first of all, be therapy applications. Such therapy applications could be long-term, such as up to 100 hours without needing to change out the cartridge, or up to 72 hours, or 24 to 40 hours, for example. Examples of applications include Hemodialysis; Hemodiariltration; Slow Continuous Ultrafiltration; Ultrafiltration; Slow Continuous Hemodialysis; Continuous Renal Replacement Therapy; plasmapherisis; and other extended therapies. Continuous Renal Replacement Therapy may include any of: CVVH (Continuous Veno-Venous Hemofiltration); CVVHD (Continuous Veno-Venous hemodialysis); CVVHDF (Continuous Veno-Venous Hemodiafiltration) and plasmapheresis. Further, it is possible that new therapies could become possible because of embodiments of the invention.

It is further possible that some applications could be short-term such as critical care applications. It is further possible that some applications could be intermittent applications in which long cartridge life is desirable. For example, applications with a service life of greater than 100 hours are possible.

Cartridges of embodiments of the invention could be manufactured in any of a range of sizes including quite small sizes. For example, the surface area of the fibers could range from about 2 $m^2$ down to about 0.03 $m^2$.

Cartridges could be used for treatment of blood in an extracorporeal blood circuit, or alternatively for treatment of blood using an implant.

In addition, the applications do not all have to be therapy applications. Embodiments of the invention could also be used for blood processing such as for blood banks or for separation of blood into components or for pharmaceutical manufacturing. Also, embodiments of the invention could use other fluids other than blood.

Applications could be applications that are known but in which less anticoagulant treatment is needed with embodiments of the invention, compared to the amount of anticoagulant needed in conventional practice. For example, in conventional practice, anticoagulant concentrations of approximately 1 IU/milliliter may be used. In embodiments of the invention, it may be possible to use anticoagulant concentrations as low as 0.25 IU/milliliter, or in some cases not use anticoagulant at all. This is advantageous economically and in other respects.

In embodiments of the invention and in Examples, there are discussed various orientations of blood flow with respect to fibers, such as parallel to fibers and perpendicular to fibers, and transitions between such types of flows are also discussed. Although many of the Examples were for axial flow along the length of a generally cylindrical cartridge, other flow orientations are also possible and are discussed. There could be flow transitions associated with those flow geometries also, and the same design considerations and analyses apply as well. The guidelines for blood flow as far as shear rate, velocity, shear rate gradient, appropriate condition of the blood-facing surface of the fiber, etc., could be used in any flow orientation or flow geometry.

Where fibers are discussed, the fibers could be either straight or wavy. The fiber bundle could be a mixture of some straight fibers and some wavy fibers. Spacer fibers, either solid or yarns, could also be included in the fiber bundle.

Coatings, such as on the housing interior or the fibers, could be placed on either the entirety of such surface or only on portions of such surface.

Although discussion has focused on fibers whose exteriors are smooth, with possibly rough interiors, it is also possible in embodiments of the invention to use so-called symmetric fibers, which are smooth on both their interiors and their exteriors.

Although mathematical derivations and calculations have been presented herein, it is not wished to be limited thereby.

All cited references are incorporated by reference herein.

Other Features and Observations

Herein, general features usable in blood processing cartridges and systems and methods for processing blood are described. They may be used independently of other features, or together with other features as deemed desirable for particular applications. In general accord with the present disclosure:

1. A cartridge for use in flow filtration, comprising:
   a housing;
   a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
   a first end barrier that joins with said fibers at first ends of said fibers and joins with a housing interior of said housing and bounds a first end plenum and separates said first end plenum from a housing midsection interior region;
   a second end barrier that joins with said fibers at second ends of said fibers and joins with said housing interior of said housing and bounds a second end plenum and separates said second end plenum from said housing midsection interior region;
   a first fluid flow compartment comprising said first end plenum and said interiors of said hollow fibers and said second end plenum, said first end plenum and said interiors of said hollow fibers and said second end plenum being in fluid communication with each other; and
   a second fluid flow compartment comprising an inter fiber space and a housing supply port and a housing discharge port, all in fluid communication with each other;
   wherein said second fluid flow compartment contains at least one design feature near a housing supply end of said cartridge that is different from a corresponding feature near a housing discharge end of said cartridge or wherein said housing discharge end does not have a corresponding feature.

2. The cartridge of characterization 1, wherein said cartridge comprises a supply distributor inside said housing near said supply port, and does not comprise a discharge distributor.

3. The cartridge of any one of characterizations 1-2, wherein said second fluid flow compartment comprises a supply distributor inside said housing near said supply port, and a discharge distributor inside said housing near said discharge port.

4. The cartridge of characterization 3, wherein an axial length of said discharge distributor is shorter than an axial length of said supply distributor.

5. The cartridge of characterization 3, wherein a flow entrance region length of said discharge distributor is shorter than a flow entrance region length of said supply distributor.

6. The cartridge of characterization 3, wherein an axial length of an axial length of a flow transition region near said housing discharge port is shorter than an axial length a flow transition region near said housing supply port.

7. The cartridge of any one of characterizations 1-6, wherein near said housing supply end of said cartridge, said fibers fan at a supply end fanning angle greater than zero, and near said housing discharge end of said cartridge, said fibers do not fan.

8. The cartridge of any one of characterizations 1-7, wherein near said supply distributor said fibers fan having a supply end fanning angle, and near said discharge distributor said fibers fan having a discharge end fanning angle that is smaller than said supply end fanning angle.

9. The cartridge of any one of characterizations 1-8, wherein near said housing supply end of said cartridge, said fibers fan having a supply end fanning factor greater than zero, and near said housing discharge end of said cartridge, said fibers do not fan.

10. The cartridge of any one of characterizations 1-9, wherein near said housing supply end of said cartridge, said fibers fan having a supply end fanning factor, and near said housing discharge end of said cartridge, said fibers fan having a discharge end fanning factor that is smaller than said supply end fanning factor.

11. The cartridge of any one of characterizations 1-10, wherein near said housing supply end of said cartridge, said fibers fan having a supply end fanning length, and near said housing discharge end of said cartridge, said fibers fan having a discharge end fanning length that is smaller than said supply end fanning length.

12. The cartridge of any one of characterizations 1-11, wherein at least some of said fibers have an outside diameter that is in the range of 100 microns to 300 microns.

13. The cartridge of any one of characterizations 1-12, wherein at least some of said fibers are wavy fibers.

14. The cartridge of any one of characterizations 1-13, wherein said plurality of fibers have a porosity in an Inter Fiber Space of between 40% and 70%.

15. The cartridge of any one of characterizations 1-14, wherein said plurality of fibers have a porosity in an Inter Fiber Space of between 50% and 62%.

16. The cartridge of any one of characterizations 1-15, wherein, said cartridge comprises a distributor that introduces or discharges blood to or from said fiber exteriors accessing substantially 360 degrees around a circumference of said cartridge, so as to create uniform or quasi-uniform blood flow in an entire cross-section of said cartridge in a space between the plurality of said fibers of said fiber array.

17. The cartridge of characterization 3, wherein said supply and discharge distributors have respective axial lengths L, and said housing midsection interior region has a radius r, and said supply distributor has a value of 2*L/r that is greater than 1.0, and said discharge distributor has a value of 2*L/r that is less than 1.0.

18. The cartridge of characterization 3, wherein the porosity in the discharge distributor is the same as that of a main portion of a fiber bundle to serve as an emboli trap.

19. The cartridge of any one of characterizations 1-18, wherein between said distributor and said barrier, said fibers fan out to increase fiber porosity by 10 to 30% compared to average porosity of fiber array at a location midway between ends of said cartridge, to provide uniform or nearly uniform blood flow velocities and shear rates.

20. A cartridge for use in flow filtration, comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other; and
a second fluid flow compartment comprising an inter fiber space and a housing supply port and a housing discharge port, all in fluid communication with each other;
wherein said fibers comprise polyethersulfone or related polymers, in combination with polyvinylpyrrolidone, and at least some of said fibers are wavy, and said fibers have an outside surface that is hemocompatible, and said fibers have said outside surface that has a root-mean-square roughness of less than 100 nanometers.

21. The cartridge of characterization 20, wherein said wavy fibers have a wavelength of waviness that is in the range of 0.4 centimeters to 1 centimeter.

22. The cartridge of any one of characterizations 20-21, wherein said wavy fibers have a half-amplitude of waviness that is in the range of 0.1 millimeter to 1 millimeter.

23. The cartridge of any one of characterizations 20-22, wherein said wavy fibers have a half-amplitude of waviness that is less than a wavelength of said waviness.

24. The cartridge of any one of characterizations 20-23, wherein at least some of said fibers have an outside diameter that is less than 300 microns.

25. The cartridge of any one of characterizations 20-24, wherein at least some of said fibers have an outside diameter that is in the range of 100 microns to 1,500 microns.

26. The cartridge of any one of characterizations 20-25, wherein said hemocompatible outside surface has a hydrated surface layer whose thickness is greater than 48 nanometers.

27. The cartridge of any one of characterizations 20-26, wherein said hydrated surface layer has sufficient hydrophilic moieties per unit surface area to prevent adsorption of fibrinogen and similar molecules.

28. The cartridge of any one of characterizations 20-27, wherein said semi-permeable membranes have pore sizes in the range of 2 nanometers to 7 nanometers.

29. The cartridge of any one of characterizations 20-28, wherein said semi-permeable membrane has a molecular weight cutoff of 50,000 Daltons or less.

30. The cartridge of any one of characterizations 20-29, wherein said fibers have an ultrafiltration coefficient of between 5 to 100 ml/hr/m$^2$/mmHg 31. The cartridge of any one of characterizations 20-30, wherein said fibers have a total external surface area of 0.03 m$^2$ to 2.0 m$^2$ for hemodialysis, 32. A cartridge for use in flow filtration, comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other;
a second fluid flow compartment comprising an inter fiber space and a housing supply port and a housing discharge port, all in fluid communication with each other; and
an air bleed connected to said second fluid flow compartment.

33. The cartridge of characterization 32, wherein said air bleed is located approximately 180 degrees circumferentially away from said housing supply port or from said housing discharge port.

34. The cartridge of any one of characterizations 32-33, wherein said housing or internal components thereof have surfaces near said air bleed that slope continuously upward toward said air bleed.

35. The cartridge of any one of characterizations 32-34, wherein said air bleed is located in fluid communication with a channel of an orbital distributor.

36. The cartridge of any one of characterizations 32-35, wherein said air bleed is connected to said housing near one of said end barriers.

37. The cartridge of any one of characterizations 32-36, wherein said cartridge contains a housing supply port air bleed near said housing supply port and a housing discharge port air bleed.

38. The cartridge of characterization 37, wherein said housing supply port air bleed has a location or design that is different from a location or design of said housing discharge port air bleed.

39. The cartridge of any one of characterizations 32-38, wherein in an intended orientation of use, said cartridge has an upwardly-located end and comprises an upward-end air bleed near an upwardly-located end of said cartridge, and has a downwardly-located end and comprises a downward-end air bleed near said downwardly-located end of said cartridge, and said upward-end air bleed is located near one of said end barriers and said downward-end air bleed is located near an orbital distributor.

40. A cartridge for use in flow filtration, comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other;
a second fluid flow compartment comprising an inter fiber space and a housing supply port and a housing discharge port, all in fluid communication with each other; and
an emboli trap in communication with said second flow compartment.

41. The cartridge of characterization 40, wherein said emboli trap is inside said housing.

42. The cartridge of any one of characterizations 40-41, wherein said emboli trap is part of a housing supply port or a housing discharge port.

43. The cartridge of any one of characterizations 40-42, wherein said emboli trap comprises an impact plate and a low-elevation place near said impact plate.

44. The cartridge of any one of characterizations 40-43, wherein said emboli trap comprises a smoothly-contoured flowpath comprising a descending portion and an ascending portion and a low-elevation place between said descending portion and said ascending portion suitable to retain emboli.

45. The cartridge of any one of characterizations 40-44, wherein said emboli trap is located near said housing supply port.

46. The cartridge of any one of characterizations 40-45, wherein said emboli trap is located near or downstream of said housing discharge port.

47. A cartridge for use in extracorporeal processing of blood, comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other; and
a second fluid flow compartment comprising an inter fiber space and a housing supply port and a housing discharge port, all in fluid communication with each other;
wherein said fibers have an external surface that is hydrophilic and has a root-mean-square surface roughness that is smaller than 100 nanometers,
wherein said hollow fibers have a molecular weight cutoff of less than 50,000 Daltons,
wherein at said housing has an interior surface that is at least partially coated with a hemocompatible material or has a surface treatment to improve its hemocompatibility.

48. The cartridge of characterization 47, wherein said coating comprises a substance that is selected from the group consisting of heparin, polyvinylpyrrolidone, polyethylene glycol, vitamin E and fluoropolymers.

49. The cartridge of any one of characterizations 47-48, wherein said housing interior surface has a root-mean-square value of surface roughness that is less than 100 nanometers.

50. The cartridge of any one of characterizations 47-49, further comprising a surface treatment underlying said coating.

51. The cartridge of any one of characterizations 47-50, wherein said housing interior is fully coated.

52. A cartridge for use in extracorporeal processing of blood, comprising:
    a housing;
    a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
    a first end barrier that joins with said fibers at first ends of said fibers and joins with a housing interior of said housing and bounds a first end plenum and separates said first end plenum from a housing midsection interior region;
    a second end barrier that joins with said fibers at second ends of said fibers and joins with said housing interior of said housing and bounds a second end plenum and separates said second end plenum from said housing midsection interior region;
    a first fluid flow compartment comprising said first end plenum and said interiors of said hollow fibers and said second end plenum, said first end plenum and said interiors of said hollow fibers and said second end plenum being in fluid communication with each other; and
    a second fluid flow compartment comprising an inter fiber space and a housing supply port and a housing discharge port, all in fluid communication with each other;
    wherein said fibers have an external surface that is hydrophilic and has a root-mean-square surface roughness that is smaller than 100 nanometers,
    wherein said hollow fibers have a molecular weight cutoff of less than 50,000 Daltons, wherein at least some of said fibers have a coating or surface treatment at some places of their exteriors but not at other places.

53. The cartridge of characterization 52, wherein said coating or surface treatment is applied on only a portion of said fibers near a flow transition region.

54. The cartridge of any one of characterizations 52-53, wherein said coating comprises a substance that is selected from the group consisting of heparin, polyvinylpyrrolidone, polyethylene glycol, vitamin E and fluoropolymers.

55. The cartridge of any one of characterizations 52-54, further comprising a surface treatment underlying said coating.

56. A cartridge for use in flow filtration, comprising:
    a housing;
    a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
    a first end barrier that joins with said fibers at first ends of said fibers and joins with a housing interior of said housing and bounds a first end plenum and separates said first end plenum from a housing midsection interior region;
    a second end barrier that joins with said fibers at second ends of said fibers and joins with said housing interior of said housing and bounds a second end plenum and separates said second end plenum from said housing midsection interior region;
    a first fluid flow compartment comprising said first end plenum and said interiors of said hollow fibers and said second end plenum, said first end plenum and said interiors of said hollow fibers and said second end plenum being in fluid communication with each other; and
    a second fluid flow compartment comprising an inter fiber space and a housing supply port and a housing discharge port, all in fluid communication with each other;
    wherein said fibers have an external surface that is hydrophilic and has a root-mean-square surface roughness that is smaller than 100 nanometers;
    wherein said hollow fibers have a molecular weight cutoff of less than 50,000 Daltons;
    wherein said cartridge has a supply distributor at a supply end of said cartridge, and an axial length of said supply distributor is chosen so that a shear rate of flow entering a fiber bundle approximately perpendicularly to said fiber bundle is between 50% and 200% of a shear rate for axial flow in said inter-fiber space.

57. A cartridge for use in flow filtration, comprising:
    a housing;
    a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
    a first end barrier that joins with said fibers at first ends of said fibers and joins with a housing interior of said housing and bounds a first end plenum and separates said first end plenum from a housing midsection interior region;
    a second end barrier that joins with said fibers at second ends of said fibers and joins with said housing interior of said housing and bounds a second end plenum and separates said second end plenum from said housing midsection interior region;
    a first fluid flow compartment comprising said first end plenum and said interiors of said hollow fibers and said second end plenum, said first end plenum and said interiors of said hollow fibers and said second end plenum being in fluid communication with each other; and
    a second fluid flow compartment comprising an inter fiber space and a housing supply port and a housing discharge port, all in fluid communication with each other;
    wherein said fibers have an external surface that is hydrophilic and has a root-mean-square surface roughness that is smaller than 100 nanometers;
    wherein said hollow fibers have a molecular weight cutoff of less than 50,000 Daltons;
    wherein said cartridge has a supply distributor at a supply end of said cartridge, and an axial length of said supply distributor is chosen so that a superficial velocity of flow entering a fiber bundle approximately perpendicularly to said fiber bundle is between 50% and 200% of a superficial velocity for axial flow in said inter-fiber space.

58. A cartridge for use in flow filtration, comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other; and
a second fluid flow compartment comprising an inter fiber space and a housing supply port and a housing discharge port, all in fluid communication with each other;
wherein said fibers have an external surface that is hydrophilic and has a root-mean-square surface roughness that is smaller than 100 nanometers;
wherein said hollow fibers have a molecular weight cutoff of less than 50,000 Daltons;
wherein said cartridge has a supply distributor at a supply end of said cartridge, and an axial length L of said supply distributor, and said housing midsection interior region has a radius r, and wherein a parameter 2*L/r has a value between 0.5 and 2.0.

59. A blood processing system, comprising:
a blood flow system, wherein said blood flow system receives blood from a patient; and
a cartridge connected to said blood flow system, said cartridge comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other; and
a second fluid flow compartment comprising an inter fiber space and a housing supply port and a housing discharge port, all in fluid communication with each other;
wherein said fibers are spaced in said housing midsection interior region between said supply distributor and said discharge distributor in a uniform or substantially uniform distribution;
wherein said hollow fibers have a molecular weight cutoff of less than 50,000 Daltons;
wherein said blood flow system introduces blood into said housing supply port of said housing and removes at least approximately said blood from said housing discharge port of said housing.

60. A blood processing system of characterization 59, wherein said blood processing system is used for a therapy selected from the group consisting of: Hemodialysis; Hemodiafiltration;
Slow Continuous Ultrafiltration; Ultrafiltration; Slow Continuous Hemodialysis; Continuous Renal Replacement Therapy; Continuous Veno-Venous Hemofiltration; Continuous Veno-Venous hemodialysis; Continuous Veno-Venous Hemodiafiltration; and plasmapheresis.

61. A blood processing system, comprising:
a blood flow system; and
a cartridge connected to said blood flow system, said cartridge comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other; and
a second fluid flow compartment comprising an inter fiber space and a housing supply port and a housing discharge port, all in fluid communication with each other;
wherein said fibers are spaced in said housing midsection interior region between said supply distributor and said discharge distributor in a uniform or substantially uniform distribution;
wherein said hollow fibers have a molecular weight cutoff of less than 50,000 Daltons;
wherein said fibers have an external surface that is hemocompatible and has a root-mean-square surface roughness that is smaller than 100 nanometers;
wherein in a cross-section of said housing and said plurality of fibers, said plurality of fibers within said housing have a porosity fraction that is between 40% and 70%;

wherein said blood flow system introduces blood into said housing supply port of said housing and removes at least approximately said blood from said housing discharge port of said housing.

62. The blood processing system of characterization 61, wherein said porosity fraction is between 50% and 62%
63. The blood processing system of any one of characterizations 61-62, wherein at least some of said fibers in said fiber array are wavy fibers.
64. The blood processing system of any one of characterizations 61-63, wherein at least some of said fibers in said fiber array are wavy fibers having a spatial period of 0.5 to 2.0 cm.
65. The blood processing system of any one of characterizations 61-64, wherein said fibers in said fiber array are straight fibers.
66. The blood processing system of any one of characterizations 61-65, wherein at least some of said fibers in said fiber array are spacer yarns.
67. The blood processing system of any one of characterizations 61-66, wherein said hollow fibers have an internal surface that has a root-mean-square surface roughness that is larger than 100 nanometers.
68. The blood processing system of any one of characterizations 61-67, further comprising an emboli trap suitable to retain blood clots, said emboli trap being located internally within said housing near said housing supply port.
69. The blood processing system of any one of characterizations 61-68, further comprising an emboli trap suitable to retain blood clots, said emboli trap being located internally within said housing near said housing discharge port.
70. The blood processing system of any one of characterizations 61-69, wherein said blood processing system is part of an extracorporeal blood circuit for treating a patient.
71. The blood processing system of any one of characterizations 61-70, wherein said blood processing system is part of an implant.
72. The blood processing system of any one of characterizations 61-71, wherein said blood processing system is used for processing blood while not being connected to a patient.
73. The blood processing system of any one of characterizations 61-72, wherein said blood processing system is used for a therapy selected from the group consisting of: Hemodialysis; Hemodiafiltration; Slow Continuous Ultrafiltration; Ultrafiltration; Slow Continuous Hemodialysis; Continuous Renal Replacement Therapy; Continuous Veno-Venous Hemofiltration; Continuous Veno-Venous hemodialysis; and Continuous Veno-Venous Hemodiafiltration; and plasmapheresis.
74. The blood processing system of any one of characterizations 61-73, wherein said blood has a shear rate that everywhere is between 300 sec$^{-1}$ and 2700 sec$^{-1}$.
75. The blood processing system of any one of characterizations 61-74, wherein said blood has a shear rate that everywhere is between 300 sec$^{-1}$ and 1000 sec$^{-1}$.
76. A blood processing system, comprising:
a blood flow system; and
a cartridge connected to said blood flow system, said cartridge comprising:
a housing;
a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a first fluid flow compartment comprising said first end plenum and said interiors of said hollow fibers and said second end plenum, said first end plenum and said interiors of said hollow fibers and said second end plenum being in fluid communication with each other; and
a second fluid flow compartment comprising an inter fiber space and a housing supply port and a housing discharge port, all in fluid communication with each other;
wherein said blood flow system introduces blood into said housing supply port of said housing and removes at least approximately said blood from said housing discharge port of said housing;
wherein said fibers are spaced in said housing middle interior region between said supply distributor and said discharge distributor in a uniform or substantially uniform distribution;
wherein at least some of said fibers in said plurality of fibers are wavy fibers, and wherein in a cross-section of said housing and said plurality of fibers.
77. The system of characterization 76, wherein at least some of said fibers in said fiber array have a spatial period of 0.5 to 2.0 cm.
78. The system of any one of characterizations 76-77, wherein said blood flows at least approximately along a longitudinal direction of said wavy fiber, past an exterior surface of said wavy fiber that is convexly curved in a first plane, having a first radius of curvature, and is convexly curved in a second plane that is perpendicular to said first plane, having a second radius of curvature.
79. The system of characterization 78, wherein said first radius of curvature is between 50 microns and 300 microns.
80. The system of characterization 78, wherein said second radius of curvature is between 0.001 m and 0.1 m.
81. The system of characterization 78, wherein a ratio of said first radius of curvature to said second radius of curvature is between 0.001 and 0.1.
82. The system of characterization 78, wherein said fiber and said blood further are in contact with an internal surface of a cylinder.
83. The system of characterization 76, wherein said blood flows past an exterior surface of said fiber that is convexly curved in a first plane, having a first radius of curvature, and is concavely curved in a second plane that is perpendicular to said first plane, having a second radius of curvature.
84. The system of characterization 83, wherein said first radius of curvature is between 50 microns and 300 microns.
85. The system of characterization 83, wherein said second radius of curvature is between 0.001 m and 0.1 m.

86. The system of characterization 83, wherein a ratio of said first radius of curvature to said second radius of curvature is between 0.001 and 0.1.

87. The system of characterization 83, wherein said fiber and said blood further are in contact with an internal surface of a cylinder.

88. The system of any one of characterizations 76-87, wherein said fiber bundle further comprises a spacer fiber.

89. The system of any one of characterizations 76-88, wherein said fibers have a molecular weight cutoff of less than 50,000 Daltons.

90. The system of any one of characterizations 76-89, wherein said fibers are hemocompatible and smooth on their exteriors.

91. The system of any one of characterizations 76-90, wherein said plurality of fibers within said housing have a porosity fraction that is between 40% and 70%

92. The system of any one of characterizations 76-91, wherein said porosity fraction is between 50% and 62%.

93. The system of any one of characterizations 76-92, wherein said blood processing system is part of an extracorporeal blood circuit for treating a patient.

94. The system of any one of characterizations 76-93, wherein said blood processing system is part of an implant.

95. The system of any one of characterizations 76-94, wherein said blood processing system is used for processing blood while not being connected to a patient.

96. A blood processing system, comprising:
   a blood flow system; and
   a cartridge connected to said blood flow system, said cartridge comprising:
      a housing;
      a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
      a first end barrier that joins with said fibers at first ends of said fibers and joins with a housing interior of said housing and bounds a first end plenum and separates said first end plenum from a housing midsection interior region;
      a second end barrier that joins with said fibers at second ends of said fibers and joins with said housing interior of said housing and bounds a second end plenum and separates said second end plenum from said housing midsection interior region;
      a first fluid flow compartment comprising said first end plenum and said interiors of said hollow fibers and said second end plenum, said first end plenum and said interiors of said hollow fibers and said second end plenum being in fluid communication with each other; and
      a second fluid flow compartment comprising an inter fiber space and a housing supply port and a housing discharge port, all in fluid communication with each other;
      wherein said fibers are spaced in said housing middle interior region between said supply distributor and said discharge distributor in a uniform or substantially uniform distribution,
      wherein said hollow fibers have a molecular weight cutoff of less than 50,000 Daltons,
      wherein said fibers have an external surface that is hydrophilic and has a root-mean-square surface roughness that is smaller than 100 nanometers;
      wherein in a cross-section of said housing and said plurality of fibers, said plurality of fibers within said housing have a porosity fraction that is between 40% and 70%;
      wherein said system is operated such that a pressure drop of dialysate flow through said cartridge is greater than 1.1 times a pressure of drop of blood flow through said cartridge.

97. The system of characterization 96, wherein at least some of said fibers in said fiber array are wavy fibers.

98. The system of characterization 97, wherein at least some of said fibers in said fiber array are spacer yarns.

99. A blood processing system, comprising:
   a blood and dialysate flow system; and
   a cartridge connected to said blood and dialysate flow system, said cartridge comprising:
      a housing;
      a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;
      wherein said cartridge defines a blood flow path in said cartridge, said blood having a blood flow average velocity where said blood is in contact with said semi-permeable membrane material;
      wherein said cartridge defines a dialysate flow path in said cartridge, said dialysate having a dialysate flow average velocity where said dialysate is in contact with said semi-permeable membrane material;
      wherein said dialysate flow average velocity is greater than said blood flow average velocity.

100. A system of characterization 99, wherein said dialysate flow average velocity is more than two times said blood flow average velocity.

101. A system of any one of characterizations 99-100, wherein said dialysate flow average velocity is more than three times said blood flow average velocity.

102. A system of any one of characterizations 99-101, wherein said dialysate flow average velocity is more than four times said blood flow average velocity.

103. A system of any one of characterizations 99-102, wherein said blood flow system causes blood to flow past said exterior of said fibers in a direction generally parallel to a long direction of said cartridge such that a local velocity of said blood is everywhere greater than 0.25 cm/sec.

104. A system of any one of characterizations 99-103, wherein said blood system is operated such that everywhere in said fiber bundle said blood has a flow velocity at least 0.2 cm/sec and has a shear rate of at least 300 $\sec^{-1}$.

105. A blood processing system, comprising:
   a blood flow system; and
   a cartridge connected to said blood flow system, said cartridge comprising:
      a housing;
      a plurality of fibers contained inside said housing, at least some of said fibers being hollow and being made of semi-permeable membranes having respective fiber interiors and fiber exteriors, said fibers being parallel or almost parallel to each other over at least a substantial portion of their lengths;

a first end barrier that joins with said fibers at first ends of said fibers and joins with a housing interior of said housing and bounds a first end plenum and separates said first end plenum from a housing midsection interior region;

a second end barrier that joins with said fibers at second ends of said fibers and joins with said housing interior of said housing and bounds a second end plenum and separates said second end plenum from said housing midsection interior region;

a first fluid flow compartment comprising said first end plenum and said interiors of said hollow fibers and said second end plenum, said first end plenum and said interiors of said hollow fibers and said second end plenum being in fluid communication with each other; and a second fluid flow compartment comprising an inter fiber space and a housing supply port and a housing discharge port, all in fluid communication with each other;

wherein said fibers are spaced in said housing middle interior region between said supply distributor and said discharge distributor in a uniform or substantially uniform distribution;

wherein said hollow fibers have a molecular weight cutoff of less than 50,000 Daltons;

wherein said fibers have an external surface that is hydrophilic and has a root-mean-square surface roughness that is smaller than 100 nanometers;

wherein in a cross-section of said housing and said plurality of fibers, said plurality of fibers within said housing have a porosity fraction that is between 40% and 70%;

wherein progressing along flow of said blood through said cartridge, near an inlet end water and small molecules leave said blood by passing from an exterior of said fibers to an interior of said fibers, and near a outlet end of said cartridge, water and small molecules enter said blood by passing from an interior of said fibers to an exterior of said fibers.

106. A blood processing system, comprising:
a blood flow system; and
a cartridge connected to said blood flow system, said cartridge comprising:
a housing;
a plurality of fibers contained inside said housing, at least some of said fibers being hollow and being made of semi-permeable membranes having respective fiber interiors and fiber exteriors;
an end barrier or barriers that joins with said fibers at ends of said fibers and joins with a housing interior of said housing and bounds a first end plenum and separates said plenum or plenums from a housing interior region;
a first fluid flow compartment comprising said plenum or plenums and said interiors of said hollow fibers, said plenum or plenums and said interiors of said hollow fibers being in fluid communication with each other; and
a second fluid flow compartment comprising an inter fiber space and a housing supply port and a housing discharge port, all in fluid communication with each other;
wherein blood flows in said second fluid flow compartment past exterior surfaces of said fibers, in a flow direction that is generally perpendicular to a local lengthwise direction of said fibers at a midpoint between ends of said fibers.

107. The system of characterization 106, wherein said fibers follow an overall path that is generally straight.

108. The system of any one of characterizations 106-107, wherein said fibers follow an overall path that is curved.

109. The system of any one of characterizations 106-108, wherein said blood flows past said fibers in a direction that is generally radial with respect to an overall geometry of said housing.

110. The system of any one of characterizations 106-109, wherein said blood flow has a shear rate that is between 300 sec$^{-1}$ and 2700 sec$^{-1}$.

111. A blood processing system, comprising:
a blood flow system; and
a cartridge connected to said blood flow system, said cartridge comprising:
a housing;
a plurality of fibers contained inside said housing, at least some of said fibers being hollow and being made of semi-permeable membranes having respective fiber lumens and fiber exteriors, said membranes having a molecular weight cutoff of approximately 50,000 Daltons;
a first fluid flow compartment comprising said lumens of said hollow fibers; and
a second fluid flow compartment comprising an inter fiber space inside said housing;
wherein blood flows in said inter fiber space at a blood flowrate;
wherein an aqueous buffer solution flows inside said fiber lumens at a solution flowrate;
wherein said blood has, based on said blood flowrate and on blood properties and on dimensional parameters of said inter fiber space, a blood flow shear rate;
wherein said aqueous buffer solution has, based on said solution flowrate and on solution properties and on dimensional parameters of said lumens, a solution flow shear rate;
wherein a ratio of said blood flow shear rate to said solution flow shear rate is between 0.5 and 2.0.

112. The system of characterization 111, wherein said ratio is between 0.67 and 1.5.

113. The system of any one of characterizations 111-112, wherein said ratio is between 0.8 and 1.2.

114. The system of any one of characterizations 111-113, wherein said solution flowrate is less than 1.2 times said blood flowrate.

115. The system of any one of characterizations 111-114, wherein flow of said blood everywhere has a shear rate that is between 300 sec$^{-1}$ and 2700 sec$^{-1}$.

116. The system of any one of characterizations 111-115, wherein said blood flows past said fibers in a direction generally parallel to said fibers.

117. The system of any one of characterizations 111-116, wherein said blood flows past said fibers in a direction generally perpendicular to said fibers.

118. The system of any one of characterizations 111-117, wherein said blood flows past said fibers in a direction that is generally radial with respect to an overall geometry of said housing.

119. The system of any one of characterizations 111-118, wherein said fibers follow an overall path that is generally straight.

120. The system of any one of characterizations 111-119, wherein said fibers follow an overall path that is curved.

121. A method of processing blood, comprising:
   providing a filtration cartridge,
      wherein said filtration cartridge comprises a plurality of semi-permeable hollow fibers enclosed within a housing, and comprises a first flow compartment comprising lumens of said fibers and comprises a second flow compartment comprising outsides of said fibers,
      wherein at least a majority of said fibers have an outside surface that is smooth having a root-mean-square roughness of less than 100 nanometers and is hemocompatible,
      wherein at least a majority of said fibers have a Molecular Weight Cutoff of less than about 50,000 Daltons,
      wherein said fibers occupy space inside said housing at a porosity fraction between 40% and 70%; and
   supplying said blood to said second flow compartment so that said blood flows outside said fibers;
   withdrawing blood from said second flow compartment; and
   withdrawing dialysate or ultrafiltrate from said first flow compartment.
122. The method of characterization 121, wherein at least a majority of said fibers are wavy fibers.
123. The method of characterization 121, wherein at least a majority of said fibers are straight fibers.
124. The method of any one of characterizations 121-123, wherein said porosity fraction is between 50% and 62%.
125. The method of any one of characterizations 121-124, wherein supplying said blood to said second flow compartment comprises causing said blood to flow through said second flow compartment such that a shear rate of said blood is between approximately 300 sec$^{-1}$ and approximately 2700 sec$^{-1}$ everywhere in said second flow compartment, and such that a local average velocity of said blood is greater than approximately 0.25 cm/sec everywhere in said second flow compartment.
126. The method of any one of characterizations 121-125, wherein a ratio of a maximum shear rate of said blood anywhere in said cartridge to a minimum shear of said blood anywhere in said cartridge does not vary by more than a factor of 4.
127. The method of any one of characterizations 121-126, wherein said blood is part of an extracorporeal blood flow circuit.
128. The method of any one of characterizations 121-127, wherein said method is used in a procedure selected from the group consisting of: Hemodialysis; Hemofiltration; Hemodiafiltration; Ultrafiltration; Slow Continuous Ultrafiltration; Slow Continuous Hemodialysis; Continuous Renal Replacement Therapy; Continuous Veno-Venous Hemodialysis; Continuous Veno-Venous Hemofiltration; Continuous Veno-Venous Hemodiafiltration; and plasmapheresis.
129. The method of any one of characterizations 121-128, wherein said method is used to treat a condition selected from the group consisting of Acute Kidney Injury, Chronic Kidney Disease, end-stage renal disease, congestive heart failure, hypervolemia, edema, and dyspnea.
130. The method of any one of characterizations 121-129, wherein said filtration cartridge is contained in an implant that is implanted in a patient.
131. The method of any one of characterizations 121-130, wherein said method is used to process said blood for a blood bank or for separation of blood into components or for pharmaceutical manufacturing.
132. The method of any one of characterizations 121-131, wherein said second compartment comprises at least one distributor.
133. The method of any one of characterizations 121-132, wherein said second compartment comprises a distributor at a supply end and does not comprise a distributor at a discharge end.
134. The method of any one of characterizations 121-133, wherein said second compartment comprises at least one orbital distributor.
135. The method of any one of characterizations 121-134, wherein said fibers fan at at least one end of said fibers.
136. The method of any one of characterizations 121-135, wherein said second flow compartment has at least one flow-related feature at a supply end that is different from a corresponding feature at a discharge end or wherein said discharge end does not have a feature corresponding to said flow-related feature at said supply end.
137. The method of any one of characterizations 121-136, wherein said fibers fan near a supply end of said second flow compartment, and near a discharge end of said second flow compartment, said fibers either do not fan or fan to a lesser extent than said fibers fan near said supply end.
138. The method of any one of characterizations 121-137, further comprising providing an emboli trap in a flow path of said blood downstream of said filtration cartridge.
139. The method of any one of characterizations 121-138, wherein said first flow compartment has only one fluid connection, said one fluid connection being used to withdraw said ultrafiltrate.
140. The method of any one of characterizations 121-139, further comprising supplying said dialysate to said first flow compartment.
141. The method of any one of characterizations 121-140, wherein said fibers are generally parallel to each other over at least a majority of their length.
142. The method of any one of characterizations 121-141, wherein said second flow compartment comprises at least one air bleed.
143. A processing system, comprising:
   a blood flow system; and
   a cartridge within said blood flow system, said cartridge comprising:
   a housing;
   a plurality of fibers contained inside said housing, at least some of said fibers being hollow and being made of semi-permeable membranes having respective fiber interiors and fiber exteriors;
   a first fluid flow compartment comprising said interiors of said hollow fibers; and
   a second fluid flow compartment comprising an inter fiber space bordering said fiber exteriors,
   wherein said fibers occupy space inside said housing at a porosity fraction of between 40% and 70%,
   wherein at least a majority of said fibers have an outside surface that is smooth having a root-mean-square roughness of less than 100 nanometers and is hemocompatible,
   wherein at least a majority of said fibers have a Molecular Weight Cutoff of less than about 50,000 Daltons, and
   wherein said blood flow system introduces blood into said second fluid flow compartment and removes processed blood from said second fluid flow compartment.
144. The processing system of characterization 143, wherein said fibers occupy space inside said housing at a porosity fraction of between 50% and 62%.

145. The processing system of any one of characterizations 143-144, wherein said fibers comprise polyethersulfone or related polymers, in combination with polyvinylpyrrolidone.

146. The processing system of any one of characterizations 143-145, wherein at least a majority of said fibers are wavy fibers.

147. The processing system of any one of characterizations 143-146, wherein at least a majority of said fibers are straight fibers.

148. The processing system of any one of characterizations 143-147, wherein said processing system supplies dialysate to said first fluid flow compartment and removes dialysate from said first fluid flow compartment.

149. The processing system of any one of characterizations 143-148, wherein said processing system removes ultrafiltrate from said first fluid flow compartment.

150. The processing system of any one of characterizations 143-149, wherein said first fluid flow compartment comprises a first header, and said interiors of said fibers, and a second header, all in fluid communication with each other.

151. The processing system of any one of characterizations 143-150, wherein said second fluid flow compartment comprises a housing supply port, and said inter fiber space, and a housing discharge port, all in fluid communication with each other.

152. The processing system of any one of characterizations 143-151, wherein said first fluid flow compartment and said second fluid flow compartment are separated by a barrier in which said fibers are potted.

153. The processing system of any one of characterizations 143-152, wherein said first fluid flow compartment and said second fluid flow compartment are separated by a first barrier and a second barrier, with first ends of said fibers being potted in said first barrier and second opposed ends of said fibers being potted in said second barrier.

154. The processing system of any one of characterizations 143-153, wherein in said second flow compartment, said blood flows generally parallel to said fibers in a majority of a flow distance in said second flow compartment.

155. The processing system of any one of characterizations 143-154, wherein in said second flow compartment, said blood flows generally perpendicular to said fibers in a majority of a flow distance in said second flow compartment.

156. The processing system of any one of characterizations 143-155, wherein dialysate flows in said first compartment, and wherein said blood flowing in said second flow compartment and said dialysate flowing in said first compartment flow in a generally opposite directions with respect to each other in a majority of their respective flowpaths inside said cartridge.

157. The processing system of any one of characterizations 143-156, wherein said second flow compartment has at least one flow-related feature at a supply end that is different from a corresponding feature at a discharge end or wherein said discharge end does not have a feature corresponding to said flow-related feature at said supply end.

158. The processing system of any one of characterizations 143-157, wherein said blood flow system causes said blood to flow through said second fluid flow compartment such that a shear rate of said blood is between approximately 300 sec$^{-1}$ and approximately 2700 sec$^{-1}$ everywhere in said second flow compartment, and such that an average local velocity of said blood is greater than approximately 0.25 cm/sec everywhere in said second flow compartment.

159. The processing system of any one of characterizations 143-145, wherein said blood flow system causes said blood to flow through said second fluid flow compartment such that a ratio of a maximum shear rate of said blood anywhere in said cartridge to a minimum shear of said blood anywhere in said cartridge is not larger than 4.

160. The processing system of any one of characterizations 143-159, wherein said processing system is used in an extracorporeal therapy wherein said processing system receives said blood from a patient and returns processed blood to said patient.

161. The processing system of any one of characterizations 143-160, wherein said processing system is used for a therapy selected from the group consisting of: Hemodialysis; Hemodiafiltration; Slow Continuous Ultrafiltration; Ultrafiltration; Slow Continuous Hemodialysis; Continuous Renal Replacement Therapy; Continuous Veno-Venous Hemofiltration; Continuous Veno-Venous hemodialysis; Continuous Veno-Venous Hemodiafiltration; and plasmapheresis.

162. The processing system of any one of characterizations 143-161, wherein said processing system is used to treat a condition selected from the group consisting of Acute Kidney Injury, Chronic Kidney Disease, end-stage renal disease, congestive heart failure, hypervolemia, edema, and dyspnea.

163. The processing system of any one of characterizations 143-162, wherein said processing system is used to process said blood while not being connected to a patient.

Although embodiments have been disclosed, it is not desired to be limited thereby. Rather, the scope should be determined only by the appended claims.

We claim:

1. A method of treating blood with dialysate comprising:
(a) providing a blood processing system comprising a blood processing cartridge comprising:
a housing having a housing interior, a housing blood supply port, a housing blood discharge port, and wherein said housing interior includes a housing midsection interior region;
a plurality of fibers contained inside said housing, at least some of said fibers being hollow fibers and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with said housing interior of said housing and bounds a first end plenum and separates said first end plenum from said housing midsection interior region;
a second end barrier that joins with said fibers at second ends of said fibers and joins with said housing interior and bounds a second end plenum and separates said second end plenum from said housing midsection interior region;
a fluid flow compartment comprising said first end plenum, said fiber interiors, and said second end plenum, said first end plenum, said fiber interiors, and said second end plenum being in fluid communication with each other; and
a blood flow compartment comprising an inter fiber space defined by said fiber exteriors and an interior housing surface along said housing midsection interior region, said housing blood supply port and said housing blood discharge port, said inter fiber space, said housing supply port, and said housing discharge port being in fluid communication with each other;

wherein at least some of said fibers have external surfaces that are hydrophilic, and said external surfaces have root-mean-square roughness values of less than 100 nanometers;

wherein at least a part of said interior housing surface along said housing midsection interior region comprises a coating or surface treatment to increase hemocompatibility; and wherein the blood processing cartridge is constructed to receive blood in the blood flow compartment so that the blood flows into the blood flow compartment via the housing supply port, in contact with said external surfaces of said fibers, and out of the blood flow compartment via the housing discharge port;

(b) connecting said blood processing system to a patient; and (c) flowing blood from the patient through the blood flow compartment along said inter fiber space and returning the blood from the blood flow compartment to the patient, and flowing dialysate through said hollow fibers.

2. A method of treating blood with dialysate comprising:
(a) providing a blood processing system comprising:
a blood flow system comprising a blood inlet line, a blood processing cartridge, and a blood outlet line; and
said blood processing cartridge comprises:
   a housing having a housing supply port and a housing discharge port;
   a plurality of fibers contained inside said housing, at least some of said fibers being hollow and being made of semi-permeable membranes having respective fiber interiors and fiber exteriors, said fibers having an external surface that is hydrophilic and has a root-mean-square surface roughness that is smaller than 100 nanometers;
   a first end barrier that joins with said fibers at first ends of said fibers and joins with a housing interior of said housing and bounds a first end plenum and separates said first end plenum from a housing midsection interior region;
   a second end barrier that joins with said fibers at second ends of said fibers and joins with said housing interior of said housing and bounds a second end plenum and separates said second end plenum from said housing midsection interior region;
   a fluid flow compartment comprising said first end plenum, said fiber interiors, and said second end plenum, said first end plenum, said fiber interiors, and said second end plenum being in fluid communication with each other; and
   a blood flow compartment comprising an inter fiber space defined by said fiber exteriors and an interior housing surface along said housing midsection interior region, said housing supply port connected to said blood inlet line, said housing discharge port connected to said blood outlet line, and said inter fiber space, said housing supply port, and said housing discharge port being in fluid communication with each other;
wherein said blood flow system is constructed to introduce blood through said blood inlet line and through said housing supply port and into said blood flow compartment and remove said blood from said housing discharge port and through said blood outlet line, and wherein said blood flows in contact with the external surface of said fibers;

(b) connecting said blood processing system to a patient; and (c) flowing blood from the patient into said blood inlet line and said housing through said housing supply port, along the external surface of said fibers, and out of said housing through said housing discharge port and into said blood outlet line, and flowing dialysate through said hollow fibers.

3. The method of treating blood of claim 2, wherein said blood has a shear rate that everywhere inside said cartridge is between 300 sec$^{-1}$ and 2700 sec$^{-1}$.

4. The method of treating blood of claim 2, wherein said blood has a shear rate that everywhere inside said cartridge is between 300 sec$^{-1}$ and 1000 sec$^{-1}$.

5. The method of treating blood of claim 2, wherein said blood has a local velocity that everywhere inside said cartridge is greater than 0.25 cm/sec.

6. The method of treating blood of claim 2, wherein flow of said blood inside said housing occurs generally parallel to a lengthwise direction of said fibers.

7. The method of treating blood of claim 2, wherein said blood flow system causes blood to flow through said cartridge at flowrate of between 75 and 300 mL/min.

8. The method of treating blood of claim 1, wherein said hollow fibers are asymmetric membranes and comprise polyethersulfone or related polymers, in combination with polyvinylpyrrolidone or polyethylene glycols.

9. The method of treating blood of claim 1, wherein said hollow fibers have internal surfaces having root-mean-square surface roughness values larger than 100 nanometers.

10. The method of treating blood of claim 1, wherein said hollow fibers are symmetric membranes and comprise a material selected from the group consisting of: cellulose triacetate and other cellulosics; polyacrilonitrile; polymethylmethacrylate; and polyester polymer alloy.

11. The method of treating blood of claim 1, wherein at least some of said fibers are wavy having a wavelength of waviness that is in the range of 0.4 centimeters to 1 centimeter.

12. The method of treating blood of claim 1, wherein at least some of said fibers are wavy having a half-amplitude of waviness that is in the range of 0.1 millimeter to 1 millimeter.

13. The method of treating blood of claim 1, wherein at least some of said fibers are straight.

14. The method of treating blood of claim 1, wherein at least some of said fibers have an outside diameter that is in the range of 100 microns to 1,500 microns.

15. The method of treating blood of claim 1, wherein said hydrophilic external surface has a hydrated surface layer whose thickness is greater than 48 nanometers.

16. The method of treating blood of claim 1, wherein said semi-permeable membranes have pore sizes in the range of 2 nanometers to 7 nanometers.

17. The method of treating blood of claim 1, wherein said semi-permeable membranes have a molecular weight cutoff of 50,000 Daltons or less.

18. The method of treating blood of claim 1, wherein said fibers have an ultrafiltration coefficient of between 5 and 100 ml/hr/m$^2$/mmHg.

19. The method of treating blood of claim 1, wherein a total surface area of said fibers is between 0.03 m$^2$ and 2.0m$^2$.

20. The method of treating blood of claim 1, wherein said blood has a shear rate that everywhere inside said cartridge is between 300 sec$^{-1}$ and 2700 sec$^{-1}$.

21. The method of treating blood of claim 1, wherein said blood has a shear rate that everywhere inside said cartridge is between 300 sec$^{-1}$ and 1000 sec$^{-1}$.

22. The method of treating blood of claim 1, wherein said blood has a local velocity that everywhere inside said cartridge is greater than 0.25 cm/sec.

23. The method of treating blood of claim 1, wherein flow of said blood inside said housing occurs generally parallel to a lengthwise direction of said fibers.

24. The method of treating blood of claim 1, wherein said blood flow system causes blood to flow through said cartridge at flowrate of between 75 and 300 mL/min.

25. The method of treating blood of claim 1, wherein the method comprises hemodialysis or hemodiafiltration.

26. The method of treating blood of claim 2, wherein the method comprises hemodialysis or hemodiafiltration.

27. A method of ultrafiltration of blood comprising:
(a) providing a blood processing system comprising a blood processing cartridge comprising:
a housing having a housing interior, a housing blood supply port, a housing blood discharge port, and wherein said housing interior includes a housing midsection interior region;
a plurality of fibers contained inside said housing, at least some of said fibers being hollow fibers and being made of semi-permeable membranes having respective fiber interiors and fiber exteriors, said fibers being parallel or almost parallel to each other over at least a substantial portion of their lengths;
a first end barrier that joins with said fibers at first ends of said fibers and joins with said housing interior of said housing and bounds a first end plenum and separates said first end plenum from said housing midsection interior region;
a second end barrier that joins with said fibers at second ends of said fibers and joins with said housing interior and bounds a second end plenum and separates said second end plenum from said housing midsection interior region;
a fluid flow compartment comprising said first end plenum, said fiber interiors, and said second end plenum, said first end plenum, said fiber interiors, and said second end plenum being in fluid communication with each other; and
a blood flow compartment comprising an inter fiber space defined by said fiber exteriors and an interior housing surface along said housing midsection interior region, said housing blood supply port and said housing blood discharge port, said inter fiber space, said housing supply port, and said housing discharge port being in fluid communication with each other;
wherein at least some of said fibers have external surfaces that are hydrophilic, and said external surfaces have root-mean-square roughness values of less than 100 nanometers;
wherein at least a part of said interior housing surface along said housing midsection interior region comprises a coating or surface treatment to increase hemocompatibility; and
wherein the blood processing cartridge is constructed to receive blood in the blood flow compartment so that the blood flows into the blood flow compartment via the housing supply port, in contact with said external surfaces of said fibers, and out of the blood flow compartment via the housing discharge port;
(b) connecting said blood processing system to a patient; and
(c) flowing blood from the patient through the blood flow compartment and returning the blood from the blood flow compartment to the patient, and collecting filtrate from said hollow fibers.

28. The method of ultrafiltration of claim 27, wherein said fibers have a pore size of about 0.2 nanometers to 5 nanometers.

29. The method of ultrafiltration of claim 27, wherein a majority of said fibers have a molecular weight cutoff of less than about 50,000 Daltons.

30. A method of ultrafiltration of blood comprising:
(a) providing a blood processing system comprising:
a blood flow system comprising a blood inlet line, a blood processing cartridge, and a blood outlet line; and
said blood processing cartridge comprises:
a housing having a housing supply port and a housing discharge port;
a plurality of fibers contained inside said housing, at least some of said fibers being hollow and being made of semi-permeable membranes having respective fiber interiors and fiber exteriors, said fibers having an external surface that is hydrophilic and has a root-mean-square surface roughness that is smaller than 100 nanometers;
a first end barrier that joins with said fibers at first ends of said fibers and joins with a housing interior of said housing and bounds a first end plenum and separates said first end plenum from a housing midsection interior region;
a second end barrier that joins with said fibers at second ends of said fibers and joins with said housing interior of said housing and bounds a second end plenum and separates said second end plenum from said housing midsection interior region;
a fluid flow compartment comprising said first end plenum, said fiber interiors, and said second end plenum, said first end plenum, said fiber interiors, and said second end plenum being in fluid communication with each other; and
a blood flow compartment comprising an inter fiber space defined by said fiber exteriors and an interior housing surface along said housing midsection interior region, said housing supply port connected to said blood inlet line, said housing discharge port connected to said blood outlet line, and said inter fiber space, said housing supply port, and said housing discharge port being in fluid communication with each other;
wherein said blood flow system is constructed to introduce blood through said blood inlet line and through said housing supply port and into said blood flow compartment and remove said blood from said housing discharge port and through said blood outlet line, and wherein said blood flows in contact with the external surface of said fibers;
(b) connecting said blood processing system to a patient; and
(c) flowing blood from the patient into said blood inlet line and said housing through said housing supply port, along the external surface of said fibers, and out of said housing through said housing discharge port and into said blood outlet line, and collecting filtrate from said hollow fibers.

31. The method of ultrafiltration of claim 30, wherein said fibers have a pore size of about 0.2 nanometers to 5 nanometers.

32. The method of ultrafiltration of claim 30, wherein a majority of said fibers have a molecular weight cutoff of less than about 50,000 Daltons.

\* \* \* \* \*